(12) United States Patent
Charrier et al.

(10) Patent No.: US 8,592,577 B2
(45) Date of Patent: Nov. 26, 2013

(54) METHODS FOR PREPARING PYRIMIDINE DERIVATIVES USEFUL AS PROTEIN KINASE INHIBITORS

(75) Inventors: Jean-Damien Charrier, Grove Wantage (GB); Steven Durrant, Abingdon (GB); Michael O'Donnell, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/497,139

(22) Filed: Mar. 20, 2012

(65) Prior Publication Data

US 2012/0271045 A1 Oct. 25, 2012

Related U.S. Application Data

(63) Continuation of application No. PCT/IB2010/002655, filed on Sep. 24, 2010.

(60) Provisional application No. 61/245,773, filed on Sep. 25, 2009.

(51) Int. Cl.
*C07D 475/00* (2006.01)
*C07D 475/10* (2006.01)
*C07D 487/04* (2006.01)

(52) U.S. Cl.
USPC ........................... 540/501; 544/258; 544/259

(58) Field of Classification Search
USPC .................................. 540/501; 544/258, 259
See application file for complete search history.

(56) References Cited

U.S. PATENT DOCUMENTS

| 3,880,855 | A | 4/1975 | Juby et al. | |
|---|---|---|---|---|
| 8,003,785 | B2 * | 8/2011 | Cai et al. ...................... | 540/501 |
| 2003/0191307 | A1 | 10/2003 | Blumenkopf et al. | |
| 2004/0176380 | A1 | 9/2004 | Hoffmann et al. | |
| 2009/0291938 | A1 * | 11/2009 | Cao et al. .................. | 514/210.21 |
| 2009/0291983 | A1 | 11/2009 | Besidski et al. | |

FOREIGN PATENT DOCUMENTS

| DE | 2418285 | | 4/1974 |
|---|---|---|---|
| DE | 2418285 | A1 | 11/1974 |
| EP | 445467 | A1 | 3/1990 |
| JP | 50-35192 | | 4/1975 |
| JP | 51-110202 | | 3/1976 |
| JP | 2003509427 | | 3/2003 |
| WO | 9744038 | | 11/1997 |
| WO | 0012497 | | 3/2000 |
| WO | 0119825 | A1 | 3/2001 |
| WO | WO0140215 | | 6/2001 |
| WO | 0276985 | | 10/2002 |
| WO | 03020722 | A1 | 3/2003 |
| WO | 2004030635 | | 4/2004 |
| WO | 2004076454 | A1 | 9/2004 |
| WO | 2004108138 | | 12/2004 |
| WO | 2005068466 | | 7/2005 |
| WO | 2005121152 | | 12/2005 |
| WO | 2005123736 | A1 | 12/2005 |
| WO | 2006058876 | A1 | 6/2006 |
| WO | 2009023269 | A2 | 2/2009 |
| WO | WO 2009023269 | * | 2/2009 |
| WO | 2009040556 | A1 | 4/2009 |
| WO | 2009042711 | A1 | 4/2009 |
| WO | 2009067547 | A1 | 5/2009 |
| WO | WO2009071480 | A2 | 6/2009 |

OTHER PUBLICATIONS

Couture, Karine; Ple, Nelly; Turck, Allain; Queguiner, Guy, "A new route to aminodiazines via a metalation reaction. Synthesis of an aza analog of nevirapine", Electronic Conference on Hyterocyclic Chemistry, [Proceedings], Jun. 24-Jul. 22, 1996(1997).

International Search Report Received in the corresponding PCT Application No. PCT/IB2010/002655 (2011).

Ple, Nelly; Turck, Alain; Couture, Karine; Queguiner, Guy, "A new route to aminodiazines via a metalation reaction. Synthesis of an aza analog of nevirapine. Diazines". Synthesis (1996), (7), 838-842.

Phillips, Oludotun, A;, Knaus, Edward, E., " Synthesis of 6,7,8,9-tetrahydro-5H-pirimido[4,5-b][1,4]diazepine-6,8-diones", Journal of Heterocyclic Chemistry (1993), 30(1), 283-5.

Boyle, Peter H., Hughes, Enid M.; Khattab, Hassan A., "Synthesis of a 2,4-diaminodihydrohomopteridine,6-acetyl-2,4-diamino-7,8-dihydro-9H-pirimido[4,5-b][1,4]diazepine, using a furazano[3,4-d]pyrimidine precursor", Tetrahedron (1991), 47(28), 5259-68.

Jordan, V. C. et al., "Tamoxifen: A most unlikely pioneering medicine.", Nature Reviews: Drug Discovery, 2, 2003, p. 205.

(Continued)

*Primary Examiner* — Bruck Kifle
(74) *Attorney, Agent, or Firm* — Rory C. Stewart

(57) ABSTRACT

A method of preparing a compound represented by Structural Formula (I):

or a pharmaceutically acceptable salt thereof, wherein the variables of Structural Formula (I) are as described in the specification and claims. Additionally, the present invention relates to compounds of Structural Formula (I), which are useful as inhibitors of protein kinase.

38 Claims, No Drawings

(56) References Cited

OTHER PUBLICATIONS

Dorwald, F. Zaragoza, Side Reactions in Organic Synthesis: A Guide to Successful Synthesis Design, Weinheim: WILEY-VCH Verlag GmbH & Co. KGaA, 2005, Preface.

D. Barrett et at., "Orally bioavailable small molecule ketoamide-based inhibitors of cathepsin K.", Bioorganic & Medicinal Chemistry Letters 14 (2004) 2543-2546.

* cited by examiner

METHODS FOR PREPARING PYRIMIDINE DERIVATIVES USEFUL AS PROTEIN KINASE INHIBITORS

CROSS-REFERENCE

This application is a continuation application of International Patent Application No. PCT/IB2010/002655, filed on Sep. 24, 2010, which in turn claims the benefit under 35 U.S.C. §119, of U.S. Application No. 61/245,773, filed on Sep. 25, 2009. The entire contents of the aforementioned application are incorporated herein.

BACKGROUND OF THE INVENTION

The search for new therapeutic agents has been greatly aided in recent years by a better understanding of the structure of enzymes and other biomolecules associated with diseases. One important class of enzymes that has been the subject of intensive study is protein kinases.

Protein kinases constitute a large family of structurally related enzymes that are responsible for the control of a variety of signal transduction processes within the cell (see Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids etc). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al, *Cell* 1992, 70, 419-429; Kunz et al, *Cell* 1993, 73, 585-596; Garcia-Bustos et al, *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., shock, heat shock, ultraviolet radiation, bacterial endotoxin, and $H_2O_2$), cytokines (e.g., interleukin-1 (IL-1) and tumor necrosis factor alpha (TNF-a), and growth factors (e.g., granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Many diseases are associated with abnormal cellular responses triggered by protein kinase-mediated events as described above. These diseases include, but are not limited to, cancer, autoimmune diseases, inflammatory diseases, bone diseases, metabolic diseases, neurological and neurodegenerative diseases, cardiovascular diseases, allergies and asthma, Alzheimer's disease and hormone related diseases. Accordingly, there has been a substantial effort in medicinal chemistry to find protein kinase inhibitors that are effective as therapeutic agents.

The Polo-like kinases (Plk) belong to a family of serine/threonine kinases that are highly conserved across the species, ranging from yeast to man (reviewed in Lowery D M et al., *Oncogene* 2005, 24; 248-259). The Plk kinases have multiple roles in cell cycle, including control of entry into and progression through mitosis. Plk1 is the best characterized of the Plk family members. Plk1 is widely expressed and is most abundant in tissues with a high mitotic index. Protein levels of Plk1 rise and peak in mitosis (Hamanaka, R et al., *J Biol Chem* 1995, 270, 21086-21091). The reported substrates of Plk1 are all molecules that are known to regulate entry and progression through mitosis, and include CDC25C, cyclin B, p53, APC, BRCA2 and the proteasome. Plk1 is upregulated in multiple cancer types and the expression levels correlate with severity of disease (Macmillan, J C et al., *Ann Surg Oncol* 2001, 8, 729-740). Plk1 is an oncogene and can transform NIH-3T3 cells (Smith, M R et al., *Biochem Biophys Res Commun* 1997, 234, 397-405). Depletion or inhibition of Plk1 by siRNA, antisense, microinjection of antibodies, or transfection of a dominant negative construct of Plk1 into cells, reduces proliferation and viability of tumour cells in vitro (Guan, R et al., *Cancer Res* 2005, 65, 2698-2704; Liu, X et al., *Proc Natl Acad Sci USA* 2003, 100, 5789-5794, Fan, Y et al., *World J Gastroenterol* 2005, 11, 4596-4599; Lane, H A et al., *J Cell Biol* 1996, 135, 1701-1713). Tumour cells that have been depleted of Plk1 have activated spindle checkpoints and defects in spindle formation, chromosome alignment and separation and cytokinesis. Loss in viability has been reported to be the result of an induction of apoptosis. In contrast, normal cells have been reported to maintain viability on depletion of Plk1. In vivo knock down of Plk1 by siRNA or the use of dominant negative constructs leads to growth inhibition or regression of tumours in xenograft models.

Plk2 is mainly expressed during the G1 phase of the cell cycle and is localized to the centrosome in interphase cells. Plk2 knockout mice develop normally, are fertile and have normal survival rates, but are around 20% smaller than wild type mice. Cells from knockout animals progress through the cell cycle more slowly than in normal mice (Ma, S et al., *Mol Cell Biol* 2003, 23, 6936-6943). Depletion of Plk2 by siRNA or transfection of kinase inactive mutants into cells blocks centriole duplication. Downregulation of Plk2 also sensitizes tumour cells to taxol and promotes mitotic catastrophe, in part by suppression of the p53 response (Burns T F et al., *Mol Cell Biol* 2003, 23, 5556-5571).

Plk3 is expressed throughout the cell cycle and increases from G1 to mitosis. Expression is upregulated in highly proliferating ovarian tumours and breast cancer and is associated with a worse prognosis (Weichert, W et al., *Br J Cancer* 2004, 90, 815-821; Weichert, W et al., *Virchows Arch* 2005, 446, 442-450). In addition to regulation of mitosis, Plk3 is believed to be involved in Golgi fragmentation during the cell cycle and in the DNA-damage response. Inhibition of Plk3 by dominant negative expression is reported to promote p53-independent apoptosis after DNA damage and suppresses colony formation by tumour cells (Li, Z et al., *J Biol Chem* 2005, 280, 16843-16850.

Plk4 is structurally more diverse from the other Plk family members. Depletion of this kinase causes apoptosis in cancer cells (L1, J et al., *Neoplasia* 2005, 7, 312-323). Plk4 knockout mice arrest at E7.5 with a high fraction of cells in mitosis and partly segregated chromosomes (Hudson, J W et al., *Current Biology* 2001, 11, 441-446).

Molecules of the protein kinase family have been implicated in tumour cell growth, proliferation and survival. Accordingly, there is a great need to develop compounds useful as inhibitors of protein kinases. The evidence implicating the Plk kinases as essential for cell division is strong. Blockade of the cell cycle is a clinically validated approach to inhibiting tumour cell proliferation and viability.

A number of Plk kinase inhibitors have been reported in the art. See, for example, US 2009/0062292, US 2008/0167289, US 2006/004014, U.S. Pat. No. 6,806,272, U.S. Pat. No. 6,861,422, WO2009/040556, WO 2009/042711, and WO 2006/058876. Considering the potential of these Plk kinase inhibitors for treating one or more of the aforementioned diseases, it would be desirable to develop new efficient synthetic methods for such inhibitors and for their derivatives.

SUMMARY OF TILE INVENTION

The present invention generally relates to a method of preparing a compound represented by Structural Formula (I):

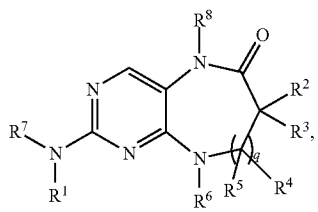

(I)

or a pharmaceutically acceptable salt thereof, wherein:

$R^1$ is —H, $C_{1-6}$ aliphatic, $C_{3-10}$ cycloaliphatic, $C_{6-10}$ aryl, 5-10 membered heteroaryl, or 3-10 membered heterocyclyl, wherein each of said aliphatic, cycloaliphatic, aryl, heteroaryl, and heterocyclyl groups represented by $R^1$ is optionally and independently substituted with one or more instances of $J^1$;

each $R^2$, $R^3$, $R^4$, and $R^5$ is independently —H, halogen, cyano, $C_{1-6}$ aliphatic, or $C_{3-10}$ cycloaliphatic, wherein each of said aliphatic and cycloaliphatic groups represented by $R^2$, $R^3$, $R^4$, and $R^5$, respectively, is optionally and independently substituted with one or more instances of $J^2$, $J^3$, $J^4$, and $J^5$, respectively;

optionally, $R^2$ and $R^3$, together with the carbon atom to which they are attached, form a $C_{3-7}$cycloaliphatic ring that is optionally substituted with one or more instances of $J^B$;

optionally, $R^3$ and $R^4$, together with the carbon atoms to which they are attached, form a $C_{3-7}$cycloaliphatic ring that is optionally substituted with one or more instances of $J^B$;

optionally, $R^4$ and $R^5$, together with the carbon atom to which they are attached, form a $C_{3-7}$cycloaliphatic ring that is optionally substituted with one or more instances of $J^B$;

$R^6$ is —H, $C_{1-6}$ aliphatic, $C_{3-10}$ cycloaliphatic, $C_{6-10}$ aryl, 5-10 membered heteroaryl, or 3-10 membered heterocyclyl, wherein each of said aliphatic, cycloaliphatic, aryl, heteroaryl, and heterocyclyl groups represented by $R^6$ is optionally and independently substituted with one or more instances of $J^6$;

$R^7$ is —H, $C_{1-6}$ aliphatic optionally substituted with one or more instanced of $J^A$, or $C_{3-8}$ cycloaliphatic optionally substituted with one or more instanced of $J^B$; or, optionally $R^7$, together with $R^1$ and the nitrogen atom to which it is attached, forms a 5-7 membered heterocyclic ring that is optionally substituted with one or more instances of $J^B$; and $R^8$ is —H or $R^9$;

$R^9$ is $C_{1-6}$ aliphatic or $C_{3-8}$cycloaliphatic, wherein said aliphatic group is independently and optionally substituted with one or more instances of $J^A$, and wherein said cycloaliphatic group is independently and optionally substituted with one or more instances of $J^B$;

each $J^1$ is independently T or $C_{1-6}$ aliphatic optionally substituted with one or more instances of T;

each of $J^2$, $J^3$, $J^4$, $J^5$, and $J^6$ is independently M, or $C_{1-6}$ aliphatic optionally substituted with one or more instances of M;

each T is independently halogen, oxo, —NO$_2$, —CN, $Q^1$, —$Z^1$—H, or —$Z^2$-$Q^2$;

each $Z^1$ is independently a unit consisting of one or more groups independently selected from the group consisting of —NR—, —O—, —S—, —C(O)—, —C(=NR)—, —C(=NOR)—, and —SO$_2$N(R)—;

each $Z^2$ is independently a unit consisting of one or more groups independently selected from the group consisting of —NR—, —O—, —S—, —C(O)—, —C(=NR)—, —C(=NOR)—, —S(O)—, and —S(O)$_2$—;

each $Q^1$ is independently $C_{3-10}$ cycloaliphatic, $C_{6-10}$ aryl, 5-10 membered heteroaryl, or 3-10 membered heterocyclyl, wherein each $Q^1$ is independently and optionally substituted with one or more instances of $J^Q$;

each $Q^2$ is independently $C_{1-6}$ aliphatic, $C_{3-10}$ cycloaliphatic, $C_{6-10}$ aryl, 5-10 membered heteroaryl, 3-10 membered heterocyclyl, or $Q^1$-$Q^1$, each of which is optionally and independently substituted with one or more instances of $J^Q$; or each $Q^2$, together with R and the nitrogen atom to which it is attached, optionally forms a 4-7 membered heterocyclic ring optionally substituted with one or more instances of $J^B$; and each $J^Q$ is independently M or $C_{1-6}$ aliphatic optionally substituted with one or more instances of M;

each M is independently halogen, oxo, —NO$_2$, —CN, —OR', —SR', —N(R')$_2$, —COR', —CO$_2$R', —CONR'$_2$, —OCOR", —OCON(R')$_2$, —NRCOR', —NRCO$_2$R', —NRCON(R')$_2$, —S(O)R", —SO$_2$R", —SO$_2$N(R')$_2$, —NRSO$_2$R", —NRSO$_2$N(R')$_2$, $C_{3-10}$ cycloaliphatic, 3-10 membered heterocyclyl, $C_{6-10}$ aryl, or 5-10 membered heteroaryl, wherein each of said cycloaliphatic, heterocyclyl, aryl and heteroaryl groups represented by M is optionally and independently substituted with one or more instances of $J^B$;

each R' is independently —H or $C_{1-6}$ aliphatic, or each R, together with $Q^2$ and the nitrogen atom to which it is attached, optionally forms a 4-7 membered heterocyclic ring optionally being substituted with one or more instances of $J^B$;

each R' is independently —H or $C_{1-6}$ aliphatic optionally substituted with one or more instances of $J^A$; or two R' groups, together with the nitrogen atom to which they are attached, form a 4-7 membered heterocyclic ring optionally being substituted with one or more instances of $J^B$;

each R" is independently $C_{1-4}$ aliphatic optionally substituted with one or more instances of $J^A$;

each $J^A$ is independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$ ($C_1$-$C_4$ alkyl), —O($C_1$-$C_4$ alkyl), $C_{3-7}$cycloalkyl, and $C_{3-7}$ cyclo(haloalkyl);

each $J^B$ is independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$ ($C_1$-$C_4$ alkyl), —O($C_1$-$C_4$ alkyl), and $C_1$-$C_4$ aliphatic that is optionally substituted with one or more instances of $J^A$; and q is 0 or 1.

The method comprises the steps of:
a) reacting a compound represented by Structural Formula (A):

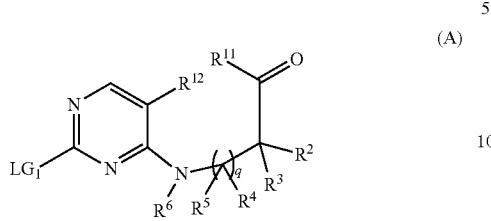

(A)

with HNR¹R⁷ under suitable conditions to form a compound represented by Structural Formula (B):

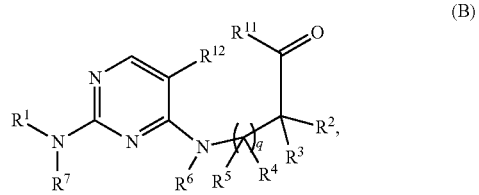

(B)

wherein: $R^{11}$ is —NHR¹³, and $R^{12}$ is halogen; or $R^{11}$ is —OR¹⁴, and $R^{12}$ is —NO₂; and $R^{13}$ is —H or $R^9$; $R^{14}$ is $C_{1-6}$ alkyl; and $LG_1$ is a suitable leaving group; and
b) i) when $R^{12}$ is —NO₂, and $R^{11}$ is —OR⁴:
  1) cyclizing the compound represented by Structural Formula (B) under suitable cyclisation conditions to form a compound represented by Structural Formula (II):

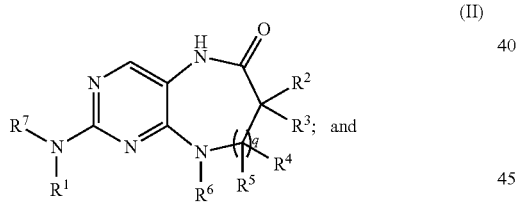

(II)

2) optionally reacting the compound represented by Structural Formula (II) with $R^9$-$LG_2$, wherein $LG_2$ is a suitable leaving group, to form the compound represented by Structural Formula (I), wherein $R^8$ is other than —H; or
ii) when $R^{12}$ is halogen, and $R^{11}$ is —NHR¹³:
  1) cyclizing the compound represented by Structural Formula (B) under suitable cyclisation conditions to form the compound represented by Structural Formula (I); and
  2) optionally, when $R^{13}$ is —H, reacting the compound produced from step b), ii), 1) with $R^9$-$LG_2$, wherein $LG_2$ is a suitable leaving group, to form the compound represented by Structural Formula (I) wherein $R^8$ is other than —H.

The compounds represented by Structural Formula (I) can inhibit protein kinases, such as Plk kinases (e.g., Plk1, Plk2, Plk3 and/or Plk4). See, for example, US 2009/0062292 and US 2008/0167289. The present invention can provide efficient synthetic methods for preparing such compounds that are useful as protein kinases inhibitors, particularly Plk inhibitors.

DETAILED DESCRIPTION OF THE INVENTION

The methods of the invention generally employ introduction of —NR¹R⁷ into the pyrimidine ring of Structural Formula (I) prior to the cyclisation step to form the ring (e.g., peperazin-2-one or diazepin-5-one) that is fused to the pyrimidine ring. Without being bound to a particular theory, early amination, particularly for aryl and heteroaryl amines, such as aniline, prior to the cyclisation can be beneficial for the convenience for purification processes of the final compounds. Generally, amines, especially aryl and heteroaryl amines, are potentially hazardous. If such materials are employed at a later stage (e.g., anilination after the cyclisation) of the production line, purifying the final products from them can be cumbersome and costy, especially in a large scale production line. For example, losing some intermediate compounds during purification processes might be better tolerable than losing some final products. Certain aspects of the methods of the invention are depicted below in schemes and preparative examples that follow. Unless otherwise indicated, all variables in the following schemes are as defined herein.

The methods of the invention employ the step of: a) reacting a compound represented by Structural Formula (A) with HNR¹R⁷ under suitable conditions to form a compound represented by Structural Formula (B):

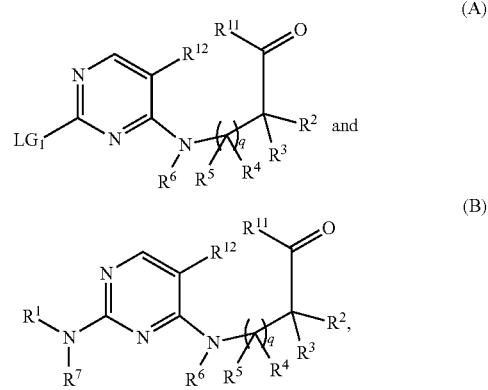

wherein $R^{11}$ is —NHR¹³, and $R^{12}$ is halogen; or $R^{11}$ is —OR⁴, and $R^{12}$ is —NO₂; and $R^{13}$ is —H or $R^9$; $R^{14}$ is $C_{1-6}$ alkyl; and $LG_1$ is a suitable leaving group. If $R^{12}$ is —NO₂, and $R^{11}$ is —OR¹⁴, the methods further comprise the step of cyclizing the compound represented by Structural Formula (B) under suitable cyclisation conditions to form a compound represented by Structural Formula (II):

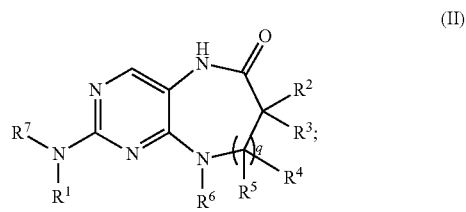

(II)

and optionally further comprise the step of reacting the compound represented by Structural Formula (II) with $R^9$-$LG_2$, wherein $LG_2$ is a suitable leaving group, to form the compound represented by Structural Formula (I), wherein $R^8$ is other than —H. If $R^{12}$ is halogen, and $R^{11}$ is —$NHR^{13}$, the methods further comprise the step of cyclizing the compound represented by Structural Formula (B) under suitable cyclisation conditions to form the compound represented by Structural Formula (I); and, when $R^{13}$ is —H, optionally further comprise the step of reacting the compound produced from the prior cyslisation step with $R^9$-$LG_2$ to form the compound represented by Structural Formula (I), wherein $R^8$ is other than —H.

Suitable conditions for the amination step a) to introduce the —$NR^1R^7$ moiety into the pyrimidine ring can be found in the art, for example, Cywin et al., "Discovery of potent and selective PKC-theta inhibitors," *Bioorganic & Medicinal Chemistry Letters*, 17(1), 225-230 (2007), and WO2006/108103. For example, the amination step can be performed in the presence of a base (e.g., organic or inorganic base), such as $NaHCO_3$, $NaCO_3$, or a tertiary amine (e.g., DIPEA: N,N-diisopropylethylamine), in any suitable solvent system, e.g., peterolium ether and dichloromethan (DCM), or mixtures thereof. Alternatively, when $R^{11}$ is —$OR^4$, and $R^{12}$ is —$NO_2$, the amination step can be performed simply by heating without a base.

Any suitable leaving group known in the art can be employed in the invention for $LG_1$ and $LG_2$, respectively. One suitable example for each $LG_1$ and $LG_2$ is halogen, such as —Cl, —Br or —I. Other suitable examples of $LG_1$ include triflate (—$OSO_2CF_3$), tosylate (O-(p-toluenesulfonyl)), mesylate (—$OSO_2$ ($CH_3$)), lower alkyl sulfones, such as methylsulfone (—SO2Me), etc. In one specific embodiment, $LG_1$ is —Cl; and $LG_2$ is —Cl, —Br, or —I.

Cyclisation between $R^{11}$ and $R^{12}$ to form the ring (e.g., peperazin-2-one or diazepin-5-one) that is fused to the pyrimidine ring can be performed in any suitable condition known in the art. For example, suitable reaction conditions for reductive cyclisation between nitro and ester groups (when is $R^{12}$ is —$NO_2$, and $R^{11}$ is —$OR^{14}$) can be found in US 2008/0167289, US 2009/0062292, US 2006/004014, U.S. Pat. No. 6,861,422, U.S. Pat. No. 6,806,272, and US2008/0009482. For example, suitable reaction conditions for cyclisation between halogen and amide groups (when $R^{12}$ is halogen, and $R^{11}$ is —$NHR^{13}$) can be found in US 2008/0009482.

In one embodiment, $R^{12}$ is —$NO_2$, and $R^{11}$ is —$OR^{14}$. In this embodiment, reductive cyclisation between the nitro and ester groups in compounds of Structural Formula (B) is performed to produce compounds represented by Structural Formula (II). Any suitable reductive cyclisation condition between nitro and ester groups known in the art can be employed in the invention. In one specific embodiment, the reductive cyclisation is performed as shown in Scheme 1:

Scheme 1

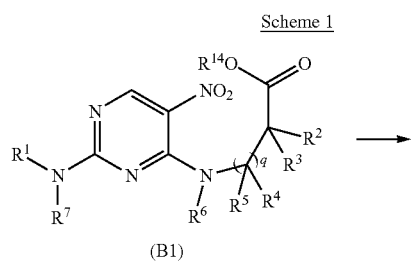

(B1)

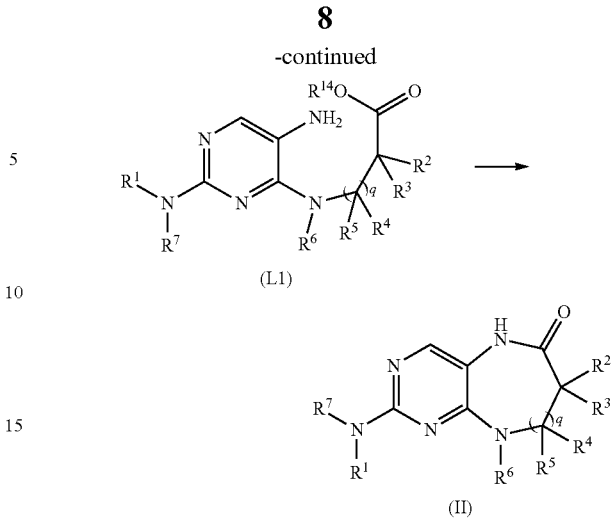

The first step involves reduction of the nitro group under suitable reduction conditions, such as iron powder, $SnCl_2$, zinc powder, indium/HCl, or $H_2$/Pd to form a compound represented by Structural Formula (L1). The second step involves cyclo-condensation between the amine and ester groups of Structural Formula (L1), resulting in the compound represented by Structural Formula (II). Cyclo-condensations typically occur in the presence of an acid or a base. In some embodiments, this two-step process occurs in situ. One example of an in situ condition involves treating the nitro compound (represented by Structural Formula (B1)) with iron powder in glacial acetic acid.

Optionally, as shown in Scheme 2, the compound represented by Structural Formula (II) can further reacts with $R^9$-$LG_2$, wherein $LG_2$ is a suitable leaving group, to form the compound represented by Structural Formula (I) wherein $R^8$ is other than H:

Scheme 2

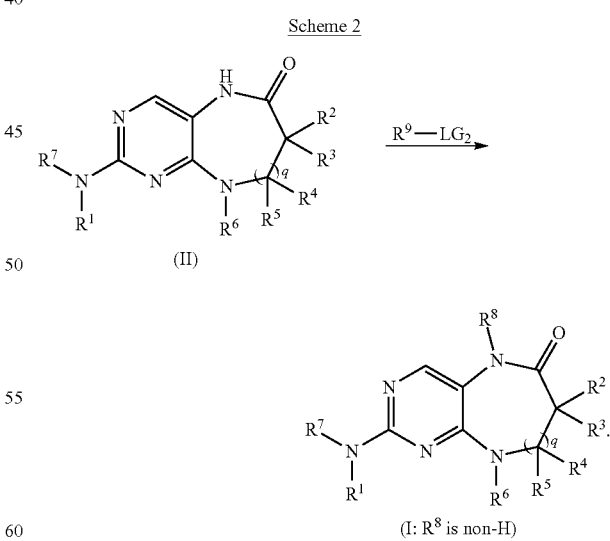

Alternatively, compounds of Structural Formula (L1) can be first functionalized to form compounds of Structural Formula (L2) which can subsequently be cyclised to form compounds of Structural Formula (I) wherein $R^8$ is other than H, as shown in Scheme 3:

Scheme 3

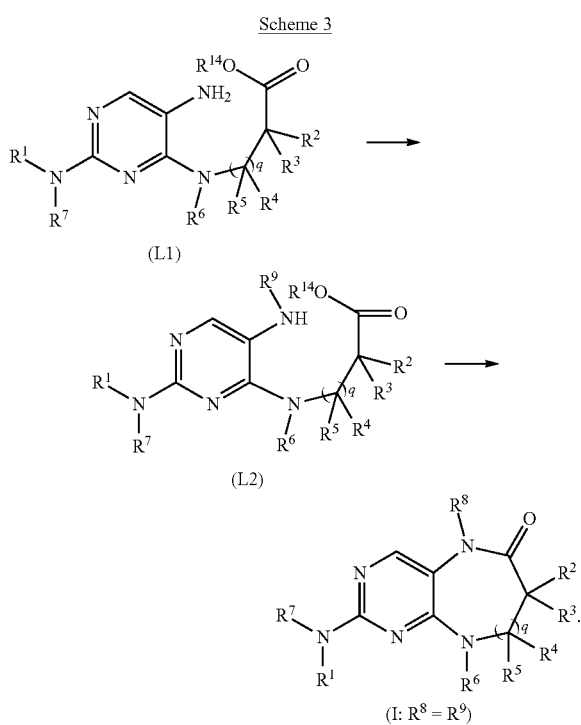

In another embodiment, $R^{12}$ is halogen, such as —Br or —I, and $R^{11}$ is —NHR$^{13}$. In this embodiment, cyclisation between halogen (e.g., —Br as exemplified in Scheme 4) and amide groups in a compound of Structural Formula (B) (e.g., a compound of Structural Formula (B2) in Scheme 4) is performed to produce the compound represented by Structural Formula (I), as shown in Scheme 4:

Scheme 4

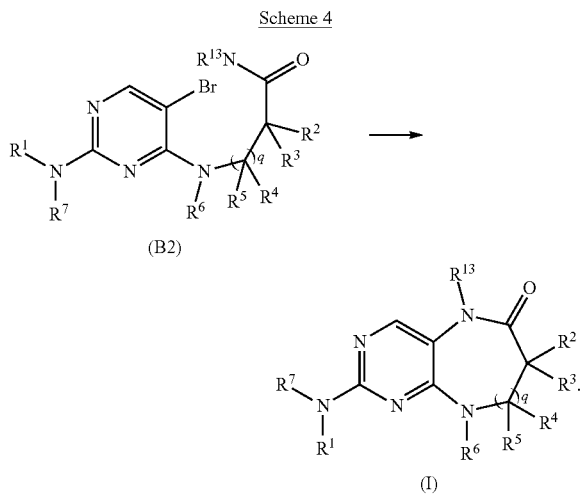

Any suitable cyclisation condition between halogen (e.g., —Br or —I) and amide groups known in the art can be employed in the invention. In one specific embodiment, the cyclisation is performed under palladium catalysis, for example, using a suitable palladium catalyst (e.g., Pd$_2$(dba)$_3$, where "dba" is tris(dibenzylideneacetone)dipalladium) and a suitable base (e.g., Xantphos).

Optionally, when $R^{13}$ is —H, the compound represented by Structural Formula (I) wherein $R^{13}$ is —H can further react with a suitable source(s) for $R^9$, e.g., $R^9$-LG$_2$, wherein LG$_2$ is a suitable leaving group, to form the compound represented by Structural Formula (I), wherein $R^8$ is other than H.

The compounds of Structural Formula (A) can be prepared by any suitable method known in the art. In one embodiment, a compound of Structural Formula (A) can be prepared via reacting a compound represented by Structural Formula (C) with a compound represented by Structural Formula (D) to form the compound represented by Structural Formula (A), wherein LG$_3$ is a suitable leaving group:

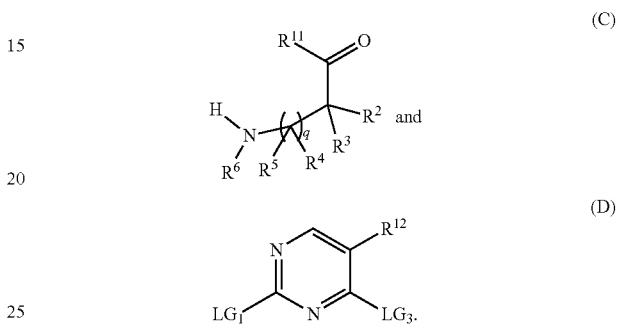

Any suitable leaving group known in the art can be employed in the invention for LG$_3$. One suitable example for LG$_3$ is halogen, such as —Cl, —Br, or —I. Other suitable examples of LG$_1$ include triflate (—OSO$_2$CF$_3$), tosylate (O-(p-toluenesulfonyl)), mesylate (—OSO$_2$(CH$_3$)), lower alkyl sulfones, such as methylsulfone (—SO$_2$Me), etc. In one specific embodiment, LG$_3$ is —Cl, —Br, or —I. In another specific embodiment, LG$_3$ is —Cl.

Suitable conditions for the reaction of the compounds of Structural formula (C) with the compounds of Structural Formula (D) to form the compounds of Structural Formula (A) can be found in the art, for example, US 2008/0062292, US 2008/0009482, and US 2008/0167289. In one embodiment, the compounds of Structural Formula (A1) are formed as shown in Scheme 5 by reaction of a 5-nitro-2,4-dichloropyrimidine of Structural Formula (D1) with an amine of Structural Formula (C1). Suitable conditions for this reaction can be found in the art, for example, US 2008/0167289 and US2008/0009482. In one example, a compound of Structural Formula (C1) is reacted with 5-nitro-2,4-dichloropyrimidine in the presence of a base (e.g., organic or inorganic base), such as NaHCO$_3$, NaCO$_3$, or a tertiary amine (e.g., DIPEA: N,N-diisopropylethylamine) in any suitable solvent system (e.g., petroleum ether, dichloromethane (DCM), acetone, or mixtures thereof), optionally with heating.

Scheme 5

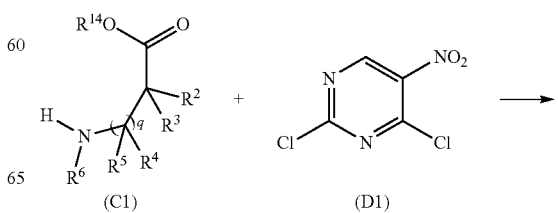

-continued

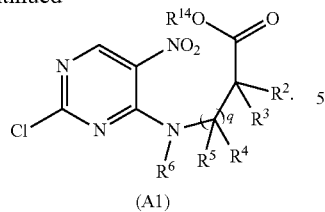

(A1)

In another embodiment, the compounds of Structural Formula (A2) are formed as shown in Scheme 6 by reaction of a 5-bromo-2,4-dichloropyrimidine of Structural Formula (D2) with an amine of Structural Formula (C2). Suitable conditions for this reaction can be found in the art, for example, US 2008/0167289 and US2008/0009482. For example, the reaction is performed by heating in the presence of a base, such as triethylamine or N,N,diisopropylethylamine (DIPEA), in a polar organic solvent, such as acetonitrile or ethanol.

Scheme 6

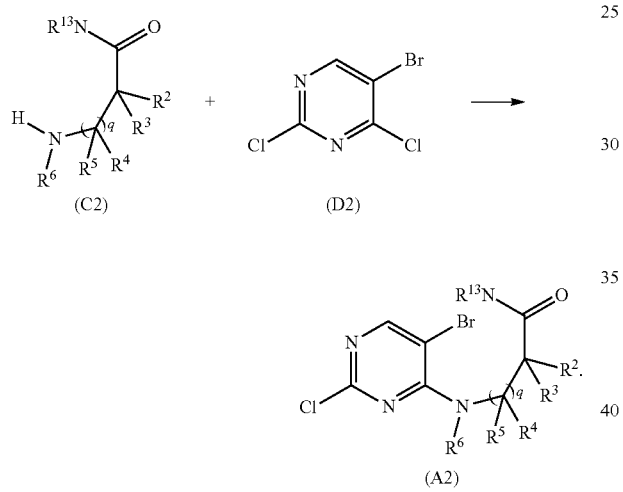

Compounds of Structural Formula (C1) may also be obtained by reaction of esters of an appropriately substituted 3-amino-propanoic acid (F1):

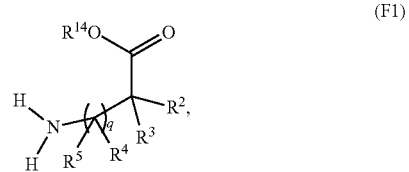

(F1)

with a ketone or aldehyde, in the presence of a suitable reducing agent, such as, for example, sodium triacetoxyborohydride, as described in US 2008/0009482. Compounds of Structural Formula (C2) may also be obtained by reaction of amides of propenoic acid (G1) with a suitable amine, as described in US 2008/0009482:

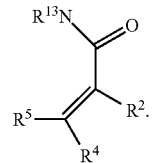

(G1)

The non-hydrogen $R^6$ group can generally be introduced during the preparation of the compounds of Structural Formulae (A) and (B) (including compounds of Structural Formulae (B1) and (B2)), as discussed above. Alternatively, the non-hydrogen $R^6$ group can be introduced after the cyclisation step to form the ring (e.g., peperazin-2'-one or diazepin-5-one) that is fused to the pyrimidine ring, as desired. For example, as shown in Scheme 7, compounds of Structural Formula (H) can react with a suitable reagent known in the art as a source for the non-hydrogen $R^6$ group (e.g., a desired $R^6X$, wherein X is halide, such as $R^6Br$, $R^6Cl$, etc.) to form compounds of Structural Formula (K).

Scheme 7

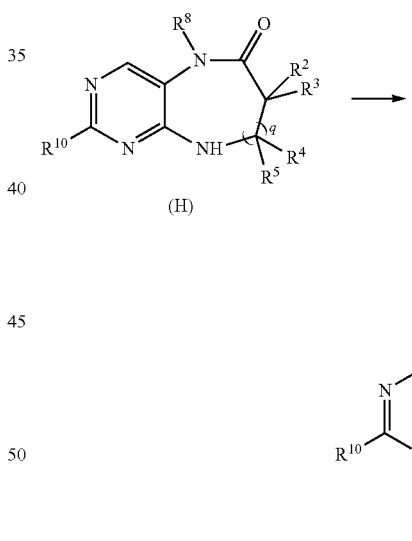

(K: $R^6$ = non-H)

In one specific embodiment, a method of the invention comprises Steps A1-C1 and optionally Step D1, of Scheme 8. In another specific embodiment, a method of the invention comprises Steps A2-C2 and optionally Step D2, of Scheme 9. Steps A1 and A2 are as described above in Schemes 5 and 6, respectively. Steps B1 and B2 are independently are as described above for the amination step a). Step C1 and optional Step D1 are each independently as described above in Scheme 1. Steps C2 and optional Step D2 are each independently as described above in Scheme 4.

Scheme 8

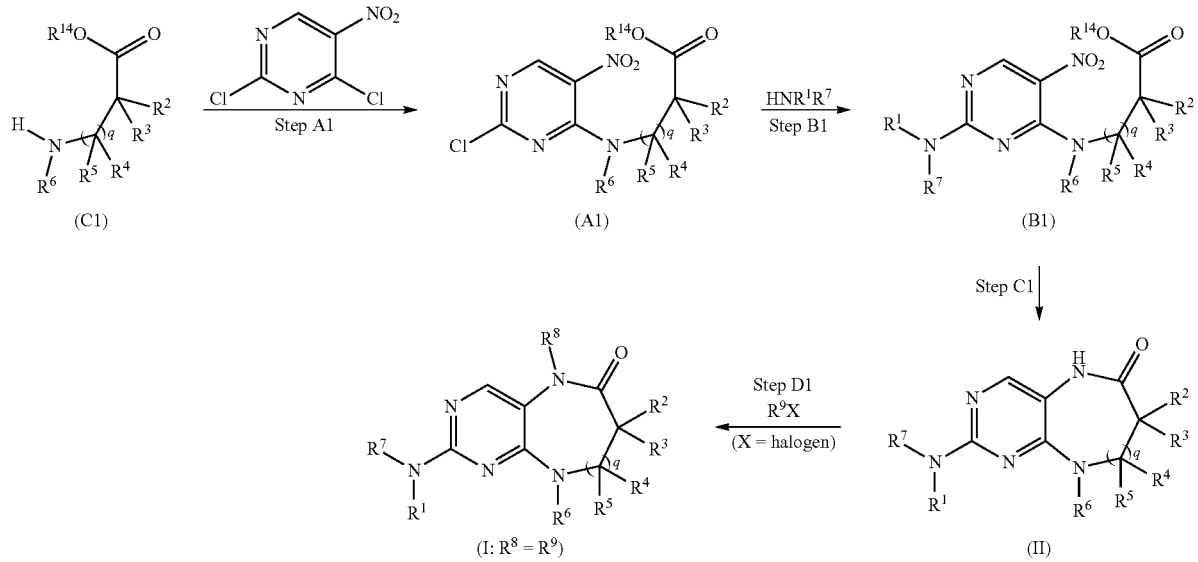

Scheme 9

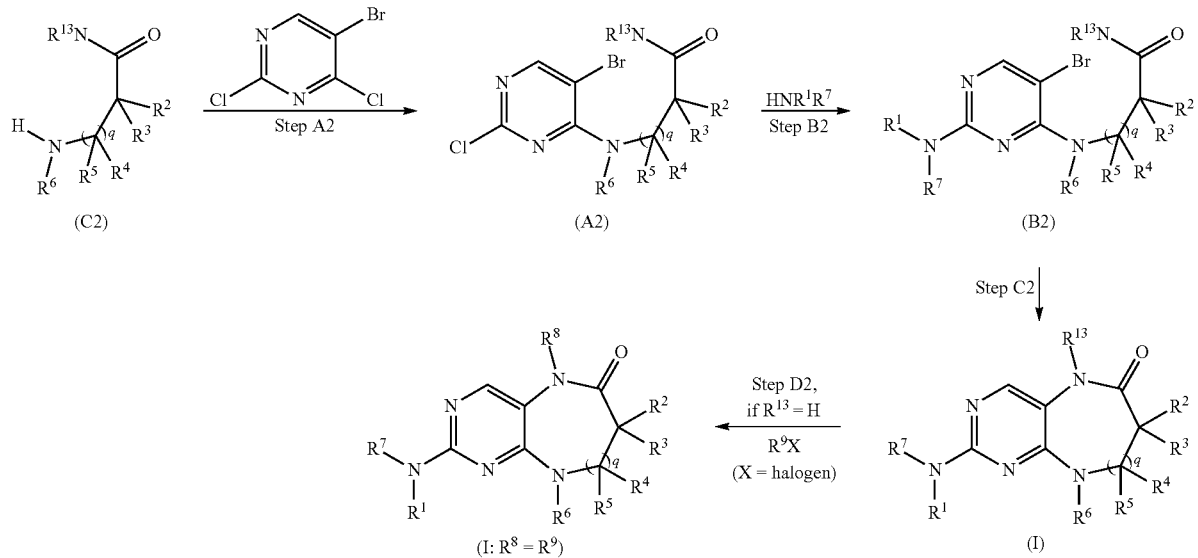

In one embodiment, the methods of the invention can be employed in preparing the compounds represented by Structural Formula (I) or pharmaceutically acceptable salts thereof, wherein values of the variables of Structural Formula (I) are as described below.

The first set of variables of Structural Formula (I) is as follows:

$R^1$ is —H, $C_{1-6}$ aliphatic, $C_{3-10}$ cycloaliphatic, $C_{6-10}$ aryl, 5-10 membered heteroaryl, or 3-10 membered heterocyclyl, wherein each of said aliphatic, cycloaliphatic, aryl, heteroaryl, and heterocyclyl groups represented by $R^1$ is optionally and independently substituted with one or more instances of $J_1$. Specifically, $R^1$ is optionally substituted $C_{1-6}$ aliphatic, optionally substituted $C_{6-10}$ aryl, or optionally substituted 5-10 membered heteroaryl. Specifically, $R^1$ is optionally substituted $C_{6-10}$ aryl or optionally substituted 5-10 membered heteroaryl. More specifically, $R^1$ is optionally substituted $C_{6-10}$ aryl or optionally substituted 5-6 membered heteroaryl. More specifically, $R^1$ is optionally substituted phenyl or optionally substituted 5-6 membered heteroaryl. More specifically, $R^1$ is optionally substituted phenyl.

Each of $R^2$, $R^3$, $R^4$, and $R^5$ is independently —H, halogen, cyano, $C_{1-6}$ aliphatic, or $C_{3-10}$ cycloaliphatic, wherein each of said aliphatic and cycloaliphatic groups represented by $R^2$, $R^3$, $R^4$, and $R^5$, respectively, is optionally and independently substituted with one or more instances of $J^2$, $J^3$, $J^4$, and $J^5$, respectively. Optionally, $R^2$ and $R^3$, together with the carbon atom to which they are attached, form a $C_{3-7}$ cycloaliphatic ring that is optionally substituted with one or more instances of $J^B$. Optionally, $R^3$ and $R^4$, together with the carbon atoms to which they are attached, form a $C_{3-7}$ cycloaliphatic ring that is optionally substituted with one or more instances of $J^B$. Optionally, $R^4$ and $R^5$, together with the carbon atom to which they are attached, form, a $C_{3-7}$ cycloaliphatic ring that is optionally substituted with one or more instances of $J^B$.

Specifically, each of $R^2$, $R^3$, $R^4$ and $R^5$ is independently —H, halogen, optionally substituted $C_{1-6}$ aliphatic, or optionally substituted $C_{3-7}$ cycloaliphatic; or optionally $R^2$ and $R^3$, $R^3$ and $R^4$, and $R^4$ and $R^5$, respectively, together with the atom to which they are bound, independently form an optionally substituted $C_{3-7}$ cycloaliphatic ring. Specifically, each of $R^2$, $R^3$, $R^4$, and $R^5$ is independently —H, halogen, optionally substituted $C_{1-6}$ aliphatic; or optionally $R^2$ and $R^3$, together with the carbon atom to which they are attached, form an optionally substituted $C_{3-6}$ cycloalkyl ring. Specifically, each of $R^2$, $R^3$, $R^4$ and $R^5$ is independently —H, or optionally substituted $C_{1-6}$ alkyl; or optionally $R^2$ and $R^3$, together with the atom to which they are bound, form an optionally substituted $C_{3-7}$ cycloalkyl ring. Specifically, each of $R^2$, $R^3$, $R^4$ and $R^5$ is independently —H, or optionally substituted $C_{1-6}$ alkyl; or optionally $R^2$ and $R^3$, together with the atom to which they are bound, form an optionally substituted $C_{3-6}$ cycloalkyl ring. More specifically, $R^2$ is —H or $C_{1-3}$ alkyl; $R^3$ is $C_{1-3}$ alkyl; $R^4$ is —H or $C_{1-3}$ alkyl; and $R^5$ is —H or $C_{1-3}$ alkyl. More specifically, $R^2$ and $R^3$ together with the atom to which they are bound form a $C_{3-7}$ cycloalkyl ring; $R^4$ is —H or $C_{1-3}$ alkyl; and $R^5$ is —H or $C_{1-3}$ alkyl. More specifically, $R^2$ is —H or $C_{1-3}$ alkyl; $R^3$ is $C_{1-3}$ alkyl; $R^4$ is —H; and $R^5$ is —H. More specifically, $R^2$ and $R^3$ together with the atom to which they are bound form a $C_{3-7}$ cycloalkyl ring; $R^4$ is —H; and $R^5$ is —H.

$R^6$ is —H, $C_{1-6}$ aliphatic, $C_{3-10}$ cycloaliphatic, $C_{6-10}$ aryl, 5-10 membered heteroaryl, or 3-10 membered heterocyclyl, wherein each of said aliphatic, cycloaliphatic, aryl, heteroaryl, and heterocyclyl groups represented by $R^6$ is optionally and independently substituted with one or more instances of $J^6$. Specifically, $R^6$ is —H, optionally substituted $C_{1-6}$ aliphatic, optionally substituted $C_{3-7}$ cycloaliphatic, optionally substituted 4-7 membered heterocyclyl, optionally substituted phenyl, or optionally substituted 5-6 membered heteroaryl. Specifically, $R^6$ is —H, optionally substituted $C_{1-6}$ aliphatic, optionally substituted $C_{3-7}$ cycloaliphatic, or optionally substituted 4-7 membered heterocyclyl. Specifically, $R^6$ is —H, optionally substituted $C_{1-6}$ aliphatic or optionally substituted $C_{3-7}$ cycloaliphatic. Specifically, $R^6$ is —H, optionally substituted $C_{1-6}$ alkyl, or optionally substituted $C_{3-7}$ cycloalkyl. Specifically, $R^6$ is —H, optionally substituted $C_{1-6}$ alkyl, or optionally substituted $C_{3-6}$ cycloalkyl. More specifically, $R^6$ is optionally substituted $C_{3-6}$ cycloalkyl. Even more specifically, $R^6$ is cyclopentyl.

$R^7$ is —H, or a $C_{1-6}$ aliphatic or $C_{3-8}$ cycloaliphatic group optionally substituted with one or more instanced of $J^4$, or, optionally $R^7$, together with $R^1$ and the nitrogen atom to which it is attached, forms a 4-7 membered heterocyclic ring that is optionally being substituted with one or more instances of $J^B$. Specifically, the heterocyclic ring formed with $R^1$ and $R^7$ is 5-6 membered. Specifically, $R^7$ is —H, or optionally substituted $C_{1-6}$ aliphatic. More specifically, $R^7$ is —H, or $C_{1-6}$ alkyl. Even more specifically, $R^7$ is —H.

$R^8$ is —H or $R^9$.

$R^9$ is $C_{1-6}$ aliphatic or $C_{3-8}$ cycloaliphatic, wherein said aliphatic group is independently and optionally substituted with one or more instances of $J^4$, and wherein said cycloaliphatic group is independently and optionally substituted with one or more instances of $J^B$;

Specifically, said aliphatic and cycloaliphatic are independently alkyl and cycloalkyl, respectively.

Specifically, $R^8$ is —H, optionally substituted $C_{1-6}$ alkyl, $C_{3-7}$ cycloalkyl, or $C_{3-7}$ cyclo(haloalkyl). Specifically, $R^8$ is —H or optionally substituted $C_{1-6}$ aliphatic. Specifically, $R^8$ is —H or optionally substituted $C_{1-16}$ alkyl. Specifically, $R^8$ is —H, $C_{1-6}$ alkyl or $C_{1-6}$ haloalkyl. Specifically, $R^8$ is —H or $C_{1-6}$ alkyl.

Each $J^1$ is independently T or $C_{1-6}$ aliphatic optionally substituted with one or more instances of T.

Each of $J^2$, $J^3$, $J^4$, $J^5$, and $J^6$ is independently M, or $C_{1-6}$ aliphatic optionally substituted with one or more instances of M.

Each T is independently halogen, oxo, —NO$_2$, —CN, $Q^1$, —$Z^1$—H, or —$Z^2$-$Q^2$. Specifically, each T is halogen, cyano, $Q^1$, —N(R)H, —OH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$. More specifically, each T is halogen, cyano, —N(R)H, —OH, —CO$_2$H, —C(O)N(R)H, —OC(O)N(R)H, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, or —N(R)C(O)N(R)Q$^2$.

Each M is independently halogen, oxo, —NO$_2$, —CN, —OR', —SR', —N(R')$_2$, —COR, —CO$_2$R$^1$, —CONR'$_2$, —OCOR", —OCON(R')$_2$, —NRCOR', —NRCO$_2$R', —NRCON(R')$_2$, —S(O)R", —SO$_2$R", —SO$_2$N(R')$_2$, —NRSO$_2$R", —NRSO$_2$N(R')$_2$, $C_{3-10}$ cycloaliphatic, 3-10 membered heterocyclyl, $C_{6-10}$ aryl, or 5-10 membered heteroaryl, wherein each of said cycloaliphatic, heterocyclyl, aryl and heteroaryl groups represented by M is optionally and independently substituted with one or more instances of $J^B$.

Each $Z^1$ is independently a unit consisting of one or more groups (e.g., up to four groups) independently selected from the group consisting of —NR—, —O—, —S—, —C(O)—, —C(=NR)—, —C(=NOR)—, and —SO$_2$N(R)—. Specifically, each $Z^1$ is independently —N(R)—, —O—, —CO$_2$—, —C(O)N(R)—, —OC(O)N(R)—, —N(R)CO$_2$—, —N(R)C(O)N(R)—, —C(O)N(R)CO$_2$—, —SO$_2$N(R)—, or —N(R)SO$_2$N(R)—.

Each $Z^2$ is independently a unit consisting of one or more groups independently selected from the group consisting of —NR—, —O—, —S—, —C(O)—, —C(=NR)—, —C(=NOR)—, —S(O)—, and —S(O)$_2$—. Specifically, each $Z^2$ is independently —N(R)—, —O—, —CO$_2$—, —OC(O)—, —C(O)N(R)—, —N(R)C(O)—, —OC(O)N(R)—, —N(R)CO$_2$—, —N(R)C(O)N(R)—, —C(O)N(R)CO$_2$—, —S(O)$_2$—, —SO$_2$N(R)—, —N(R)SO$_2$—, or —N(R)SO$_2$N(R)—.

Each $Q^1$ is independently $C_{3-10}$ cycloaliphatic, $C_{6-10}$ aryl, 5-10 membered heteroaryl, or 3-10 membered heterocyclyl, wherein each $Q^1$ is independently and optionally substituted with one or more instances of $J^Q$. Specifically, each $Q^1$ is independently optionally substituted $C_{3-7}$ cycloalkyl, optionally substituted phenyl, optionally substituted 5-6 membered heteroaryl, or optionally substituted 4-7 membered heterocyclyl. More specifically, each $Q^1$ is independently optionally substituted $C_{3-7}$ cycloalkyl, optionally substituted phenyl, optionally substituted 5-6 membered heteroaryl, or optionally substituted 4-7 membered heterocyclyl.

Each $Q^2$ is independently $C_{1-6}$ aliphatic, $C_{3-10}$ cycloaliphatic, $C_{6-10}$ aryl, 5-10 membered heteroaryl, 3-10 membered heterocyclyl, or $Q^1$-$Q^1$, each of which is optionally and independently substituted with one or more instances of $J^Q$; or each $Q^2$, together with R and the nitrogen atom to which is attached, optionally forms a 4-7 membered heterocyclic ring optionally being substituted with one or more instances of $J^B$. Specifically, each $Q^2$ is independently optionally substituted $C_{1-6}$ alkyl, optionally substituted $C_{3-7}$cycloalkyl, optionally substituted phenyl, optionally substituted 5-6 membered heteroaryl, or optionally substituted 4-7 membered heterocyclyl, or each $Q^2$, together with R and the nitrogen atom to which it is attached, optionally and independently forms an optionally substituted 4-7 membered heterocyclic ring.

Each $J^Q$ is independently M or $C_{1-6}$ aliphatic optionally substituted with one or more instances of M. Specifically, values of $J^Q$ for each of the $C_{3-7}$cycloalkyl, phenyl, 5-6 membered heteroaryl, and 4-7 membered heterocyclyl groups represented by $Q^1$ independently include halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), —O(C$_1$-C$_4$ alkyl), C$_1$-C$_4$ alkyl, C$_1$-C$_4$ haloalkyl; C$_1$-C$_4$ cyanoalkyl, C$_1$-C$_4$ aminoalkyl, C$_1$-C$_4$ hydroxyalkyl, and C$_2$-C$_4$ alkoxyalkyl. Specifically, values of $J^Q$ for the $C_{1-6}$ aliphatic (e.g., $C_{1-6}$ alkyl) represented by $Q^2$ include halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$ (C$_1$-C$_4$ alkyl), and —O(C$_1$-C$_4$ alkyl). Values of $J^Q$ for each of the cycloalkyl, aryl, heteroaryl, and heterocyclyl groups represented by $Q^2$ independently include halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$ (C$_1$-C$_4$ alkyl), —O(C$_1$-C$_4$ alkyl), C$_1$-C$_4$ alkyl, C$_1$-C$_4$ haloalkyl; C$_1$-C$_4$ cyanoalkyl, C$_1$-C$_4$ aminoalkyl, C$_1$-C$_4$ hydroxyalkyl, and C$_2$-C$_4$ alkoxyalkyl.

Each R is independently —H or $C_{1-6}$ aliphatic, or each R, together with $Q^2$ and the nitrogen atom to which it is attached, optionally forms a 4-7 membered heterocyclic ring optionally substituted with one or more instances of $J^B$. Specifically, the $C_{1-4}$ aliphatic group is $C_{1-4}$ alkyl. Specifically, each R is independently —H, —CH$_3$ or —CH$_2$CH$_3$, or each R, together with $Q^2$ and the nitrogen atom to which it is attached, optionally forms a 4-7 membered heterocyclic ring optionally substituted with one or more instances of $J^B$.

Each R' is independently —H or $C_{1-6}$ aliphatic optionally substituted with one or more instances of $J^4$; or two R' groups, together with the nitrogen atom to which they are attached, form a 4-7 membered heterocyclic ring optionally being substituted with one or more instances of $J^B$. Specifically, the $C_{1-4}$ aliphatic group is $C_{1-4}$ alkyl.

Each R" is independently $C_{1-4}$ aliphatic optionally substituted with one or more instances of $J^4$. Specifically, the $C_{1-4}$ aliphatic group is $C_{1-4}$alkyl.

Each $J^4$ is independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$ (C$_1$-C$_4$ alkyl), —O(C$_1$-C$_4$ alkyl), C$_{3-7}$cycloalkyl, and C$_{3-7}$ cyclo(haloalkyl).

Each $J^B$ is independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$ (C$_1$-C$_4$ alkyl), —O(C$_1$-C$_4$ alkyl), and C$_1$-C$_4$ aliphatic that is optionally substituted with one or more instances of $J^4$.

A second set of variables of Structural Formula (I) is as follows:
$R^6$ is —H, optionally substituted $C_{1-6}$ aliphatic, optionally substituted $C_{3-7}$ cycloaliphatic, optionally substituted 3-7 membered heterocyclyl, optionally substituted phenyl, or optionally substituted 5-6 membered heteroaryl.
$R^7$ is —H or optionally substituted $C_{1-6}$ aliphatic
$R^8$ is —H or optionally substituted $C_{1-6}$ aliphatic.

Values, including specific values, of the remaining variables are as described above in the first set of variables of Structural Formula (I).

A third set of variables of Structural Formula (I) is as follows:
$R^1$ is optionally substituted $C_{1-6}$ aliphatic, optionally substituted $C_{6-10}$ aryl, or optionally substituted 5-10 membered heteroaryl.

Values, including specific values, of the remaining variables are as described above in the first set of variables of Structural Formula (I).

A fourth set of variables of Structural Formula (I) is as follows:
$R^7$ is —H or optionally substituted $C_{1-6}$ aliphatic.

Values, including specific values, of the remaining variables are as described above in the first set of variables of Structural Formula (I).

A fifth set of variables of Structural Formula (I) is as follows:
$R^1$ is optionally substituted $C_{1-6}$ aliphatic, optionally substituted $C_{6-10}$ aryl, or optionally substituted 5-10 membered heteroaryl.
$R^7$ is —H or optionally substituted $C_{1-6}$ aliphatic.

Values, including specific values, of the remaining variables are as described above in the first set of variables of Structural Formula (I).

A sixth set of variables of Structural Formula (I) is as follows:
$R^6$ is —H, optionally substituted $C_{1-6}$ aliphatic, optionally substituted $C_{3-7}$ cycloaliphatic, optionally substituted 4-7 membered heterocyclyl, optionally substituted phenyl, or optionally substituted 5-6 membered heteroaryl.

Values, including specific values, of the remaining variables are as described above in the first set of variables of Structural Formula (I).

A seventh set of variables of Structural Formula (I) is as follows:
Values of $R^1$ and $R^7$, wherever applicable, are independently as described above in the second, third, fourth, or fifth set of variables of Structural Formula (I).
$R^6$ is —H, optionally substituted $C_{1-6}$ aliphatic, optionally substituted $C_{3-7}$ cycloaliphatic, optionally substituted 4-7 membered heterocyclyl, optionally substituted phenyl, or optionally substituted 5-6 membered heteroaryl.

Values, including specific values, of the remaining variables are as described above in the first set of variables of Structural Formula (I).

An eighth set of variables of Structural Formula (I) is as follows:
Each of $R^2$, $R^3$, $R^4$ and $R^5$ is independently —H, halogen, optionally substituted $C_{1-6}$ aliphatic, or optionally substituted $C_{3-7}$cycloaliphatic; or optionally $R^2$ and $R^3$, $R^3$ and $R^4$, and $R^4$ and $R^5$, respectively, together with the atom to which they are bound, independently form an optionally substituted $C_{3-7}$cycloaliphatic ring.

Values, including specific values, of the remaining variables are as described above in the first set of variables of Structural Formula (I).

A ninth set of variables of Structural Formula (I) is as follows:
Values of $R^1$, $R^6$ and $R^7$, wherever applicable, are independently as described above in the second, third, fourth, fifth, sixth, or seventh set of variables of Structural Formula (I).

Each of $R^2$, $R^3$, $R^4$ and $R^5$ is independently —H, halogen, optionally substituted $C_{1-6}$ aliphatic, or optionally substituted $C_{3-7}$cycloaliphatic; or optionally $R^2$ and $R^3$, $R^3$ and $R^4$, and $R^4$ and $R^5$, respectively, together with the atom to which they are bound, independently form an optionally substituted $C_{3-7}$cycloaliphatic ring.

Values, including specific values, of the remaining variables are as described above in the first set of variables of Structural Formula (I).

A tenth set of variables of Structural Formula (I) is as follows:

$R^8$ is —H or optionally substituted $C_{1-6}$ aliphatic.

Values, including specific values, of the remaining variables are as described above in the first set of variables of Structural Formula (I).

An eleventh set of variables of Structural Formula (I) is as follows:

Values of $R^1$, $R^2$, $R^3$, $R^4$, $R^5$, $R^6$ and $R^7$, wherever applicable, are independently as described above in the second, third, fourth, fifth, sixth, seventh, eighth, or ninth set of variables of Structural Formula (I).

$R^8$ is —H or optionally substituted $C_{1-6}$ aliphatic.

Values, including specific values, of the remaining variables are as described above in the first set of variables of Structural Formula (I).

A twelfth set of variables of Structural Formula (I) is as follows:

Each $Z^1$ is independently —N(R)—, —O—, —S—, —CO$_2$—, —C(O)N(R)—, —OC(O)N(R)—, —N(R)CO$_2$—, —N(R)C(O)N(R)—, —C(O)N(R)CO$_2$—, —SO$_2$N(R)—, or —N(R)SO$_2$N(R)—.

Each $Z^2$ is independently —N(R)—, —O—, —S—, —CO$_2$—, —OC(O)—, —C(O)N(R)—, —N(R)C(O)—, —OC(O)N(R)—, —N(R)CO$_2$—, —N(R)C(O)N(R)—, —C(O)N(R)CO$_2$—, —S(O)$_2$—, —SO$_2$N(R)—, —N(R)SO$_2$—, or —N(R)SO$_2$N(R)—.

Values, including specific values, of the remaining variables are as described above in the first set of variables of Structural Formula (I).

A thirteenth set of variables of Structural Formula (I) is as follows:

Values of $R^1$, $R^2$, $R^3$, $R^4$, $R^5$, $R^6$, $R^7$, and $R^8$, wherever applicable, are independently as described above in the second, third, fourth, fifth, sixth, seventh, eighth, ninth, tenth, eleventh, or twelfth set of variables of Structural Formula (I).

Each $Z^1$ is independently —N(R)—, —O—, —S—, —CO$_2$—, —C(O)N(R)—, —OC(O)N(R)—, —N(R)CO$_2$—, —N(R)C(O)N(R)—, —C(O)N(R)CO$_2$—, —SO$_2$N(R)—, or —N(R)SO$_2$N(R)—.

Each $Z^2$ is independently —N(R)—, —O—, —S—, —CO$_2$—, —OC(O)—, —C(O)N(R)—, —N(R)C(O)—, —OC(O)N(R)—, —N(R)CO$_2$—, —N(R)C(O)N(R)—, —C(O)N(R)CO$_2$—, —S(O)$_2$—, —SO$_2$N(R)—, —N(R)SO$_2$—, or —N(R)SO$_2$N(R)—.

Values, including specific values, of the remaining variables are as described above in the first set of variables of Structural Formula (I).

A fourteenth set of variables of Structural Formula (I) is as follows:

$R^1$ is $C_{1-4}$ alkyl substituted with $Q^1$ and optionally further substituted with one or more substituents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl). Alternatively, $R^1$ is $C_{6-10}$ aryl or 5-6 membered heteroaryl, each optionally and independently substituted with one or more substituents independently selected from the group consisting of T and $C_{1-6}$ aliphatic optionally substituted with one or more instances of T; and wherein each T is halogen, cyano, $Q^1$, —N(R)H, —OH, —SH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —SQ$^2$, —CO$_2$Q$^2$, —OC(O) Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$. Specifically, $R^1$ is phenyl optionally substituted with one or more substituents independently selected from the group consisting of T and $C_{1-6}$ aliphatic optionally substituted with one or more instances of T; and wherein each T is halogen, cyano, —N(R)H, —OH, —CO$_2$H, —C(O)N(R)H, —OC(O)N(R)H, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O) N(R)CO$_2$Q$^2$, or —N(R)C(O)N(R)Q$^2$.

Values, including specific values, of the remaining variables are as described above in the first set of variables of Structural Formula (I).

A fifteenth set of variables of Structural Formula (I) is as follows:

$R^1$ is $C_{1-4}$alkyl substituted with $Q^1$ and optionally further substituted with one or more substituents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$ ($C_1$-$C_4$ alkyl), and —O($C_1$-$C_4$ alkyl). Alternatively, $R^1$ is $C_{6-10}$ aryl or 5-6 membered heteroaryl, each optionally and independently substituted with one or more substituents independently selected from the group consisting of T and $C_{1-6}$ aliphatic optionally substituted with one or more instances of T; and wherein each T is halogen, cyano, $Q^1$, —N(R)H, —OH, —SH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —SQ$^2$, —CO$_2$Q$^2$, —OC(O) Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$. Specifically, $R^1$ is phenyl optionally substituted with one or more substituents independently selected from the group consisting of T and $C_{1-6}$ aliphatic optionally substituted with one or more instances of T; and wherein each T is halogen, cyano, —N(R)H, —OH, —CO$_2$H, —C(O)N(R)H, —OC(O)N(R)H, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O) N(R)CO$_2$Q$^2$, or —N(R)C(O)N(R)Q$^2$.

$R^7$ is —H, or optionally substituted $C_{1-6}$ aliphatic.

Values, including specific values, of the remaining variables are as described above in the first set of variables of Structural Formula (I).

A sixteenth set of variables of Structural Formula (I) is as follows:

$R^1$ is $C_{1-4}$alkyl substituted with $Q^1$ and optionally further substituted with one or more substituents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$ ($C_1$-$C_4$ alkyl), and —O($C_1$-$C_4$ alkyl). Alternatively, $R^1$ is $C_{6-10}$ aryl or 5-6 membered heteroaryl, each optionally and independently substituted with one or more substituents independently selected from the group consisting of T and $C_{1-6}$ aliphatic optionally substituted with one or more instances of T; and wherein each T is halogen, cyano, $Q^1$, —N(R)H, —OH, —SH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —SQ$^2$, —CO$_2$Q$^2$, —OC(O) Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$. Specifically, $R^1$ is phenyl optionally substituted with one or more substituents independently selected from the group consisting of T and $C_{1-6}$ aliphatic optionally substituted with one or more instances of T; and wherein each T is halogen, cyano, —N(R)H, —OH, —CO$_2$H, —C(O)N(R)H, —OC(O)N(R)H, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, or —N(R)C(O)N(R)Q$^2$.

$R^6$ is —H, optionally substituted $C_{1-6}$ aliphatic, optionally substituted $C_{3-7}$ cycloaliphatic, optionally substituted 4-7 membered heterocyclyl, optionally substituted phenyl, or optionally substituted 5-6 membered heteroaryl.

$R^7$ is —H, or optionally substituted $C_{1-6}$ aliphatic.

Values, including specific values, of the remaining variables are as described above in the first set of variables of Structural Formula (I).

A seventeenth set of variables of Structural Formula (I) is as follows:

$R^1$ is $C_{1-4}$ alkyl substituted with $Q^1$ and optionally further substituted with one or more substituents independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl). Alternatively, $R^1$ is $C_{6-10}$ aryl or 5-6 membered heteroaryl, each optionally and independently substituted with one or more substituents independently selected from the group consisting of T and $C_{1-6}$ aliphatic optionally substituted with one or more instances of T; and wherein each T is halogen, cyano, $Q^1$, —N(R)H, —OH, —SH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —SQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$. Specifically, $R^1$ is phenyl optionally substituted with one or more substituents independently selected from the group consisting of T and $C_{1-6}$ aliphatic optionally substituted with one or more instances of T; and wherein each T is halogen, cyano, —N(R)H, —OH, —CO$_2$H, —C(O)N(R)H, —OC(O)N(R)H, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, or —N(R)C(O)N(R)Q$^2$.

Each of $R^2$, $R^3$, $R^4$ and $R^5$ is independently —H, halogen, optionally substituted $C_{1-6}$ aliphatic, or optionally substituted $C_{3-7}$ cycloaliphatic; or optionally $R^2$ and $R^3$, $R^3$ and $R^4$, and $R^4$ and $R^5$, respectively, together with the atom to which they are bound, independently form an optionally substituted $C_{3-7}$ cycloaliphatic ring.

$R^6$ is —H, optionally substituted $C_{1-6}$ aliphatic, optionally substituted $C_{3-7}$ cycloaliphatic, optionally substituted 3-7 membered heterocyclyl, optionally substituted phenyl, or optionally substituted 5-6 membered heteroaryl.

$R^7$ is —H, or optionally substituted $C_{1-6}$ aliphatic.

Values, including specific values, of the remaining variables are as described above in the first set of variables of Structural Formula (I).

An eighteenth set of variables of Structural Formula (I) is as follows:

$R^1$ is $C_{1-4}$ alkyl substituted with $Q^1$ and optionally further substituted with one or more substituents independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl). Alternatively, $R^1$ is $C_{6-10}$ aryl or 5-6 membered heteroaryl, each optionally and independently substituted with one or more substituents independently selected from the group consisting of T and $C_{1-6}$ aliphatic optionally substituted with one or more instances of T; and wherein each T is halogen, cyano, $Q^1$, —N(R)H, —OH, —SH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —SQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$. Specifically, $R^1$ is phenyl optionally substituted with one or more substituents independently selected from the group consisting of T and $C_{1-6}$ aliphatic optionally substituted with one or more instances of T; and wherein each T is halogen; cyano, —N(R)H, —OH, —CO$_2$H, —C(O)N(R)H, —OC(O)N(R)H, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, or —N(R)C(O)N(R)Q$^2$.

Each of $R^2$, $R^3$, $R^4$ and $R^5$ is independently —H, halogen, optionally substituted $C_{1-6}$ aliphatic, or optionally substituted $C_{3-7}$ cycloaliphatic; or optionally $R^2$ and $R^3$, $R^3$ and $R^4$, and $R^4$ and $R^5$, respectively, together with the atom to which they are bound, independently form an optionally substituted $C_{3-7}$ cycloaliphatic ring.

$R^6$ is —H, or optionally substituted $C_{1-6}$ aliphatic, optionally substituted $C_{3-7}$ cycloaliphatic, optionally substituted 3-7 membered heterocyclyl, optionally substituted phenyl, or optionally substituted 5-6 membered heteroaryl.

$R^7$ is —H, or optionally substituted $C_{1-6}$ aliphatic.

$R^8$ is —H, or optionally substituted $C_{1-6}$ aliphatic.

Values, including specific values, of the remaining variables are as described above in the first set of variables of Structural Formula (I).

A nineteenth set of variables of Structural Formula (I) is as follows:

$R^1$ is $C_{1-4}$ alkyl substituted with $Q^1$ and optionally further substituted with one or more substituents independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_6$H, —CO$_2$(C$_1$-C$_4$ alkyl), and —O(C$_1$-C$_4$ alkyl). Alternatively, $R^1$ is $C_{6-10}$ aryl or 5-6 membered heteroaryl, each optionally and independently substituted with one or more substituents independently selected from the group consisting of T and $C_{1-6}$ aliphatic optionally substituted with one or more instances of T; and wherein each T is halogen, cyano, $Q^1$, —N(R)H, —OH, —SH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —SQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$. Specifically, $R^1$ is phenyl optionally substituted with one or more substituents independently selected from the group consisting of T and $C_{1-6}$ aliphatic optionally substituted with one or more instances of T; and wherein each T is halogen, cyano, —N(R)H, —OH, —CO$_2$H, —C(O)N(R)H, —OC(O)N(R)H, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, or —N(R)C(O)N(R)Q$^2$.

Each of $R^2$, $R^3$, $R^4$ and $R^5$ is independently —H, halogen, optionally substituted $C_{1-6}$ aliphatic, or optionally substituted $C_{3-7}$ cycloaliphatic; or optionally $R^2$ and $R^3$, $R^3$ and $R^4$, and $R^4$ and $R^5$, respectively, together with the atom to which they are bound, independently form an optionally substituted $C_{3-7}$ cycloaliphatic ring.

$R^6$ is —H, optionally substituted $C_{1-6}$ aliphatic, optionally substituted $C_{3-7}$ cycloaliphatic, optionally substituted 3-7 membered heterocyclyl, optionally substituted phenyl, or optionally substituted 5-6 membered heteroaryl.

$R^7$ is —H, or $C_{1-6}$ alkyl.

Values, including specific values, of the remaining variables are as described above in the first set of variables of Structural Formula (I).

A twentieth set of variables of Structural Formula (I) is as follows:

Values, including specific values, of $R^1$, $R^2$, $R^3$, $R^4$, $R^5$, and $R^6$ are independently as described above in any set of fourteenth through nineteenth sets of variables of Structural Formula (I).

$R^7$ is —H.

Values, including specific values, of the remaining variables are as described above in the first set of variables of Structural Formula (I).

A twenty first set of variables of Structural Formula (I) is as follows:

Values, including specific values, of $R^1$, $R^2$, $R^3$, $R^4$, and $R^5$ are independently as described above in any set of fourteenth through nineteenth sets of variables of Structural Formula (I).

$R^6$ is —H, optionally substituted $C_{1-6}$ alkyl, or optionally substituted $C_{3-7}$ cycloalkyl.

$R^7$ is —H, or $C_{1-6}$ alkyl. Specifically, $R^7$ is —H.

Values, including specific values, of the remaining variables are as described above in the first set of variables of Structural Formula (I).

A twenty second set of variables of Structural Formula (I) is as follows:

Values, including specific values, of $R^1$, $R^2$, $R^3$, $R^4$, and $R^5$ are independently as described above in any set of fourteenth through nineteenth sets of variables of Structural Formula (I).

$R^6$ is —H, optionally substituted $C_{1-6}$ alkyl, or optionally substituted $C_{3-7}$ cycloalkyl.

$R^7$ is —H, or $C_{1-6}$ alkyl. Specifically, $R^7$ is —H.

$R^8$ is —H or $C_{1-6}$ alkyl.

Values, including specific values, of the remaining variables are as described above in the first set of variables of Structural Formula (I).

A twenty third set of variables of Structural Formula (I) is as follows:

$R^1$ is $C_{1-4}$ alkyl substituted with $Q^1$ and optionally further substituted with one or more substituents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl). Alternatively, $R^1$ is $C_{6-10}$ aryl or 5-6 membered heteroaryl, each optionally and independently substituted with one or more substituents independently selected from the group consisting of T and $C_{1-6}$ aliphatic optionally substituted with one or more instances of T; and wherein each T is halogen, cyano, $Q^1$, —N(R)H, —OH, —SH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —SQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$. Specifically, $R^1$ is phenyl optionally substituted with one or more substituents independently selected from the group consisting of T and $C_{1-6}$ aliphatic optionally substituted with one or more instances of T; and wherein each T is halogen, cyano, —N(R)H, —OH, —CO$_2$H, —C(O)N(R)H, —OC(O)N(R)H, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, or —N(R)C(O)N(R)Q$^2$.

Each of $R^2$, $R^3$, $R^4$ and $R^5$ is independently —H, or optionally substituted $C_{1-6}$ alkyl; or optionally $R^2$ and $R^3$, together with the atom to which they are bound, form an optionally substituted $C_{3-7}$ cycloalkyl ring.

$R^6$ is —H, optionally substituted $C_{1-6}$ alkyl, or optionally substituted $C_{3-7}$ cycloalkyl.

$R^7$ is —H, or $C_{1-6}$ alkyl.

$R^8$ is —H or $C_{1-6}$ alkyl.

Values, including specific values, of the remaining variables are as described above in the first set of variables of Structural Formula (I).

A twenty fourth set of variables of Structural Formula (I) is as follows:

$R^1$ is $C_{1-4}$ alkyl substituted with $Q^1$ and optionally further substituted with one or more substituents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl). Alternatively, $R^1$ is $C_{6-10}$ aryl or 5-6 membered heteroaryl, each optionally and independently substituted with one or more substituents independently selected from the group consisting of T and $C_{1-6}$ aliphatic optionally substituted with one or more instances of T; and wherein each T is halogen, cyano, $Q^1$, —N(R)H, —OH, —SH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —SQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$. Specifically, $R^1$ is phenyl optionally substituted with one or more substituents independently selected from the group consisting of T and $C_{1-6}$ aliphatic optionally substituted with one or more instances of T; and wherein each T is halogen, cyano, —N(R)H, —OH, —CO$_2$H, —C(O)N(R)H, —OC(O)N(R)H, —N(R)Q$^2$, —OQ$^2$, CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, or —N(R)C(O)N(R)Q$^2$.

i) $R^2$ is —H or $C_{1-3}$ alkyl; $R^3$ is $C_{1-3}$ alkyl; $R^4$ is —H or $C_{1-3}$ alkyl; and $R^5$ is —H or $C_{1-3}$ alkyl; or ii) $R^2$ and $R^3$ together with the atom to which they are bound form a $C_{3-7}$ cycloalkyl ring; $R^4$ is —H or $C_{1-3}$ alkyl; and $R^5$ is —H or $C_{1-3}$ alkyl.

$R^6$ is —H, optionally substituted $C_{1-6}$ alkyl, or optionally substituted $C_{3-7}$ cycloalkyl.

$R^7$ is —H, or $C_{1-6}$ alkyl.

$R^8$ is —H or $C_{1-6}$ alkyl.

Values, including specific values, of the remaining variables are as described above in the first set of variables of Structural Formula (I).

A twenty fifth set of variables of Structural Formula (I) is as follows:

$R^1$ is $C_{1-4}$ alkyl substituted with $Q^1$ and optionally further substituted with one or more substituents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl). Alternatively, $R^1$ is $C_{6-10}$ aryl or 5-6 membered heteroaryl, each optionally and independently substituted with one or more substituents independently selected from the group consisting of T and $C_{1-6}$ aliphatic optionally substituted with one or more instances of T; and wherein each T is halogen, cyano, $Q^1$, —N(R)H, —OH, —SH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —SQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —$SO_2N(R)Q^2$, —$N(R)SO_2Q^2$, or —$N(R)SO_2N(R)Q^2$. Specifically, $R^1$ is phenyl optionally substituted with one or more substituents independently selected from the group consisting of T and $C_{1-6}$ aliphatic optionally substituted with one or more instances of T; and wherein each T is halogen, cyano, —N(R)H, —OH, —$CO_2H$, —C(O)N(R)H, —OC(O)N(R)H, —$N(R)Q^2$, —$OQ^2$, —$CO_2Q^2$, —$OC(O)Q^2$, —$C(O)N(R)Q^2$, —$N(R)C(O)Q^2$, —$N(R)CO_2Q^2$, —$OC(O)N(R)Q^2$, —$C(O)N(R)CO_2Q^2$, or —$N(R)C(O)N(R)Q^2$.

i) $R^2$ is —H or $C_{1-3}$ alkyl; $R^3$ is $C_{1-3}$alkyl; $R^4$ is —H; and $R^5$ is —H; or ii) $R^2$ and $R^3$ together with the atom to which they are bound form a $C_{3-7}$ cycloalkyl ring; $R^4$ is —H; and $R^5$ is —H.

$R^6$ is —H, optionally substituted $C_{1-6}$ alkyl, or optionally substituted $C_{3-7}$ cycloalkyl.

$R^7$ is —H, or $C_{1-6}$ alkyl.

$R^8$ is —H or $C_{1-6}$ alkyl.

Values, including specific values, of the remaining variables are as described above in the first set of variables of Structural Formula (I).

A twenty sixth set of variables of Structural Formula (I) is as follows:

$R^1$ is phenyl optionally substituted with one or more substituents independently selected from the group consisting of T and $C_{1-6}$ aliphatic optionally substituted with one or more instances of T; and wherein each T is halogen, cyano, —N(R)H, —OH, —$CO_2H$, —C(O)N(R)H, —OC(O)N(R)H, —$N(R)Q^2$, —$OQ^2$, —$CO_2Q^2$, —$OC(O)Q^2$, —$C(O)N(R)Q^2$, —$N(R)C(O)Q^2$, —$N(R)CO_2Q^2$, —$OC(O)N(R)Q^2$, —$C(O)N(R)CO_2Q^2$, or —$N(R)C(O)N(R)Q^2$.

i) $R^2$ is —H or $C_{1-3}$ alkyl; $R^3$ is $C_{1-3}$alkyl; $R^4$ is —H; and $R^5$ is —H; or ii) $R^2$ and $R^3$ together with the atom to which they are bound form a $C_{3-7}$cycloalkyl ring; $R^4$ is —H; and $R^5$ is —H.

$R^6$ is —H, optionally substituted $C_{1-6}$ alkyl, or optionally substituted $C_{3-7}$ cycloalkyl.

$R^7$ is —H, or $C_{1-6}$ alkyl.

$R^8$ is —H, or $C_{1-6}$ alkyl.

Values, including specific values, of the remaining variables are as described above in the first set of variables of Structural Formula (I).

A twenty seventh set of variables of Structural Formula (I) is as follows:

Values, including specific values, of $R^1$, $R^2$, $R^3$, $R^4$, $R^5$, $R^6$, and $R^8$ are independently as described above in the twenty sixth set of variables of Structural Formula (I).

$R^7$ is —H.

Values, including specific values, of the remaining variables are as described above in the first set of variables of Structural Formula (I).

A twenty eighth set of variables of Structural Formula (I) is as follows:

Values, including specific values, of $R^1$, $R^2$, $R^3$, $R^4$, and $R^5$ are independently as described above in the twenty sixth set of variables of Structural Formula (I).

$R^6$ is optionally substituted $C_{3-6}$cycloalkyl $R^7$ is —H.

Values, including specific values, of the remaining variables are as described above in the first set of variables of Structural Formula (I).

A twenty ninth set of variables of Structural Formula (I) is as follows:

$R^1$ is optionally substituted aryl or optionally substituted heteroaryl. Values, including specific values, of the remaining variables of Structural Formula (I) are as described above in any set of the first through twenty eighth sets of variables of Structural Formula (I).

A thirtieth set of variables of Structural Formula (I) is as follows:

q is 1.

Values, including specific values, of the remaining variables of Structural Formula (I) are as described above in any set of the first through twenty sixth sets of variables of Structural Formula (I).

A thirty first set of t of variables of Structural Formula (I) is as follows:

$R^1$ is optionally substituted aryl or optionally substituted heteroaryl.

q is 1

Values, including specific values, of the remaining variables of Structural Formula (I) are as described above in any set of the first through twenty sixth sets of variables of Structural Formula (I).

In another embodiment, the methods of the invention can be employed in preparing the compounds represented by Structural Formula (III) or pharmaceutically acceptable salts thereof, wherein values of the variables of Structural Formula (III) are as described below:

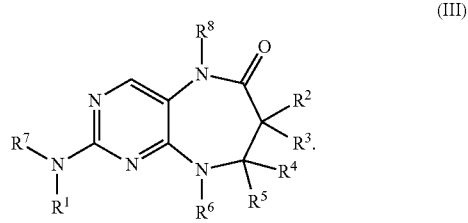

(III)

In a first set of variables of Structural Formula (III), values, including specific values, of variables of Structural Formula (III) are independently as described above in any set of the first through twenty eighth sets of variables of Structural Formula (I).

A second set of variables of Structural Formula (III) is as follows:

$R^6$ is —H, $C_{1-6}$ aliphatic, or $C_{3-7}$cycloaliphatic, wherein each of the $C_{1-6}$ aliphatic and $C_{3-7}$cycloaliphatic groups is optionally and independently substituted with one or more instances of $J^6$.

Values, including specific values, of variables of Structural Formula (III) are independently as described above in the first set of variables of Structural Formula (I).

A third set of variables of Structural Formula (III) is as follows:

$R^1$ is optionally substituted $C_{6-10}$ aryl or optionally substituted 5-10 membered heteroaryl.

Each $Z^1$ is independently —N(R)—, —O—, —S—, —$CO_2$—, —C(O)N(R)—, —OC(O)N(R)—, —$N(R)CO_2$—, —N(R)C(O)N(R)—, —$C(O)N(R)CO_2$—, —$SO_2N(R)$—, or —$N(R)SO_2N(R)$—.

Each $Z^2$ is independently —N(R)—, —O—, —S—, —$CO_2$—, —OC(O)—, —C(O)N(R)—, —N(R)C(O)—, —OC(O)N(R)—, —$N(R)CO_2$—, —N(R)C(O)N(R)—, —$C(O)N(R)CO_2$—, —S(O)—, —$S(O)_2$—, —$SO_2N(R)$—, —$N(R)SO_2$—, or —$N(R)SO_2N(R)$—.

Each $Q^1$ is independently optionally substituted $C_{3-7}$cycloalkyl, optionally substituted phenyl, optionally substituted 5-6 membered heteroaryl, or optionally substituted 4-7 membered heterocyclyl.

Each of $R^2$ and $R^3$ is independently —H, halogen, cyano, or $C_{1-6}$ aliphatic, or optionally $R^2$ and $R^3$, together with the carbon atom(s) to which they are bound, independently form a $C_{3-7}$cycloalkyl ring, wherein each of said aliphatic and cycloalkyl ring is independently and optionally substituted with one or more substituents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$ ($C_1$-$C_4$ alkyl), and —O($C_1$-$C_4$ alkyl).

$R^6$ is —H, $C_{1-6}$ aliphatic or $C_{3-7}$cycloaliphatic, each of which is optionally and independently substituted with one or more substituents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$ ($C_1$-$C_4$ alkyl), and —O($C_1$-$C_4$ alkyl).

Each of $R^7$ and $R^8$ is independently —H or $C_{1-6}$ alkyl.

Values, including specific values, of the remaining variables of Structural Formula (I) are as described above in the first set of variables of Structural Formula (I).

In another embodiment, the methods of the invention can be employed in preparing the compounds represented by Structural Formula (IV) or pharmaceutically acceptable salts thereof, wherein values of the variables of Structural Formula (IV) are as described below:

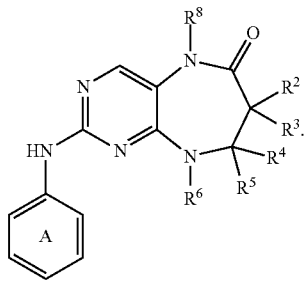

(IV)

In a first set of variables of Structural Formula (IV), values, including specific values, of variables of Structural Formula (IV) are independently as described above in any set of the first through twenty sixth sets of variables of Structural Formula (I).

In a second set of variables of Structural Formula (IV), values, including specific values, of variables of Structural Formula (IV) are independently as described above in the second or third set of variables of Structural Formula (III).

A third set of variables of Structural Formula (IV) is as follows:

Phenyl ring A is optionally substituted with one or more substitutents independently selected from the group consisting of T and $C_{1-6}$ aliphatic optionally substituted with one or more instances of T.

Each T is halogen, cyano, $Q^1$, —N(R)H, —OH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$-C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$.

$Q^1$ is $C_{3-7}$ cycloalkyl, phenyl, 5-6 membered heteroaryl, or 4-7 membered heterocyclyl, each optionally and independently substituted with one or more substitutents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$ ($C_1$-$C_4$ alkyl), —O($C_1$-$C_4$ alkyl), $C_1$-$C_4$ alkyl, $C_1$-$C_4$ haloalkyl; $C_1$-$C_4$ cyanoalkyl, $C_1$-$C_4$ aminoalkyl, $C_1$-$C_4$ hydroxyalkyl, and $C_2$-$C_4$ alkoxyalkyl.

Each $Q^2$ is independently $C_{1-6}$ alkyl, $C_{3-7}$ cycloalkyl, phenyl, 5-6 membered heteroaryl, or 4-7 membered heterocyclyl, or each $Q^2$, together with R, optionally and independently forms an optionally substituted, 4-7 membered heterocyclic ring; wherein said $C_{1-6}$ alkyl represented by $Q^2$ is optionally substituted with one or more substitutents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$ ($C_1$-$C_4$ alkyl), and —O($C_1$-$C_4$ alkyl); and wherein each of said cycloalkyl, aryl, heteroaryl, and heterocyclyl groups represented by $Q^2$ is optionally and independently substituted with one or more substitutents independently selected from the group consisting of halogen, oxo, —CN, —OH, —NH$_2$, —NH($C_1$-$C_4$ alkyl), —N($C_1$-$C_4$ alkyl)$_2$; —OCO($C_1$-$C_4$ alkyl), —CO($C_1$-$C_4$ alkyl), —CO$_2$H, —CO$_2$ ($C_1$-$C_4$ alkyl), —O($C_1$-$C_4$ alkyl), $C_1$-$C_4$ alkyl, $C_1$-$C_4$ haloalkyl; $C_1$-$C_4$ cyanoalkyl, $C_1$-$C_4$ aminoalkyl, $C_1$-$C_4$ hydroxyalkyl, and $C_2$-$C_4$ alkoxyalkyl.

Each of $R^2$ and $R^3$ is independently —H, halogen, optionally substituted $C_{1-6}$ aliphatic; or optionally $R^2$ and $R^3$, together with the carbon atom to which they are attached, form an optionally substituted $C_{3-6}$cycloalkyl ring.

$R^6$ is optionally substituted —H, optionally substituted $C_{1-6}$ alkyl, or optionally substituted $C_{3-6}$cycloalkyl.

Each of $R^7$ and $R^8$ is independently —H or $C_{1-6}$ alkyl.

Values, including specific values, of the remaining variables of Structural Formula (I) are as described above in the first set of variables of Structural Formula (I).

A fourth set of variables of Structural Formula (IV) is as follows:

Phenyl ring A is substituted with one or more substituents independently selected from the group consisting of —C(O)N(R)H, —C(O)N(R)Q$^2$, —N(R)C(O)Q$^2$, —CO$_2$H, —CO$_2$Q$^2$, —OC(O)Q$^2$, —N(R)CO$_2$Q$^2$, —OC(O)N(R)Q$^2$, and —N(R)C(O)N(R)Q$^2$; and optionally further substituted with one or one or more substituents independently selected from the group consisting of halogen, —CN, —OH, —NH$_2$, —NH($C_1$-$C_4$ alkyl), —N($C_1$-$C_4$ alkyl)$_2$, —O($C_1$-$C_4$ alkyl), $C_1$-$C_4$ alkyl, $C_1$-$C_4$ haloalkyl; $C_1$-$C_4$ cyanoalkyl, $C_1$-$C_4$ aminoalkyl, $C_1$-$C_4$ hydroxyalkyl, and $C_2$-$C_4$ alkoxyalkyl.

Each $Q^2$ is independently $C_{1-6}$ alkyl, $C_{3-7}$cycloalkyl, phenyl, 5-6 membered heteroaryl, or 4-7 membered heterocyclyl, or each $Q^2$, together with R, optionally and independently forms an optionally substituted, 4-7 membered heterocyclic ring; wherein said $C_{1-6}$ alkyl represented by $Q^2$ is optionally substituted with one or more substitutents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$ ($C_1$-$C_4$ alkyl), and —O($C_1$-$C_4$ alkyl); and wherein each of said cycloalkyl, aryl, heteroaryl, and heterocyclyl groups represented by $Q^2$ is optionally and independently substituted with one or more substitutents independently selected from the group consisting of halogen, oxo, —CN, —OH, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$ ($C_1$-$C_4$ alkyl), —O($C_1$-$C_4$ alkyl), $C_1$-$C_4$ alkyl, $C_1$-$C_4$ haloalkyl; $C_1$-$C_4$ cyanoalkyl, $C_1$-$C_4$ aminoalkyl, $C_1$-$C_4$ hydroxyalkyl, and $C_2$-$C_4$ alkoxyalkyl.

Each of $R^2$ and $R^3$ is independently —H, halogen, optionally substituted $C_{1-6}$ aliphatic; or optionally $R^2$ and $R^3$, together with the carbon atom to which they are attached, form an optionally substituted $C_{3-6}$cycloalkyl ring.

R⁶ is optionally substituted —H, optionally substituted C₁₋₆ alkyl, or optionally substituted C₃₋₆ cycloalkyl.

Each of R⁷ and R⁸ is independently —H or C₁₋₆ alkyl.

Values, including specific values, of the remaining variables of Structural Formula (I) are as described above in the first set of variables of Structural Formula (I).

A fifth set of variables of Structural Formula (IV) is as follows:

Phenyl ring A is substituted with —OC(O)Q², —C(O)N(R)Q², or —N(R)C(O)Q², and optionally further substituted with one or one or more substituents independently selected from the group consisting of halogen, —CN, —OH, —NH₂, —NH(C₁-C₄ alkyl), —N(C₁-C₄ alkyl)₂, —O(C₁-C₄ alkyl), C₁-C₄ alkyl, C₁-C₄ haloalkyl; C₁-C₄ cyanoalkyl, C₁-C₄ aminoalkyl, C₁-C₄ hydroxyalkyl, and C₂-C₄ alkoxyalkyl.

Each Q² is independently C₁₋₆ alkyl, C₃₋₇cycloalkyl, phenyl, 5-6 membered heteroaryl, or 4-7 membered heterocyclyl, or each Q², together with R, optionally and independently forms an optionally substituted, 4-7 membered heterocyclic ring; wherein said C₁₋₆ alkyl represented by Q² is optionally substituted with one or more substitutents independently selected from the group consisting of halogen, oxo, —CN, —OH, —NH₂, —NH(C₁-C₄ alkyl), —N(C₁-C₄ alkyl)₂, —OCO(C₁-C₄ alkyl), —CO(C₁-C₄ alkyl), —CO₂H, —CO₂(C₁-C₄ alkyl), and —O(C₁-C₄ alkyl); and wherein each of said cycloalkyl, aryl, heteroaryl, and heterocyclyl groups represented by Q² is optionally and independently-substituted with one or more substitutents independently selected from the group consisting of halogen, oxo, —CN, —OH, —NH₂, —NH(C₁-C₄ alkyl), —N(C₁-C₄ alkyl)₂, —OCO(C₁-C₄ alkyl), —CO(C₁-C₄ alkyl), —CO₂H, —CO₂ (C₁-C₄ alkyl), —O(C₁-C₄ alkyl), C₁-C₄ alkyl, C₁-C₄ haloalkyl; C₁-C₄ cyanoalkyl, C₁-C₄ aminoalkyl, C₁-C₄ hydroxyalkyl, and C₂-C₄ alkoxyalkyl.

Each of R² and R³ is independently —H, halogen, optionally substituted C₁₋₆ aliphatic; or optionally R² and R³, together with the carbon atom to which they are attached, form an optionally substituted C₃₋₆ cycloalkyl ring.

R⁶ is optionally substituted —H, optionally substituted C₁₋₆ alkyl, or optionally substituted C₃₋₆cycloalkyl.

Each of R⁷ and R⁸ is independently —H or C₁₋₆ alkyl.

Values, including specific values, of the remaining variables of Structural Formula (I) are as described above in the first set of variables of Structural Formula (I).

A sixth set of variables of Structural Formula (IV) is as follows:

R⁶ is C₅₋₆ cycloalkyl.

Values, including specific values, of the remaining variables of Structural Formula (IV) are independently as described in the second, third or fourth set of variables of Structural Formula (IV).

A seventh set of variables of Structural Formula (IV) is as follows:

R² is —H or C₁₋₃alkyl, and R³ is C₁₋₃alkyl; or R² and R³ together with the atom to which they are bound form a C₃₋₆cycloalkyl ring.

R⁶ is C₅₋₆cycloalkyl.

Values, including specific values, of the remaining variables of Structural Formula (IV) are independently as described in the second, third or fourth set of variables of Structural Formula (IV).

In yet another embodiment, the methods of the invention can be employed in preparing the compounds represented by any one of the following structural formulae, or pharmaceutically acceptable salts thereof:

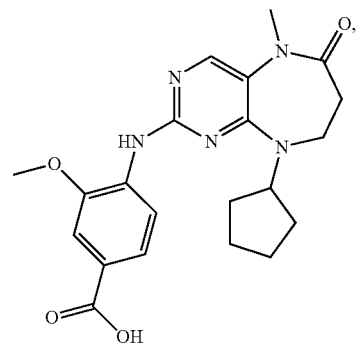

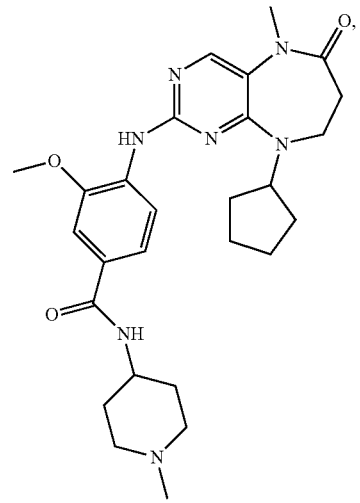

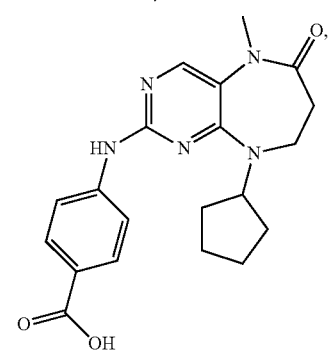

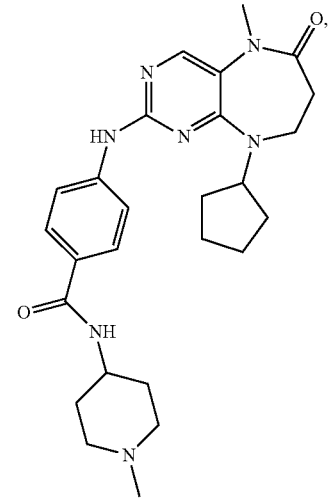

31
-continued
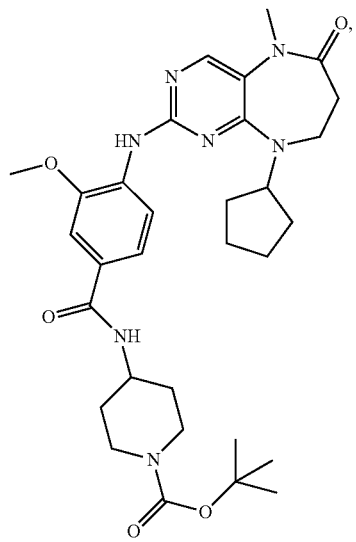
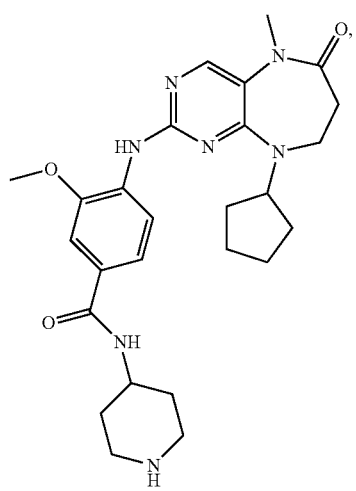
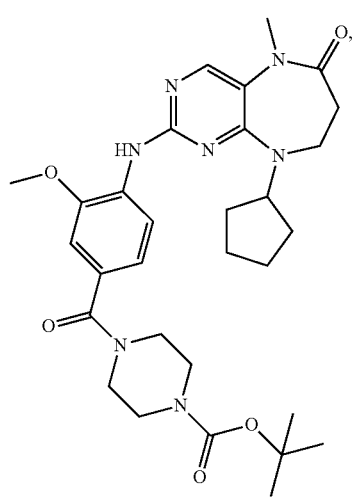
32
-continued
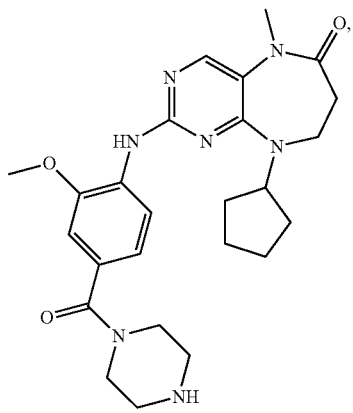
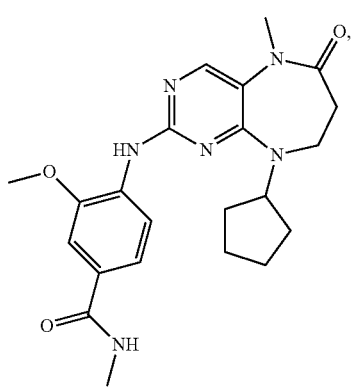
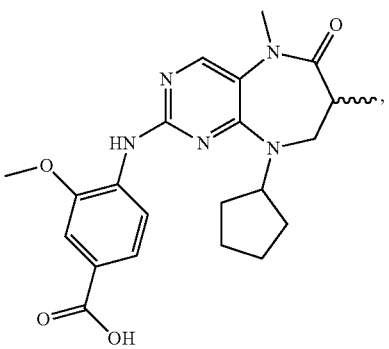
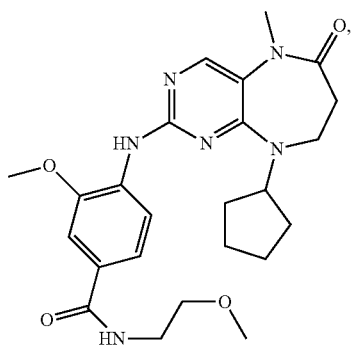

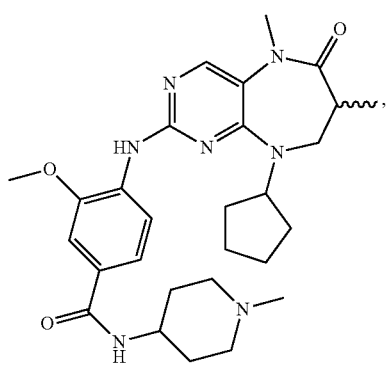
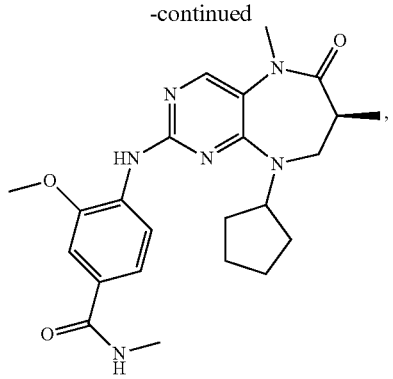
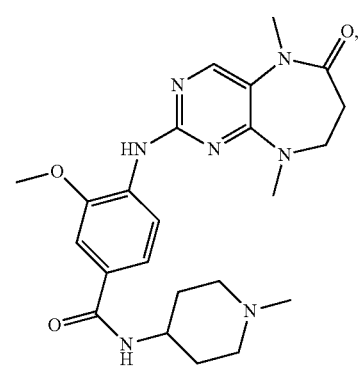
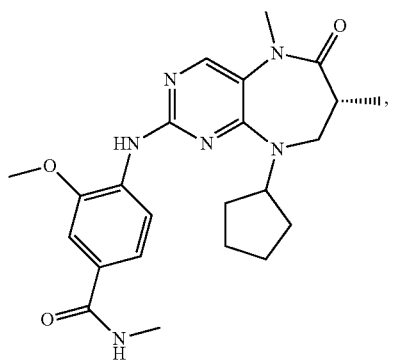
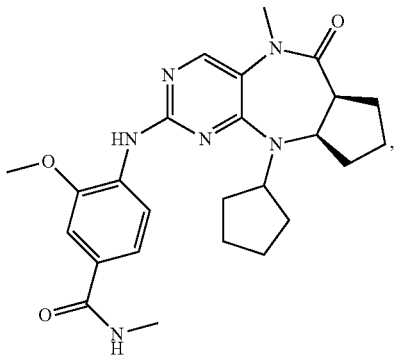
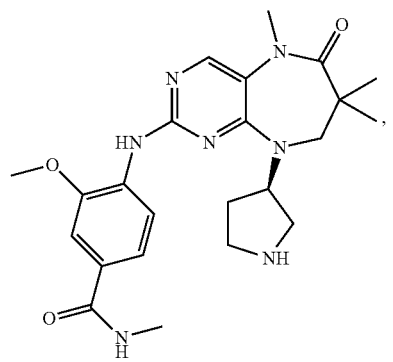
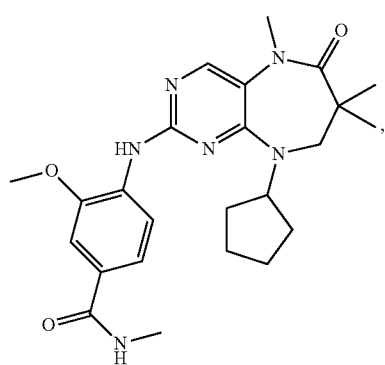
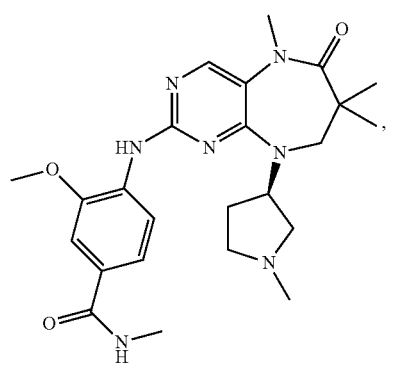

35
-continued
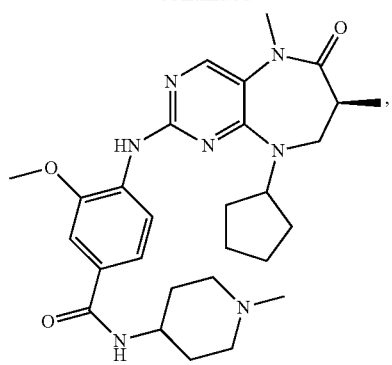
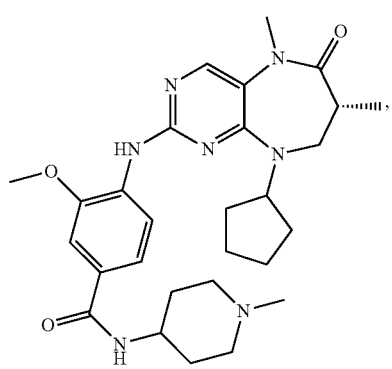
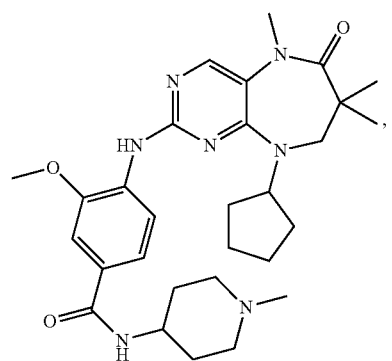
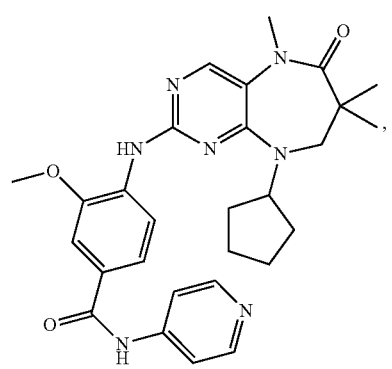
36
-continued
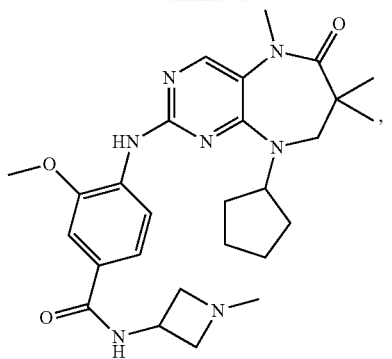
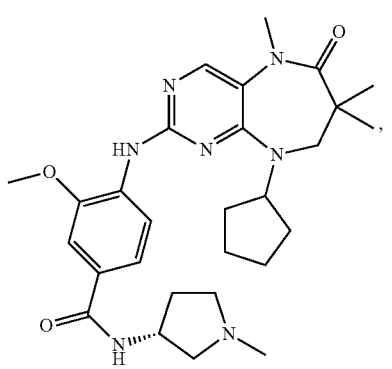
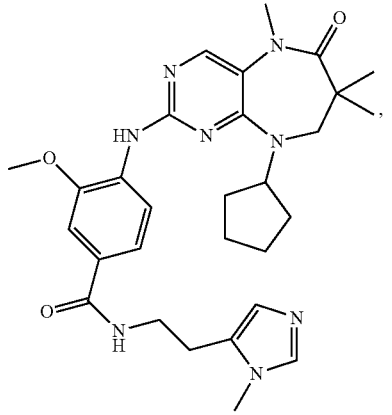
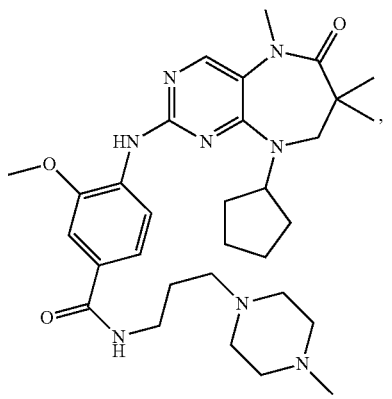

-continued
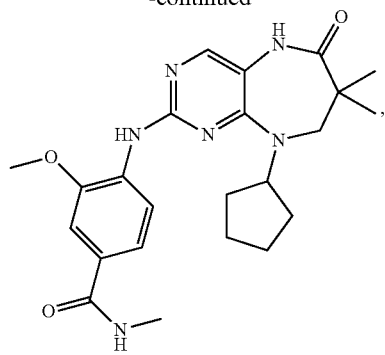
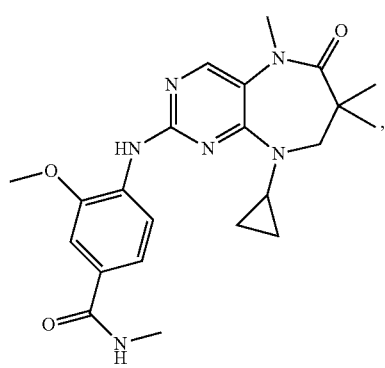
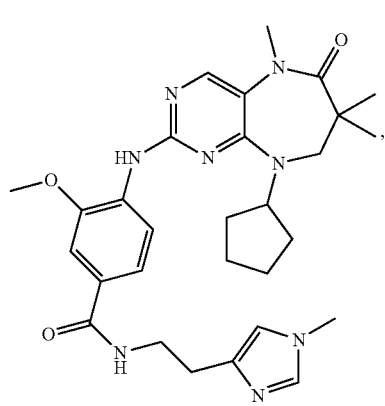
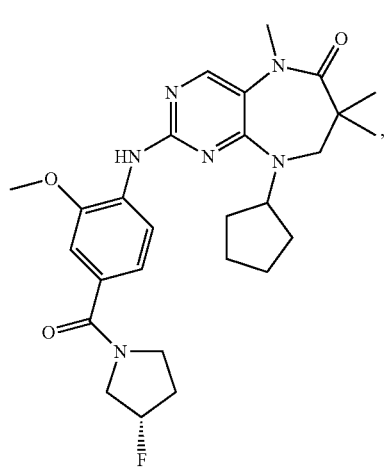
-continued
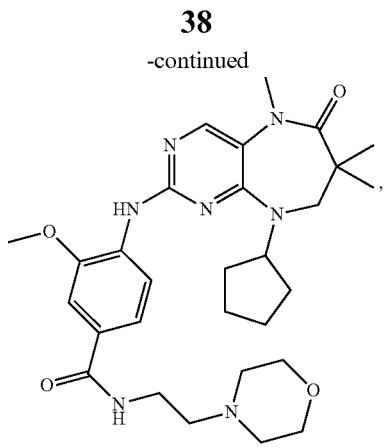
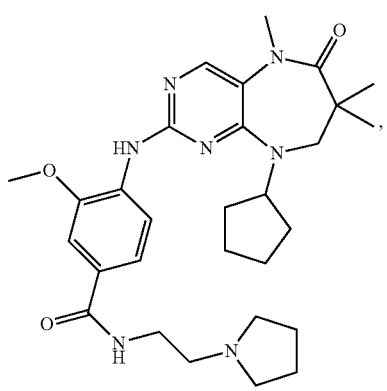
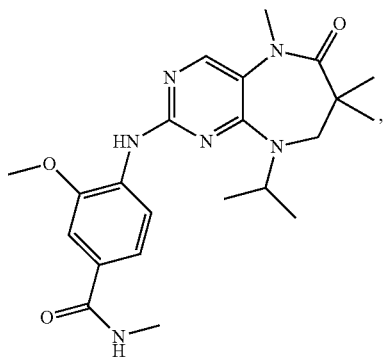
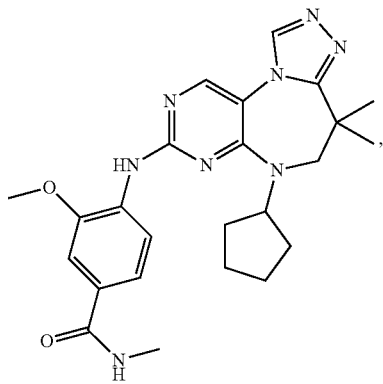

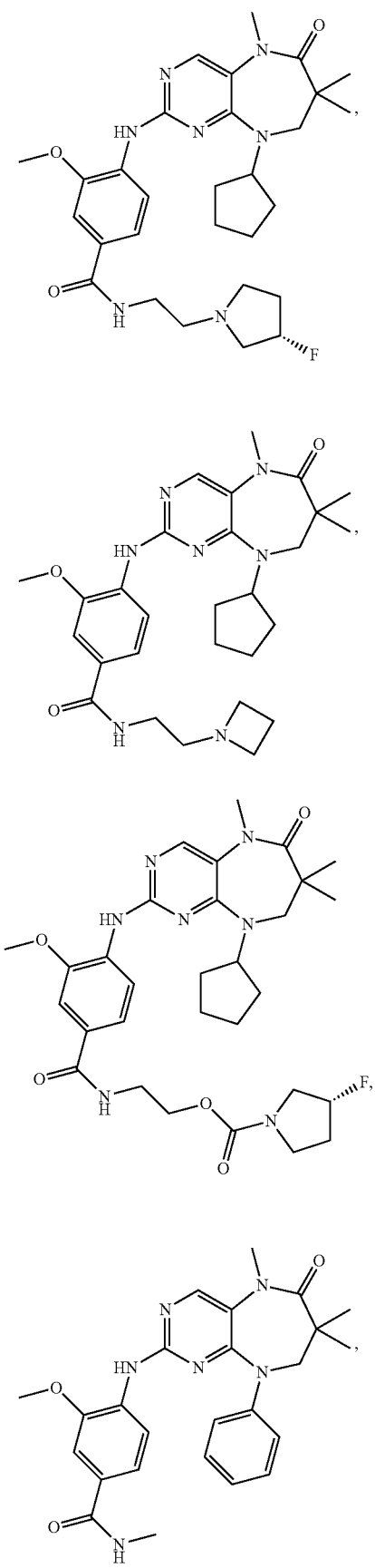
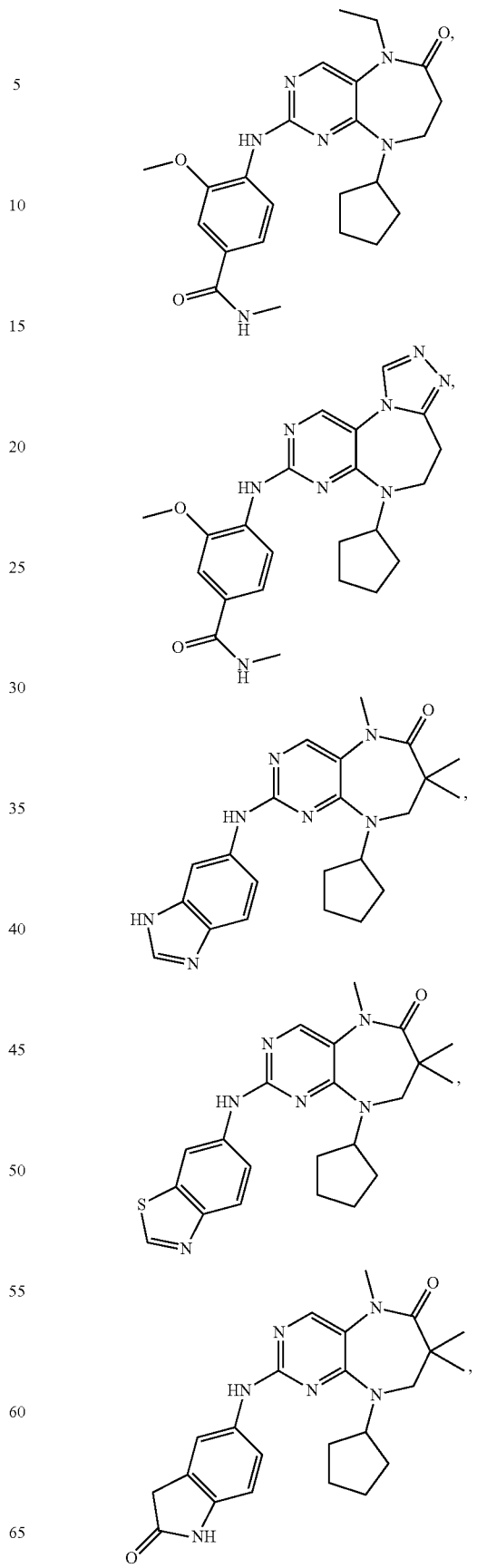

41
-continued
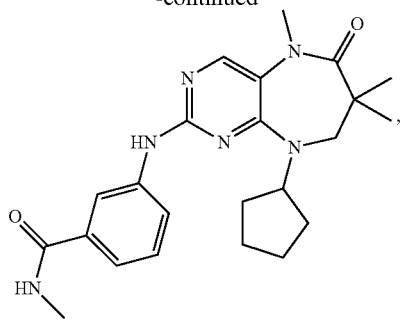
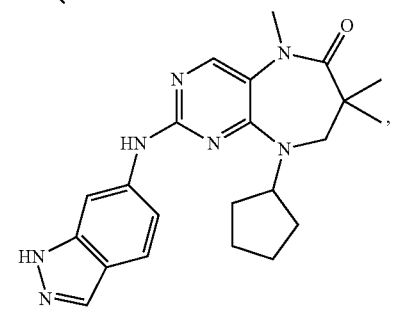
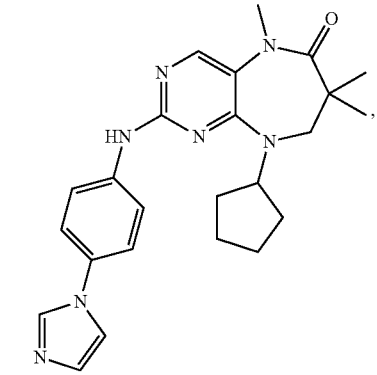
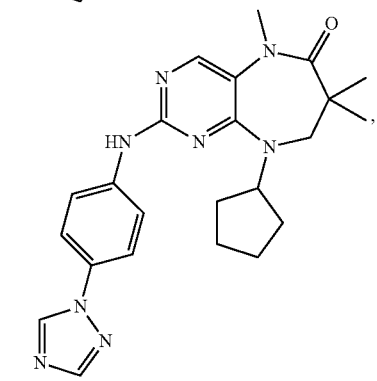
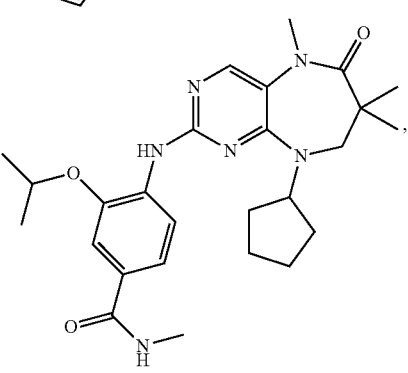
42
-continued
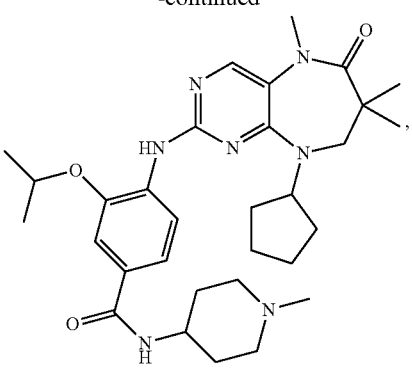
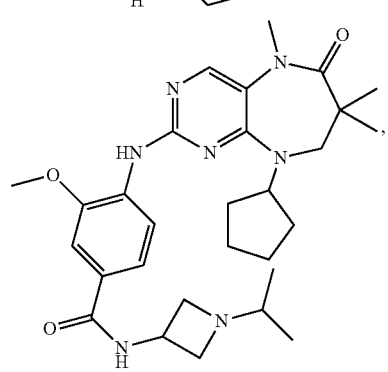
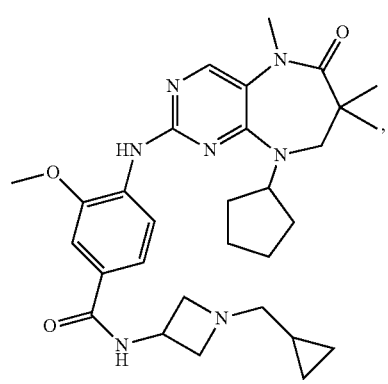
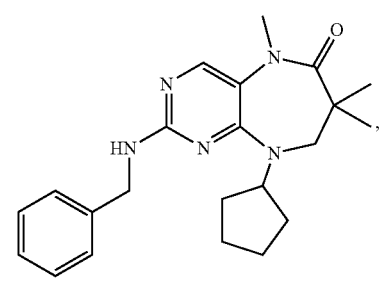
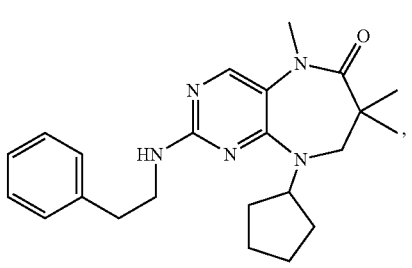

43
-continued
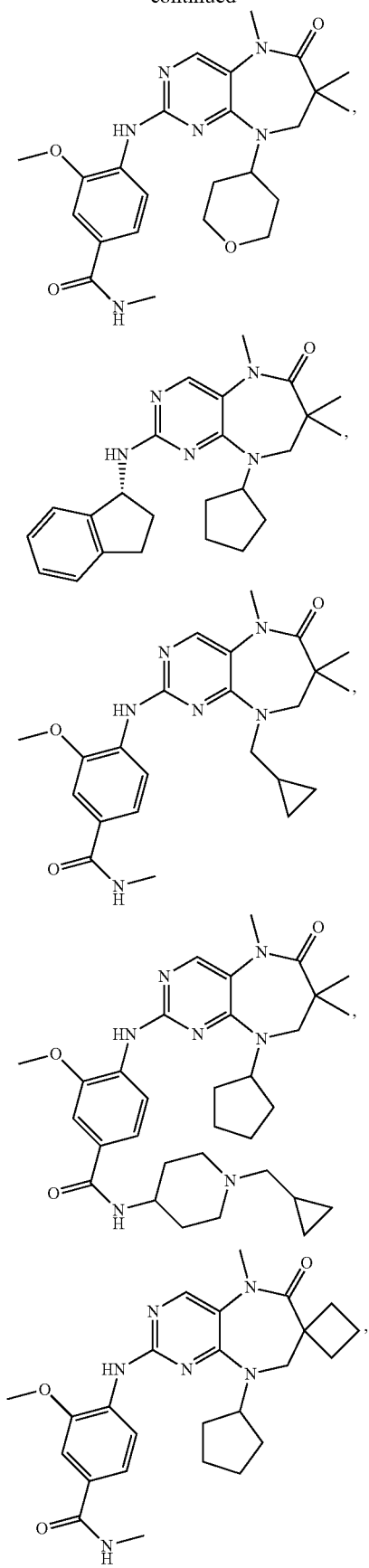
44
-continued
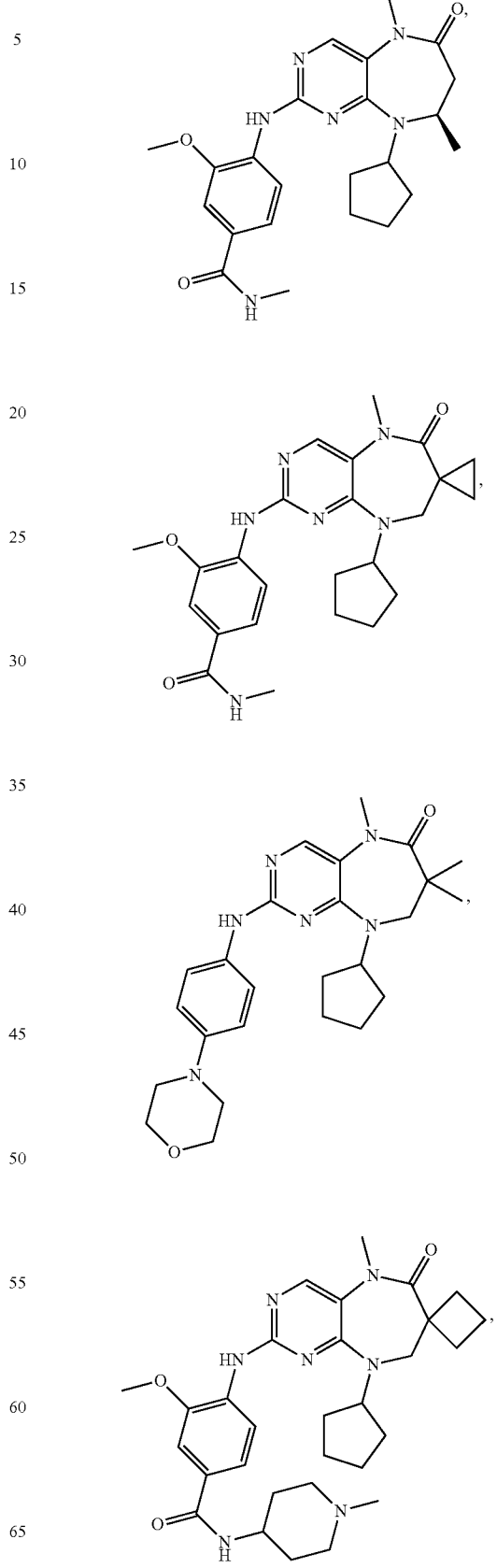

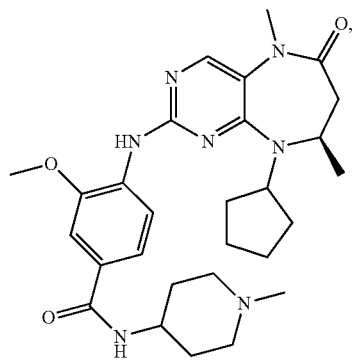
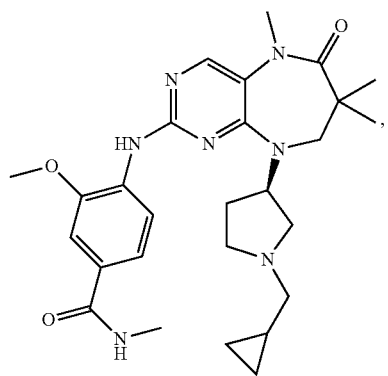
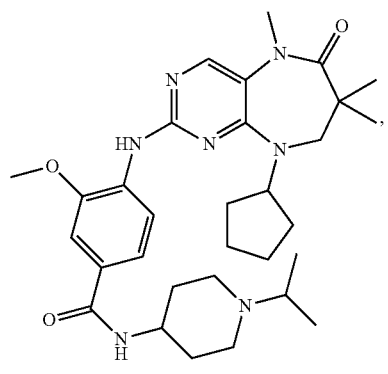
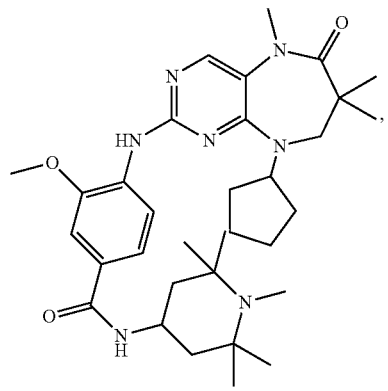
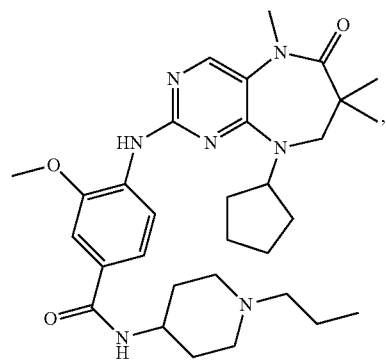
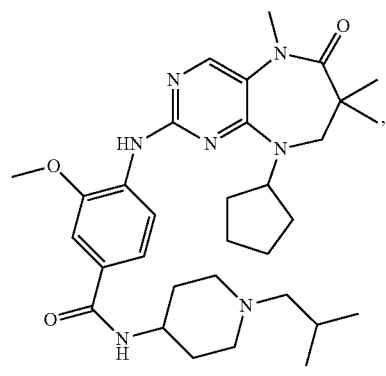
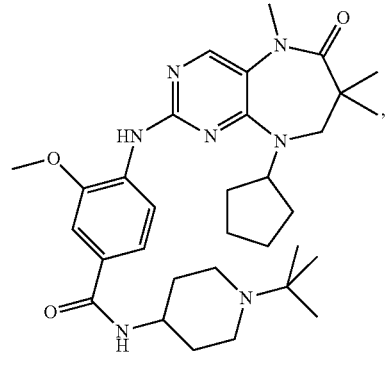
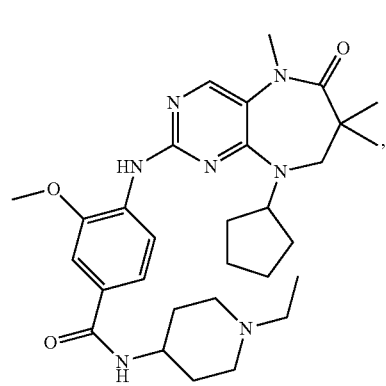

-continued
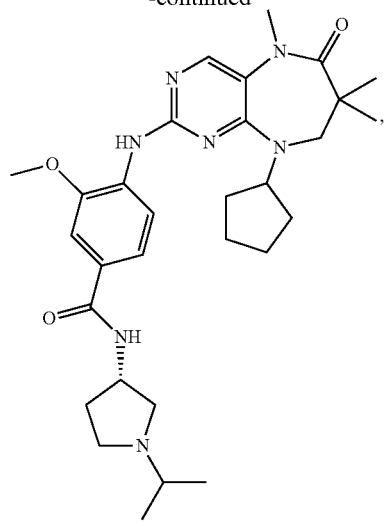
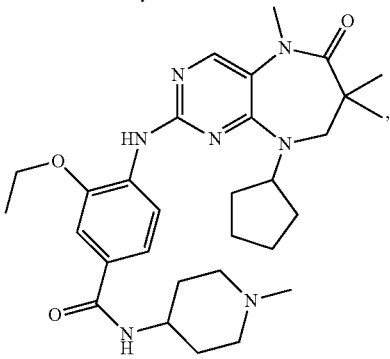
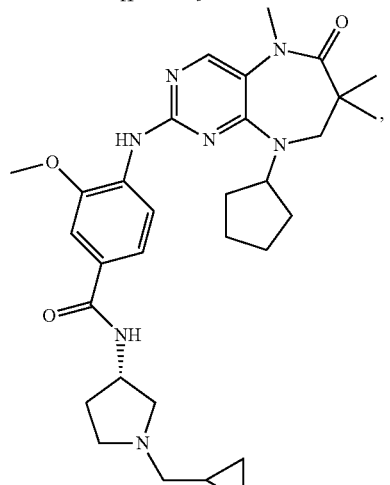
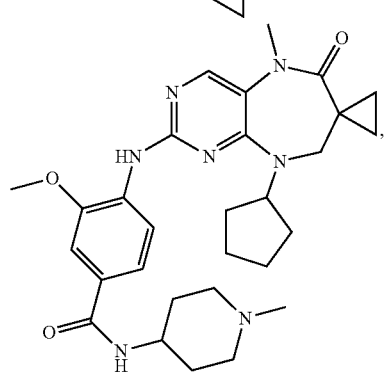
-continued
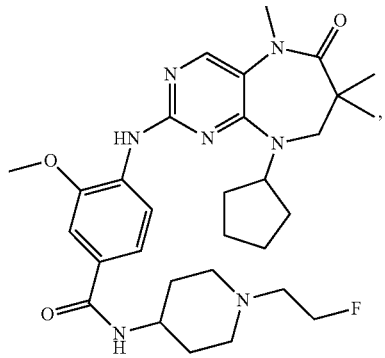
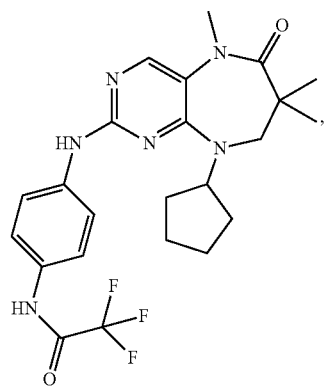
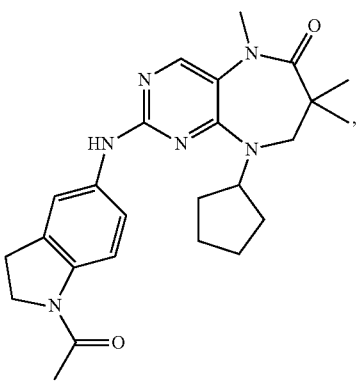
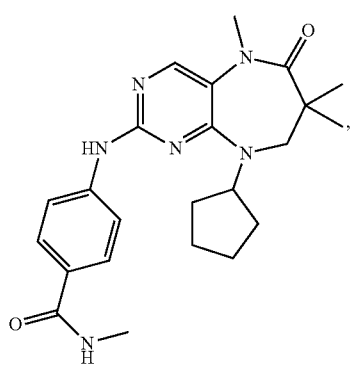

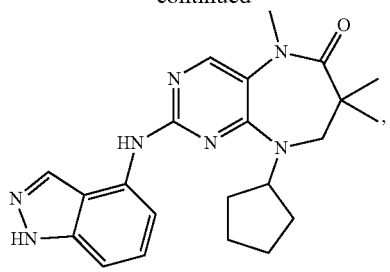
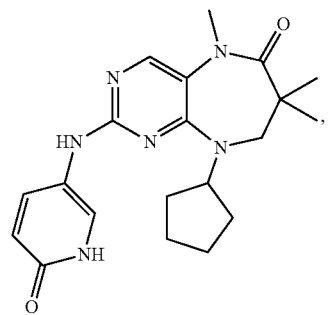
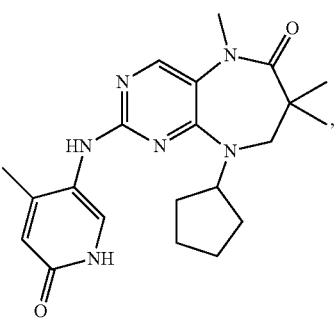
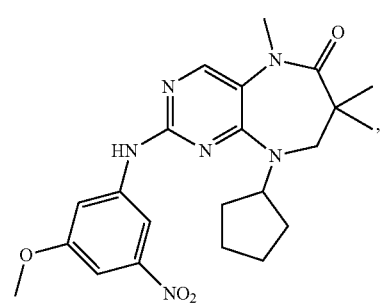
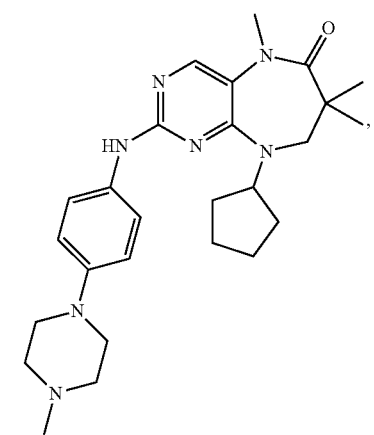
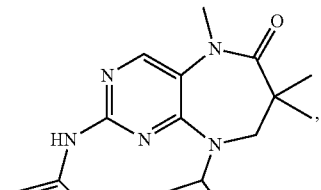
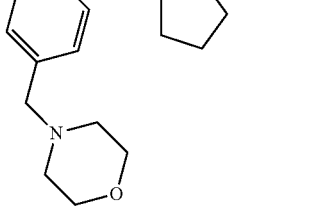
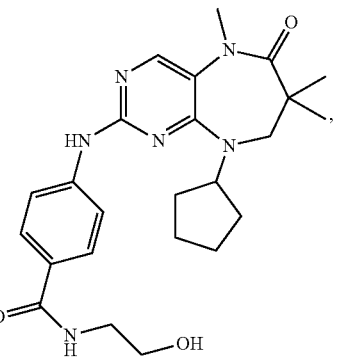
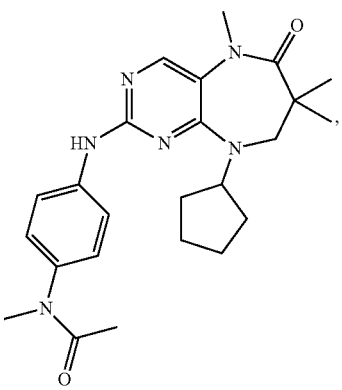
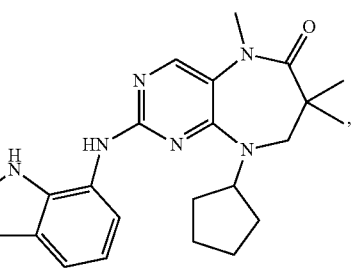
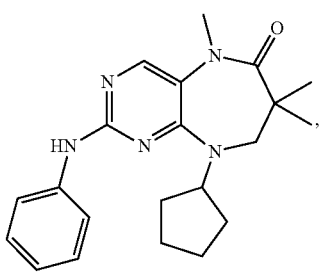

51
-continued
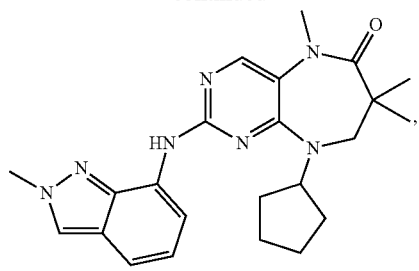
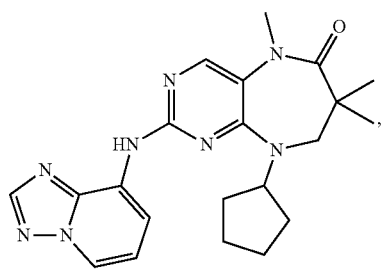
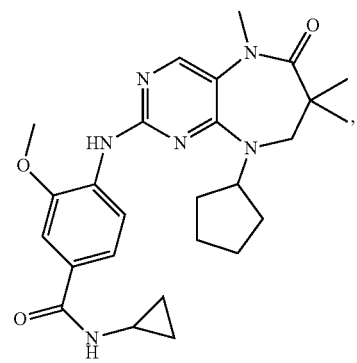
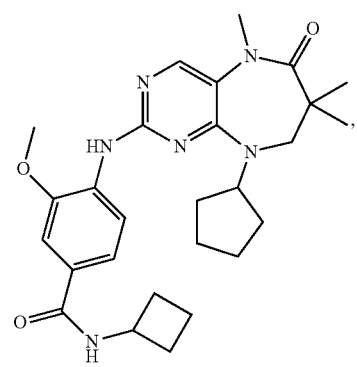
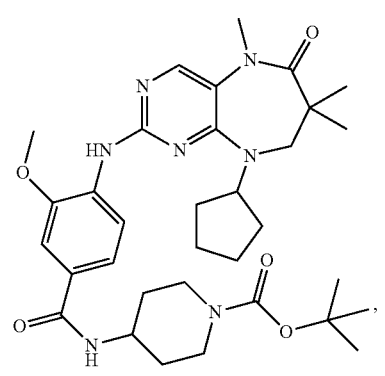
52
-continued
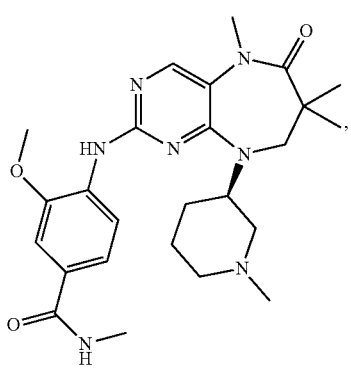
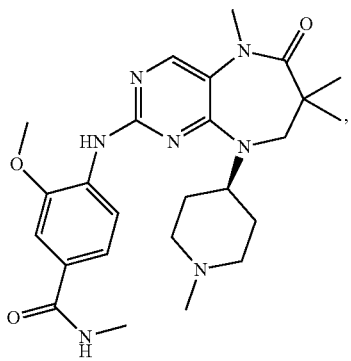
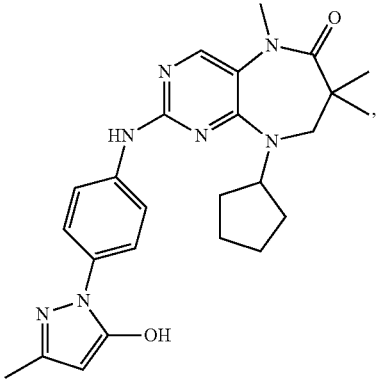
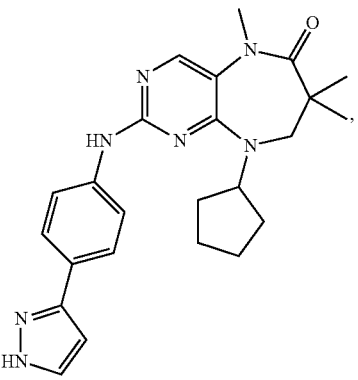

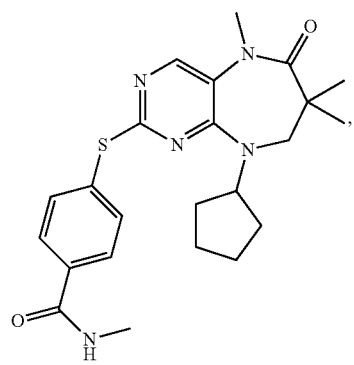
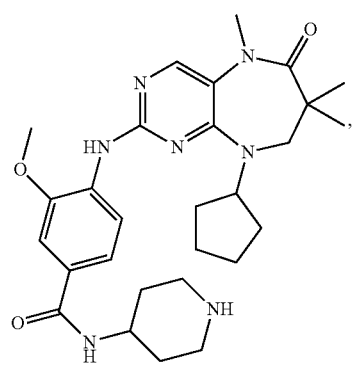
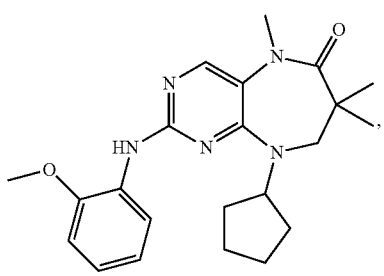
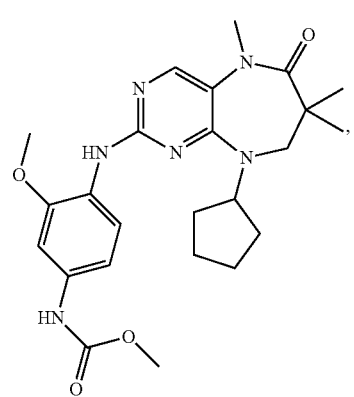
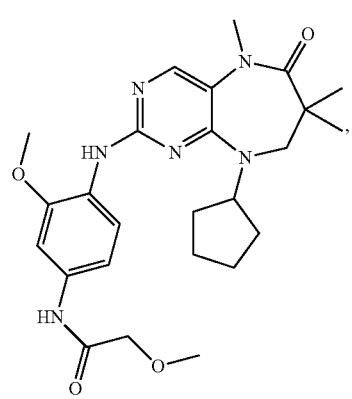
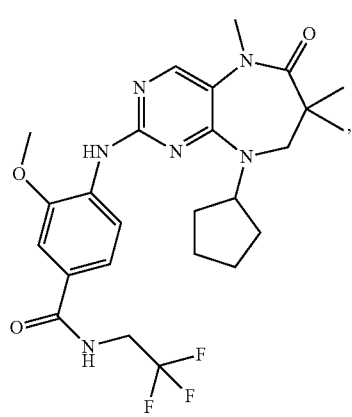
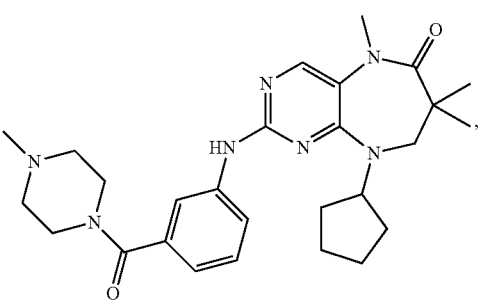
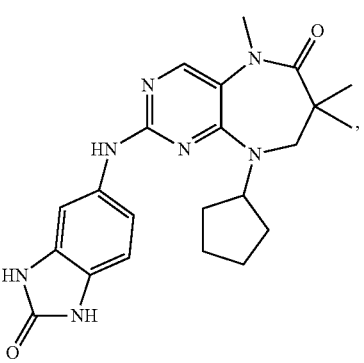

55
-continued
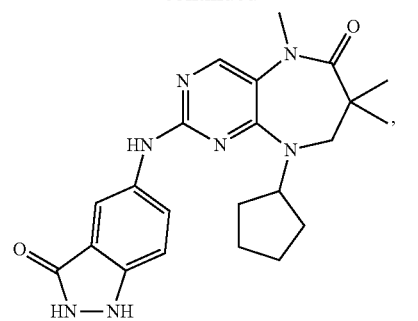
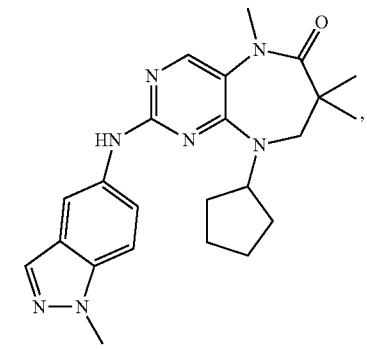
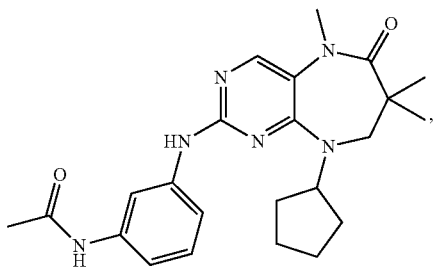
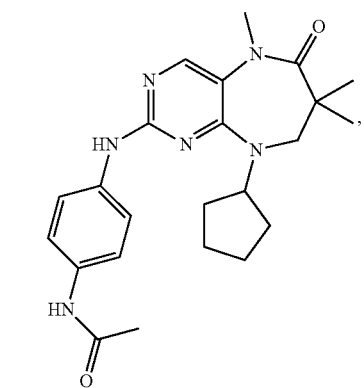
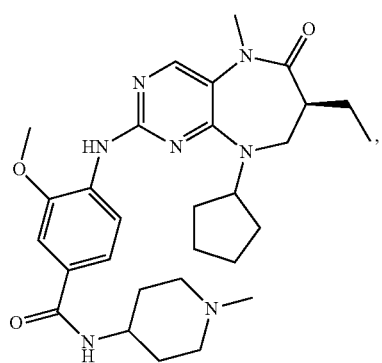
56
-continued
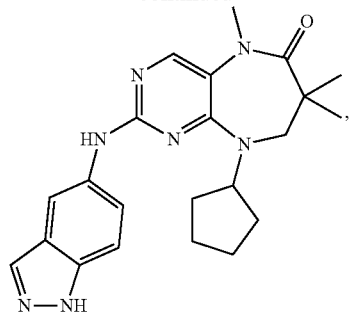
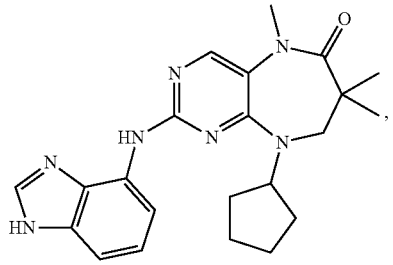
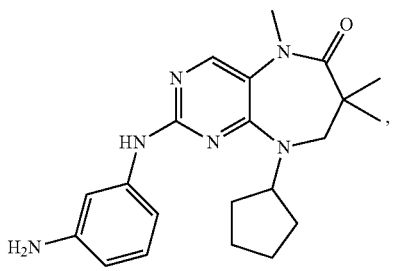
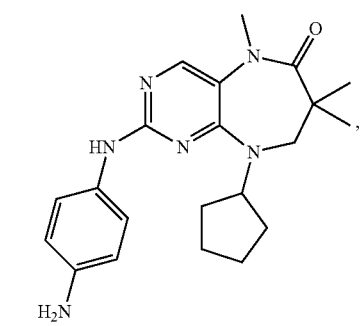
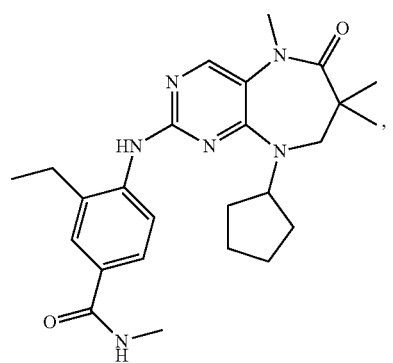

57
-continued
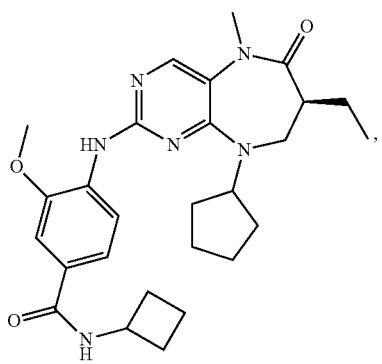
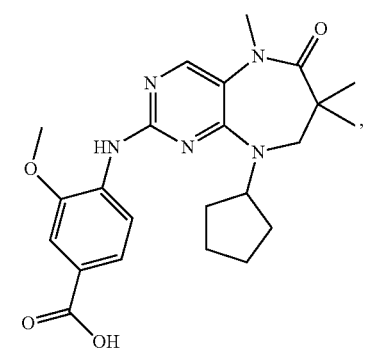
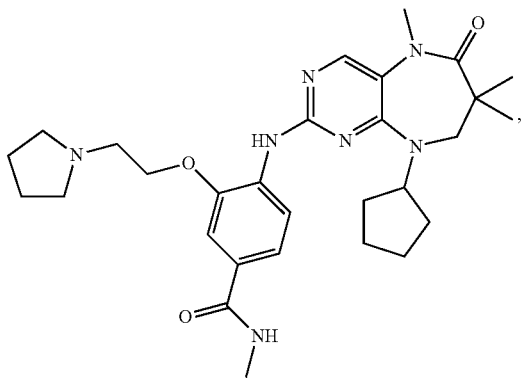
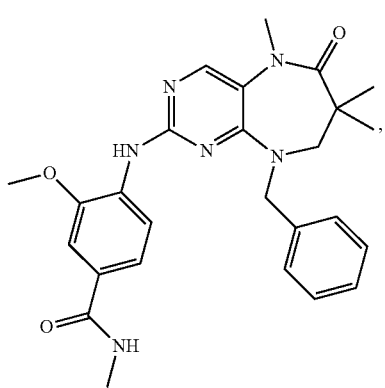
58
-continued
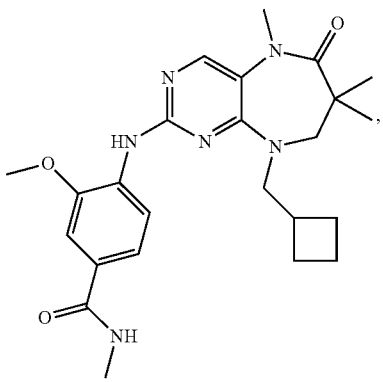
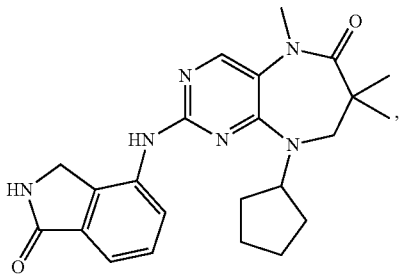
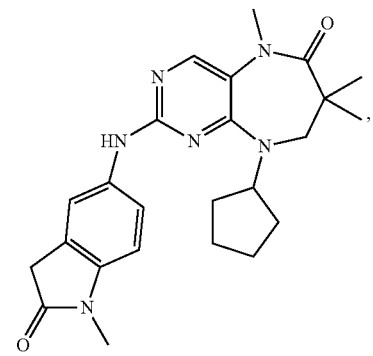
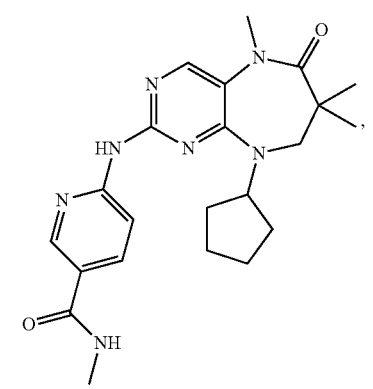
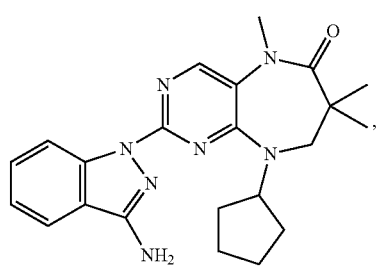

59
-continued
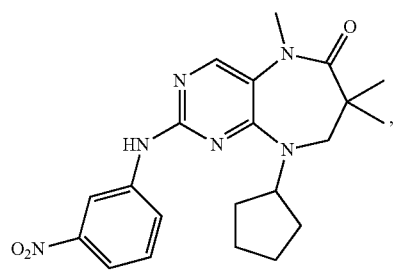
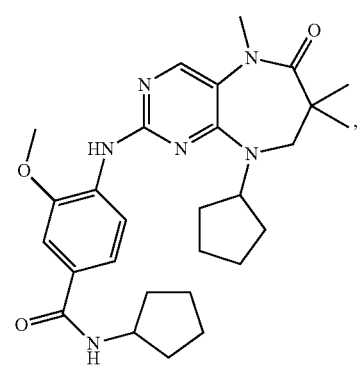
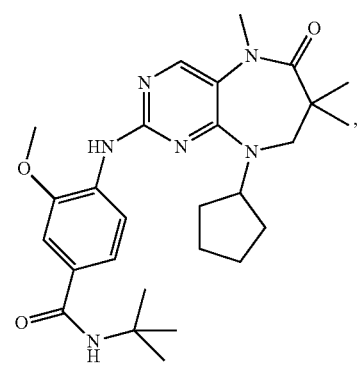
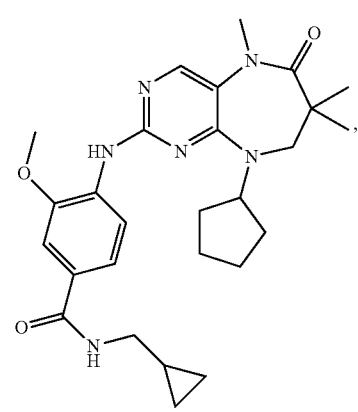
60
-continued
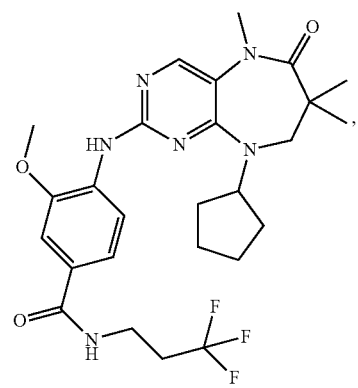
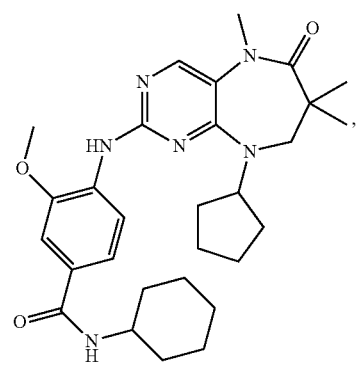
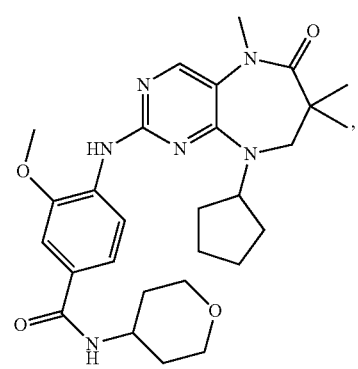
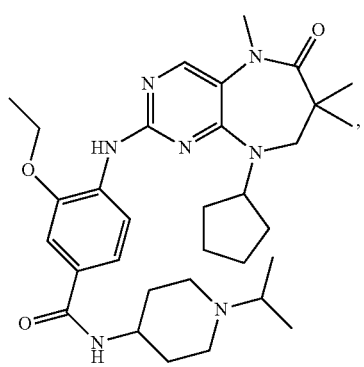

61
-continued
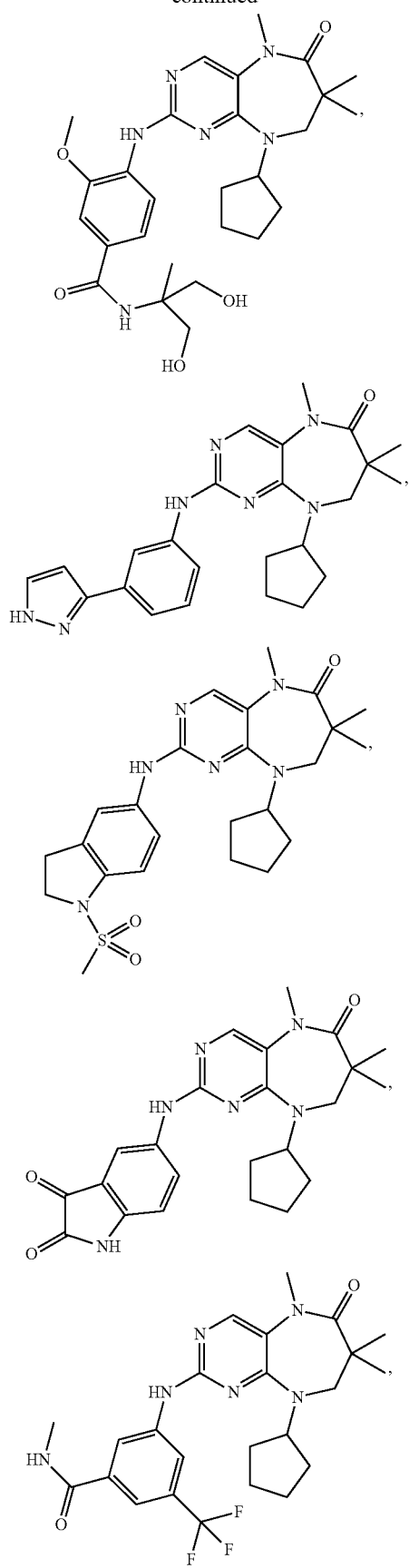
62
-continued
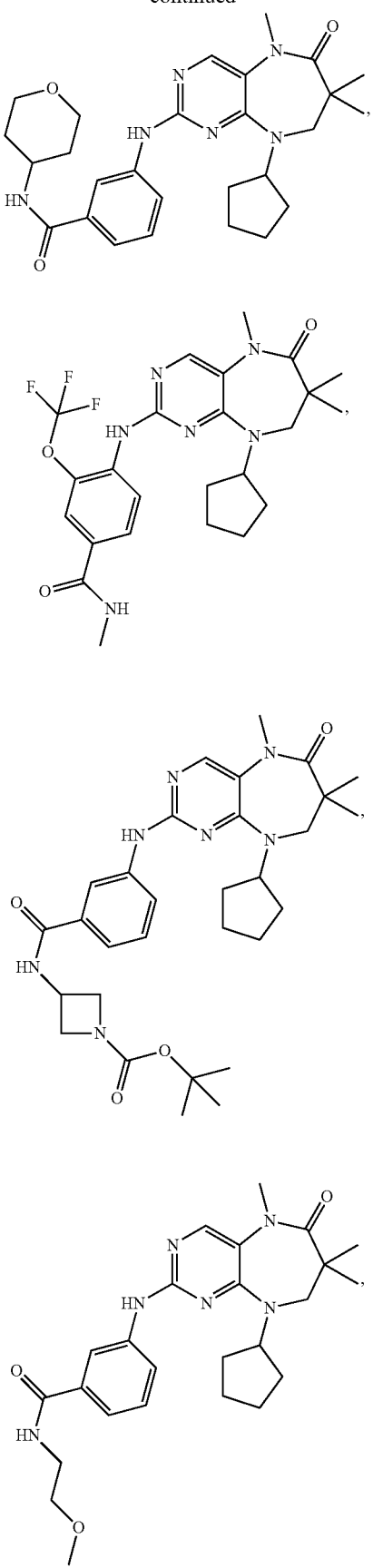

63
-continued
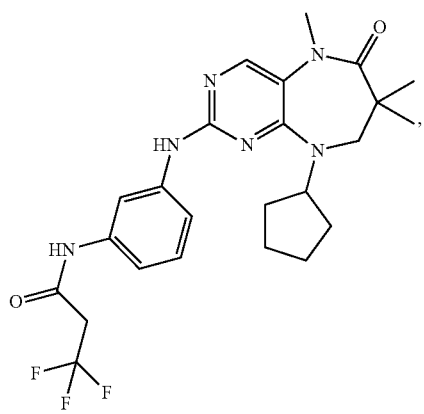
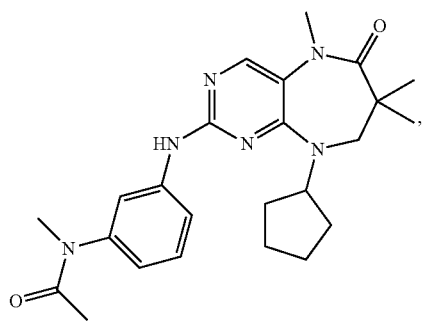
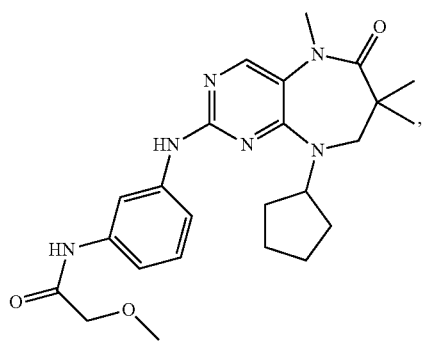
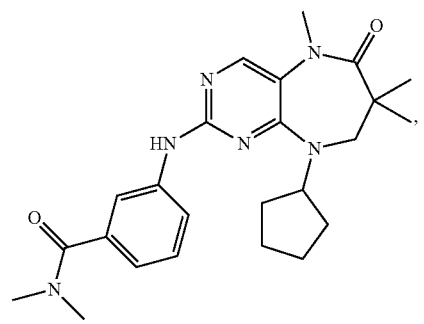
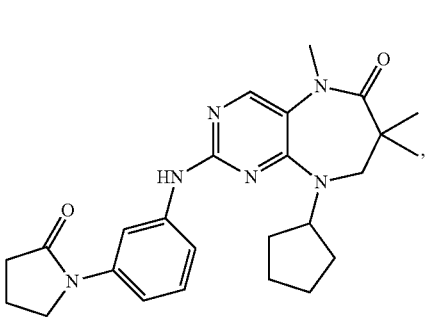
64
-continued
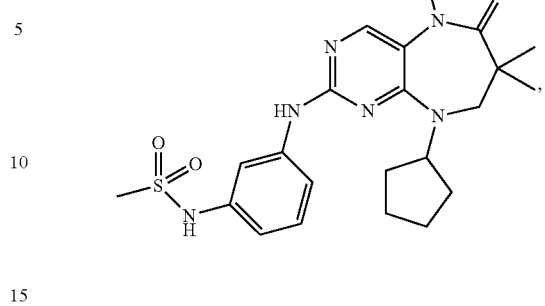
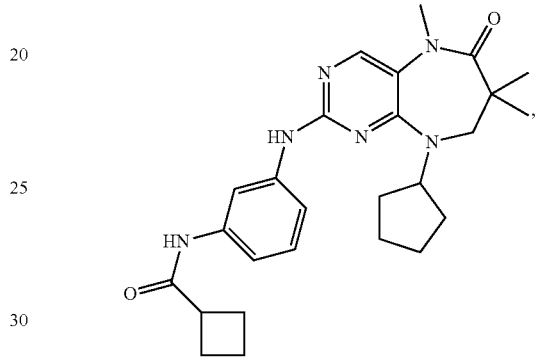
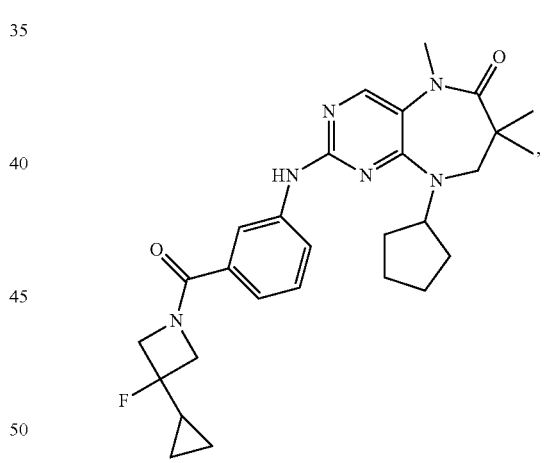
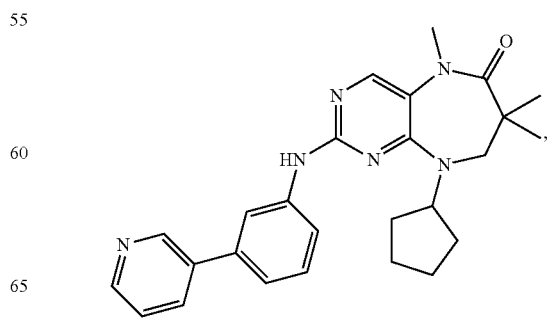

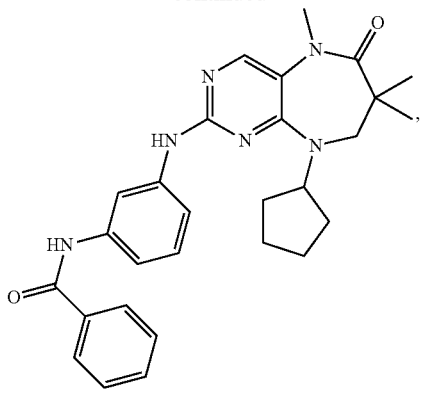
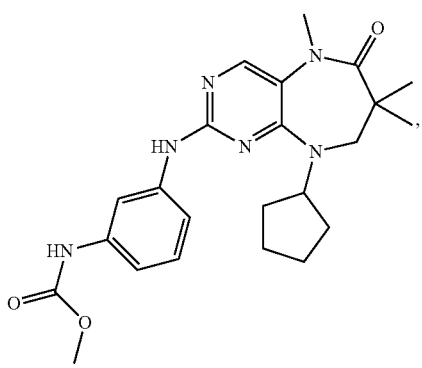
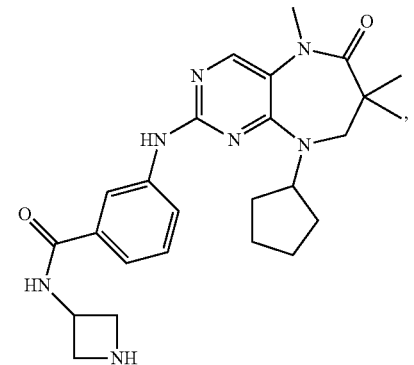
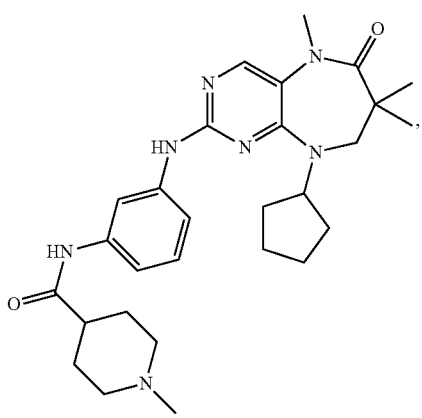
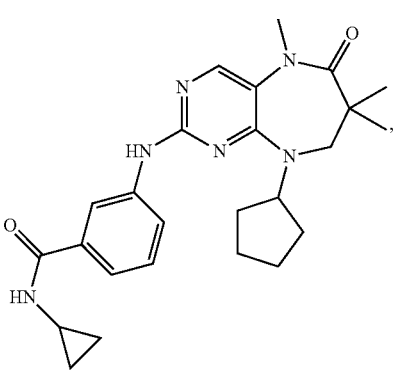
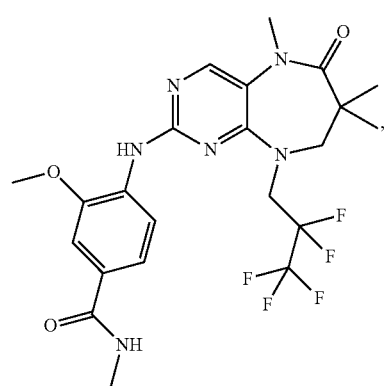
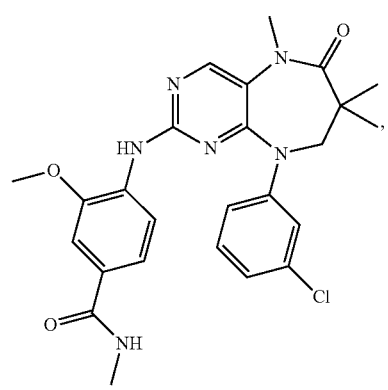

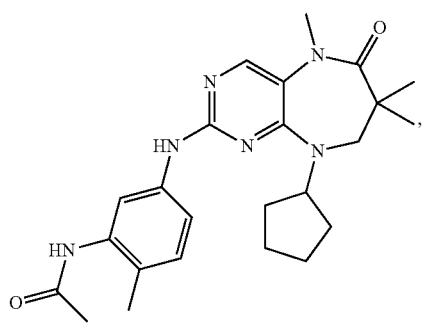
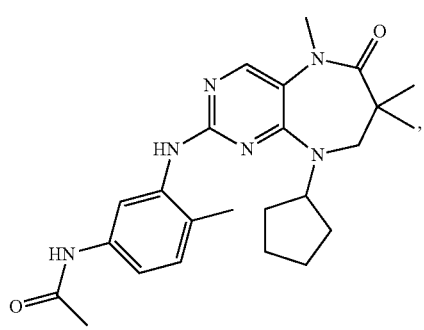
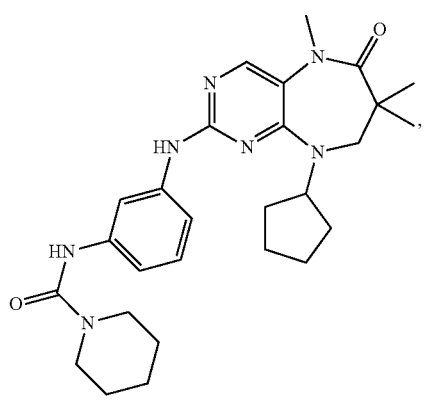
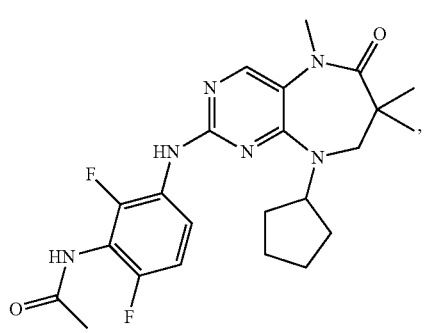
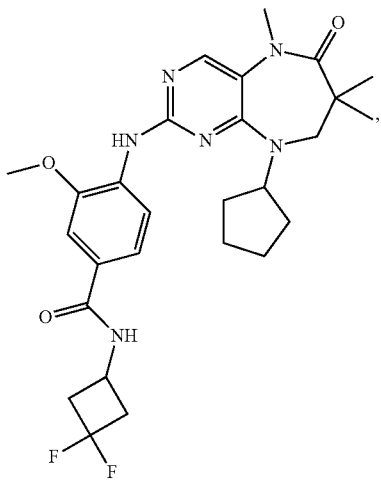
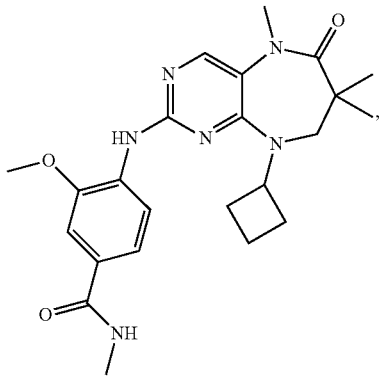
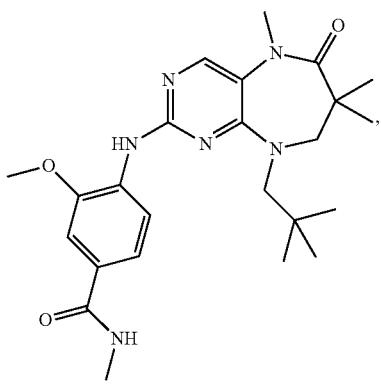
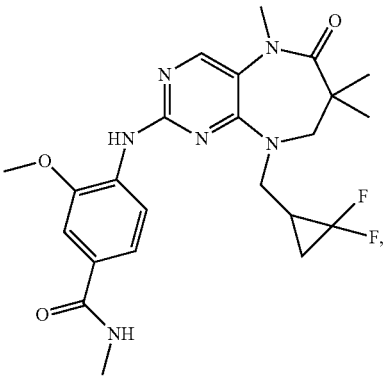

69
-continued
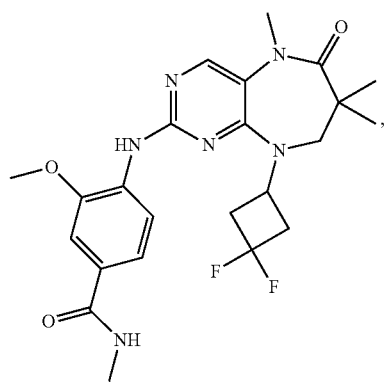
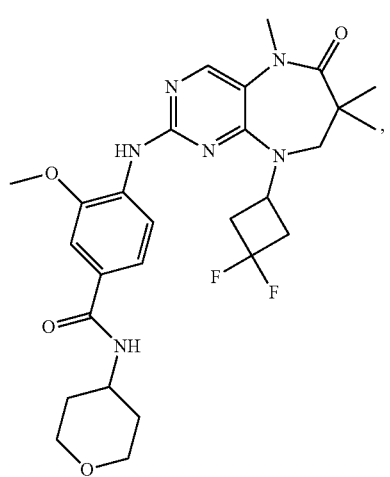
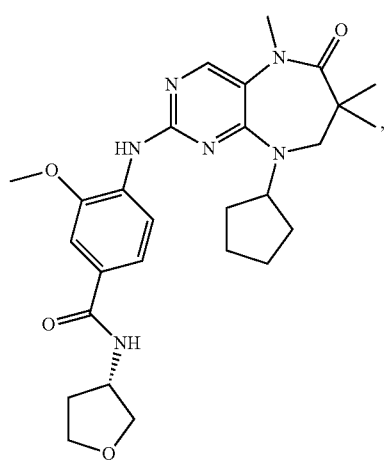
70
-continued
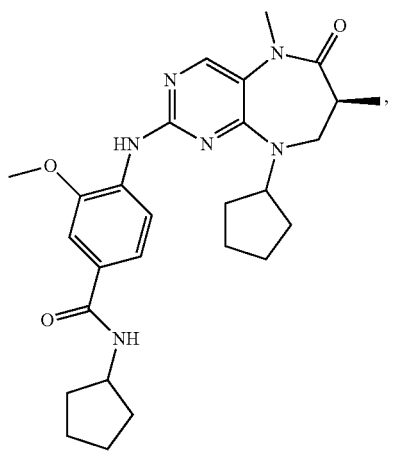
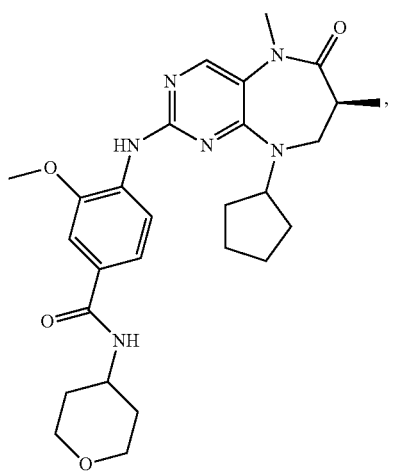
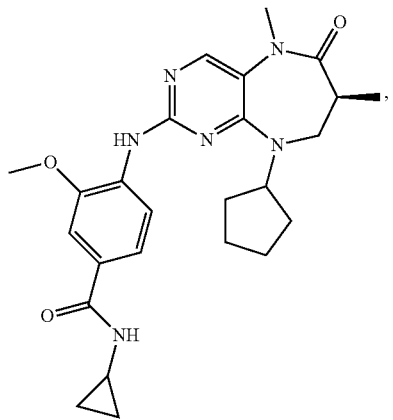

71
-continued
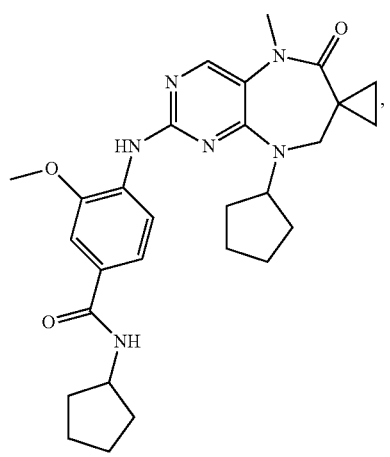
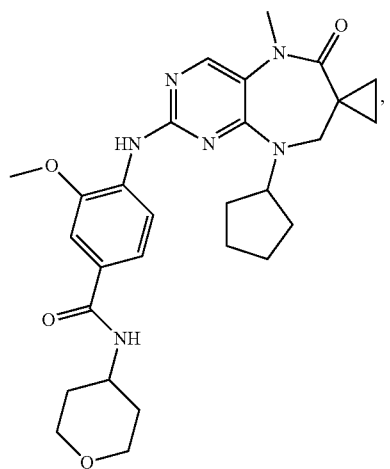
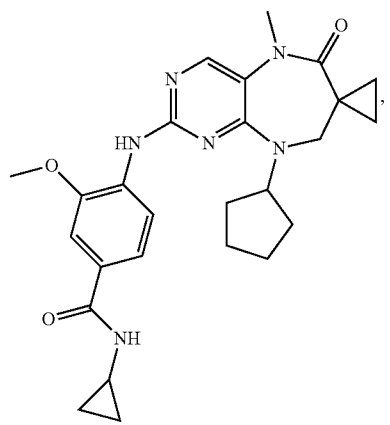
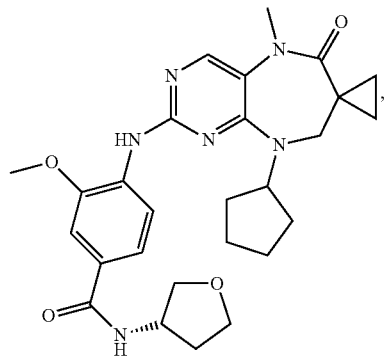
72
-continued
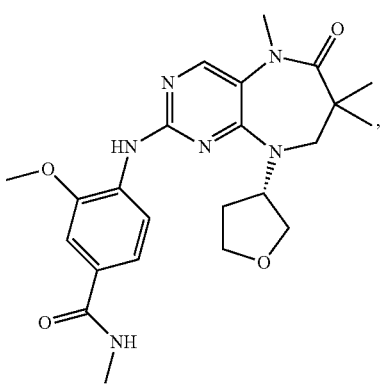
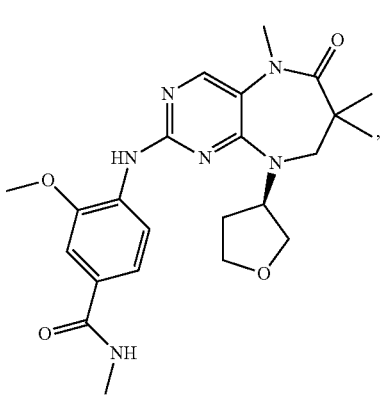
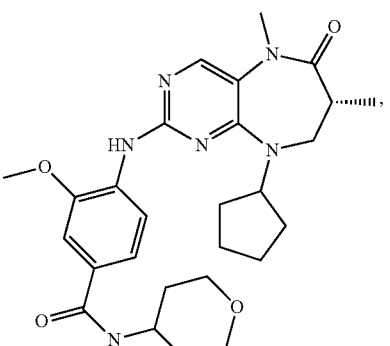
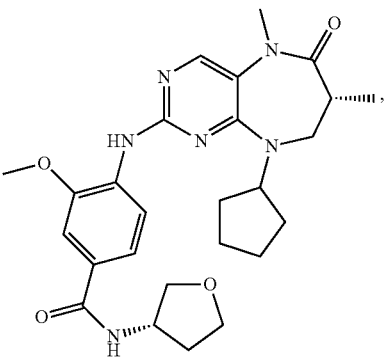

73
-continued
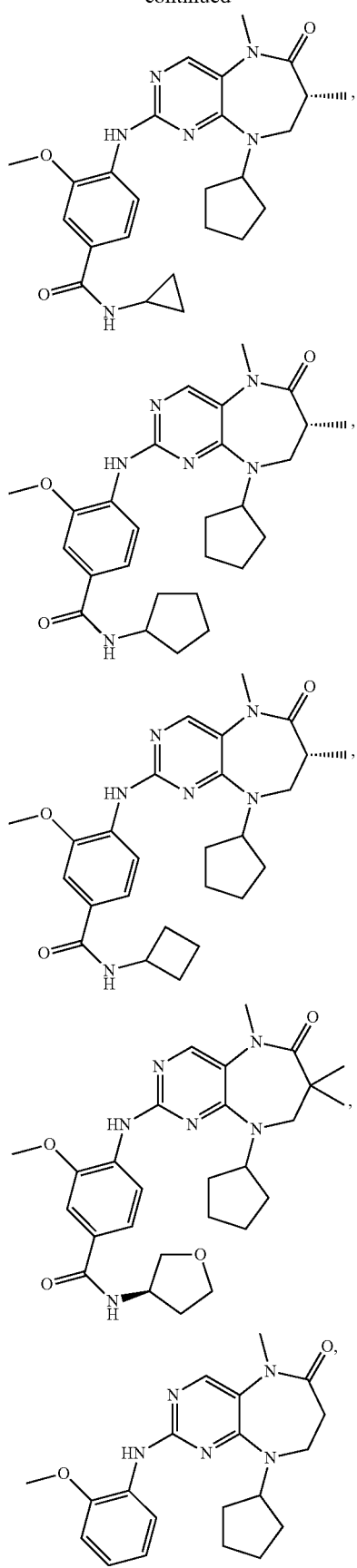
74
-continued
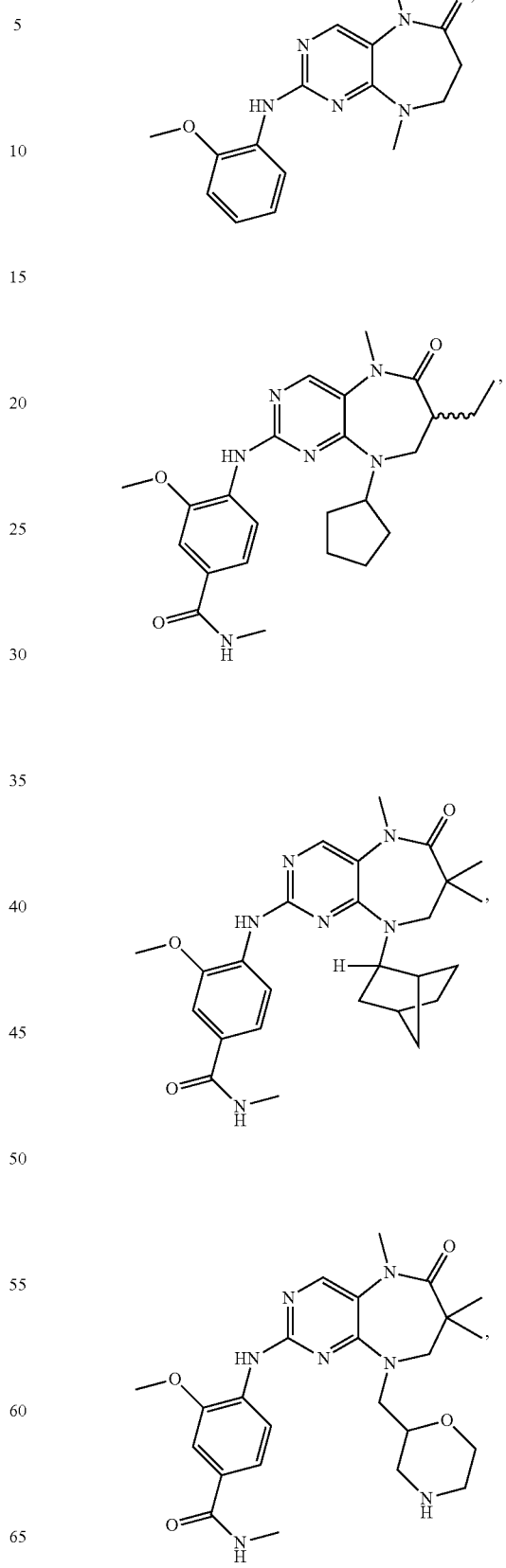

75
-continued
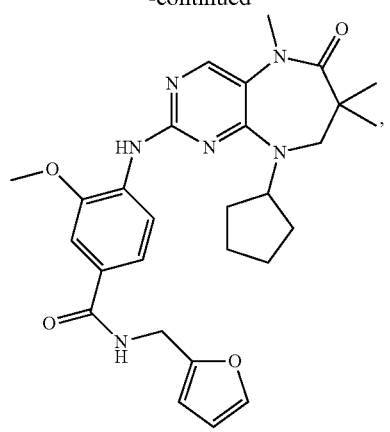
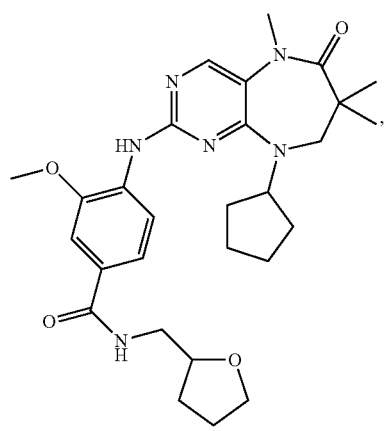
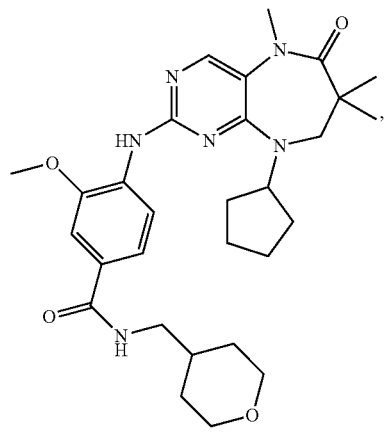
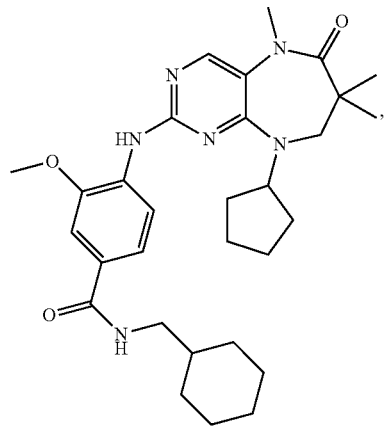
76
-continued
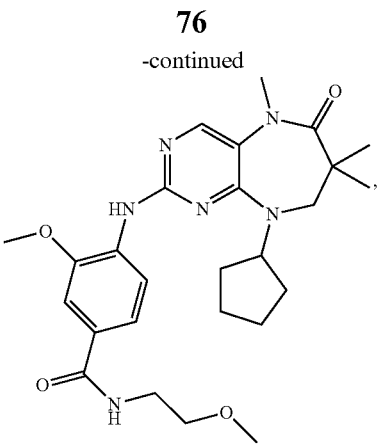
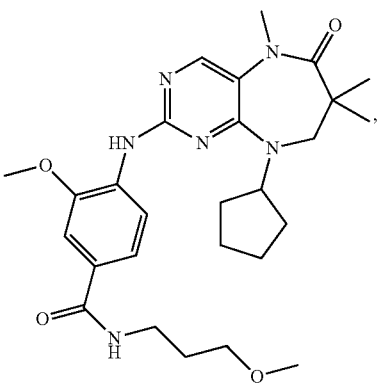
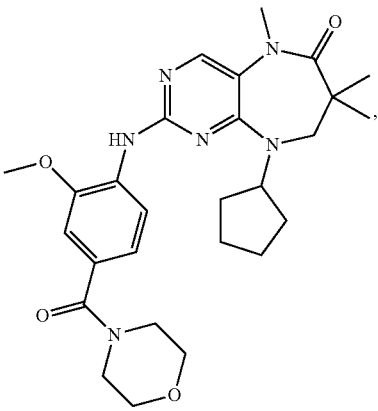
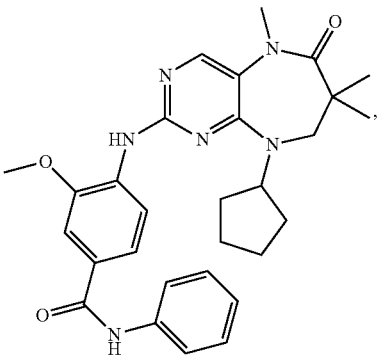

77
-continued
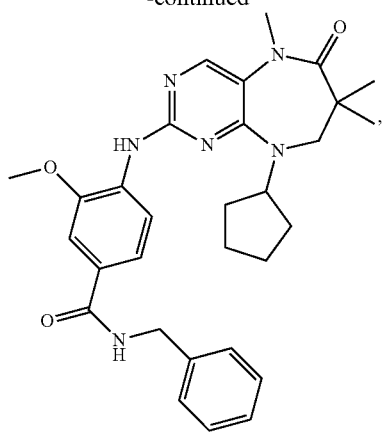
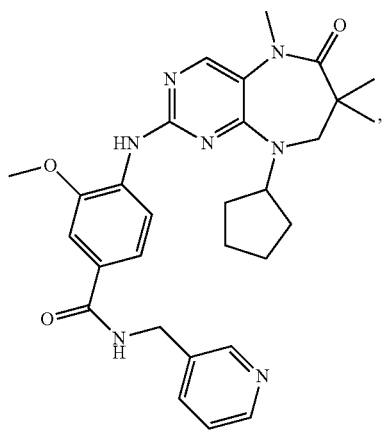
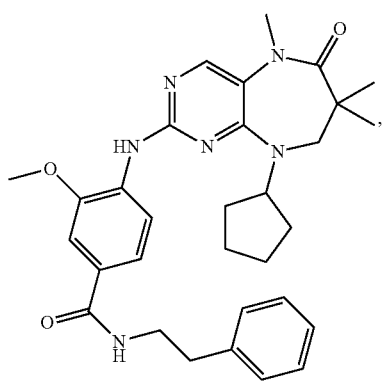
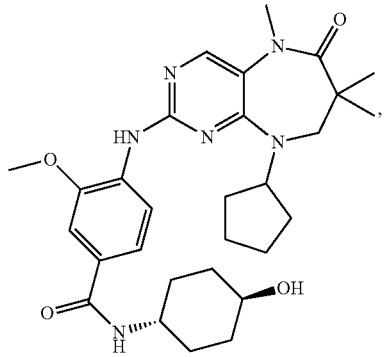
78
-continued
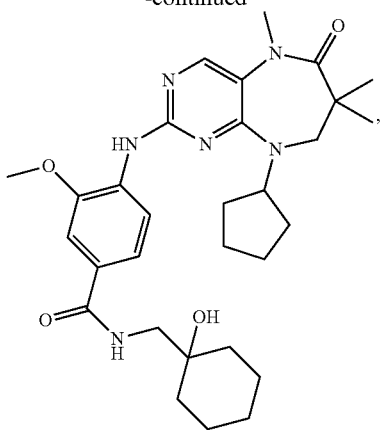
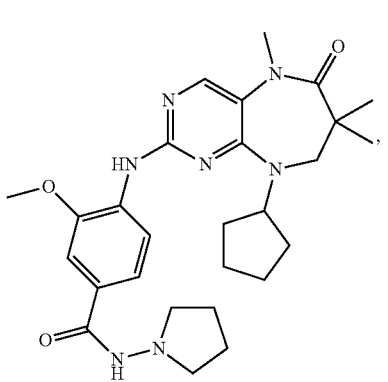
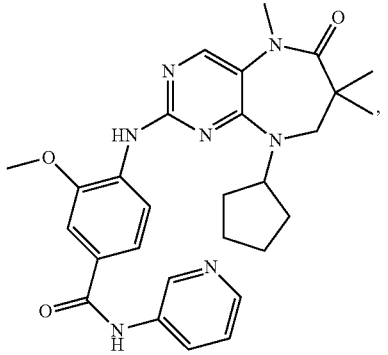
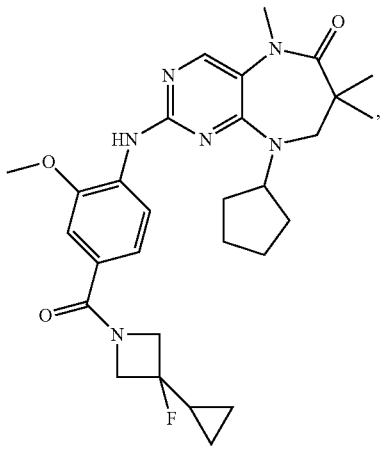

79
-continued
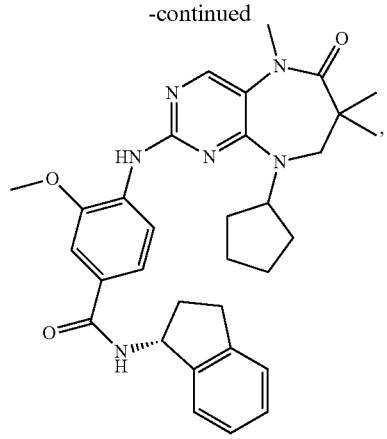
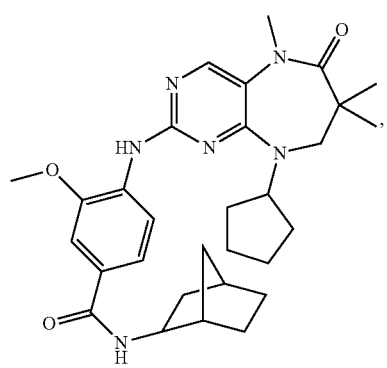
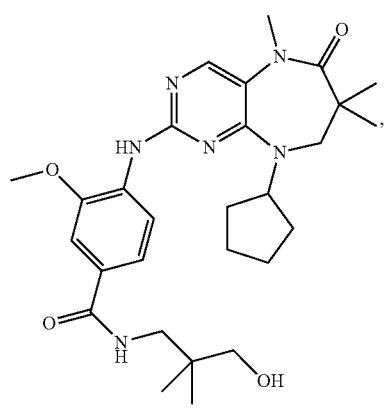
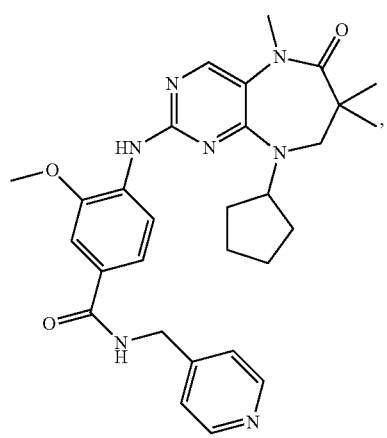
80
-continued
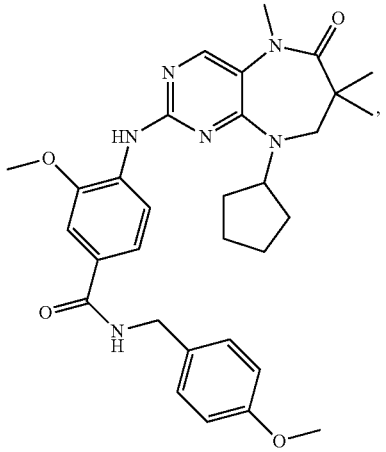
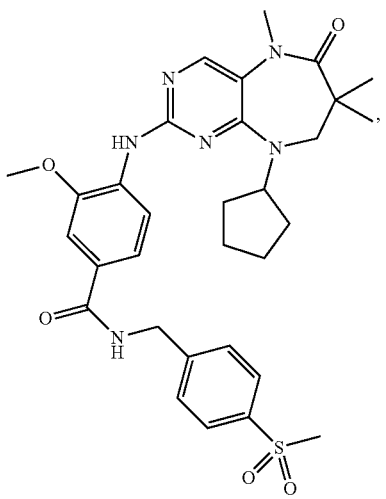
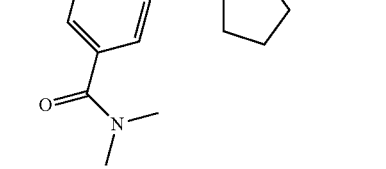

81
-continued
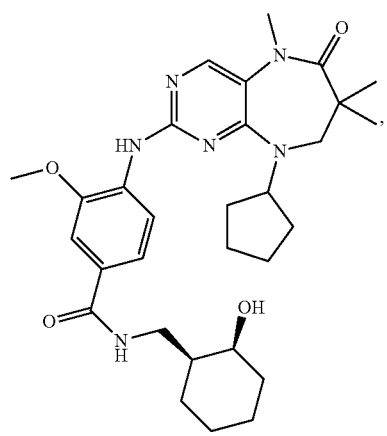
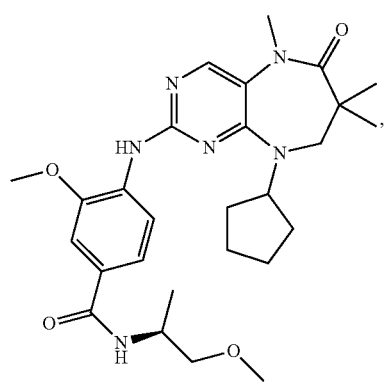
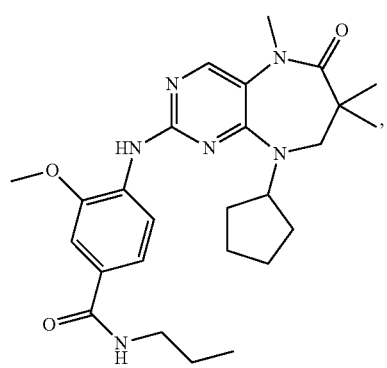
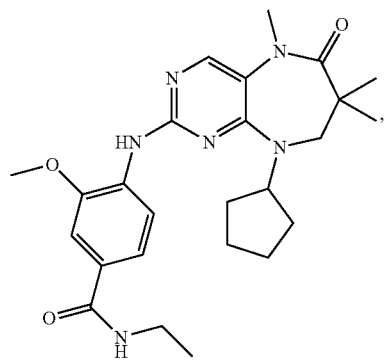
82
-continued
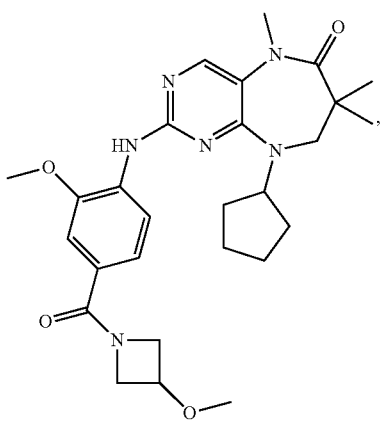
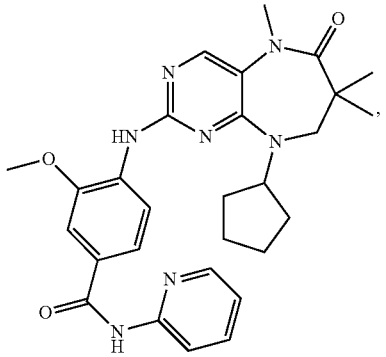
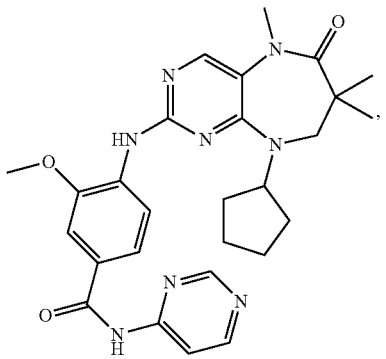
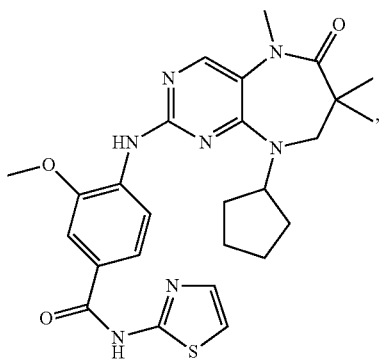

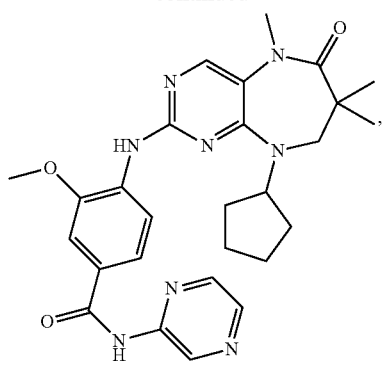
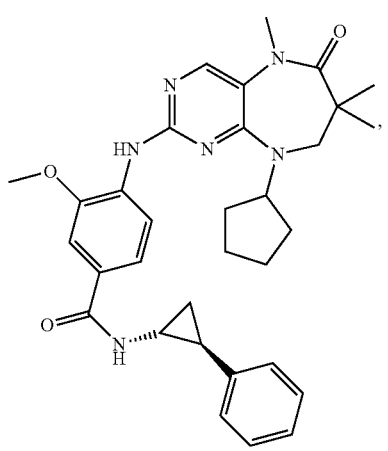
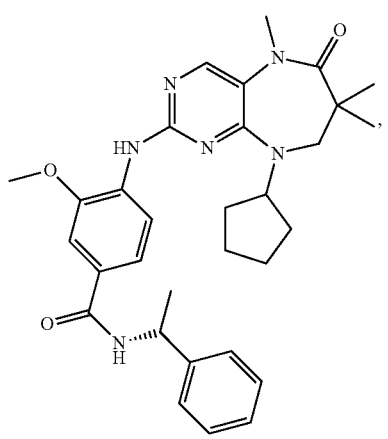
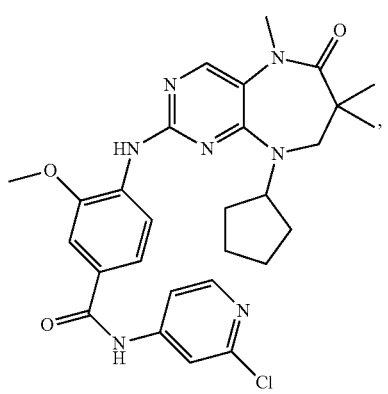
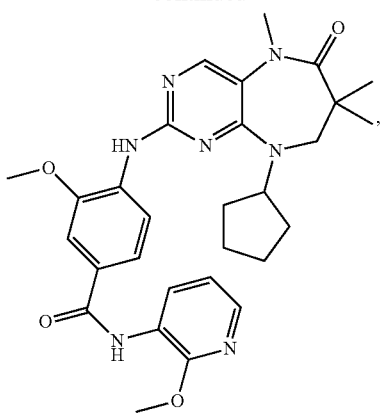
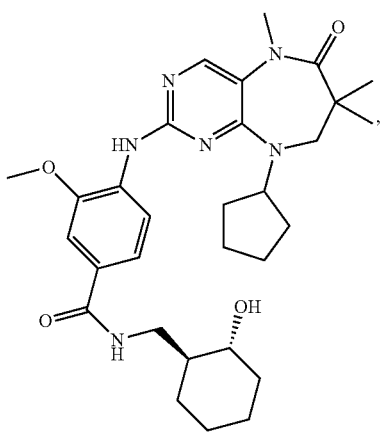
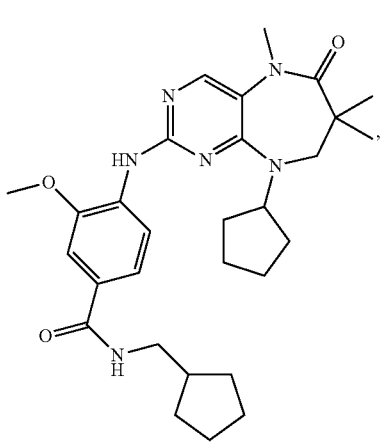
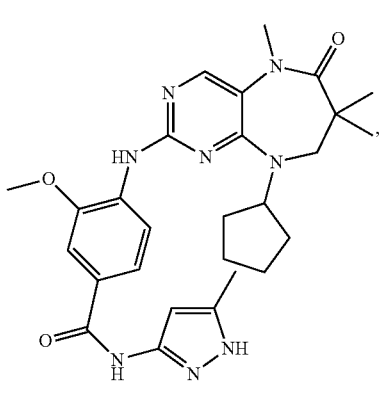

85
-continued
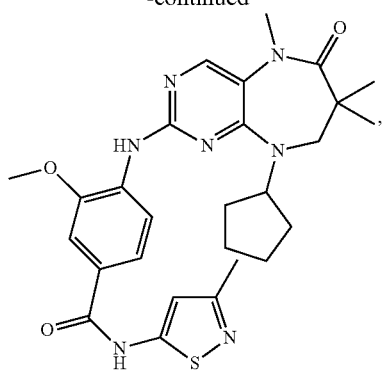
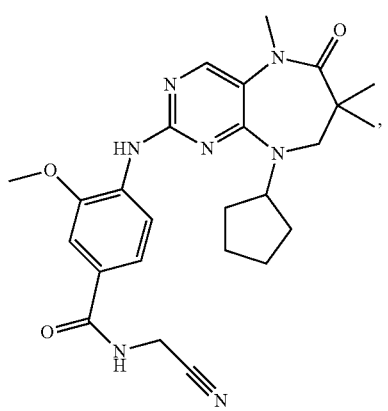
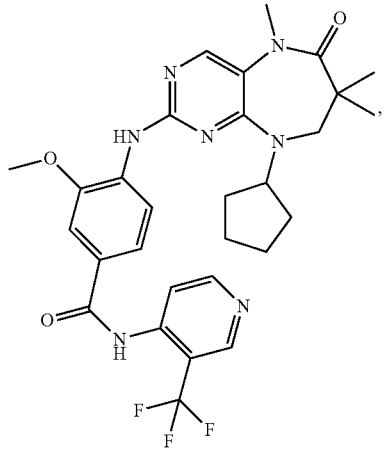
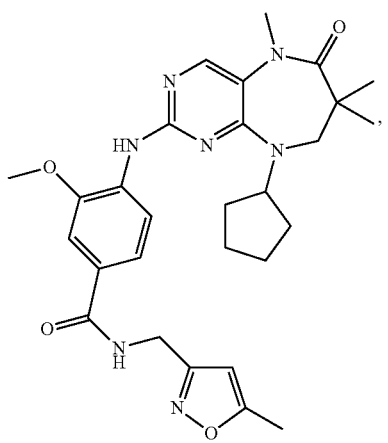
86
-continued
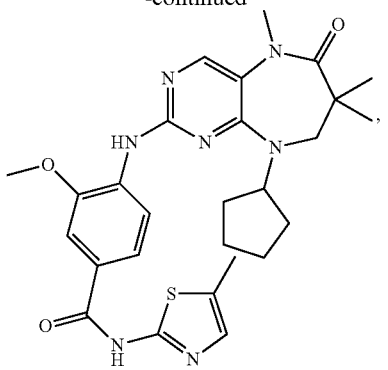
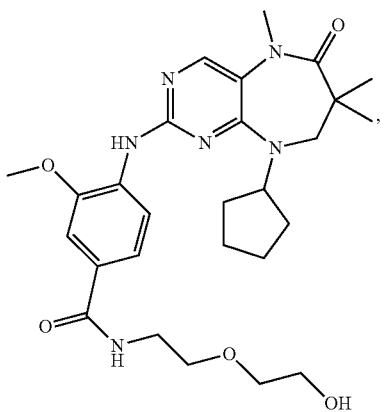
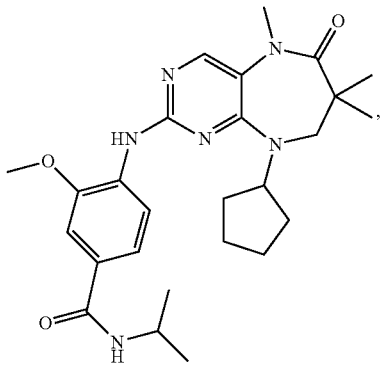
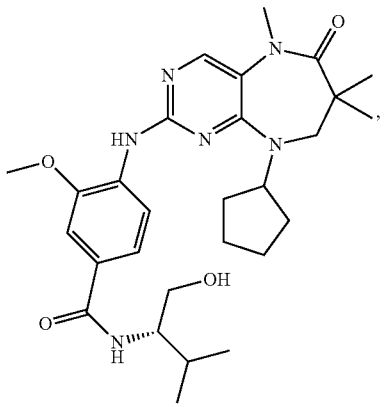

87
-continued
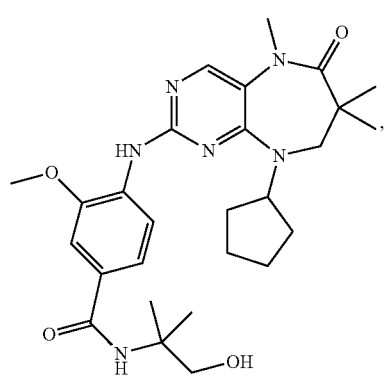
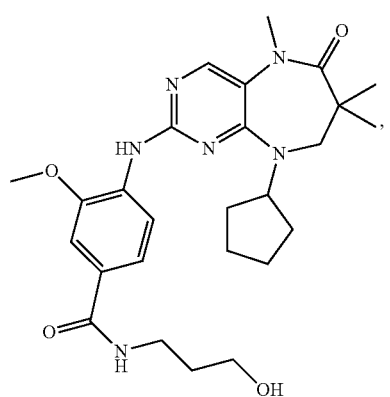
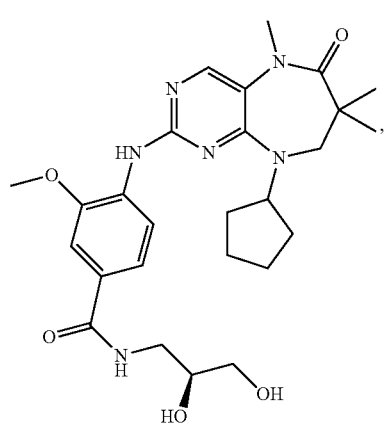
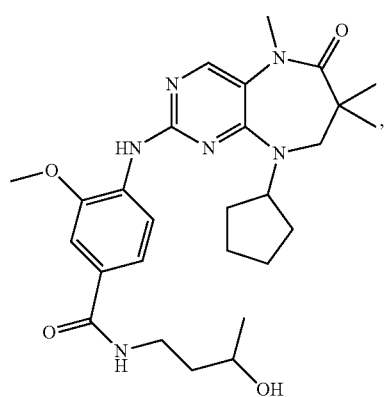
88
-continued
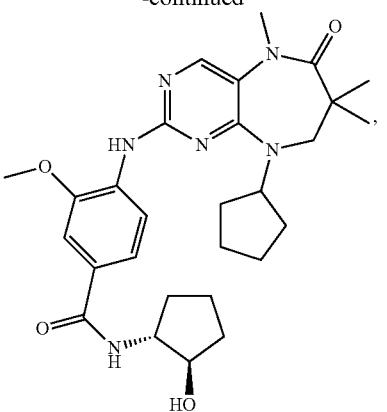
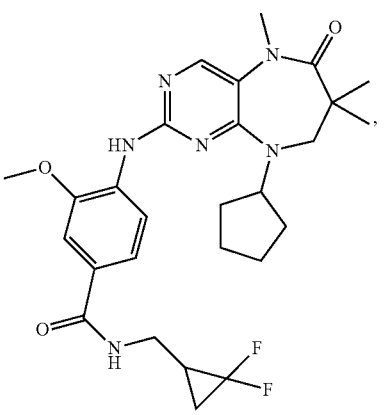
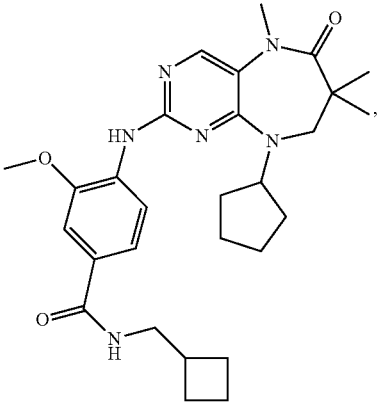
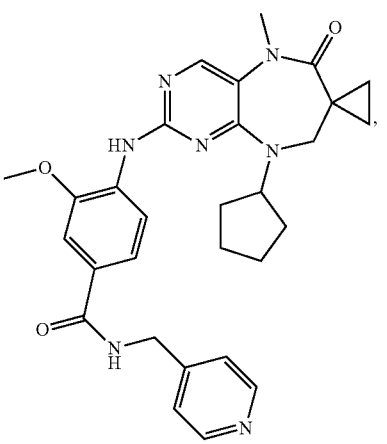

89
-continued
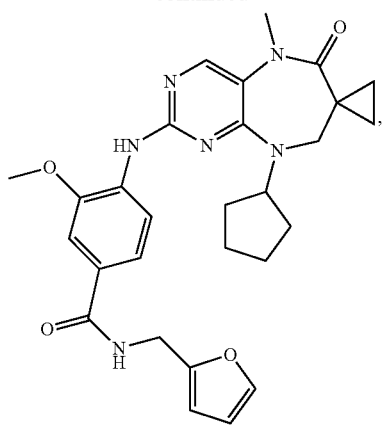
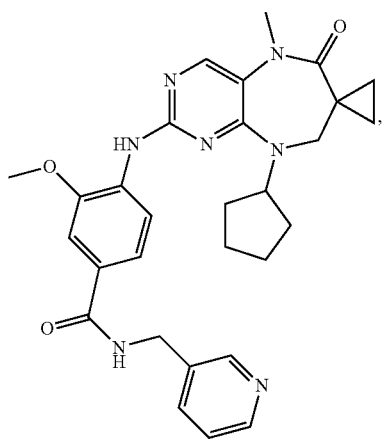
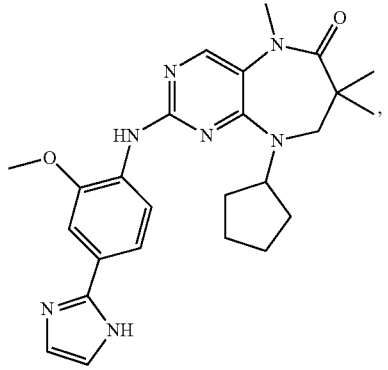
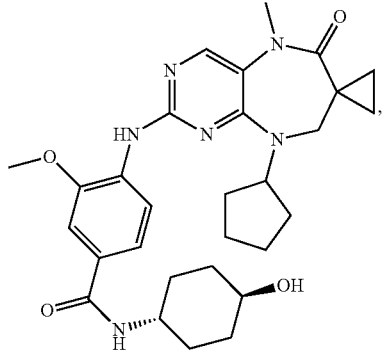
90
-continued
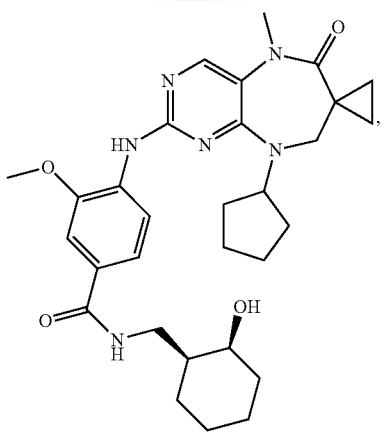
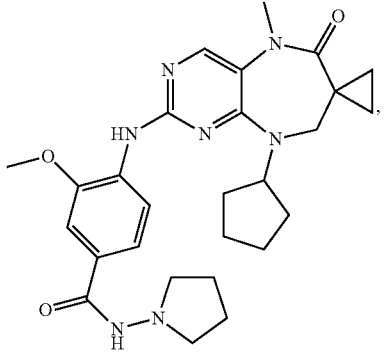
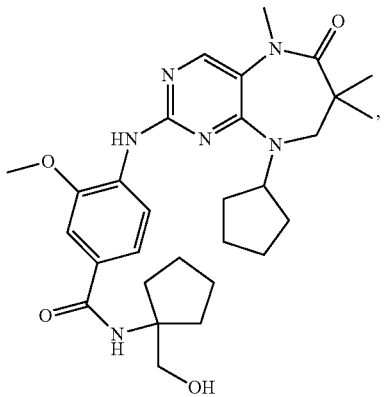
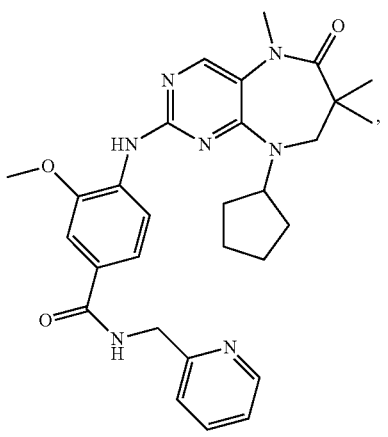

-continued
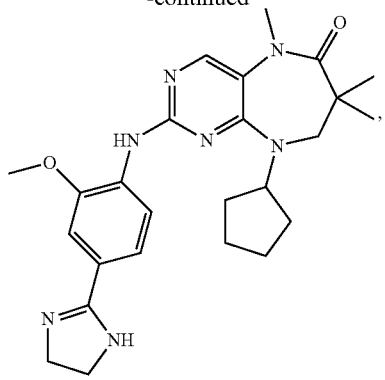
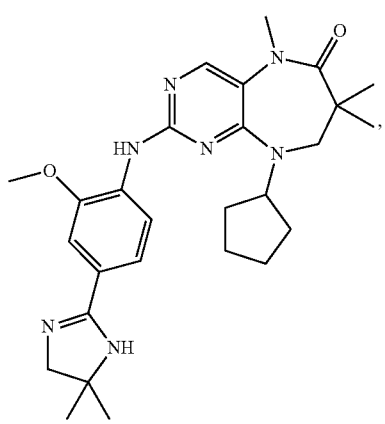
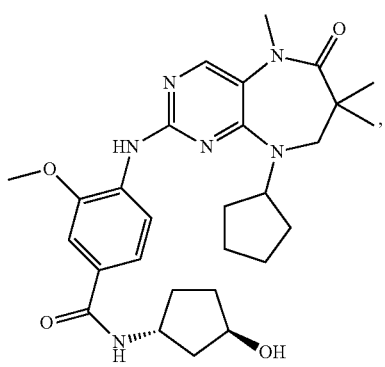
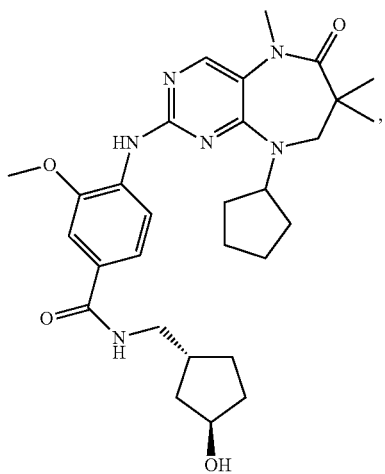
-continued
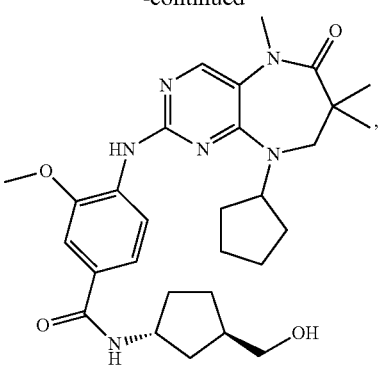
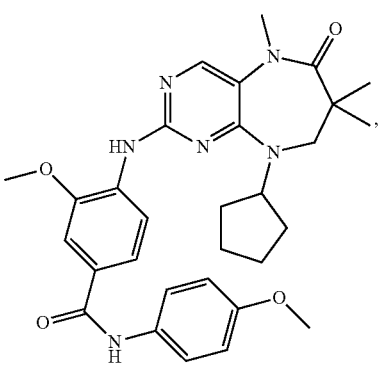
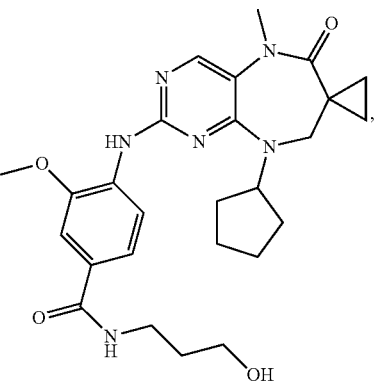
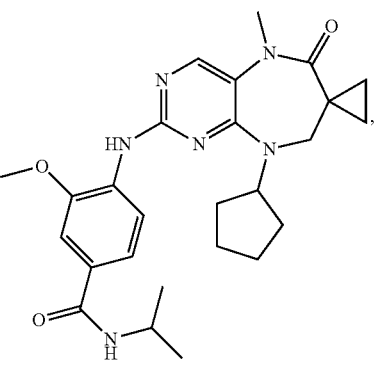

93
-continued
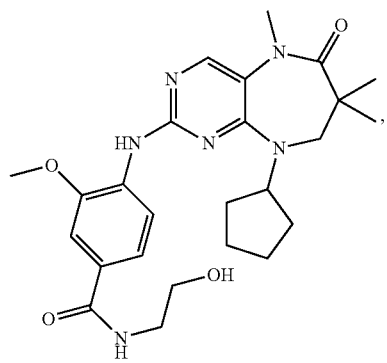
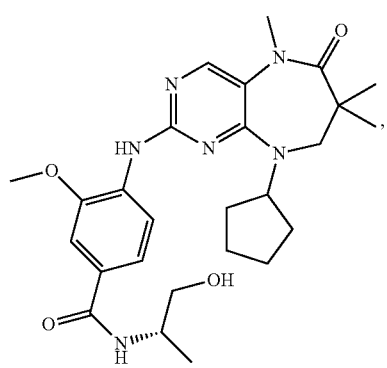
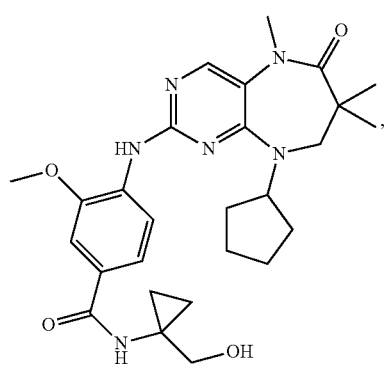
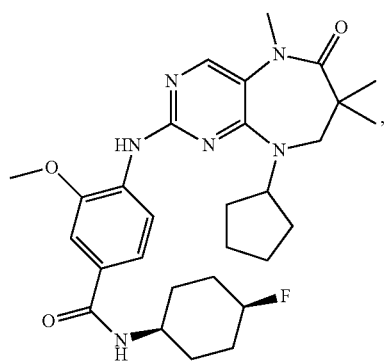
94
-continued
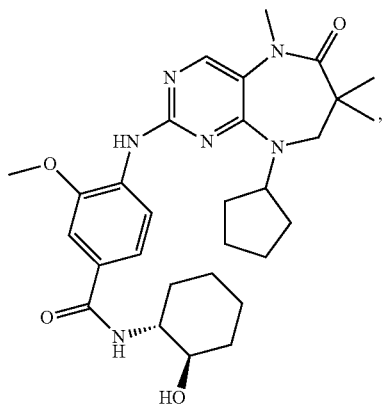
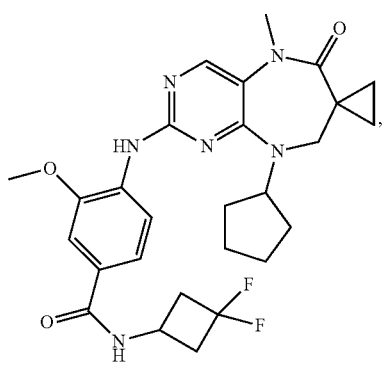
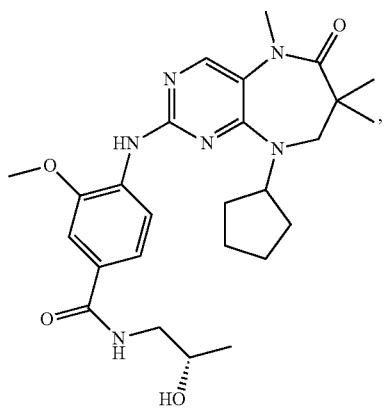
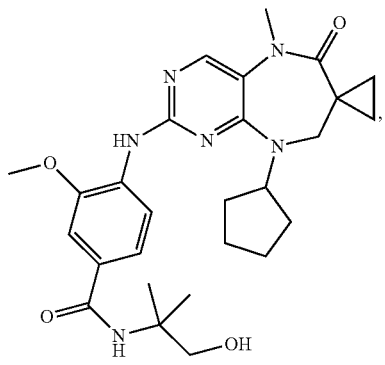

95
-continued
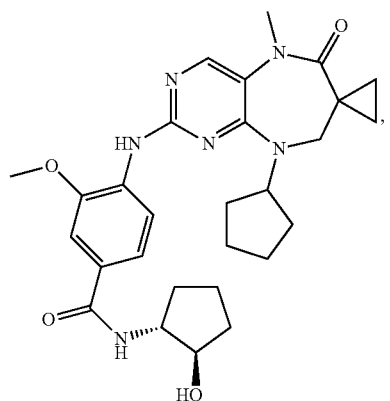
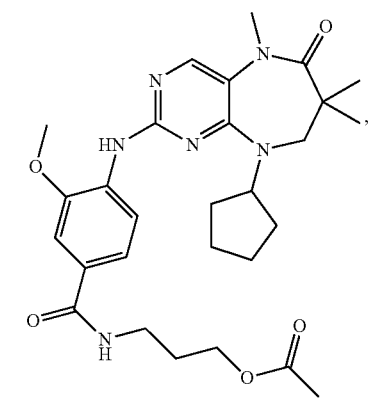
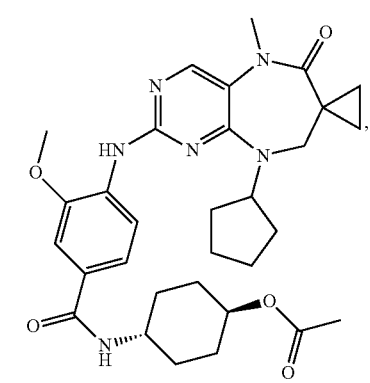
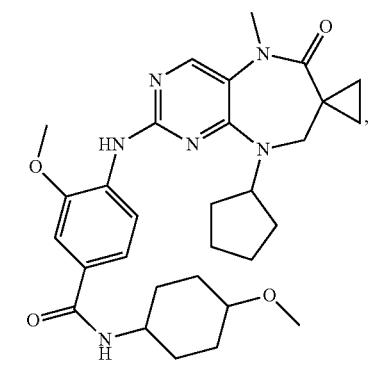
96
-continued
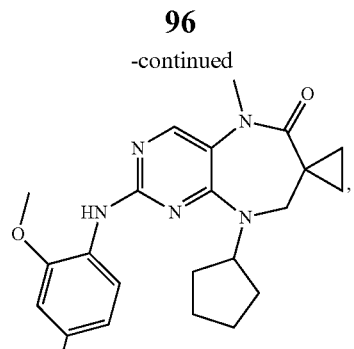
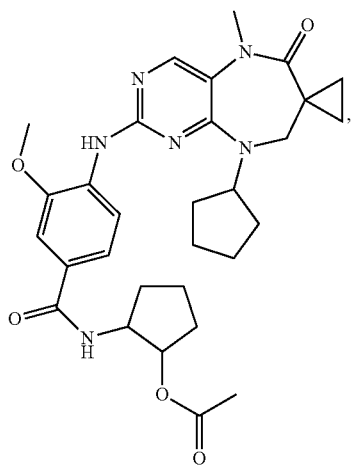
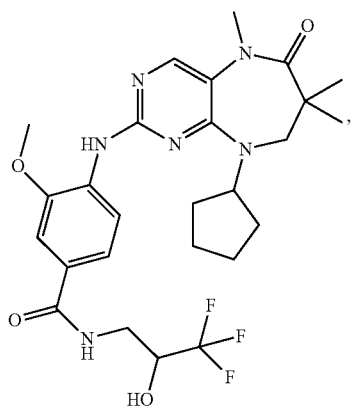
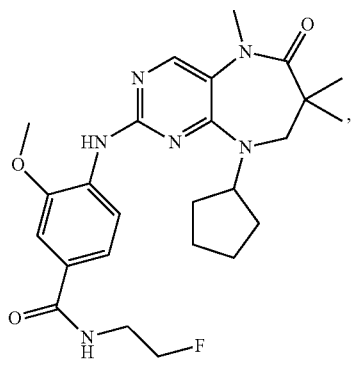

97
-continued
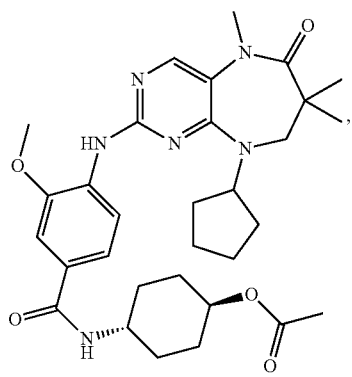
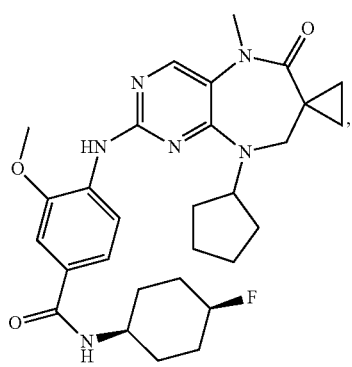
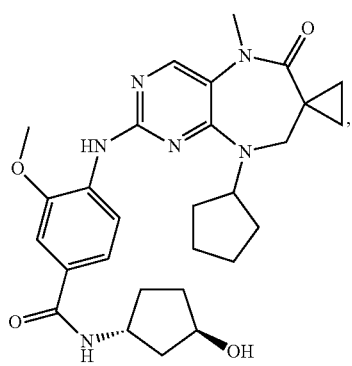
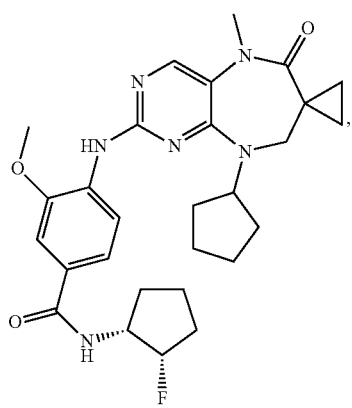
98
-continued
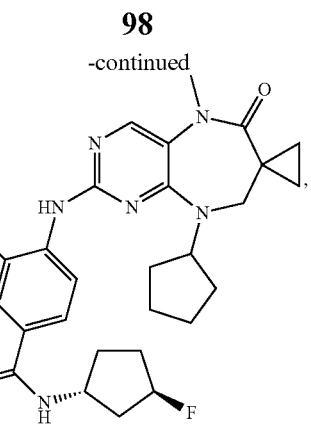
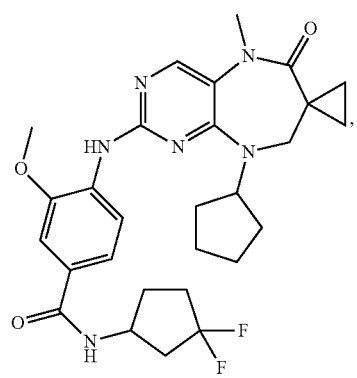
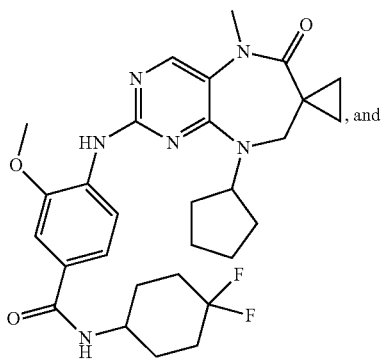
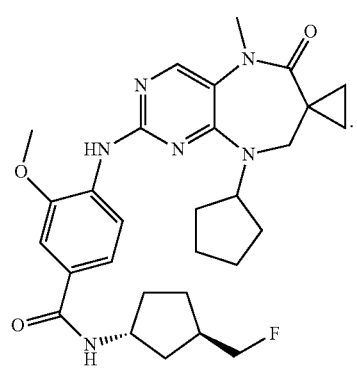
In yet another embodiment, the methods of the invention can be employed in preparing the compounds represented by any one of the following structural formulae, or pharmaceutically acceptable salts thereof:

| 99 | 100 |
|---|---|
| 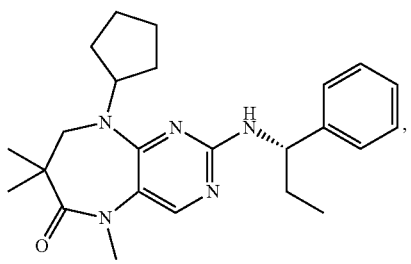 | 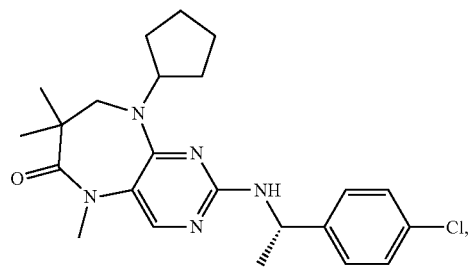 |
| 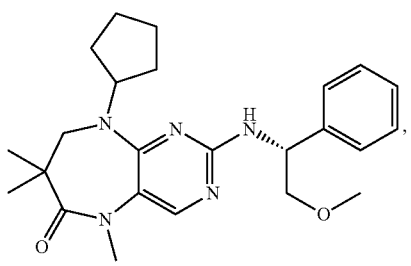 | 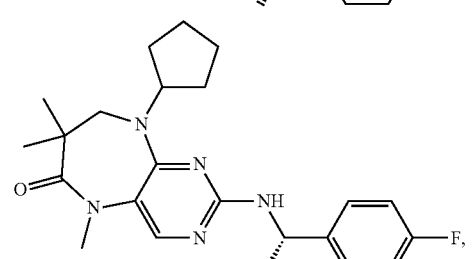 |
| 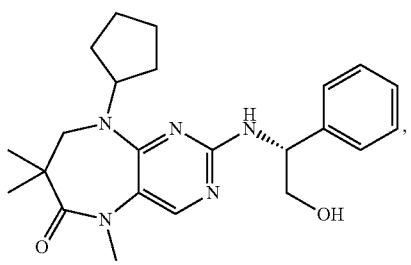 | 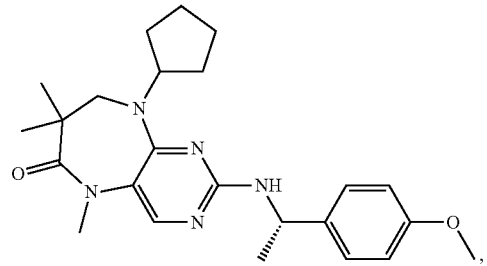 |
| 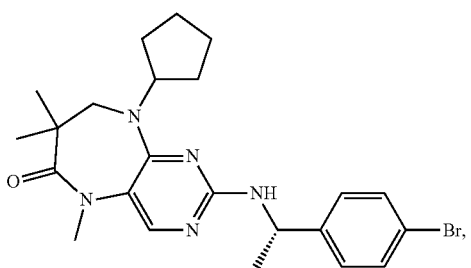 | 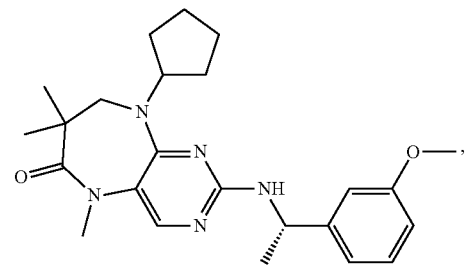 |
| 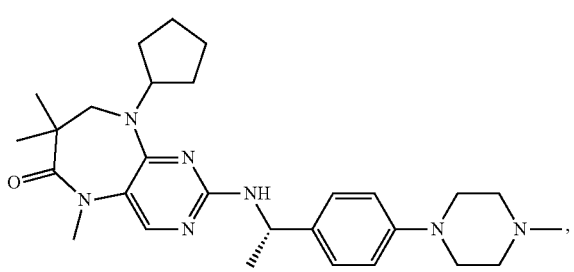 | 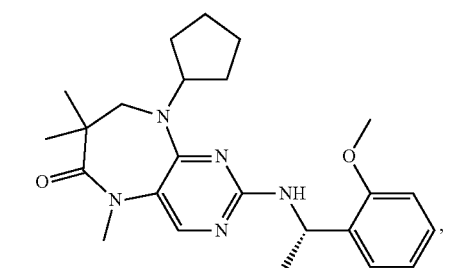 |
| 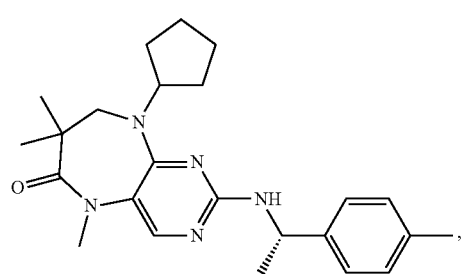 | 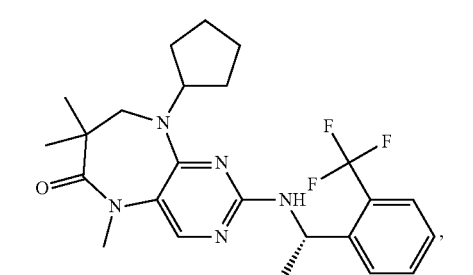 |

101
-continued
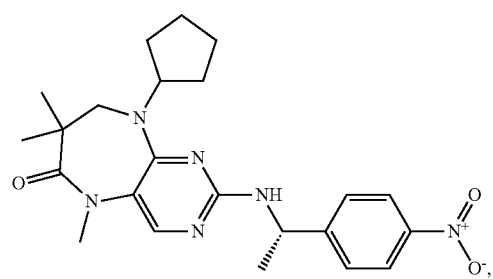
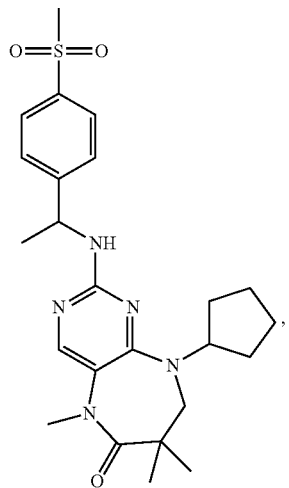
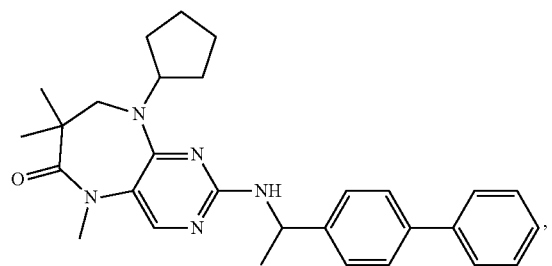
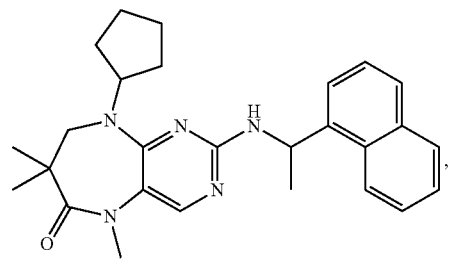
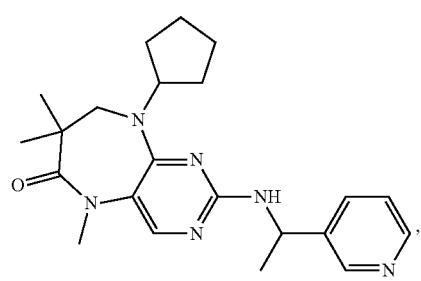
102
-continued
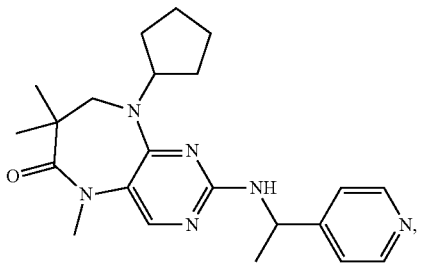
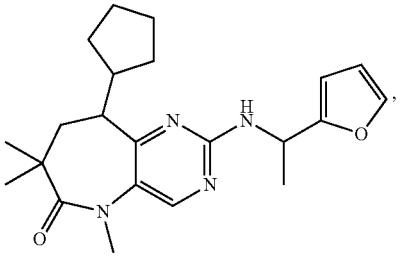
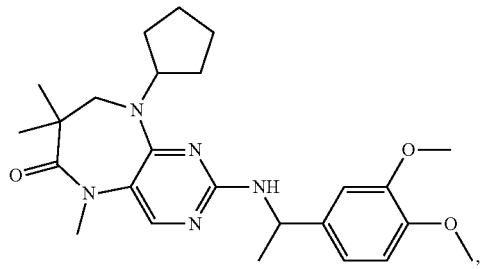
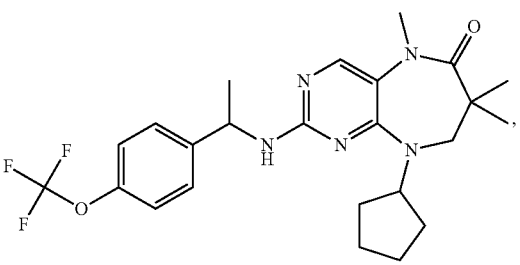
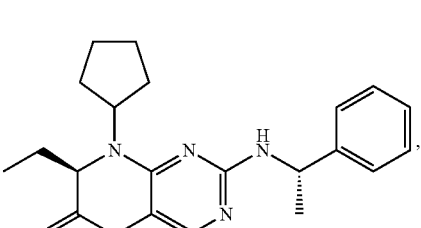
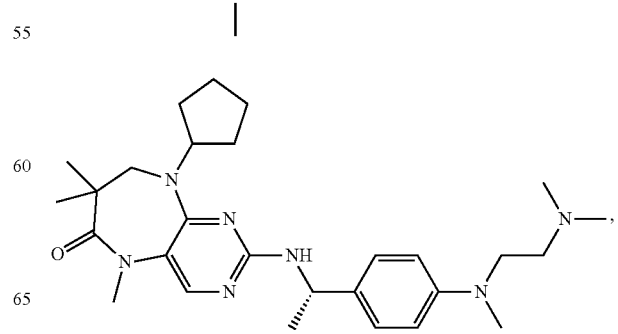

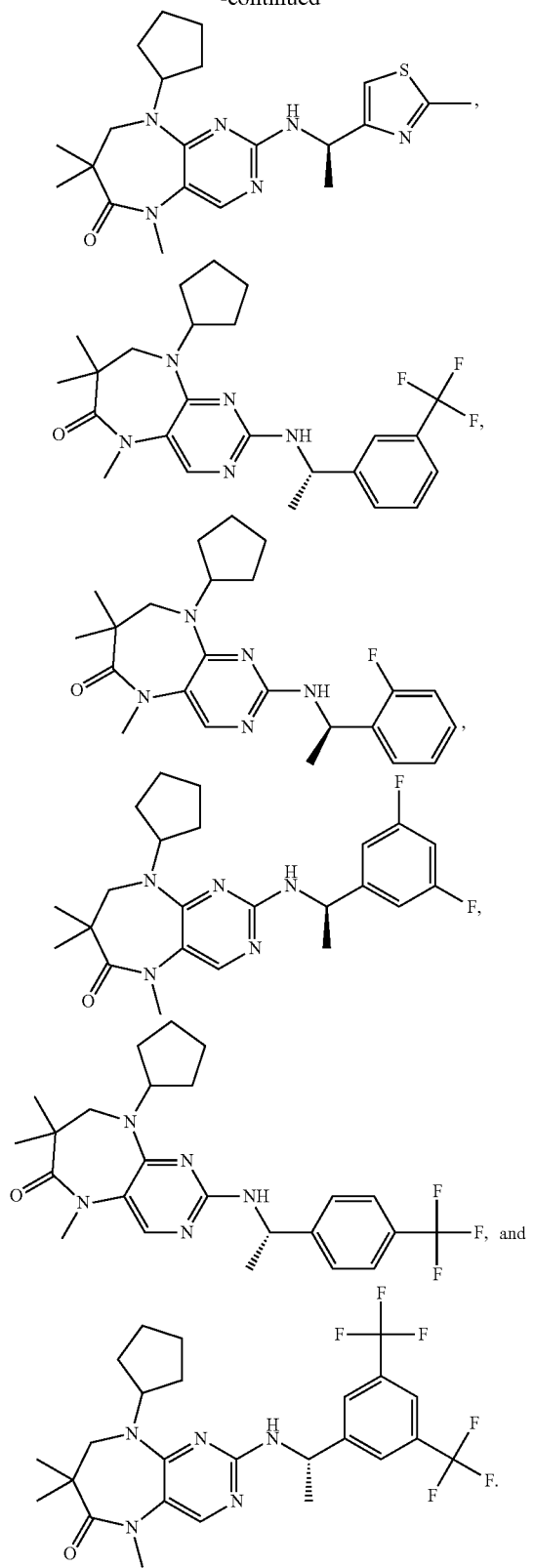
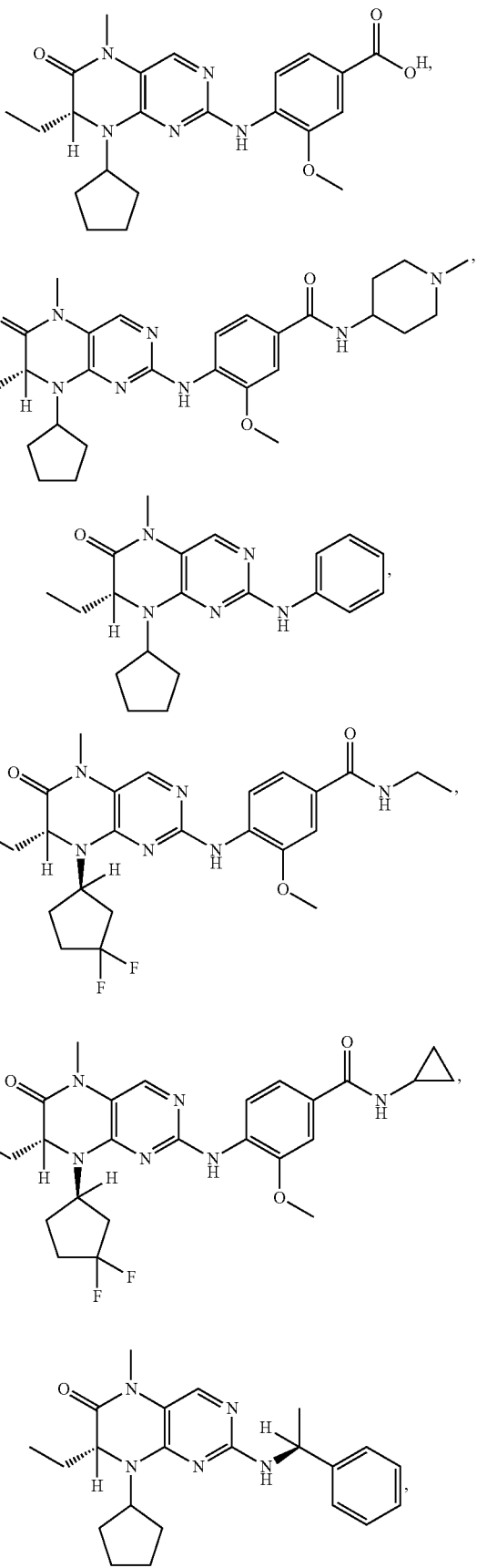
In yet another embodiment, the methods of the invention can be employed in preparing the compounds represented by any one of the following structural formulae, or pharmaceutically acceptable salts thereof:

105
-continued
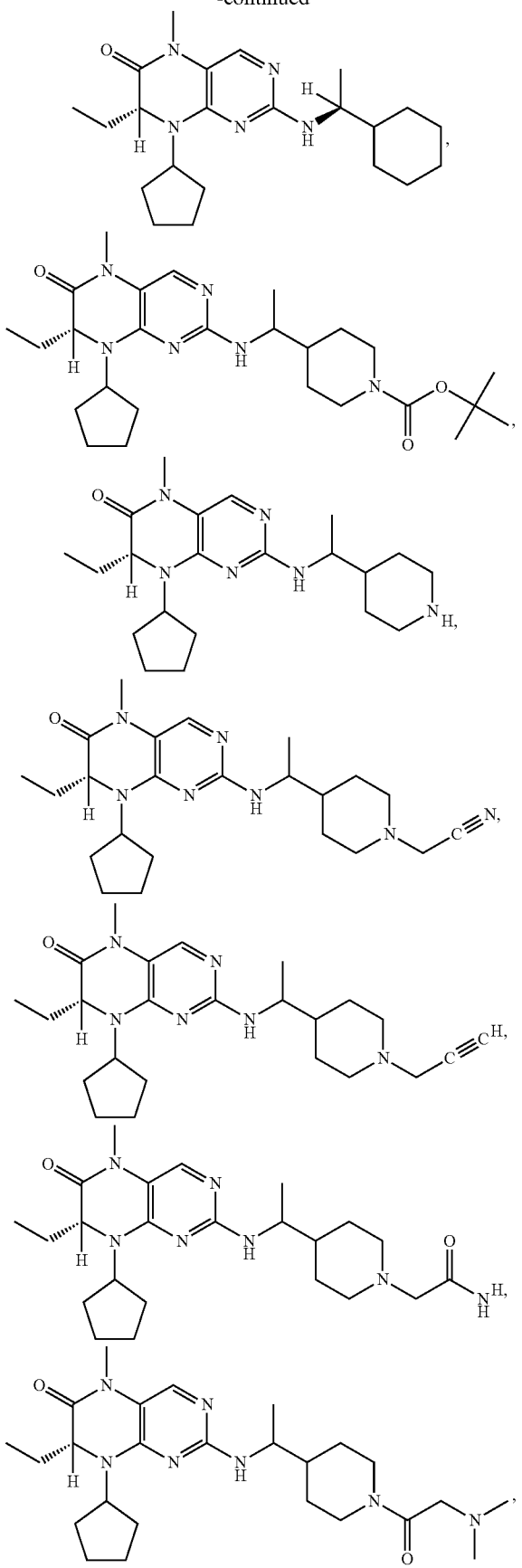
106
-continued
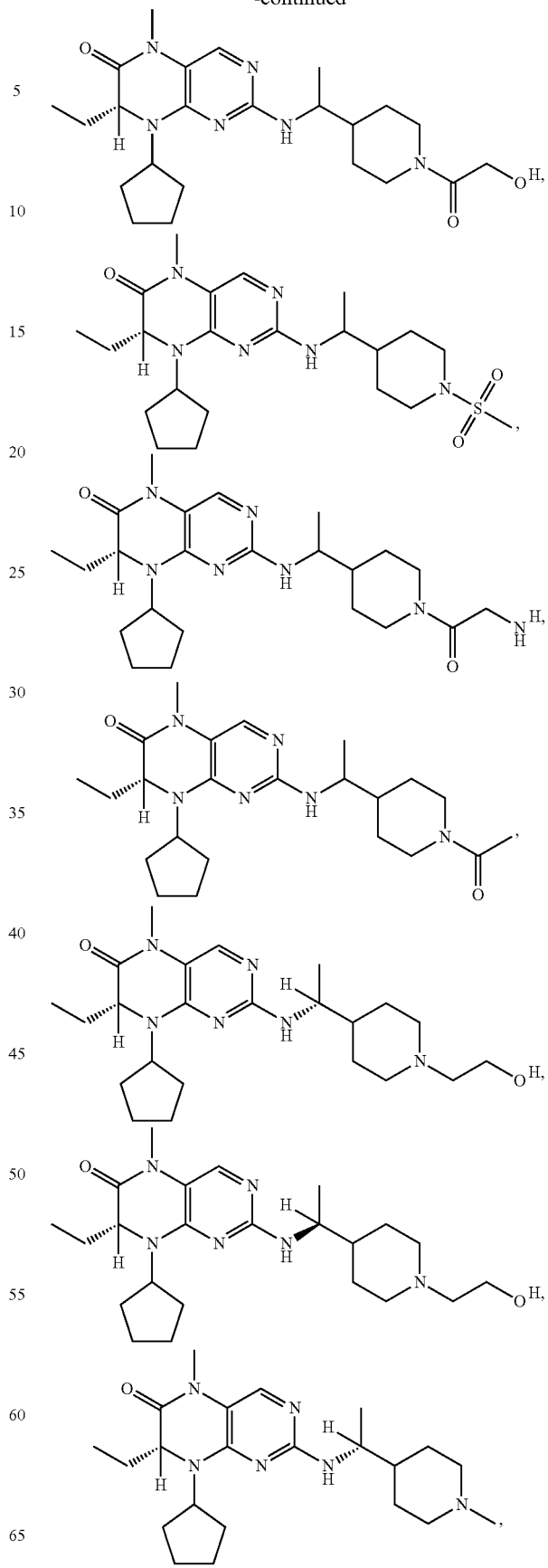

-continued

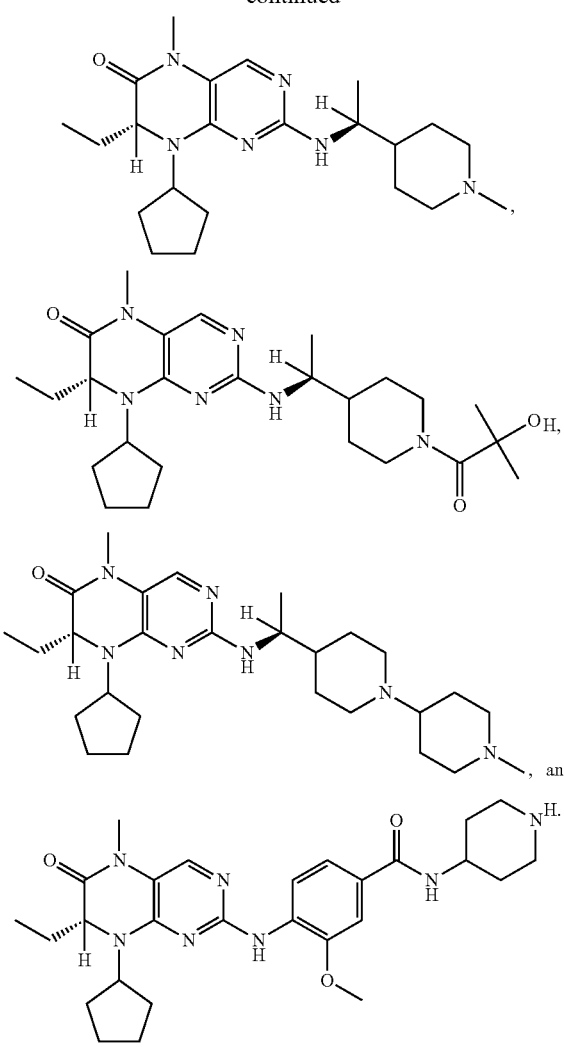

, and

In yet another embodiment, the methods of the invention can be employed in preparing the compound represented by the following structural formula, or a pharmaceutically acceptable salt thereof:

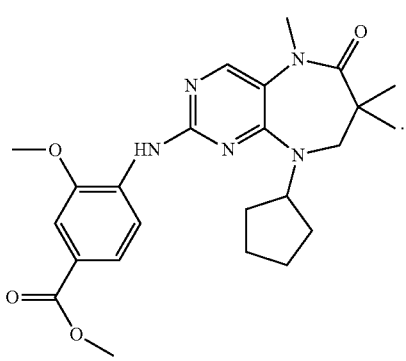

In yet another embodiment, the methods of the invention can be employed in preparing the compound represented by the following structural formula, or a pharmaceutically acceptable salt thereof:

Additional examples of compounds that can be prepared by the methods of the invention can be found in, for example, US 2008/0167289, US 2008/0009492, US 2006/004014, U.S. Pat. No. 6,806,272, U.S. Pat. No. 6,861,422, WO2009/040556, WO 2009/042711, and WO 2006/058876.

In some embodiments, the methods of the invention further comprise the step of reacting a compound of Structural Formula (C):

(C)

with a compound of Structural Formula (D):

under suitable conditions to form the compound represented by Structural Formula (A). $LG_3$ is a suitable leaving group, such as a halogen. Specifically, $LG_3$ is —Cl. Details of this reaction are as described above.

It will be appreciated by those skilled in the art that in the processes of the present invention certain functional groups such as hydroxyl or amino groups in the starting reagents or intermediate compounds may need to be protected by protecting groups. Thus, the preparation of the compounds described above may involve, at various stages, the addition and removal of one or more protecting groups. The protection and deprotection of functional groups is described in "Protective Groups in Organic Chemistry." edited by J. W. F. McOmie, Plenum Press (1973) and "Protective Groups in Organic Synthesis," 3rd edition, T. W. Greene and P. G. M. Wuts, Wiley Interscience, and "Protecting Groups," 3rd edition, P. J. Kocienski, Thieme (2005)

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B.

and March, J., John Wiley & Sons, New York: 2001, the entire contents of which are hereby incorporated by reference.

As described herein, compounds of the invention may optionally be substituted with one or more substituents, such as illustrated generally below, or as exemplified by particular classes, subclasses, and species of the compounds described above. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted. For example, if X is optionally substituted $C_1$-$C_3$ alkyl or phenyl; X may be either optionally substituted $C_1$-$C_3$ alkyl or optionally substituted phenyl. Likewise, if the term "optionally substituted" follows a list, said term also refers to all of the substitutable groups in the prior list unless otherwise indicated. For example: if X is $C_1$-$C_3$ alkyl or phenyl wherein X is optionally and independently substituted by $J^X$, then both $C_1$-$C_3$ alkyl and phenyl may be optionally substituted by $J^X$. As is apparent to one having ordinary skill in the art, groups such as H, halogen, $NO_2$, CN, $NH_2$, OH, or $OCF_3$ would not be substitutable groups.

The phrase "up to", as used herein, refers to zero or any integer number that is equal or less than the number following the phrase. For example, "up to 3" means any one of 0, 1, 2, and 3. As described herein, a specified number range of atoms includes any integer therein. For example, a group having from 1-4 atoms could have 1, 2, 3, or 4 atoms.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "aliphatic" or "aliphatic group", as used herein, means a straight-chain (i.e., unbranched), or branched, hydrocarbon chain that is completely saturated or that contains one or more units of unsaturation but is non-aromatic. Unless otherwise specified, aliphatic groups contain 1-10 aliphatic carbon atoms. In some embodiments, aliphatic groups contain 1-6 aliphatic carbon atoms. In other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl and acetylene.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds. Each of the "alkyl", "alkenyl" or "alkynyl" as used herein can be optionally substituted as set forth below. In some embodiments, the "alkyl" is $C_1$-$C_6$ alkyl or $C_1$-$C_4$ alkyl. In some embodiments, the "alkenyl" is $C_2$-$C_6$ alkenyl or $C_2$-$C_4$ alkenyl. In some embodiments, the "alkynyl" is $C_2$-$C_6$ alkynyl or $C_2$-$C_4$ alkynyl.

The term "cycloaliphatic" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle" (or "heterocyclyl," or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 7 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" (or "aryl ring" or "aryl group") used alone or as part of a larger moiety as in "aralkyl", "aralkoxy", "aryloxyalkyl", or "heteroaryl" refers to carbocyclic aromatic ring systems. The term "aryl" may be used interchangeably with the terms "aryl ring" or "aryl group". "Carbocyclic aromatic ring" groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring" or "carbocyclic aromatic", as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl", "heteroaromatic", "heteroaryl ring", "heteroaryl group", "aromatic heterocycle" or "heteroaromatic group", used alone or as part of a larger moiety as in "heteroaralkyl" or "heteroarylalkoxy", refer to heteroaromatic ring groups having five to fourteen members, in which one or more ring carbons is replaced by a heteroatom such as, N, S, or O. In some embodiments, heteroaryl rings comprise up to three heteroatoms selected from N, S and O within the ring. In other embodiments, heteroaryl rings comprise up to two heteroatoms selected from N, S and O within the ring system. In yet other embodiments, heteroaryl rings comprise up to two heteroatoms selected from N and O within the ring system. Heteroaryl rings include monocyclic heteroaromatic rings and polycyclic aromatic rings in which a monocyclic aromatic ring is fused to one or more other aromatic rings. Also included within the scope of the term "heteroaryl", as it is used herein, is a group in which an aromatic ring is "fused" to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo", "cyclic", "cyclic group" or "cyclic moiety", include mono-, bi-, and tri-cyclic ring systems including cycloaliphatic, heterocycloaliphatic, aryl, or heteroaryl, each of which has been previously defined.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "bridge" refers to a bond or an atom or an unbranched chain of atoms connecting two different parts of a molecule. The two atoms that are connected through the bridge (usually but not always, two tertiary carbon atoms) are denoted as "bridgeheads".

As used herein, the term "spiro" refers to ring systems having one atom (usually a quaternary carbon) as the only common atom between two rings.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

As used herein an optionally substituted aralkyl can be substituted on both the alkyl and the aryl portion. Unless otherwise indicated as used herein optionally substituted aralkyl is optionally substituted on the aryl portion.

In some embodiments, an aliphatic group and a heterocyclic ring may independently contain one or more substituents. Suitable substituents on the saturated carbon of an aliphatic group or of a non-aromatic heterocyclic ring are selected from those described above, for example, in the definition of $J^A$ and $J^B$. Other suitable substituents include those listed as suitable for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, wherein each R* is independently selected from hydrogen or an optionally substituted $C_{1-6}$ aliphatic. Optional substituents on the aliphatic group of R* are selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo $C_{1-4}$ aliphatic), or halo($C_{1-4}$ aliphatic), wherein each of the foregoing $C_{1-4}$ aliphatic groups of R* is unsubstituted.

In some embodiments, optional substituents on the nitrogen of a heterocyclic ring include those described above. Examples of such suitable substituents include —OH, —NH$_2$, —NH(C$_1$-C$_4$ alkyl), —N(C$_1$-C$_4$ alkyl)$_2$, —CO(C$_1$-C$_4$ alkyl), —CO$_2$H, —CO$_2$ (C$_1$-C$_4$ alkyl), —O(C$_1$-C$_4$ alkyl), and C$_1$-C$_4$ aliphatic that is optionally substituted with one or more substituents independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$ (C$_1$-C$_4$ alkyl), —O(C$_1$-C$_4$ alkyl), C$_{3-7}$cycloalkyl, and C$_{3-7}$cyclo(haloalkyl). Other suitable substituents include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted $C_{1-6}$ aliphatic, optionally substituted phenyl, optionally substituted —O(Ph), optionally substituted —CH$_2$ (Ph), optionally substituted —(CH$_2$)$_2$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, $C_{1-4}$ aliphatic, OH, O($C_{1-4}$ aliphatic), NO$_2$, CN, CO$_2$H, CO$_2$ ($C_{1-4}$ aliphatic), O(halo $C_{1-4}$ aliphatic), or halo($C_{1-4}$ aliphatic), wherein each of the foregoing $C_{1-4}$ aliphatic groups of R$^+$ is unsubstituted.

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those described above. Specific examples include halogen, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$ (C$_1$-C$_4$ alkyl), —O(C$_1$-C$_4$ alkyl), and C$_1$-C$_4$ aliphatic that is optionally substituted with one or more substituents independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$ (C$_1$-C$_4$ alkyl), —O(C$_1$-C$_4$ alkyl), C$_{3-7}$ cycloalkyl, and C$_{3-7}$cyclo(haloalkyl). Other suitable substituents include: halogen; —R$^\circ$; —OR$^\circ$; —SR$^\circ$; 1,2-methylenedioxy; 1,2-ethylenedioxy; phenyl (Ph) optionally substituted with Ro; —O(Ph) optionally substituted with R$^\circ$; —(CH$_2$)$_{1-2}$(Ph), optionally substituted with R$^\circ$; —CH=CH (Ph), optionally substituted with R$^\circ$; —NO$_2$; —CN; —N(R$^\circ$)$_2$; —NR$^\circ$C(O)R$^\circ$; —NR$^\circ$C(S)R$^\circ$; —NR$^\circ$C(O)N(R$^\circ$)$_2$; —NR$^\circ$C(S)N(R$^\circ$)$_2$; —NR$^\circ$CO$_2$R$^\circ$; —NR$^\circ$NR$^\circ$C(O)R$^\circ$; —NR$^\circ$NR$^\circ$C(O)N(R$^\circ$)$_2$; —NR$^\circ$NR$^\circ$CO$_2$R$^\circ$; —C(O)C(O)R$^\circ$; —C(O)CH$_2$C(O)R$^\circ$; —CO$_2$R$^\circ$; —C(O)R$^\circ$; —C(S)R$^\circ$; —C(O)N(R$^\circ$)$_2$; —C(S)N(R$^\circ$)$_2$; —OC(O)N(R$^\circ$)$_2$; —OC(O)R$^\circ$; —C(O)N(OR$^\circ$)R$^\circ$; —C(NOR$^\circ$)R$^\circ$; —S(O)$_2$R$^\circ$; —S(O)$_3$R$^\circ$; —SO$_2$N(R$^\circ$)$_2$; —S(O)R$^\circ$; —NR$^\circ$SO$_2$N(R$^\circ$)$_2$; —NR$^\circ$SO$_2$R$^\circ$; —N(OR$^\circ$)R$^\circ$; —C(=NH)—N(R$^\circ$)$_2$; or —(CH$_2$)$_{0-2}$NHC(O)R$^\circ$; wherein each independent occurrence of R$^\circ$ is selected from hydrogen, optionally substituted $C_{1-6}$ aliphatic, an unsubstituted 5-6 membered heteroaryl or heterocyclic ring, phenyl, —O(Ph), or —CH$_2$ (Ph), or, two independent occurrences of R$^\circ$, on the same substituent or different substituents, taken together with the atom(s) to which each R$^\circ$ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R$^\circ$ are selected from NH$_2$, NH(C$_{1-4}$ aliphatic), N(C$_{1-4}$ aliphatic)$_2$, halogen, $C_{1-4}$ aliphatic, OH, O($C_{1-4}$ aliphatic), NO$_2$, CN, CO$_2$H, CO$_2$ ($C_{1-4}$ aliphatic), O(haloC$_{1-4}$ aliphatic), or haloC$_{1-4}$ aliphatic, CHO, N(CO)(C$_{1-4}$ aliphatic), C(O)N (C$_{1-4}$ aliphatic), wherein each of the foregoing $C_{1-4}$ aliphatic groups of R$^\circ$ is unsubstituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

The term "unsaturated", as used herein, means that a moiety has one or more units of unsaturation.

As detailed above, in some embodiments, two independent occurrences of R$^\circ$ (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R$^\circ$ (or R$^+$, or any other variable similarly defined herein) are taken together with the atom(s) to which each variable is bound include, but are not limited to the following: a) two independent occurrences of R$^\circ$ (or R$^+$, or any other variable similarly defined herein) that are bound to the same atom and are taken together with that atom to form a ring, for example, N(R$^\circ$)$_2$, where both occurrences of R$^\circ$ are taken together with the nitrogen atom to form a piperidin-1-yl, piperazin-1-yl, or morpholin-4-yl group; and b) two independent occurrences of R$^\circ$ (or R$^+$, or any other variable similarly defined herein) that are bound to different atoms and are taken together with both of those atoms to form a ring, for example where a phenyl group is substituted with two occurrences of

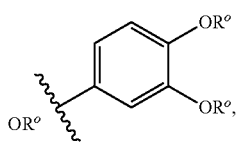

these two occurrences of R° are taken together with the oxygen atoms to which they are bound to form a fused 6-membered oxygen containing ring:

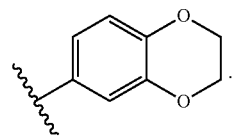 [SMILES: *c1ccc2c(c1)OCCO2]

It will be appreciated that a variety of other rings can be formed when two independent occurrences of R° (or R+, or any other variable similarly defined herein) are taken together with the atom(s) to which each variable is bound and that the examples detailed above are not intended to be limiting.

As used herein, an "amino" group refers to —NH$_2$.

The term "hydroxyl" or "hydroxy" or "alcohol moiety" refers to —OH.

As used herein, an "oxo" refers to =O.

As used herein, the term "alkoxy", or "alkylthio", as used herein, refers to an alkyl group, as previously defined, attached to the molecule through an oxygen ("alkoxy" e.g., —O-alkyl) or sulfur ("alkylthio" e.g., —S-alkyl) atom.

As used herein, the terms "halogen", "halo", and "hal" mean F, Cl, Br, or I.

As used herein, the term "cyano" or "nitrile" refer to —CN or —C≡N.

The terms "alkoxyalkyl", "alkoxyalkenyl", "alkoxyaliphatic", and "alkoxyalkoxy" mean alkyl, alkenyl, aliphatic or alkoxy, as the case may be, substituted with one or more alkoxy groups.

The terms "haloalkyl", "haloalkenyl", "haloaliphatic", and "haloalkoxy" mean alkyl, alkenyl, aliphatic or alkoxy, as the case may be, substituted with one or more halogen atoms. This term includes perfluorinated alkyl groups, such as —CF$_3$ and —CF$_2$CF$_3$.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. In some embodiments, the cyanoalkyl is (NC)-alkyl-.

The terms "aminoalkyl", "aminoalkenyl", "aminoaliphatic", and "aminoalkoxy" mean alkyl, alkenyl, aliphatic or alkoxy, as the case may be, substituted with one or more amino groups, wherein the amino group is as defined above.

The terms "hydroxyalkyl", "hydroxyaliphatic", and "hydroxyalkoxy" mean alkyl, aliphatic or alkoxy, as the case may be, substituted with one or more —OH groups.

The terms "alkoxyalkyl", "alkoxyaliphatic", and "alkoxyalkoxy" mean alkyl, aliphatic or alkoxy, as the case may be, substituted with one or more alkoxy groups. For example, an "alkoxyalkyl" refers to an alkyl group such as (alkyl-O)-alkyl-, wherein alkyl has been defined above.

The term "protecting group" and "protective group" as used herein, are interchangeable and refer to an agent used to temporarily block one or more desired functional groups in a compound with multiple reactive sites. In certain embodiments, a protecting group has one or more, or specifically all, of the following characteristics: a) is added selectively to a functional group in good yield to give a protected substrate that is b) stable to reactions occurring at one or more of the other reactive, sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. For example, a substituent drawn as

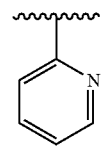

also represents

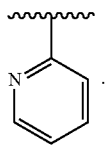

Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium analogs, can also be therapeutically useful.

The terms "a bond" and "absent" are used interchangeably to indicate that a group is absent.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The compounds described herein can exist in free form, or, where appropriate, as salts. Those salts that are pharmaceutically acceptable are of particular interest since they are useful in administering the compounds described above for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound, which are, within the scope of sound medical judgment, suitable for use in humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminium. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds described herein, the methods of the invention can be employed for preparing pharmaceutically acceptable solvates (e.g., hydrates) and clathrates of these compounds.

As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule e.g., a solvent or water) trapped within.

In addition to the compounds described herein, the methods of the invention can be employed for preparing pharmaceutically acceptable derivatives or prodrugs of these compounds.

A "pharmaceutically acceptable derivative or prodrug" includes any pharmaceutically acceptable ester, salt of an ester, or other derivative or salt thereof, of a compound described herein, which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —$NO_2$, —ONO, or —$ONO_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

Pharmaceutically acceptable prodrugs of the compounds described above include, without limitation, esters, amino acid esters, phosphate esters, metal salts and sulfonate esters.

The compounds described above are useful as protein kinase inhibitors, such as Plk (Plk1, Plk2, Plk3, and/or Plk4) inhibitors. Thus, these compounds can inhibit the activity of such protein kinase(s) in a patient. Generally, inhibiting such protein kinase activity can treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease.

Particularly, the compounds described above are useful for the treatment of diseases, disorders, and conditions characterized by excessive or abnormal cell proliferation. Such diseases include a proliferative or hyperproliferative disease, and a neurodegenerative disease. Examples of proliferative and hyperproliferative diseases include, without limitation, cancer.

The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" also includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myiloma, myelodysplastic syndrome), Hodgkin's disease, non-Hodgkin's lymphoma [malignant lymphoma]hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

More particularly, the compounds described above are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. Specific examples of diseases and conditions where the compounds described herein and their compositions are useful include hematopoietic disorders, in particular, acute-myelogenous leukemia (AML), chronic-myelogenous leukemia (CML), acute-promyelocytic leukemia (APL), and acute lymphocytic leukemia (ALL). Examples of neurodegenerative diseases include, without limitation, Alzheimer's disease.

The compounds described above can be particularly useful for treating a protein-kinase mediated condition, such as a Plk-mediated disease. The term "protein kinase-mediated condition," as used herein, means any disease or other deleterious condition in which a protein kinase plays a role. Such conditions include, without limitation, autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. The term "Plk-mediated condition", as used herein means any disease or other deleterious condition in which Plk plays a role. Such conditions include, without limitation, a proliferative or hyperproliferative disease, or a neurodegenerative disease.

As used herein, a "patient" means an animal, preferably a human.

An "effective amount" of a compound for treating or preventing a protein kinase-mediated disease/condition (e.g., a Plk-mediated disease/condition) is the amount effective in order to treat said disease/condition. The compounds described above may be administered using any amount and any route of administration effective for treating or lessening the severity of said disease. For example, the compounds can be administered in a dosage of between 0.01-100 mg/kg body weight/day.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of the compound will also depend upon the particular compound in the composition.

Depending upon the particular protein kinase-mediated conditions to be treated or prevented, additional drugs, which are normally administered to treat or prevent that condition, may be administered together with the protease inhibitors described herein. For example, chemotherapeutic agents or other anti-proliferative agents may be combined with the protein kinase inhibitors of this invention to treat proliferative diseases.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

Examples of known chemotherapeutic agents include, but are not limited to, Gleevec™, adriamycin, dexamethasone, vincristine, cyclophosphamide, fluorouracil, topotecan, taxol, interferons, and platinum derivatives. Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

As inhibitors of protein kinases, the compounds described above are also useful in biological samples. For example, the compounds are useful in inhibiting protein kinase activity in a biological sample. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

The compounds described above are also useful the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Protein kinase inhibition assays are known in the art. For example, detailed conditions for Plk1, Plk2, Plk3, and Plk4 are set forth in US 2008/0167289 and US 2009/0062292.

In treating or preventing one or more conditions/diseases described above, the compounds described above can be formulated in pharmaceutically acceptable formulations that optionally further comprise a pharmaceutically acceptable carrier, adjuvant or vehicle.

As described herein, the pharmaceutically acceptable compositions comprise a compound described above in an effective amount, and additionally comprise a pharmaceutically acceptable carrier, adjuvant, or vehicle, which includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds described above, and pharmaceutically acceptable compositions thereof can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Any orally acceptable dosage form including, but not limited to, capsules, tablets, aqueous suspensions or solutions, can be used for the oral administration. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Liquid dosage forms for oral administration include, but are not limited to, pharmaceutically acceptable emulsions, microemulsions, solutions, suspensions, syrups and elixirs. In addition to the active compounds (the compounds described above), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Sterile injectable forms may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In order to prolong the effect of the active compounds administered, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the active compound with suitable non-irritating excipients or carriers such as cocoa butter, polyethylene glycol or a suppository wax which are solid at ambient temperature but liquid at body temperature and therefore melt in the rectum or vaginal cavity and release the active compound.

Dosage forms for topical or transdermal administration include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, transdermal patches, which have the added advantage of providing controlled delivery of a compound to the body, can also be used. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Alternatively, the compounds described above and pharmaceutically acceptable compositions thereof may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds described above and pharmaceutically acceptable compositions thereof can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. The amount of the active compound in a unit dosage form will vary depending upon, for example, the host treated, and the particular mode of administration, for example, from 0.01 mg/kg body weight/day to 100 mg/kg body weight/day.

EXEMPLIFICATION

Example 1

Methyl 4-(9-cyclopentyl-5,7,7-trimethyl-6-oxo-6,7,8,9-tetrahydro-5H-pyrimido[4,5-b][1,4]diazepin-2-yl amino)-3-methoxybenzoate

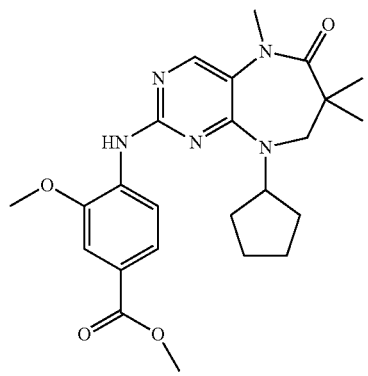

Method A: Methyl 3-(cyclopentylamino)-2,2-dimethylpropanoate hydrochloride

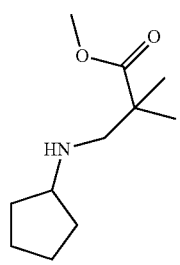

1,3,5-tricyclopentyl-1,3,5-triazinane (112.9 g, 387.3 mmol) and (1-methoxy-2-methyl-prop-1-enoxy)-trimethylsilane (202.6 g, 1.162 mol) in DCM (1 L) was stirred at 0° C. followed by dropwise addition of trifluoromethanesulfonic acid (4 mL, 45 mmol). The mixture was stirred at ambient temperature overnight. Mixture was diluted with sat. bicarbonate aqueous solution and extracted twice with DCM. Organics layers were combined, washed with brine, dried (MgSO4), filtered and solvents removed to leave a reddish mobile oil which was filtered through a silica plug (800 ml silica) eluting with 0-5% MeOH:EtOAc.

This mobile red oil was dissolved in ether (500 ml) cooled to 0° C., followed by slow addition of HCl in ether and stirred for 2 hours. Petroleum ether (500 ml) was added and pink solid isolated by filtration (160.62 g). The mother liquors were concentrated and the addition of HCl in ether repeated and pink solid was isolated as before. Solids combined to give methyl 3-(cyclopentylamino)-2,2-dimethylpropanoate hydrochloride as a slightly pink solid (255.35 g, 92%). NMR CDCl$_3$ 1.45 (6H, s), 1.6-1.67 (2H, m), 1.87-1.97 (2H, m), 2.0-2.1 (2H, m), 2.1-2.2 (2H, m), 3.08 (2H, s), 3.50-3.57 (1H, m), 3.77 (3H, s)

Method B: tert-butyl 3-(cyclopentylamino)-2,2-dimethylpropanoate

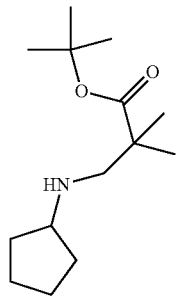 [SMILES: CC(C)(C)OC(=O)C(C)(C)CNC1CCCC1]

Methyl 3-(cyclopentylamino)-2,2-dimethyl-propanoate hydrochloride (3 g, 12.73 mmol) was dissolved in DCM and washed with aqueous bicarbonate solution, then brine and concentrated to an oil. This oil was dissolved in THF (10 ml) and added to a 1M solution of potassium butoxide (12.73 mL of 1 M, 12.73 mmol) in THF at 0° C. Reaction mixture turned to thick paste and was diluted with THF (20 ml) and stirred at ambient temperature for 1 hr. A further 2 ml of 1M butoxide added and stirred for 1 hr. The mixture was concentrated to a paste, diluted with ethylacetate and washed with water (×2), brine and concentrated to give tert-butyl 3-(cyclopentylamino)-2,2-dimethylpropanoate as an oil (2.6 g, 85%). NMR CDCl$_3$ 1.18-1.2 (6H, m), 1.27-1.35 (2H, m), 1.46 (9H, s), 1.50-1.58 (2H, m), 1.63-1.72 (2H, m), 1.78-1.87 (2H, m), 2.62 (2H, s), 3.02-3.08 (1H, m); MS (ES+) 242.1

Method C: tert-butyl 3-((2-chloro-5-nitropyrimidin-4-yl)(cyclopentyl)amino)-2,2-dimethylpropoate

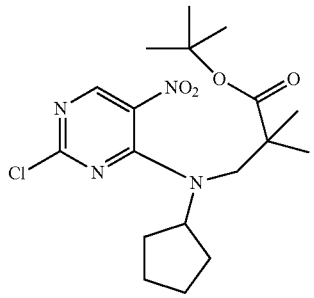 [SMILES: CC(C)(C)OC(=O)C(C)(C)CN(c1nc(Cl)ncc1[N+](=O)[O-])C1CCCC1]

tert-butyl 3-(cyclopentylamino)-2,2-dimethyl-propanoate (21.44 g, 76.39 mmol) was suspended in petroleum ether (296.4 mL):DCM (118.6 mL) and sodium bicarbonate (25.67 g, 305.6 mmol) were added. The reaction mixture was cooled to 0° C. and 2,4-dichloro-5-nitro-pyrimidine (14.82 g, 76.39 mmol) was added portionwise. The mixture was stirred at ambient temperature overnight. The mixture was filtered to remove inorganics, concentrated to give a viscous yellow oil and purified by column chromatography (800 ml silica) eluting with 5% ethyl acetate: petrol. The oil thus obtained oil was dissolved in ether and triturated with petroleum ether to give tert-butyl 3-((2-chloro-5-nitropyrimidin-4-yl) (cyclopentyl) amino)-2,2-dimethylpropoate as a yellow crystalline solid (24.4 g, 80%). NMR CDCl₃ 1.18 (6H, s), 1.46 (9H, s), 1.52-1.58 (2H, m), 1.63-1.70 (2H, m), 1.72-1.80 (2H, m), 1.92-1.98 (2H, m), 2.62 (2H, s), 3.58-3.65 (1H, m), 3.92 (2H, s), 8.9 (1H, s); MS (ES+) 399.1

Method D: Methyl 4-(4-((3-tert-butoxy-2,2-dimethyl-3-oxopropyl) (cyclopentyl)amino)-5-nitropyridin-2-ylamino)-3-methoxybenzoate

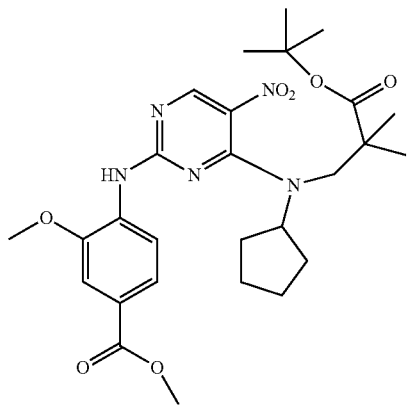 [SMILES: COC(=O)c1ccc(Nc2ncc([N+](=O)[O-])c(N(CC(C)(C)C(=O)OC(C)(C)C)C3CCCC3)n2)c(OC)c1]

tert-butyl 3-[(2-chloro-5-nitro-pyrimidin-4-yl)-cyclopentyl-amino]-2,2-dimethyl-propanoate (1.5 g, 3.760 mmol), methyl 4-amino-3-methoxy-benzoate (817.5 mg, 4.512 mmol) and DIPEA (728.9 mg, 982.3 µL, 5.640 mmol) in 4-methylpentan-2-ol were treated under microwave at 140 C for 2 hours. The mixture was concentrated and purification by flash chromatography, eluting with 5% ethylacetate/petether to remove impurities followed by 10% ethylacetate/pet ether to elute product, gave methyl 4-(4-((3-tert-butoxy-2,2-dimethyl-3-oxopropyl) (cyclopentyl)amino)-5-nitropyridin-2-ylamino)-3-methoxybenzoate as a yellow oil (1.25 g, 61%). NMR CDCl₃ 1.18 (6H, s), 1.46 (9H, s), 1.52-1.58 (2H, m), 1.63-1.70 (2H, m), 1.72-1.80 (2H, m), 1.92-1.98 (2H, m), 3.62-3.68 (1H, m), 3.85-4.0 (8H, m), 7.55 (1H, s), 7.72-7.75 (1H, m), 8.12 (1H, brs), 8.5 (1H, d), 8.97 (1H, s); MS (ES+) 544.1 (ES-) 542.1

Method E: Methyl 4-(9-cyclopentyl-7,7-dimethyl-6-oxo-6,7,8,9-tetrahydro-5H-pyrimido[4,5-b][1,4]diazpine-2-ylamino0-3-methoxybenzoate

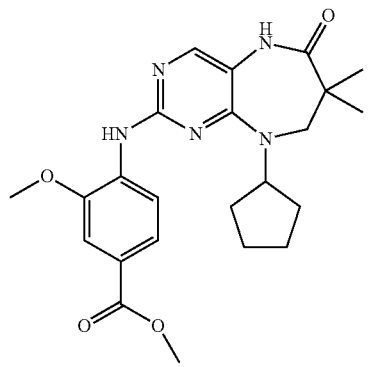

Methyl 4-(4-((3-tert-butoxy-2,2-dimethyl-3-oxopropyl) (cyclopentyl)amino)-5-nitropyridin-2-ylamino)-3-methoxybenzoate (1.2 g, 2.207 mmol) in DCM (15 mL) was treated with dropwise addition of TFA (5.033 g, 3.401 mL, 44.14 mmol). The mixture was stirred at rt for 3 hours and concentrated to an oil, redissolved in DCM and concentrated. This process was repeated until a yellow solid was obtained. This solid was suspended in acetic acid (20 mL) and Fe (184.8 mg, 3.310 mmol) was added. The mixture was heated to 60° C. for 1 hour, filtered through celite and concentrated. Purification by flash chromatography on silica gel, eluting with 2% methanol/DCM to remove impurities followed by 15% methanol/DCM, gave methyl 4-(9-cyclopentyl-7,7-dimethyl-6-oxo-6,7,8,9-tetrahydro-5H-pyrimido[4,5-b][1,4]diazepine-2-ylamino-3-methoxybenzoate as a pale yellow solid (650 mg, 67%). NMR CDCl₃ 1.32 (6H, s), 1.52-1.62 (2H, m), 1.72-1.85 (4H, m), 2.02-2.08 (2H, m), 3:32 (2H, s), 3.92 (3H, s), 3.98 (3H, s), 5.32-5.4 (1H, m), 7.23-7.26 (1H, brs), 7.55 (1H, s), 7.72-7.77 (3H, m), 8.53 (1H, d); MS (ES+) 440.1

Method F: Methyl 4-(9-cyclopentyl-5,7,7-trimethyl-6-oxo-6,7,8,9-tetrahydro-5H-pyrimido[4,5-b][1,4]diazepin-2-ylamino)-3-methoxybenzoate

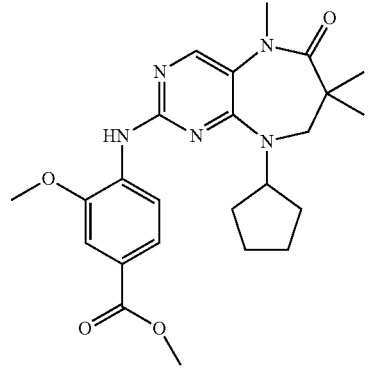

Methyl 4-(9-cyclopentyl-7,7-dimethyl-6-oxo-6,7,8,9-tetrahydro-5H-pyrimido[4,5-b][1,4]diazepine-2-ylamino-3-methoxybenzoate and dicesium carbonate (118.6 mg, 0.3640 mmol) were mixed in DMF. MeI (103.3 mg, 45.31 µL, 0.7280 mmol) was then added and the reaction mixture was stirred at room temperature overnight. The mixture was diluted with ethylacetate, filtered through small pad of celite, washed twice with water, dried and concentrated to a yellow solid. Purification by flash chromatography on silica gel, eluting with 1% methanol/DCM, gave methyl 4-(9-cyclopentyl-5,7,7-trimethyl-6-oxo-6,7,8,9-tetrahydro-5H-pyrimido[4,5-b][1,4]diazepin-2-ylamino)-3-methoxybenzoate as a pale yellow solid (47 mg, 56%). NMR CDCl₃ 1.25 (6H, s), 1.53-1.58 (2H, m), 1.69-1.83 (4H, m), 2.02-2.08 (2H, m), 3.33 (3H, s), 3.4 (2H, s), 3.92 (3H, s), 3.98 (3H, s), 5.27-5.34 (1H, m), 7.23-7.26 (1H, brs), 7.55 (1H, s), 7.72-7.77 (2H, m), 7.88 (1H, s), 8.56 (1H, d); MS (ES+) 454.1 (ES-) 452.1

Method G:
3-(Cyclopentylamino)-N,2,2-trimethylpropanamide

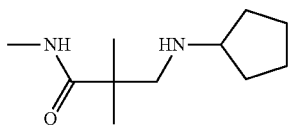

Methyl 3-(cyclopentylamino)-2,2-dimethyl-propanoate hydrochloride (3 g, 12.73 mmol) was dissolved in methanamine, 33 wt % in EtOH (15 mL) and heated to 90° C. in a sealed tube overnight. The reaction was allowed to cool to ambient temperature and the solvent removed in vacuo. The crude product was purified by column chromatography (0-5% MeOH/EtOAc+1% NH4OH) to give the sub-title compound as a colourless oil (1.18 g, 47%); 1H NMR (400.0 MHz, DMSO) d 1.02 (s, 6H), 1.22-1.33 (m, 2H), 1.39-1.51 (m, 2H), 1.53-1.72 (m, 2H), 2.48 (s, 4H), 2.56 (d, J=4.5 Hz, 3H), 2.89-2.96 (m, 1H) and 8.07 (br s, 1H); MS ES(+) 199.1, ES (−) not seen.

Method H: 3-[(5-bromo-2-chloro-pyrimidin-4-yl)-cyclopentyl-amino]-N,2,2-trimethyl-propanamide

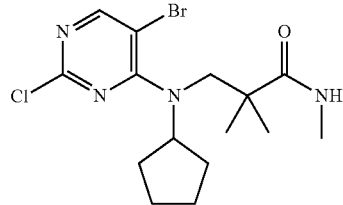 [SMILES: CNC(=O)C(C)(C)CN(c1nc(Cl)ncc1Br)C1CCCC1]

3-(cyclopentylamino)-N,2,2-trimethyl-propanamide (665 mg, 3.353 mmol) and 5-bromo-2,4-dichloro-pyrimidine (666 mg, 373.7 µL, 2.921 mmol) were dissolved in EtOH (10 mL) and DIPEA (511.4 mg, 691.9 µL, 3.957 mmol) was added. The reaction was allowed to stir at reflux temperature overnight. The solvent was removed in vacuo. The crude residue was purified by column chromatography (0-100% EtOAc/Petrol) to give the sub-title product as a brown oil (266 mg, 23%); ¹H NMR (400.0 MHz, DMSO) d 1.03 (s, 6H), 1.54-1.83 (m, 8H), 2.57 (s, 3H), 3.68 (s, 2H), 4.23 (quin, 1H), 7.53 (d, 1H), 8.63 (s, 1H); MS ES(+) 391.0, ES (−) 389.0.

Method I: Methyl 4-(5-bromo-4-(cyclopentyl(2,2-dimethyl-3-(methylamino)-3-oxopropyl)amino)pyrimidin-2-ylamino)-3-methoxybenzoate

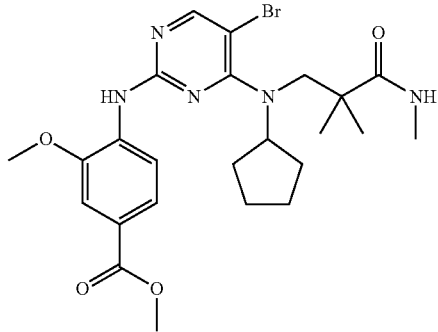

3-[(5-bromo-2-chloro-pyrimidin-4-yl)-cyclopentyl-amino]-N,2,2-trimethyl-propanamide (266 mg, 0.6825 mmol) and methyl 4-amino-3-methoxy-benzoate (185.5 mg, 1.024 mmol) were dissolved in EtOH (2 mL) and Water (8 mL) and treated with HCl (134.5 µL of 37% w/v, 1.365 mmol). Heat at 90° C. overnight. Cool to ambient temperature and remove solvent in vacuo. The reaction mixture was diluted with EtOAc/NaHCO3 and extracted with EtOAc. The combined organic extracts were dried (Na2SO4), filter and concentrated. The crude residue was purified by column chromatography (0 to 100% EtOAc/Petrol) to give the sub-title compound as a beige oil (84 mg, 23%); NMR (400.0 MHz, DMSO) d 0.97 (s, 6H), 1.44-1.69 (m, 8H), 2.45 (d; J=4.4 Hz, 3H), 3.58 (br s, 2H), 3.84 (s, 3H), 3.96 (s, 3H), 4.11 (quin, 1H), 7.32-7.34 (m, 1H), 7.52 (d, J=1.8 Hz, 1H), 7.61 (d, 1H), 8.07 (s, 1H), 8.38 (s, 1H) and 8.43 (d, J=8.5 Hz, 1H); MS ES(+) 536.0, ES (−) 534.1.

Method J: Methyl 4-[(9-cyclopentyl-5,7,7-trimethyl-6-oxo-8H-pyrimido[4,5-b][1,4]diazepin-2-yl)amino]-3-methoxy-benzoate

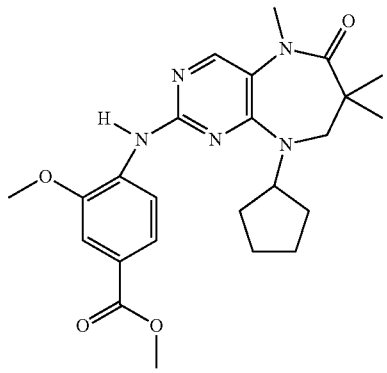

Methyl 4-(5-bromo-4-(cyclopentyl(2,2-dimethyl-3-(methylamino)-3-oxopropyl)amino)pyrimidin-2-ylamino)-3-methoxybenzoate (84 mg, 0.1572 mmol) and Cs2CO3 (74.25 mg, 0.2279 mmol) were dissolved in dioxane (2 mL) and Pd2(dba)3 (4.319 mg, 0.004716 mmol) and Xantphos (7.279 mg, 0.01258 mmol) were added. Heat to 100° C. overnight. The Xantphos and Pd2(dba)3 were replenished and the reaction heated under microwave conditions (120° C. for 30 minutes.) The solvent was removed in vacuo and the crude residue purified by column chromatography (0 to 100% EtOAc/Petrol) to give the title compound as a beige solid (42 mg, 59%); ¹H NMR (400.0 MHz, DMSO) d 1.25 (s, 6H), 1.72-1.82 (m, 4H), 1.85-1.95 (m, 2H), 1.98-2.04 (m, 2H), 3.35 (s, 3H), 3.54 (s, 2H), 3.99 (s, 3H), 4.11 (s, 3H), 5.34 (quin, 1H), 7.66 (s, 1H), 7.74 (d, 1H), 7.98 (s, 1H), 8.17 (s, 1H) and 8.64 (d, 1H); MS ES(+) 454.1, ES (−) 452.1.

All references provided herein are incorporated herein in its entirety by reference. As used herein, all abbreviations, symbols and conventions are consistent with those used in the contemporary scientific literature. See, e.g., Janet S: Dodd, ed., *The ACS Style Guide: A Manual for Authors and Editors,* 2nd Ed., Washington, D.C.: American Chemical Society, 1997.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a compound represented by Structural Formula (I), or a pharmaceutically acceptable salt thereof:

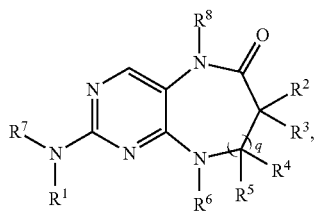

wherein:
- $R^1$ is —H, $C_{1-6}$ aliphatic, $C_{3-10}$ cycloaliphatic, $C_{6-10}$ aryl, 5-10 membered heteroaryl, or 3-10 membered heterocyclyl, wherein each of said aliphatic, cycloaliphatic, aryl, heteroaryl, and heterocyclyl groups represented by $R^1$ is optionally and independently substituted with one or more instances of $J^1$;
- each $R^2$, $R^3$, $R^4$, and $R^5$ is independently —H, halogen, cyano, $C_{1-6}$ aliphatic, or $C_{3-10}$ cycloaliphatic, wherein each of said aliphatic and cycloaliphatic groups represented by $R^2$, $R^3$, $R^4$, and $R^5$, respectively, is optionally and independently substituted with one or more instances of $J^2$, $J^3$, $J^4$, and $J^5$, respectively;
- optionally, $R^2$ and $R^3$, together with the carbon atom to which they are attached, form a $C_{3-7}$ cycloaliphatic ring that is optionally substituted with one or more instances of $J^B$;
- optionally, $R^3$ and $R^4$, together with the carbon atoms to which they are attached, form a $C_{3-7}$ cycloaliphatic ring that is optionally substituted with one or more instances of $J^B$;
- optionally, $R^4$ and $R^5$, together with the carbon atom to which they are attached, form a $C_{3-7}$ cycloaliphatic ring that is optionally substituted with one or more instances of $J^B$;
- $R^6$ is —H, $C_{1-6}$ aliphatic, $C_{3-10}$ cycloaliphatic, $C_{6-10}$ aryl, 5-10 membered heteroaryl, or 3-10 membered heterocyclyl, wherein each of said aliphatic, cycloaliphatic, aryl, heteroaryl, and heterocyclyl groups represented by $R^6$ is optionally and independently substituted with one or more instances of $J^6$;
- $R^7$ is —H, $C_{1-6}$ aliphatic optionally substituted with one or more instanced of $J^4$, or $C_{3-8}$ cycloaliphatic optionally substituted with one or more instanced of $J^B$; or, optionally $R^7$, together with $R^1$ and the nitrogen atom to which it is attached, forms a 5-7 membered heterocyclic ring that is optionally substituted with one or more instances of $J^B$; and
- $R^8$ is —H or $R^9$;
- $R^9$ is $C_{1-6}$ aliphatic or $C_{3-8}$ cycloaliphatic, wherein said aliphatic group is independently and optionally substituted with one or more instances of $J^4$, and wherein said cycloaliphatic group is independently and optionally substituted with one or more instances of $J^B$;
- each $J^1$ is independently T or $C_{1-6}$ aliphatic optionally substituted with one or more instances of T;
- each of $J^2$, $J^3$, $J^4$, $J^5$, and $J^6$ is independently M, or $C_{1-6}$ aliphatic optionally substituted with one or more instances of M;
- each T is independently halogen, oxo, —$NO_2$, —CN, $Q^1$, —$Z^1$—H, or —$Z^2$-$Q^2$;
- each $Z^1$ is independently a unit consisting of one or more groups independently selected from the group consisting of —NR—, —O—, —S—, —C(O)—, —C(=NR)—, —C(=NOR)—, and —$SO_2$N(R)—;
- each $Z^2$ is independently a unit consisting of one or more groups independently selected from the group consisting of —NR—, —O—, —S—, —C(O)—, —C(=NR)—, —C(=NOR)—, —S(O)—, and —$S(O)_2$—;
- each $Q^1$ is independently $C_{3-10}$ cycloaliphatic, $C_{6-10}$ aryl, 5-10 membered heteroaryl, or 3-10 membered heterocyclyl, wherein each $Q^1$ is independently and optionally substituted with one or more instances of $J^Q$;
- each $Q^2$ is independently $C_{1-6}$ aliphatic, $C_{3-10}$ cycloaliphatic, $C_{6-10}$ aryl, 5-10 membered heteroaryl, 3-10 membered heterocyclyl, or $Q^1$-$Q^1$, each of which is optionally and independently substituted with one or more instances of $J^Q$; or each $Q^2$, together with R and the nitrogen atom to which it is attached, optionally forms a 4-7 membered heterocyclic ring optionally substituted with one or more instances of $J^B$; and
- each $J^Q$ is independently M or $C_{1-6}$ aliphatic optionally substituted with one or more instances of M;
- each M is independently halogen, oxo, —$NO_2$, —CN, —OR', —SR', —N(R')$_2$, —COR', —$CO_2$R', —CONR'$_2$, —OCOR'', —OCON(R')$_2$, —NRCOR', —$NRCO_2$R', —NRCON(R')$_2$, —S(O)R'', —$SO_2$R'', —$SO_2$N(R')$_2$, —$NRSO_2$R'', —$NRSO_2$N(R')$_2$, $C_{3-10}$ cycloaliphatic, 3-10 membered heterocyclyl, $C_{6-10}$ aryl, or 5-10 membered heteroaryl, wherein each of said cycloaliphatic, heterocyclyl, aryl and heteroaryl groups represented by M is optionally and independently substituted with one or more instances of $J^B$;
- each R is independently —H or $C_{1-6}$ aliphatic, or each R, together with $Q^2$ and the nitrogen atom to which it is attached, optionally forms a 4-7 membered heterocyclic ring optionally being substituted with one or more instances of $J^B$;
- each R' is independently —H or $C_{1-6}$ aliphatic optionally substituted with one or more instances of $J^4$; or two R' groups, together with the nitrogen atom to which they are attached, form a 4-7 membered heterocyclic ring optionally being substituted with one or more instances of $J^B$;
- each R'' is independently $C_{1-4}$ aliphatic optionally substituted with one or more instances of $J^4$;
- each $J^4$ is independently selected from the group consisting of halogen, oxo, —CN, —OH, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), —O($C_1$-$C_4$ alkyl), $C_{3-7}$ cycloalkyl, and $C_{3-7}$ cyclo(haloalkyl);
- each $J^B$ is independently selected from the group consisting of halogen, oxo, —CN, —OH, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), —O($C_1$-$C_4$ alkyl), and $C_1$-$C_4$ aliphatic that is optionally substituted with one or more instances of $J^4$; and
- q is 0 or 1;

comprising the steps of:

a) reacting a compound represented by Structural Formula (A):

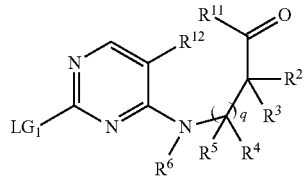
(A)

with $HNR^1R^7$ under suitable conditions to form a compound represented by Structural Formula (B):

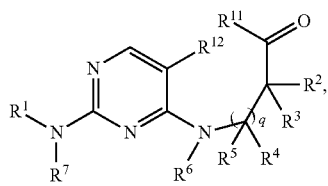
(B)

wherein:

$R^{11}$ is —$NHR^{13}$, and $R^{12}$ is halogen; and $R^{13}$ is —H or $R^9$;

and $LG_1$ is a suitable leaving group; and 1) cyclizing the compound represented by Structural Formula (B) under suitable cyclisation conditions to form the compound represented by Structural Formula (I); and 2) optionally, when $R^{13}$ is —H, reacting the compound produced from step b), ii), 1) with $R^9$-$LG_2$, wherein $LG_2$ is a suitable leaving group, to form the compound represented by Structural Formula (I), wherein $R^8$ is other than —H.

2. The method of claim 1, wherein $R^1$ is optionally substituted $C_{1-6}$ aliphatic, optionally substituted $C_{6-10}$ aryl, or optionally substituted 5-10 membered heteroaryl.

3. The method of claim 2, wherein $R^7$ is —H, or optionally substituted $C_{1-6}$ aliphatic.

4. The method of any one of claims 1-3, wherein $R^6$ is —H, optionally substituted $C_{1-6}$ aliphatic, optionally substituted $C_{3-7}$ cycloaliphatic, optionally substituted 3-7 membered heterocyclyl, optionally substituted phenyl, or optionally substituted 5-6 membered heteroaryl.

5. The method of claim 1, wherein each of $R^2$, $R^3$, $R^4$ and $R^5$ is independently —H, halogen, optionally substituted $C_{1-6}$ aliphatic, or optionally substituted $C_{3-7}$ cycloaliphatic; or optionally $R^2$ and $R^3$, $R^3$ and $R^4$, and $R^4$ and $R^5$, respectively, together with the atom to which they are bound, independently form an optionally substituted $C_{3-7}$ cycloaliphatic ring.

6. The method of claim 5, wherein $R^8$ is —H, or optionally substituted $C_{1-6}$ aliphatic.

7. The method of claim 1, further comprising the step of reacting a compound represented by Structural Formula (C):

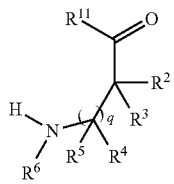
(C)

with a compound represented by Structural Formula (D):

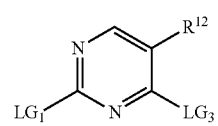
(D)

to form the compound represented by Structural Formula (A), wherein $LG_3$ is a suitable leaving group.

8. The method of claim 7, wherein each of $LG_1$ and $LG_2$ independently is halogen.

9. The method of claim 8, wherein $LG_1$ and $LG_2$ are both —Cl.

10. The method of claim 9, wherein $R^{14}$ is $C_{1-6}$ alkyl.

11. The method of claim 9, wherein $R^{12}$ is —Br or —I, and $R^{13}$ is $C_{1-6}$ alkyl.

12. The method of claim 11, wherein $R^{12}$ is —Br.

13. The method of claim 9, wherein:

each $Z^1$ is independently —N(R)—, —O—, —S—, —$CO_2$—, —C(O)N(R)—, —OC(O)N(R)—, —N(R)$CO_2$—, —N(R)C(O)N(R)—, —C(O)N(R)$CO_2$—, —$SO_2$N(R)—, or —N(R)$SO_2$N(R)—; and each $Z^2$ is independently —N(R)—, —O—, —S—, —$OC_2$—, —OC(O)—, —C(O)N(R)—, —N(R)C(O)—, —OC(O)N(R)—, —N(R)$CO_2$—, —N(R)C(O)N(R)—, —C(O)N(R)$CO_2$—, —S(O)$_2$—, —$SO_2$N(R)—, —N(R)$SO_2$—, or —N(R)$SO_2$N(R)—.

14. The method of claim 13, wherein $R^1$ is $C_{1-4}$ alkyl substituted with $Q^1$ and optionally further substituted with one or more substituents independently selected from the group consisting of halogen, oxo, —CN, —OH, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and —O($C_1$-$C_4$ alkyl).

15. The method of claim 13, wherein $R^1$ is $C_{6-10}$ aryl or 5-6 membered heteroaryl, each optionally and independently substituted with one or more substituents independently selected from the group consisting of T and $C_{1-6}$ aliphatic optionally substituted with one or more instances of T; and wherein each T is halogen, cyano, $Q^1$, —N(R)H, —OH, —SH, —$CO_2$H, —C(O)N(R)H, —OC(O)N(R)H, —N(R)C(O)N(R)H, —$SO_2$N(R)H, —N(R)$SO_2$N(R)H, —S(O)$_2Q^2$, —N(R)$Q^2$, —$OQ^2$, —$SQ^2$, —$CO_2Q^2$, —OC(O)$Q^2$, —C(O)N(R)$Q^2$, —N(R)C(O)$Q^2$, —N(R)$CO_2Q^2$, —OC(O)N(R)$Q^2$, —C(O)N(R)$CO_2Q^2$, —N(R)C(O)N(R)$Q^2$, —$SO_2$N(R)$Q^2$, —N(R)$SO_2Q^2$, or —N(R)$SO_2$N(R)$Q^2$.

16. The method of claim 14 or 15, wherein $R^7$ is —H, or $C_{1-6}$ alkyl.

17. The method of claim 16, wherein $R^6$ is —H, optionally substituted $C_{1-6}$ alkyl, or optionally substituted $C_{3-7}$ cycloalkyl.

18. The method of claim 17, wherein $R^8$ is —H, or $C_{1-6}$ alkyl.

19. The method of claim 18, wherein each of $R^2$, $R^3$, $R^4$ and $R^5$ is independently —H, or optionally substituted $C_{1-6}$ alkyl; or optionally $R^2$ and $R^3$, together with the atom to which they are bound, form an optionally substituted $C_{3-7}$ cycloalkyl ring.

20. The method of claim 19, wherein:
  i) $R^2$ is —H or $C_{1-3}$ alkyl; $R^3$ is $C_{1-3}$ alkyl; $R^4$ is —H or $C_{1-3}$ alkyl; and $R^5$ is —H or $C_{1-3}$ alkyl; or
  ii) $R^2$ and $R^3$ together with the atom to which they are bound form a $C_{3-7}$ cycloalkyl ring; $R^4$ is —H or $C_{1-3}$ alkyl; and $R^5$ is —H or $C_{1-3}$ alkyl.

21. The method of claim 20, wherein $R^4$ and $R^5$ are both —H.

22. The method of claim 15, wherein $R^1$ is phenyl optionally substituted with one or more substituents independently selected from the group consisting of T and $C_{1-6}$ aliphatic optionally substituted with one or more instances of T; and wherein each T is halogen, cyano, —N(R)H, —OH, —CO$_2$H, —C(O)N(R)H, —OC(O)N(R)H, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, or —N(R)C(O)N(R)Q$^2$.

23. The compound of claim 22, wherein $R^7$ is —H.

24. The method of claim 23, wherein $R^6$ is optionally substituted $C_{3-6}$ cycloalkyl.

25. The method of claim 24, wherein $R^1$ is optionally substituted aryl or optionally substituted heteroaryl.

26. The method of claim 25, wherein q is 1.

27. A method of preparing a compound by Structural Formula (III):

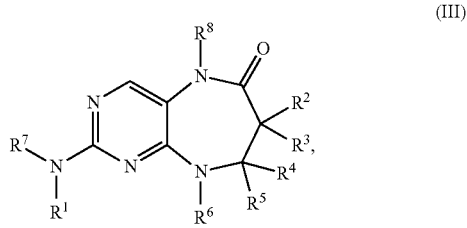

(III)

or a pharmaceutically acceptable salt thereof, wherein:
  $R^1$ is —H, $C_{1-6}$ aliphatic, $C_{3-10}$ cycloaliphatic, $C_{6-10}$ aryl, 5-10 membered heteroaryl, or 3-10 membered heterocyclyl, wherein each of said aliphatic, cycloaliphatic, aryl, heteroaryl, and heterocyclyl groups represented by $R^1$ is optionally and independently substituted with one or more instances of $J^1$;
  each $R^2$, $R^3$, $R^4$, and $R^5$ is independently —H, halogen, cyano, $C_{1-6}$ aliphatic, or $C_{3-10}$ cycloaliphatic, wherein each of said aliphatic and cycloaliphatic groups represented by $R^2$, $R^3$, $R^4$, and $R^5$, respectively, is optionally and independently substituted with one or more instances of $J^2$, $J^3$, $J^4$, and $J^5$, respectively;
  optionally, $R^2$ and $R^3$, together with the carbon atom to which they are attached, form a $C_{3-7}$ cycloaliphatic ring that is optionally substituted with one or more instances of $J^B$;
  optionally, $R^3$ and $R^4$, together with the carbon atoms to which they are attached, form a $C_{3-7}$ cycloaliphatic ring that is optionally substituted with one or more instances of $J^B$;
  optionally, $R^4$ and $R^5$, together with the carbon atom to which they are attached, form a $C_{3-7}$ cycloaliphatic ring that is optionally substituted with one or more instances of $J^B$;
  $R^6$ is —H, $C_{1-6}$ aliphatic, or $C_{3-10}$ cycloaliphatic, wherein each of said aliphatic and cycloaliphatic groups represented by $R^6$ is optionally and independently substituted with one or more instances of $J^6$;
  $R^7$ is —H, $C_{1-6}$ aliphatic optionally substituted with one or more instanced of $J^A$, or $C_{3-8}$ cycloaliphatic optionally substituted with one or more instanced of $J^B$; or, optionally $R^7$, together with $R^1$ and the nitrogen atom to which it is attached, forms a 5-7 membered heterocyclic ring that is optionally substituted with one or more instances of $J^B$; and
  $R^8$ is —H or $R^9$;
  $R^9$ is $C_{1-6}$ aliphatic, or $C_{3-8}$ cycloaliphatic, wherein said aliphatic group is independently and optionally substituted with one or more instances of $J^A$, and wherein said cycloaliphatic group is independently and optionally substituted with one or more instances of $J^B$;
  each $J^1$ is independently T or $C_{1-6}$ aliphatic optionally substituted with one or more instances of T;
  each of $J^2$, $J^3$, $J^4$, $J^5$, and $J^6$ is independently M, or $C_{1-6}$ aliphatic optionally substituted with one or more instances of M;
  each T is independently halogen, oxo, —NO$_2$, —CN, $Q^1$, —$Z^1$—H, or —$Z^2$-$Q^2$;
  each $Z^1$ is independently a unit consisting of one or more groups independently selected from the group consisting of —NR—, —O—, —S—, —C(O)—, —C(=NR)—, —C(=NOR)—, and —SO$_2$N(R)—;
  each $Z^2$ is independently a unit consisting of one or more groups independently selected from the group consisting of —NR—, —O—, —S—, —C(O)—, —C(=NR)—, —C(=NOR)—, —S(O)—, and —S(O)$_2$—;
  each $Q^1$ is independently $C_{3-10}$ cycloaliphatic, $C_{6-10}$ aryl, 5-10 membered heteroaryl, or 3-10 membered heterocyclyl, wherein each $Q^1$ is independently and optionally substituted with one or more instances of $J^Q$;
  each $Q^2$ is independently $C_{1-6}$ aliphatic, $C_{3-10}$ cycloaliphatic, $C_{6-10}$ aryl, 5-10 membered heteroaryl, 3-10 membered heterocyclyl, or $Q^1$-$Q^1$, each of which is optionally and independently substituted with one or more instances of $J^Q$; or each $Q^2$, together with R and the nitrogen atom to which it is attached, optionally forms a 4-7 membered heterocyclic ring optionally substituted with one or more instances of $J^B$; and
  each $J^Q$ is independently M or $C_{1-6}$ aliphatic optionally substituted with one or more instances of M;
  each M is independently halogen, oxo, —NO$_2$, —CN, —OR', —SR', —N(R')$_2$, —COR', —CO$_2$R', —CONR'$_2$, —OCOR'', —OCON(R')$_2$, —NRCOR', —NRCO$_2$R', —NRCON(R')$_2$, —S(O)R'', —SO$_2$R'', —SO$_2$N(R')$_2$, —NRSO$_2$R'', —NRSO$_2$N(R')$_2$, $C_{3-10}$ cycloaliphatic, 3-10 membered heterocyclyl, $C_{6-10}$ aryl, or 5-10 membered heteroaryl, wherein each of said cycloaliphatic, heterocyclyl, aryl and heteroaryl groups represented by M is optionally and independently substituted with one or more instances of $J^B$;
  each R is independently —H or $C_{1-6}$ aliphatic, or each R, together with $Q^2$ and the nitrogen atom to which it is attached, optionally forms a 4-7 membered heterocyclic ring optionally being substituted with one or more instances of $J^B$;
  each R' is independently —H or $C_{1-6}$ aliphatic optionally substituted with one or more instances of $J^A$; or two R' groups, together with the nitrogen atom to which they are attached, form a 4-7 membered heterocyclic ring optionally being substituted with one or more instances of $J^B$;

each R" is independently $C_{1-4}$ aliphatic optionally substituted with one or more instances of $J^A$; and each $J^A$ is independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), —O(C$_1$-C$_4$ alkyl), $C_{3-7}$ cycloalkyl, and $C_{3-7}$ cyclo(haloalkyl);

each $J^B$ is independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), —O(C$_1$-C$_4$ alkyl), and $C_1$-C$_4$ aliphatic that is optionally substituted with one or more instances of $J^A$;

comprising the steps of:

a) reacting a compound represented by Structural Formula (A):

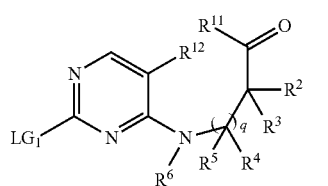

(A)

with HNR$^1$R$^7$ under suitable conditions to form a compound represented by Structural Formula (B):

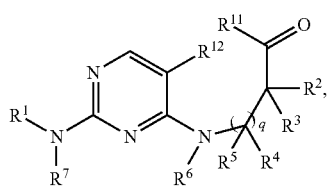

(B)

wherein:

q is 1;

R$^{11}$ is —NHR$^{13}$, and R$^{12}$ is halogen; and

R$^{13}$ is H or R$^9$;

LG$_1$ is a suitable leaving group; and 1) cyclizing the compound represented by Structural Formula (B) under suitable cyclisation conditions to form the compound represented by Structural Formula (I); and 2) optionally, when R$^{13}$ is —H, reacting the compound produced from step b), ii), 1) with R$^9$-LG$_2$, wherein LG$_2$ is a suitable leaving group, to form the compound represented by Structural Formula (I) wherein R$^8$ is R$^9$.

28. The method of claim 27, wherein:

R$^1$ is optionally substituted $C_{6-10}$ aryl or optionally substituted 5-10 membered heteroaryl;

each Z$^1$ is independently —N(R)—, —O—, —S—, —CO$_2$—, —C(O)N(R)—, —OC(O)N(R)—, —N(R)CO$_2$—, —N(R)C(O)N(R)—, —C(O)N(R)CO$_2$—, —SO$_2$N(R)—, or —N(R)SO$_2$N(R)—;

each Z$^2$ is independently —N(R)—, —O—, —S—, —CO$_2$—, —OC(O)—, —C(O)N(R)—, —N(R)C(O)—, —OC(O)N(R)—, —N(R)CO$_2$—, —N(R)C(O)N(R)—, —C(O)N(R)CO$_2$—, —S(O)—, —S(O)$_2$—, —SO$_2$N(R)—, —N(R)SO$_2$—, or —N(R)SO$_2$N(R)—;

each Q$^1$ independently is optionally substituted $C_{3-7}$ cycloalkyl, optionally substituted phenyl, optionally substituted 5-6 membered heteroaryl, or optionally substituted 4-7 membered heterocyclyl;

each of R$^2$ and R$^3$, R$^4$ and R$^5$ is independently —H, halogen, cyano, or $C_{1-6}$ aliphatic, or optionally R$^2$ and R$^3$, R$^3$ and R$^4$, and R$^4$ and R$^5$, respectively, together with the carbon atom(s) to which they are bound, independently form a $C_{3-7}$ cycloalkyl ring, wherein each of said aliphatic and cycloalkyl ring is independently and optionally substituted with one or more substituents independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl);

R$^6$ is —H, $C_{1-6}$ aliphatic or $C_{3-7}$ cycloaliphatic, each of which is optionally and independently substituted with one or more substituents independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl); and each of R$^7$ and R$^8$ is independently —H or $C_{1-6}$ alkyl.

29. The method of claim 28, wherein the compound produced by the method is represented by Structural Formula (IV):

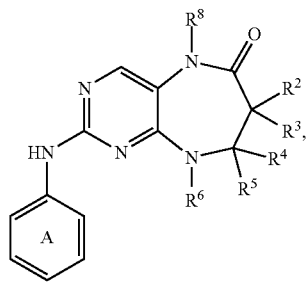

(IV)

or a pharmaceutically acceptable salt thereof, wherein:

phenyl ring A is optionally substituted with one or more substitutents independently selected from the group consisting of T and $C_{1-6}$ aliphatic optionally substituted with one or more instances of T;

each T is halogen, cyano, Q$^1$, —N(R)H, —OH, —CO$_2$H, —C(O)N(R)H, —OC(O)N(R)H, —N(R)C(O)N(R)H, —SO$_2$N(R)H, —N(R)SO$_2$N(R)H, —S(O)$_2$Q$^2$, —N(R)Q$^2$, —OQ$^2$, —CO$_2$Q$^2$, —OC(O)Q$^2$, —C(O)N(R)Q$^2$, —N(R)C(O)Q$^2$, —N(R)CO$_2$Q$^2$, —OC(O)N(R)Q$^2$, —C(O)N(R)CO$_2$Q$^2$, —N(R)C(O)N(R)Q$^2$, —SO$_2$N(R)Q$^2$, —N(R)SO$_2$Q$^2$, or —N(R)SO$_2$N(R)Q$^2$;

Q¹ is C$_{3-7}$ cycloalkyl, phenyl, 5-6 membered heteroaryl, or 4-7 membered heterocyclyl, each optionally and independently substituted with one or more substitutents independently selected from the group consisting of halogen, oxo, —CN, —OH, —NH$_2$, —NH(C$_1$-C$_4$ alkyl), —(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), —O(C$_1$-C$_4$ alkyl), C$_1$-C$_4$ alkyl, C$_1$-C$_4$ haloalkyl; C$_1$-C$_4$ cyanoalkyl, C$_1$-C$_4$ aminoalkyl, C$_1$-C$_4$ hydroxyalkyl, and C$_2$-C$_4$ alkoxyalkyl;

each Q² is independently C$_{1-6}$ alkyl, C$_{3-7}$ cycloalkyl, C$_{6-10}$ aryl, 5-10 membered heteroaryl, or 4-7 membered heterocyclyl, or each Q², together with R, optionally and independently forms an optionally substituted, 4-7 membered heterocyclic ring; wherein said C$_{1-6}$ alkyl represented by Q² is optionally substituted with one or more substitutents independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl); and wherein each of said cycloalkyl, aryl, heteroaryl, and heterocyclyl groups represented by Q² is optionally and independently substituted with one or more substitutents independently selected from the group consisting of halogen, oxo, —CN, —OH, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), —O(C$_1$-C$_4$ alkyl), C$_1$-C$_4$ alkyl, C$_1$-C$_4$ haloalkyl; C$_1$-C$_4$ cyanoalkyl, C$_1$-C$_4$ aminoalkyl, C$_1$-C$_4$ hydroxyalkyl, and C$_2$-C$_4$ alkoxyalkyl;

each of R² and R³ is independently —H, halogen, or optionally substituted C$_{1-6}$ aliphatic; or optionally R² and R³, together with the carbon atom to which they are attached, form an optionally substituted C$_{3-6}$ cycloalkyl ring; and R⁶ is optionally substituted —H, optionally substituted C$_{1-6}$ alkyl, or optionally substituted C$_{3-6}$ cycloalkyl.

30. The method of claim 29, wherein R⁶ is C$_{5-6}$ cycloalkyl.

31. The method of claim 30, wherein:
i) R² is —H or C$_{1-3}$ alkyl; and R³ is C$_{1-3}$ alkyl; or
ii) R² and R³ together with the atom to which they are bound form a C$_{3-6}$ cycloalkyl ring.

32. The method of any one of claims 29-31, wherein phenyl ring A is substituted with one or more substituents independently selected from the group consisting of —C(O)N(R)H, —C(O)N(R)Q², —N(R)C(O)Q², —CO$_2$H, —CO$_2$Q², —OC(O)Q², —N(R)CO$_2$Q², —OC(O)N(R)Q², and —N(R)C(O)N(R)Q²; and optionally further substituted with one or one or more substituents independently selected from the group consisting of halogen, —CN, —OH, —NH$_2$, —NH(C$_1$-C$_4$ alkyl), —N(C$_1$-C$_4$ alkyl)$_2$, —O(C$_1$-C$_4$ alkyl), C$_1$-C$_4$ alkyl, C$_1$-C$_4$ haloalkyl; C$_1$-C$_4$ cyanoalkyl, C$_1$-C$_4$ aminoalkyl, C$_1$-C$_4$ hydroxyalkyl, and C$_2$-C$_4$ alkoxyalkyl.

33. The method of claim 32, wherein phenyl ring A is substituted with —OC(O)Q², —C(O)N(R)Q², or —N(R)C(O)Q², and optionally further substituted with one or one or more substituents independently selected from the group consisting of halogen, —CN, —OH, —NH$_2$, —NH(C$_1$-C$_4$ alkyl), —N(C$_1$-C$_4$ alkyl)$_2$, —O(C$_1$-C$_4$ alkyl), C$_1$-C$_4$ alkyl, C$_1$-C$_4$ haloalkyl; C$_1$-C$_4$ cyanoalkyl, C$_1$-C$_4$ aminoalkyl, C$_1$-C$_4$ hydroxyalkyl, and C$_2$-C$_4$ alkoxyalkyl.

34. The method of claim 1, wherein the compound of Formula (I) is represented by any one of the following structural formulae:

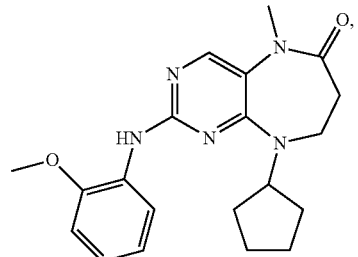

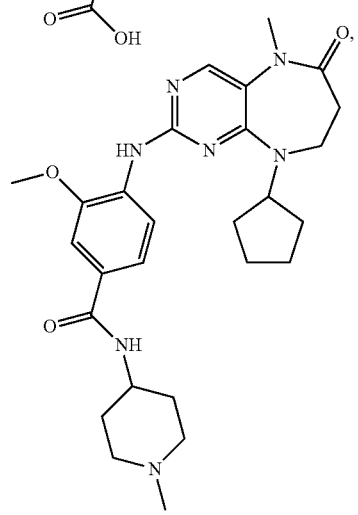

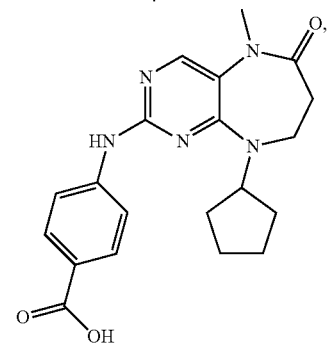

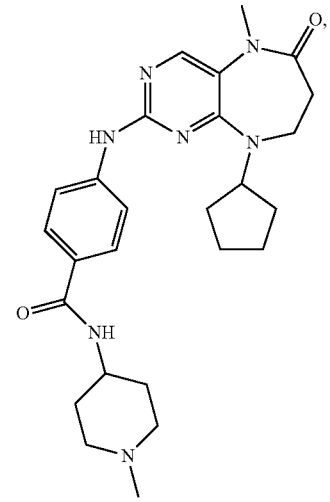

143
-continued
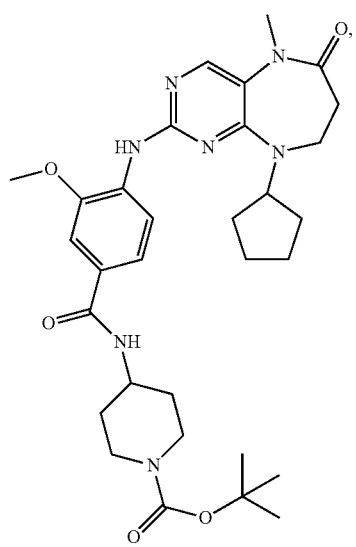
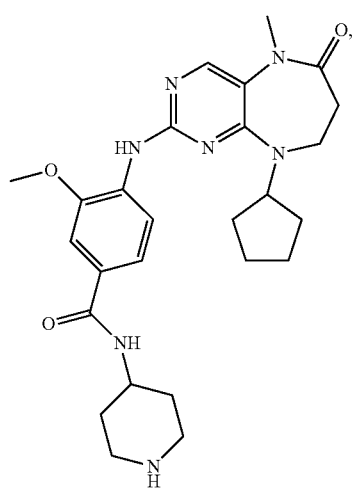
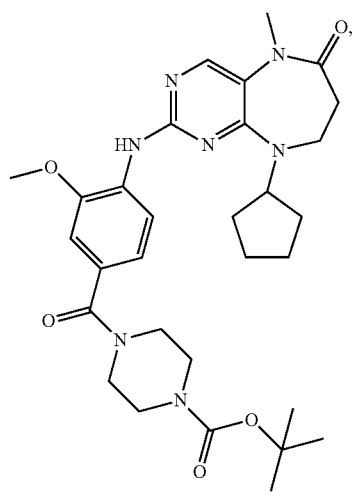
144
-continued
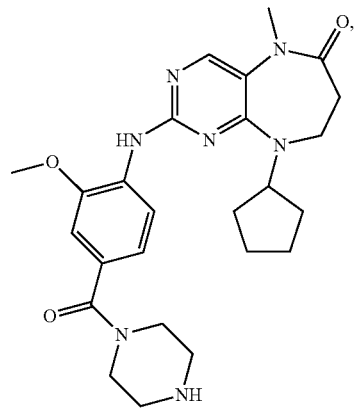
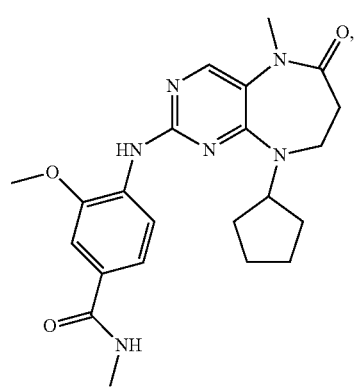
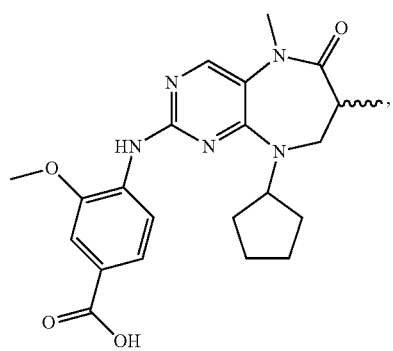
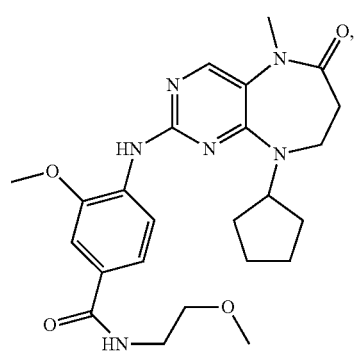

145
-continued
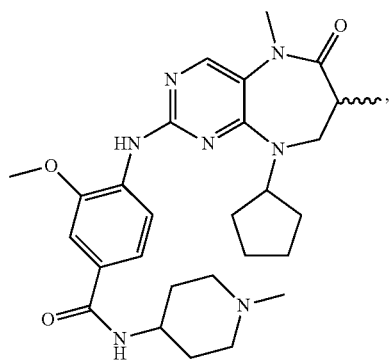
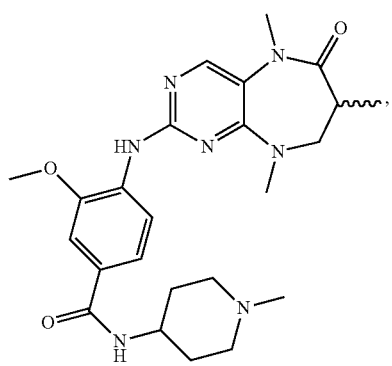
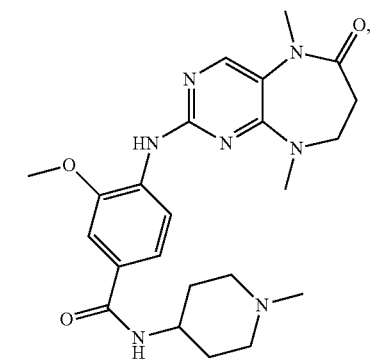
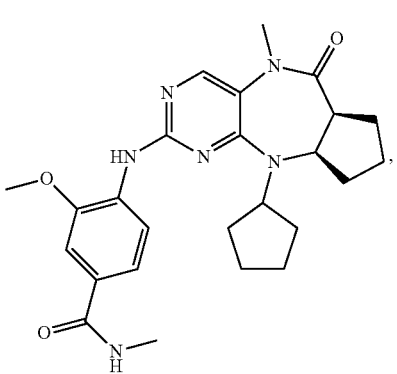
146
-continued
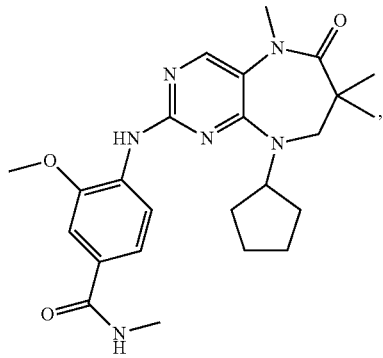
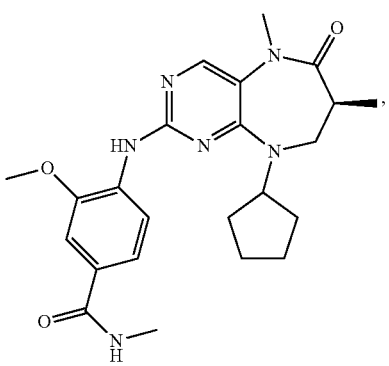
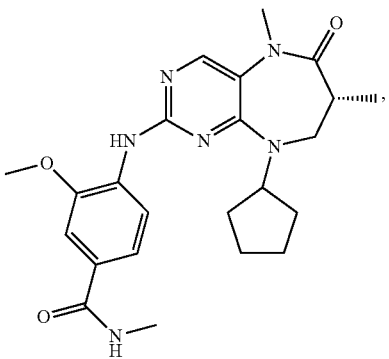
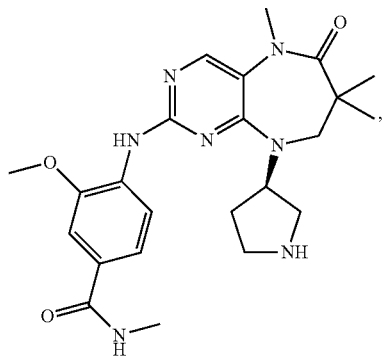

147
-continued

148
-continued

149
-continued
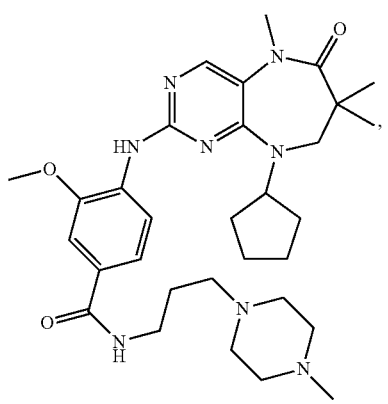
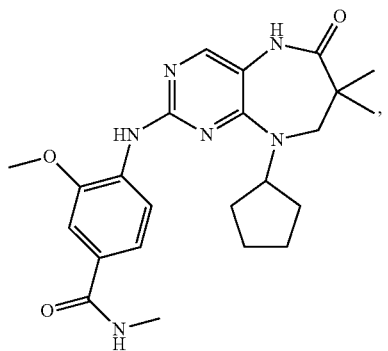
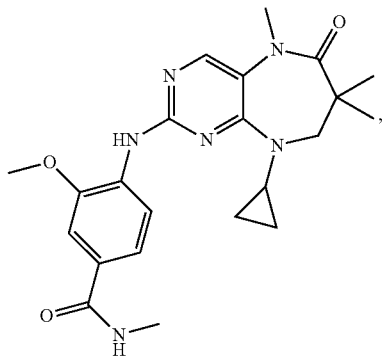
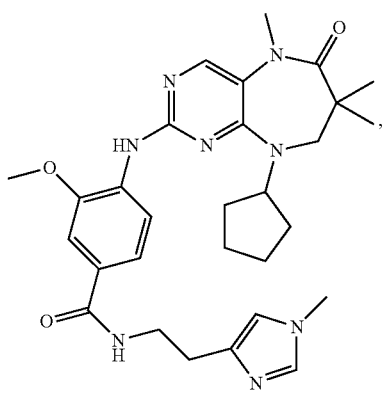
150
-continued
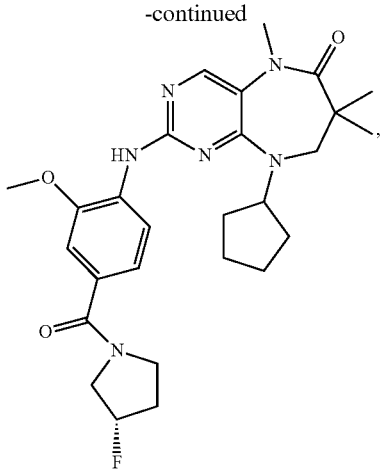
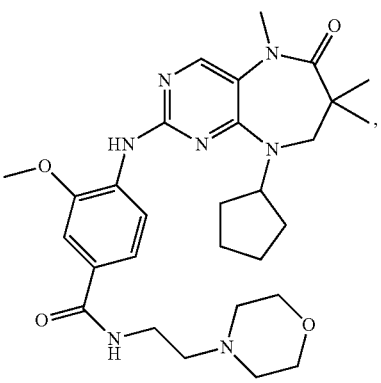
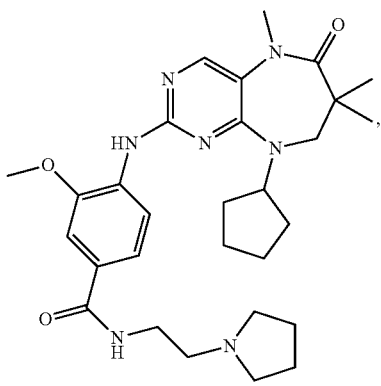
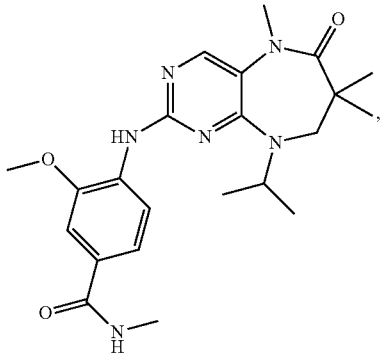

151
-continued
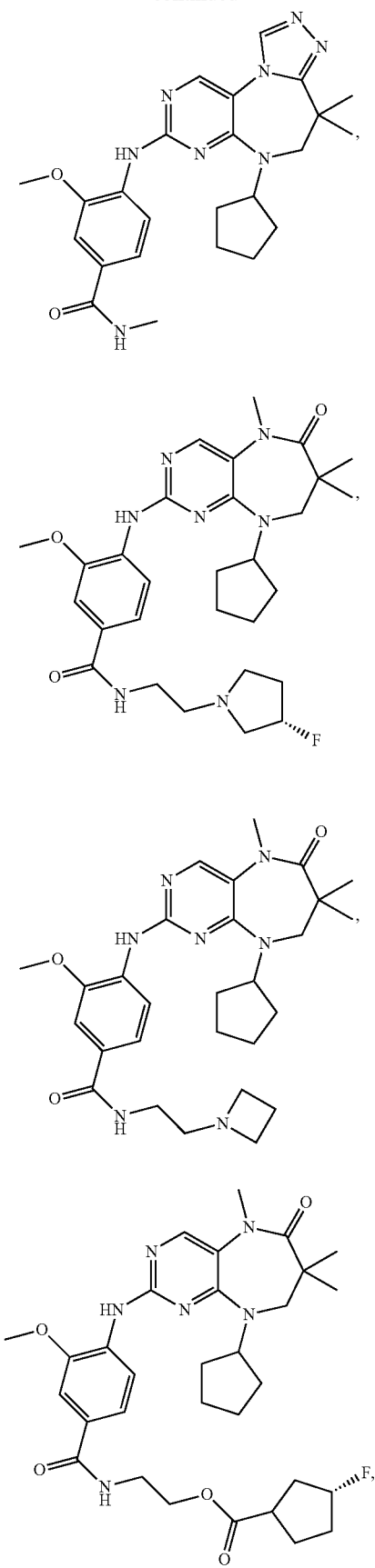
152
-continued
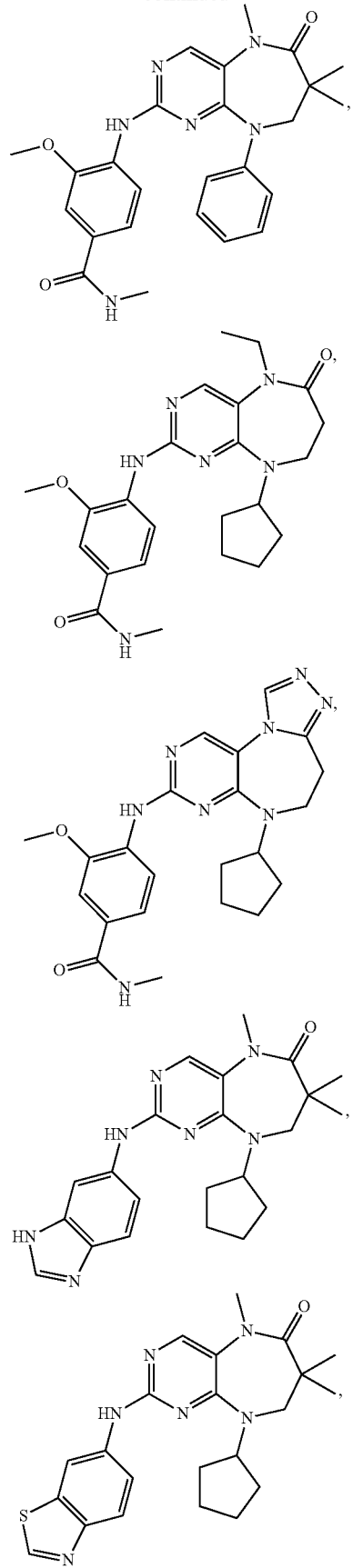

153
-continued
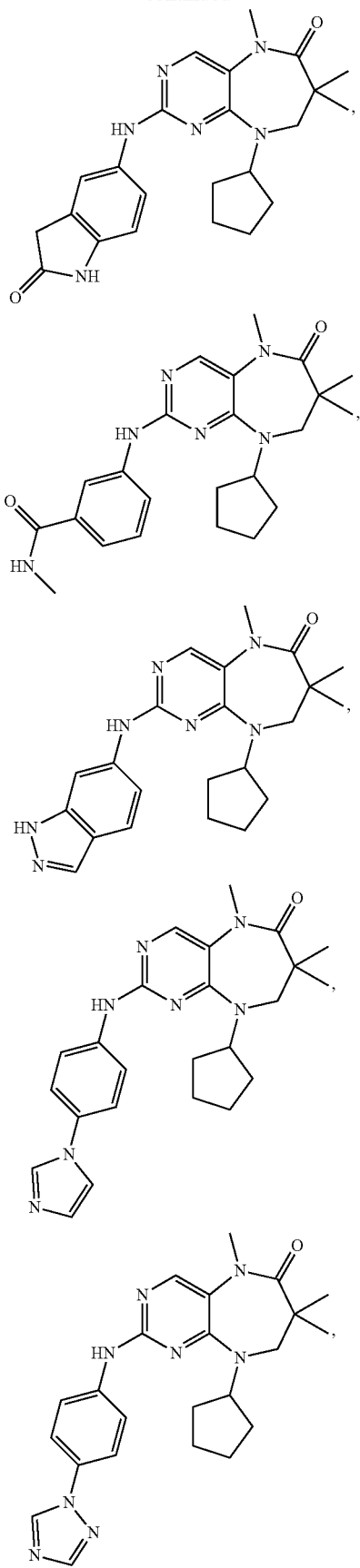
154
-continued
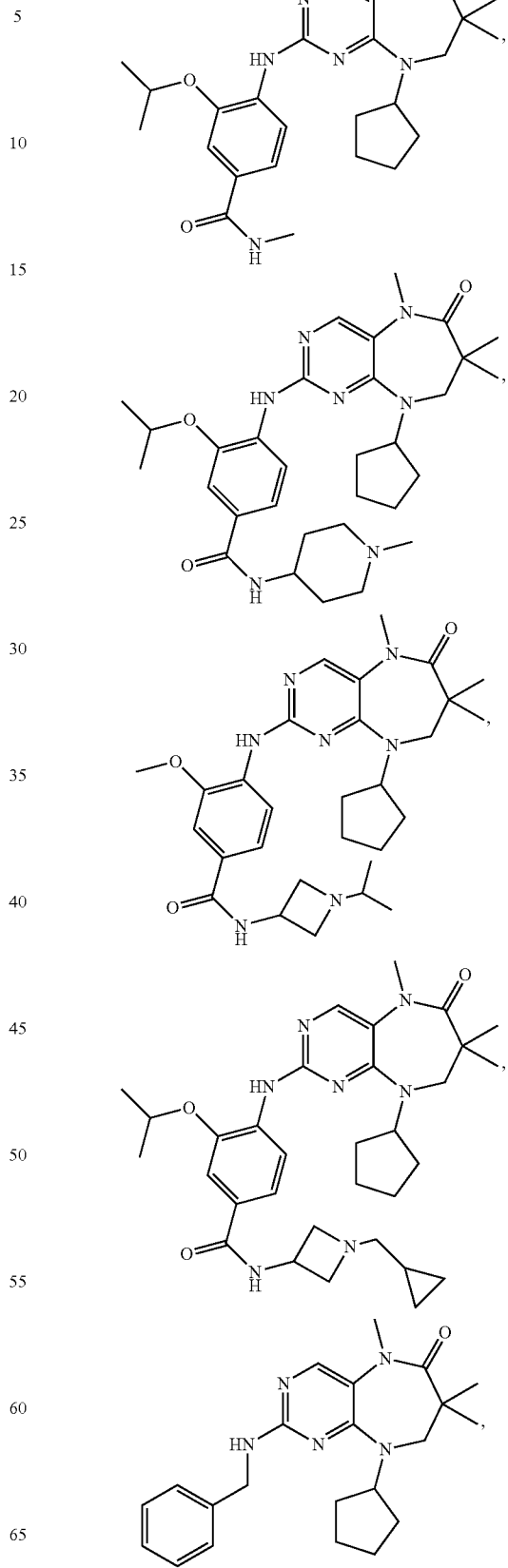

155
-continued
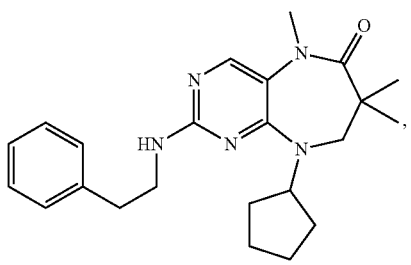
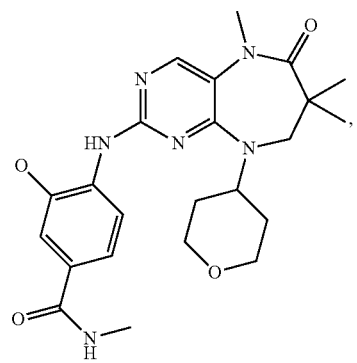
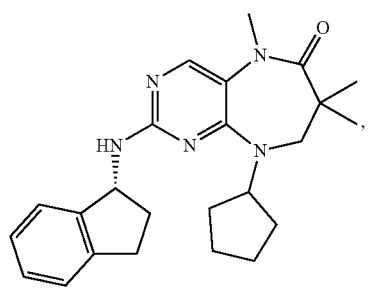
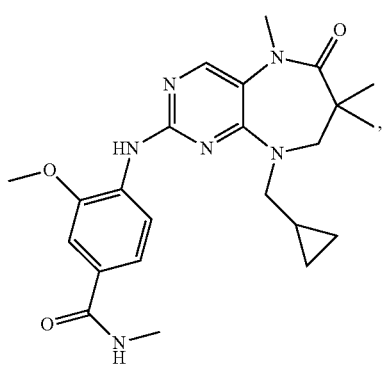
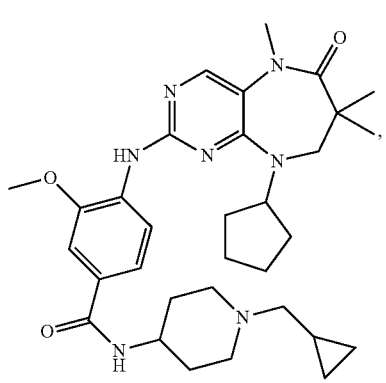
156
-continued
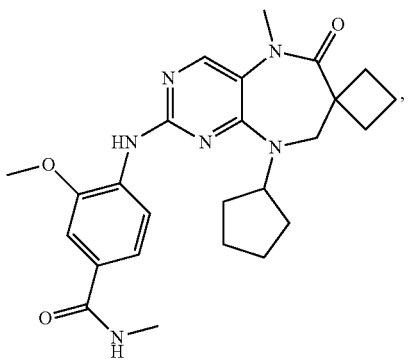
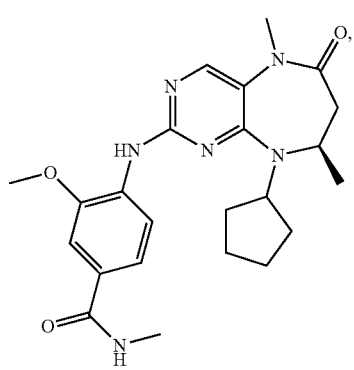
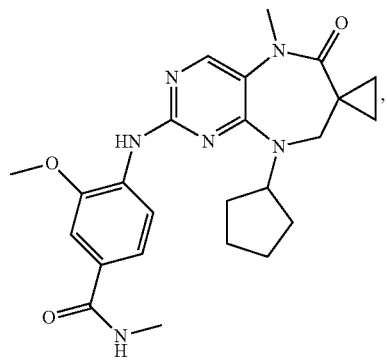
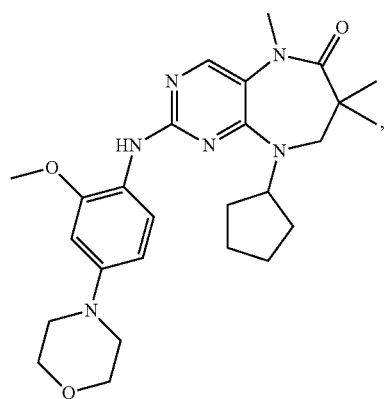

157
-continued
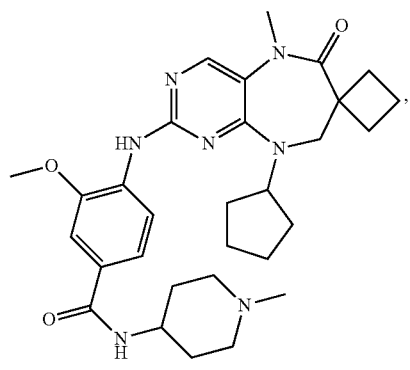
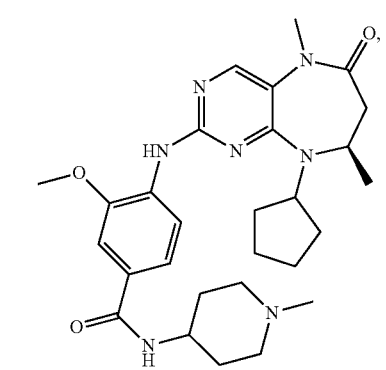
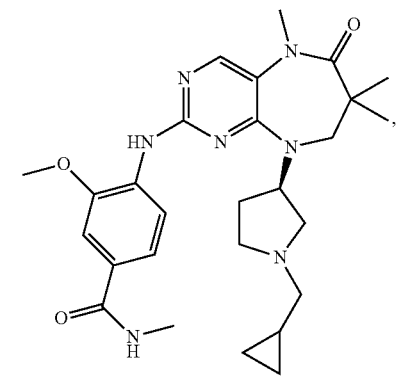
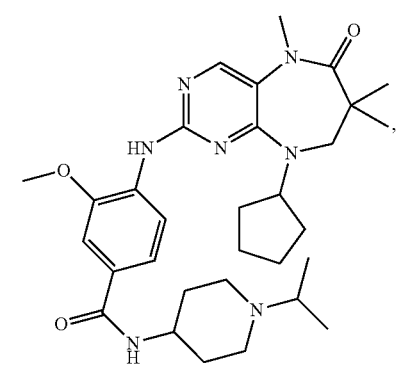
158
-continued
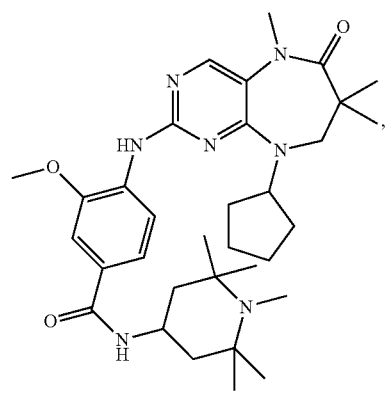
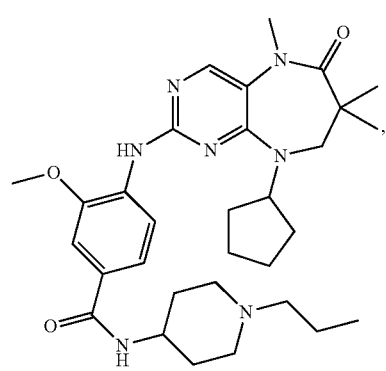
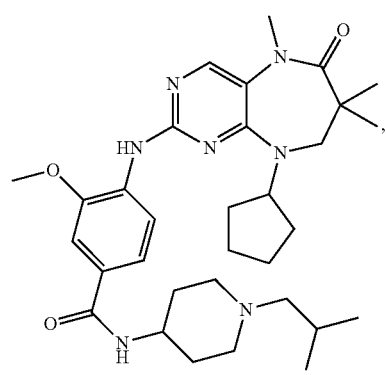
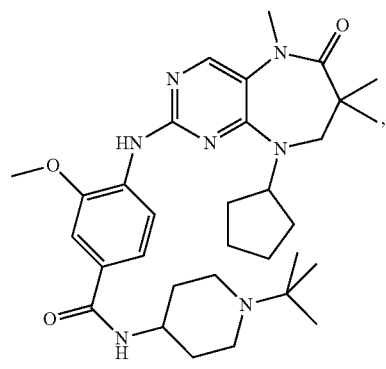

159
-continued
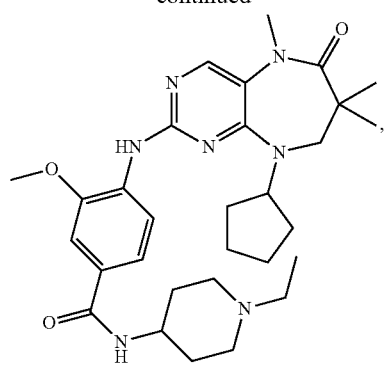
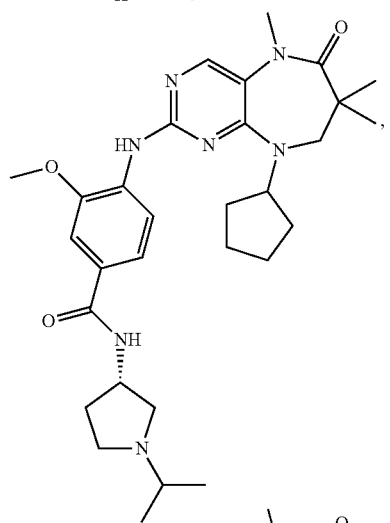
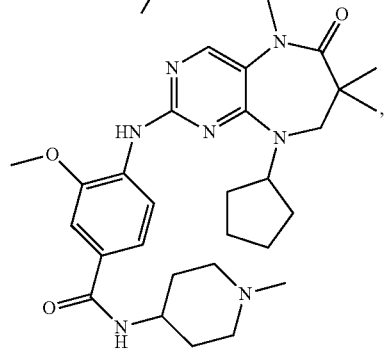
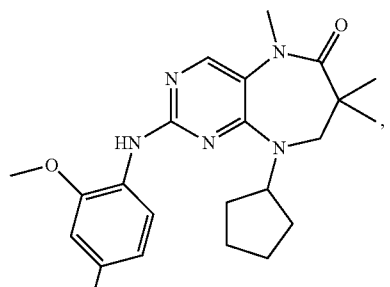
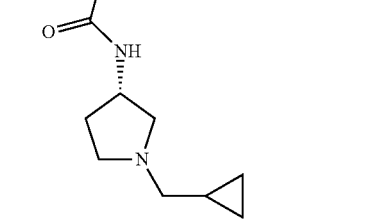
160
-continued
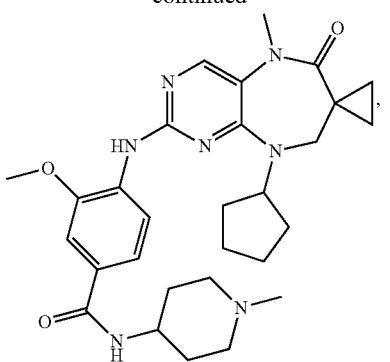
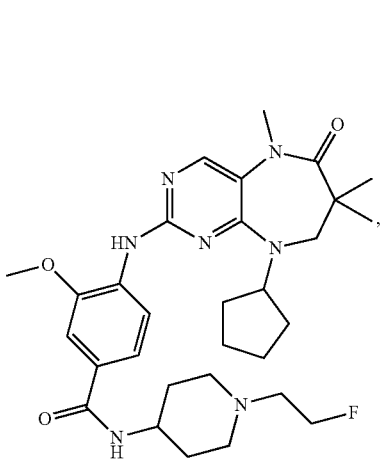
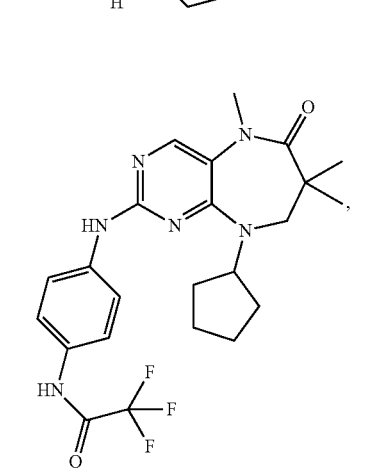
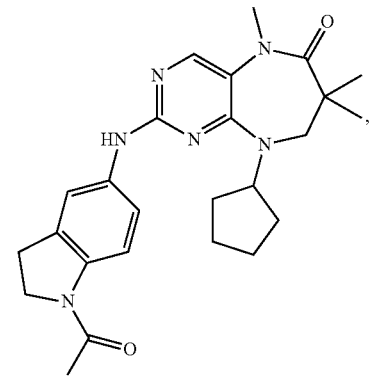

161
-continued
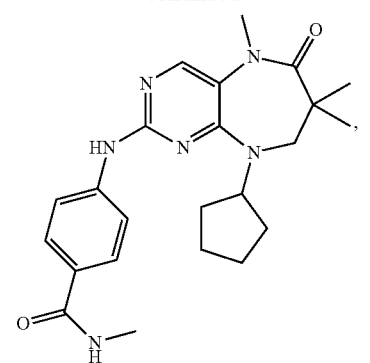
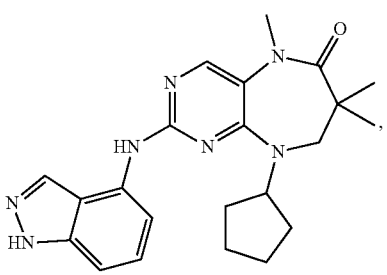
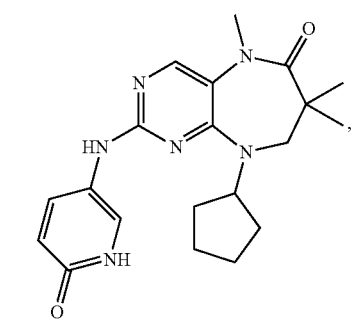
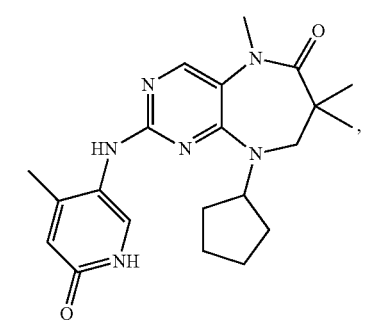
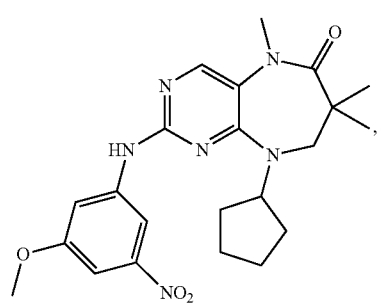
162
-continued
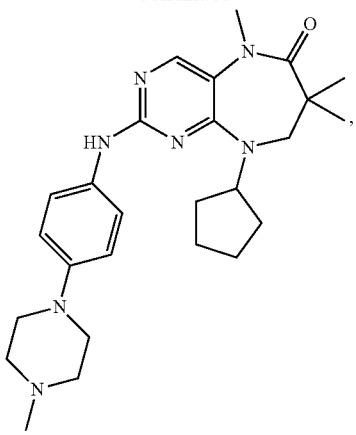
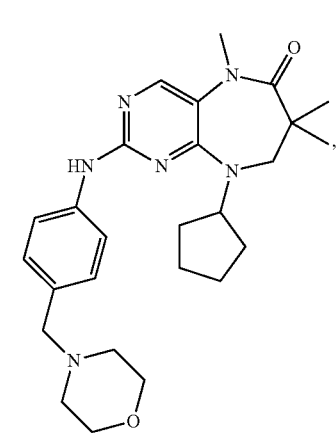
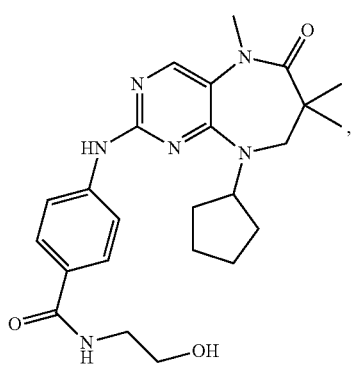
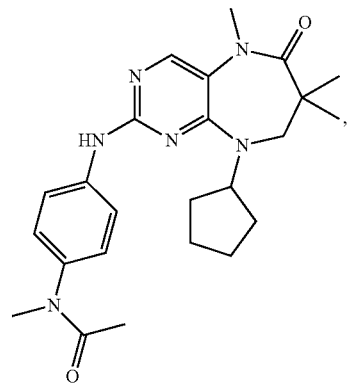

163
-continued
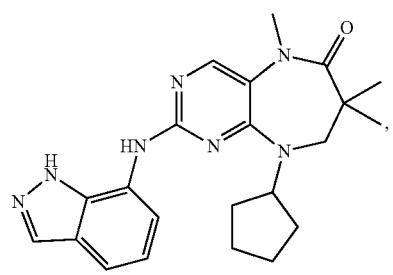
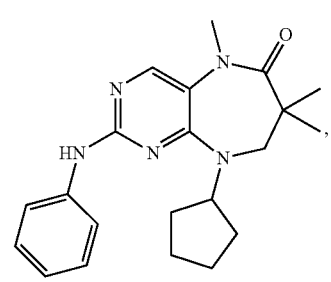
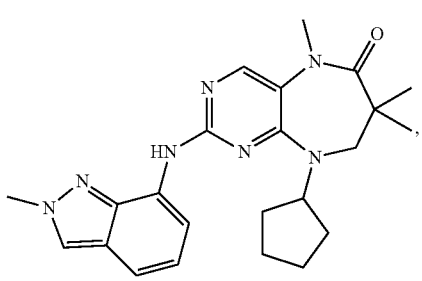
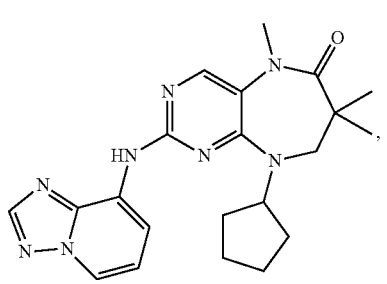
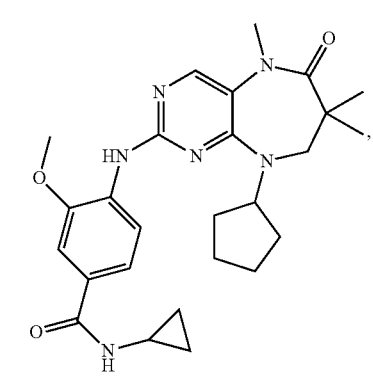
164
-continued
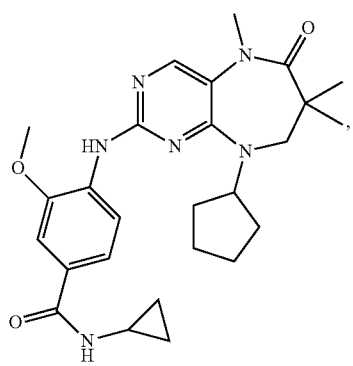
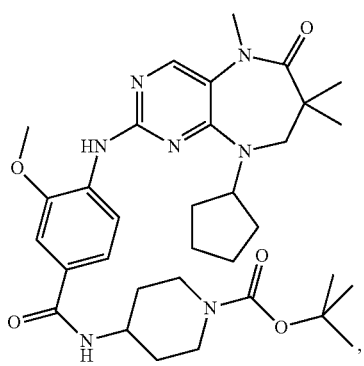
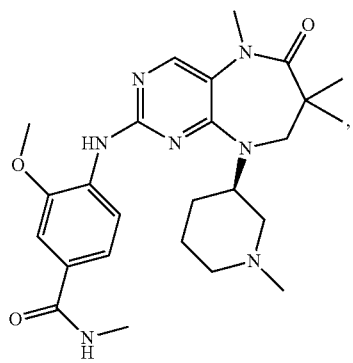
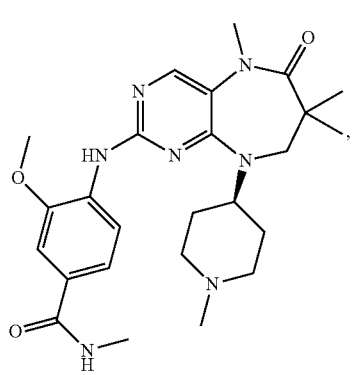

165
-continued
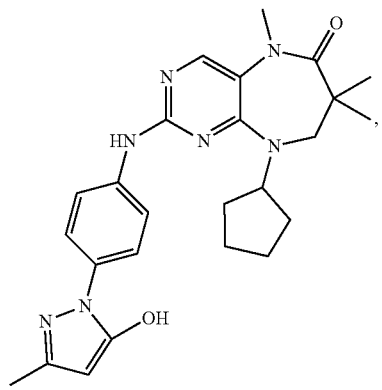
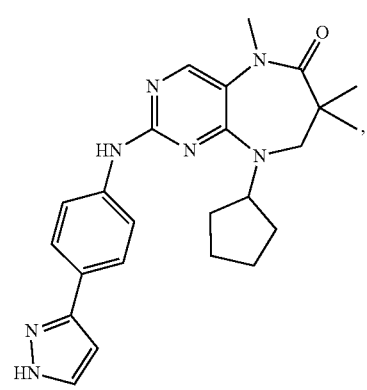
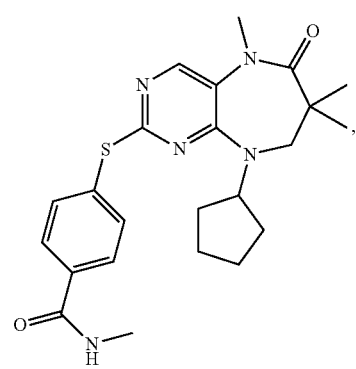
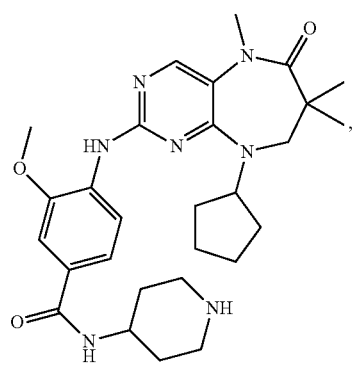
166
-continued
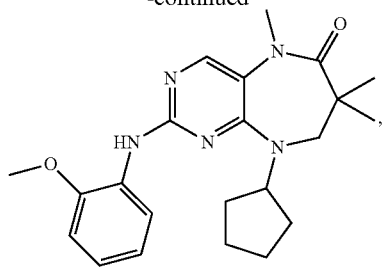
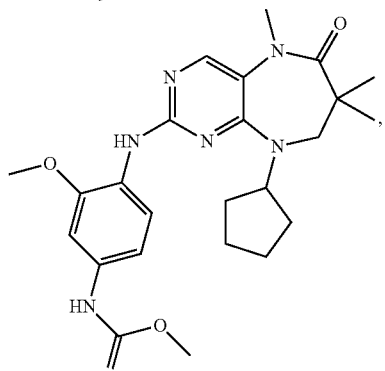
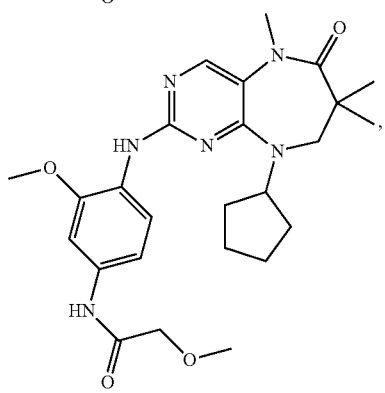
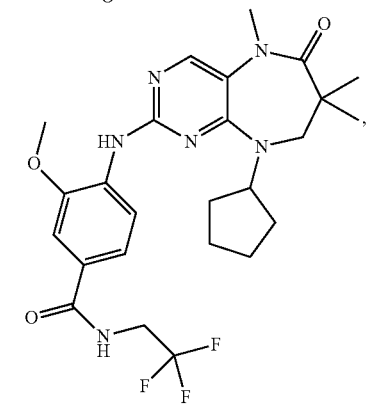
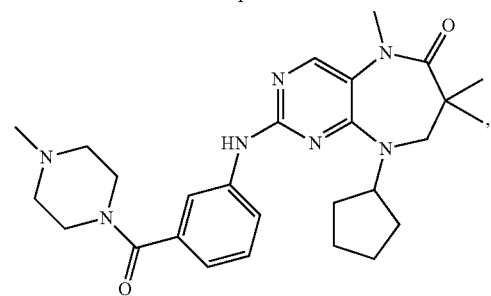

167
-continued
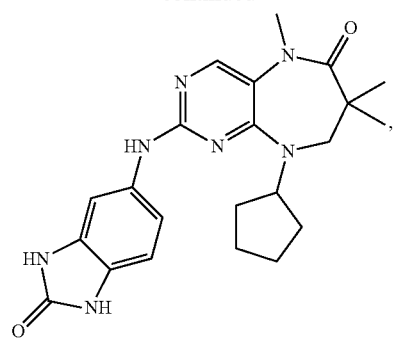
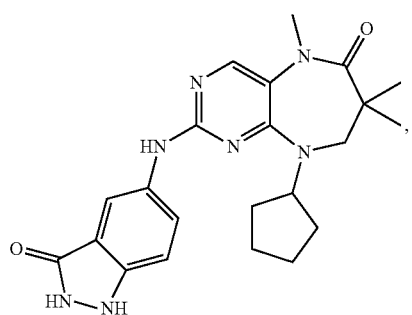
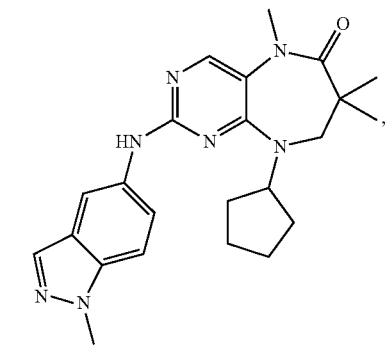
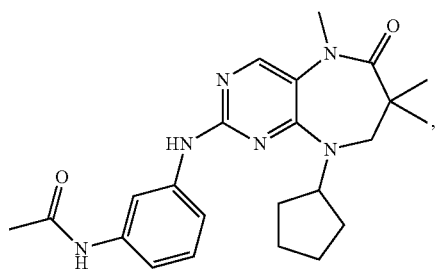
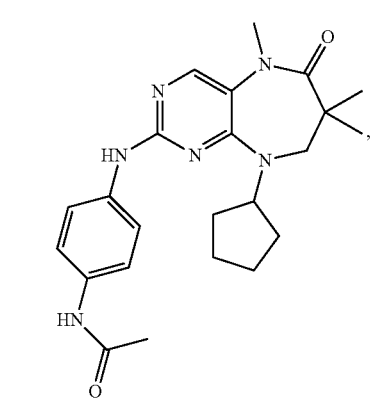
168
-continued
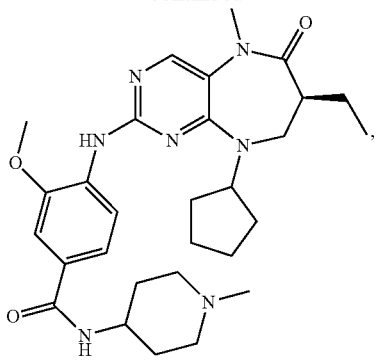
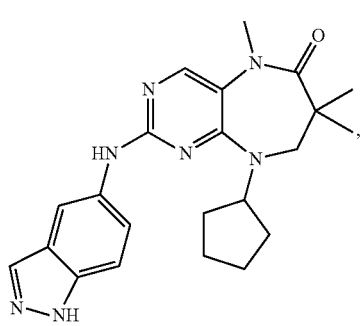
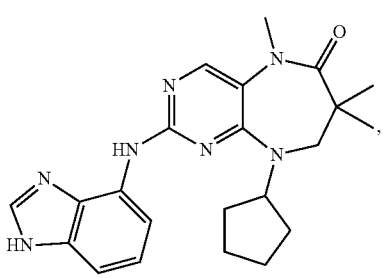
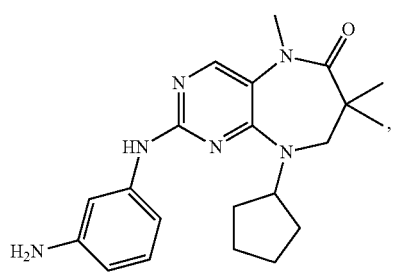
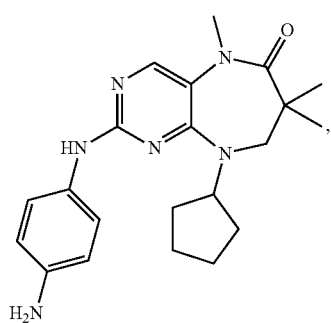

169
-continued
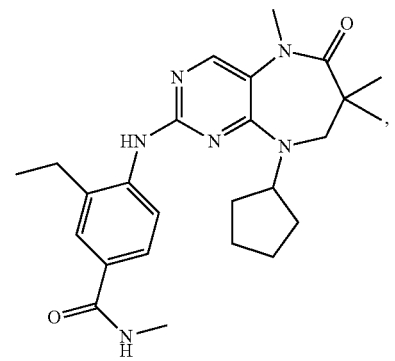
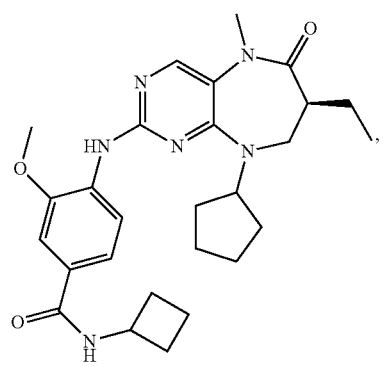
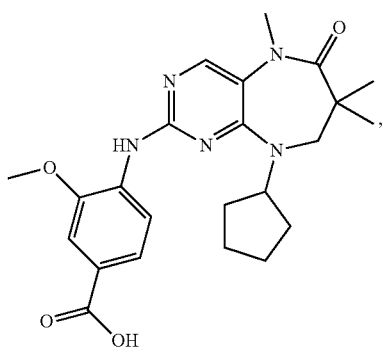
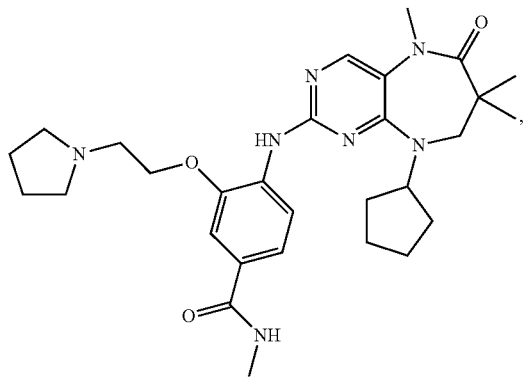
170
-continued
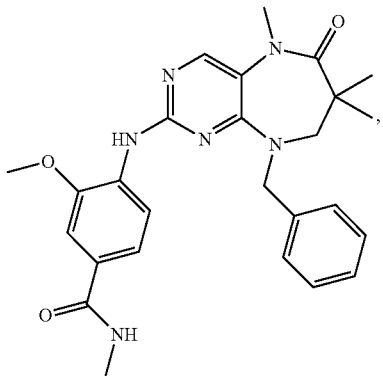
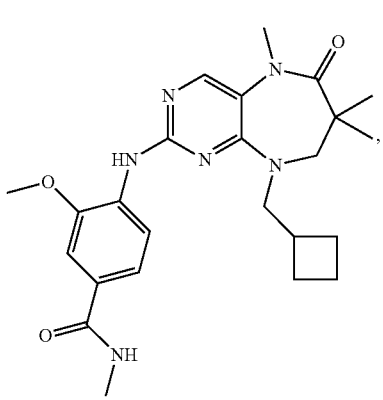
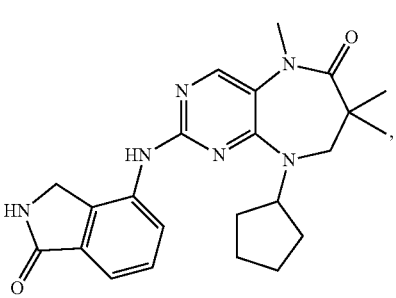
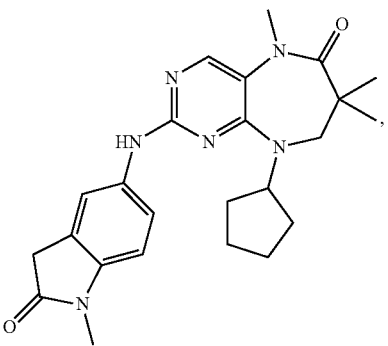

171
-continued
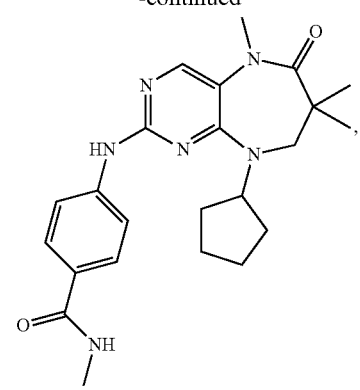
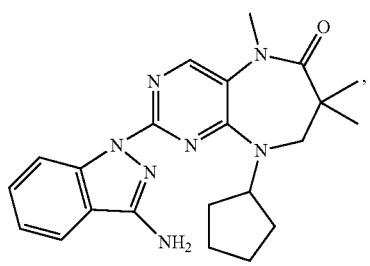
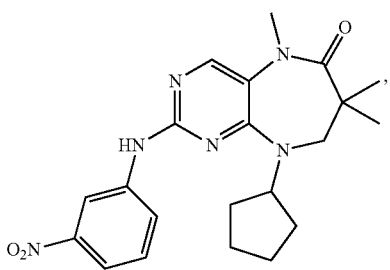
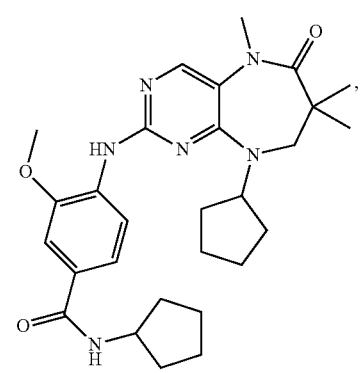
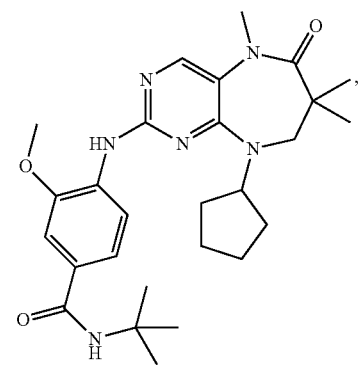
172
-continued
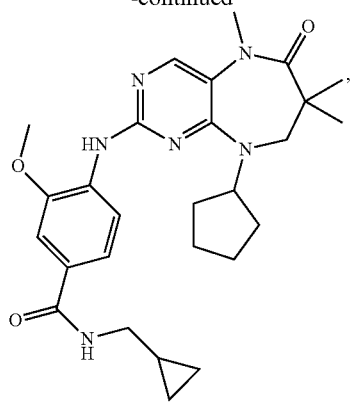
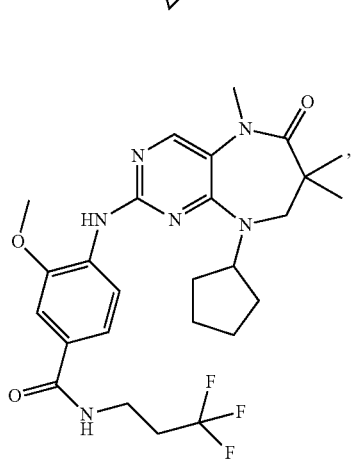
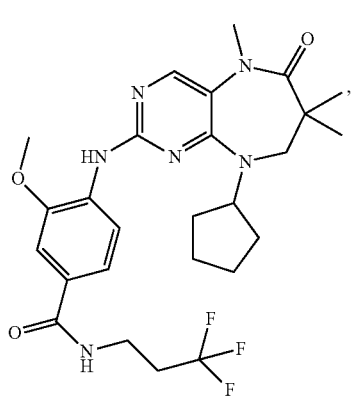
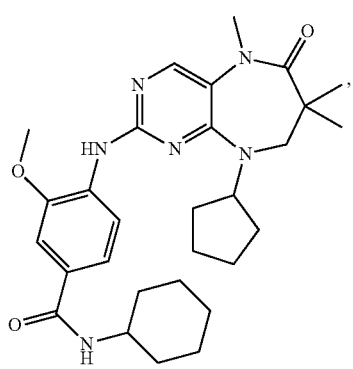
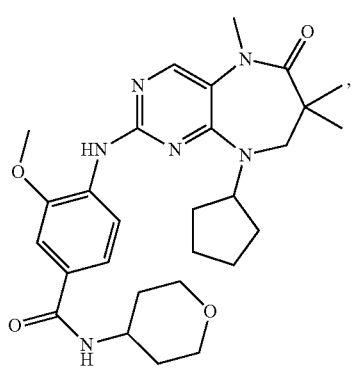

173
-continued
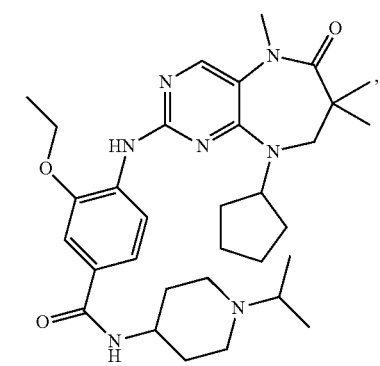
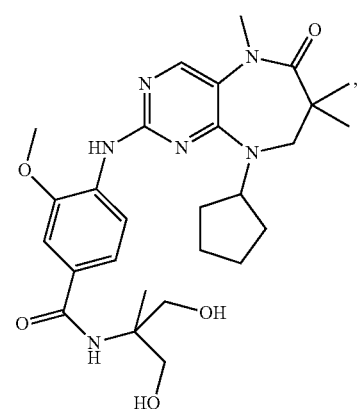
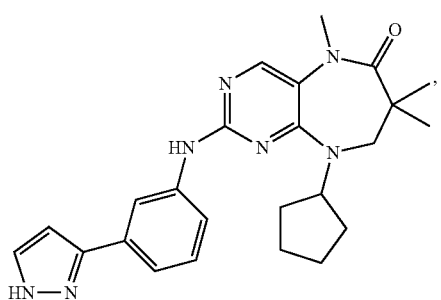
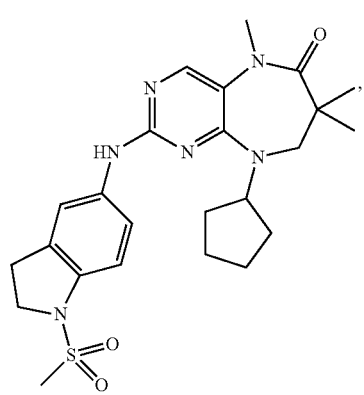
174
-continued
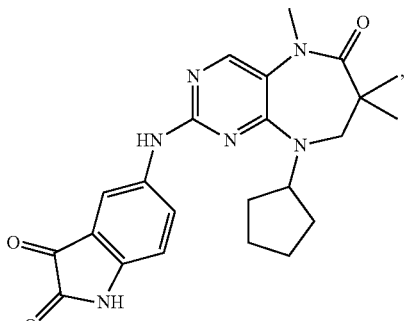
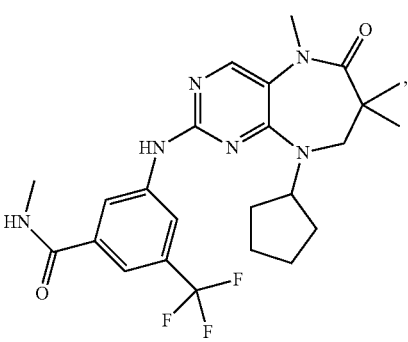
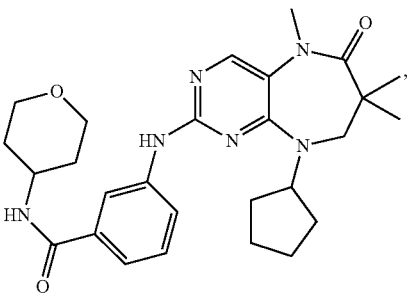
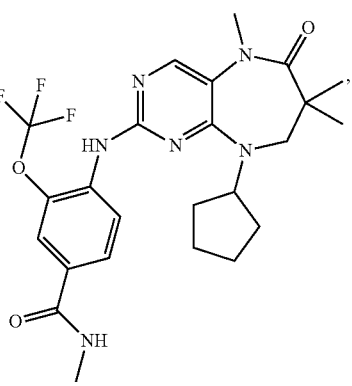

175
-continued
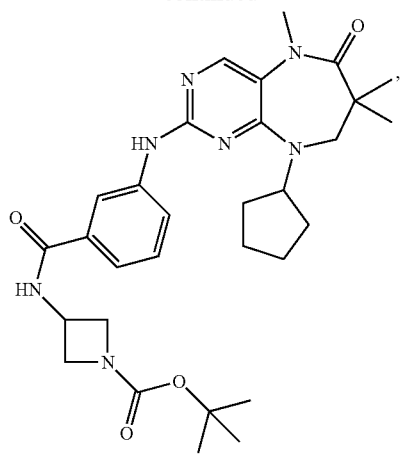
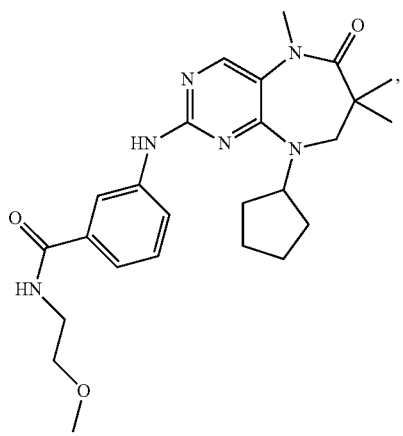
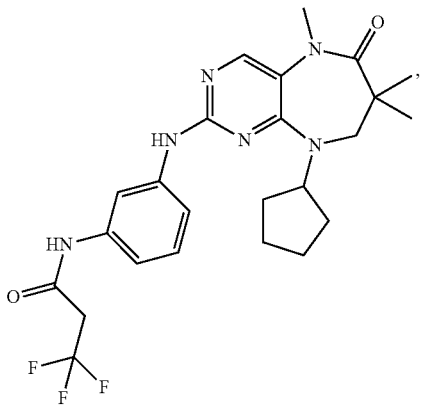
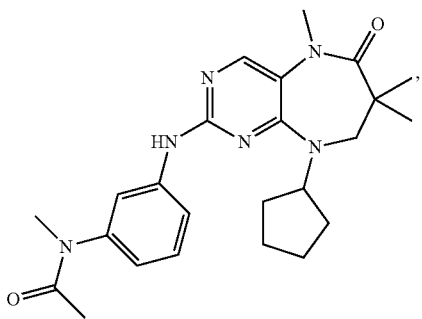
176
-continued
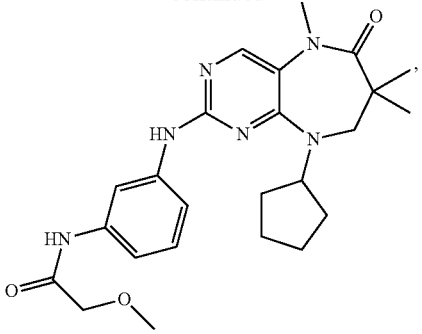
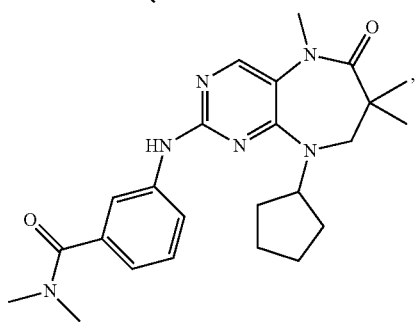
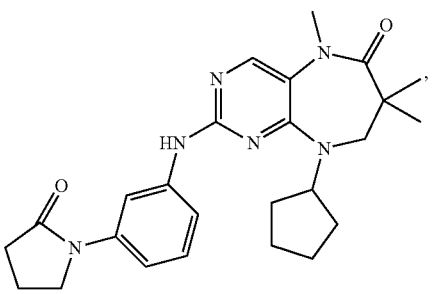
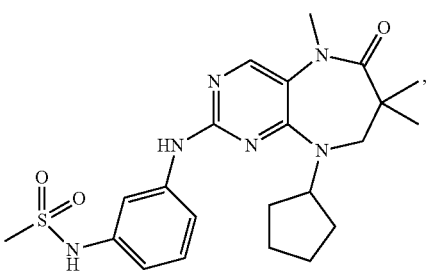
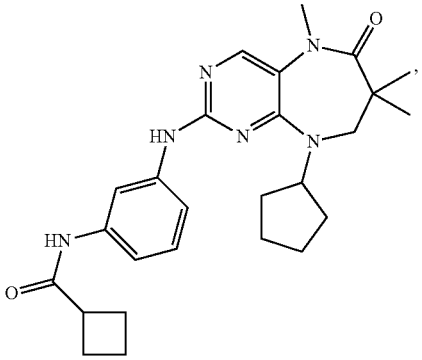

177
-continued
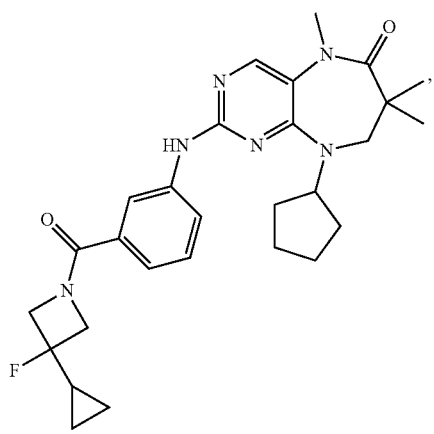
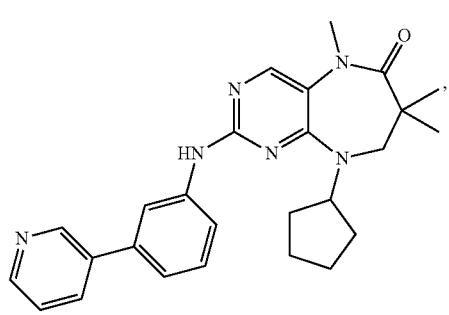
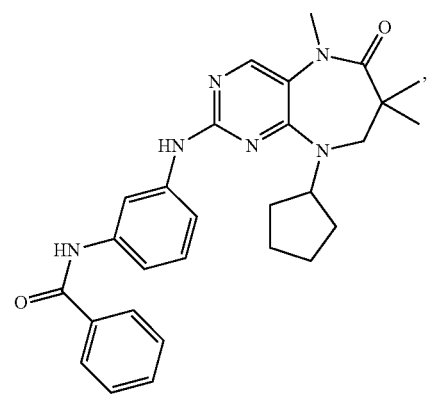
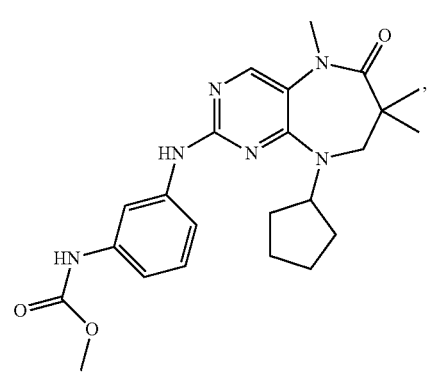
178
-continued
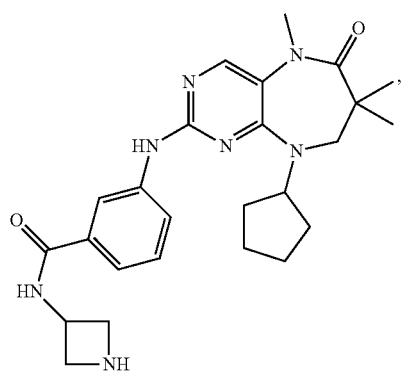
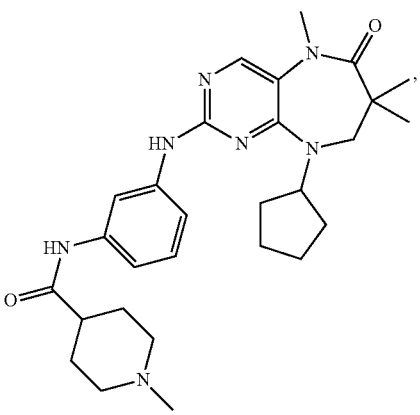
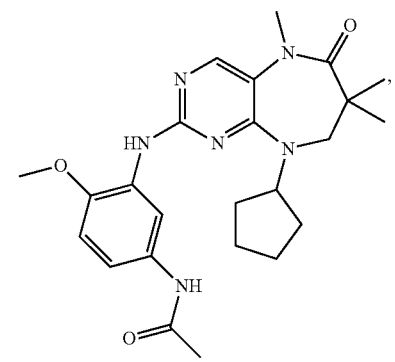
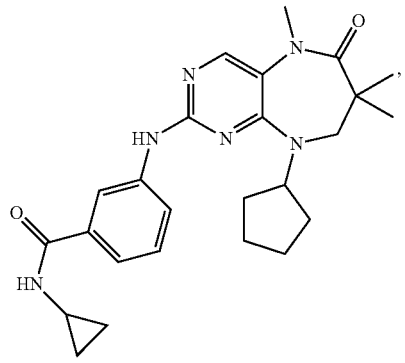

179
-continued
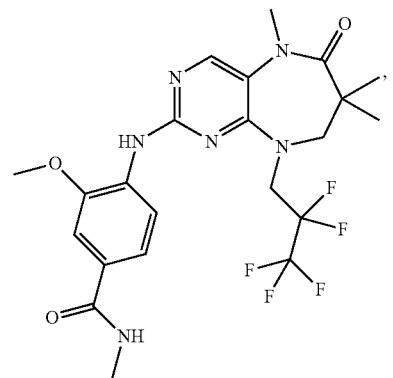
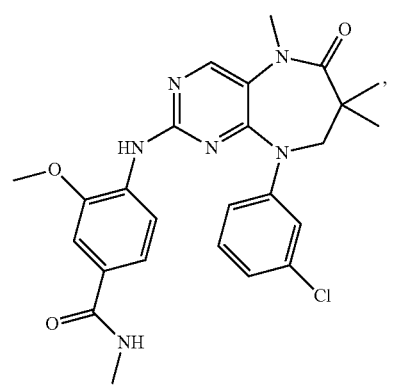
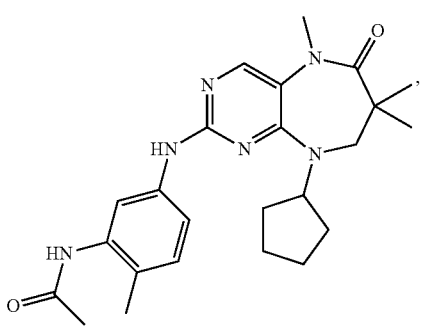
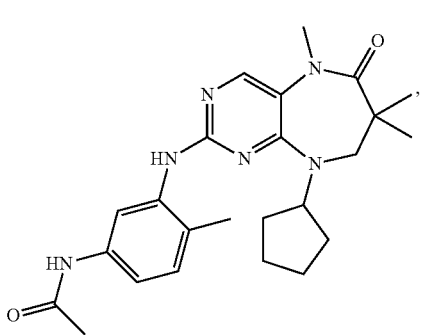
180
-continued
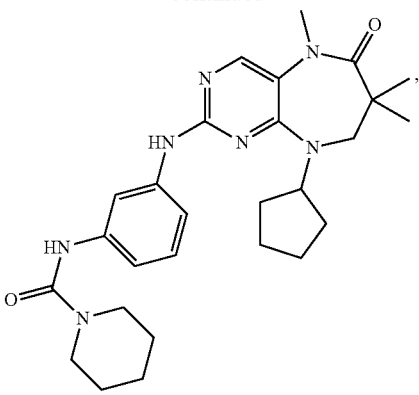
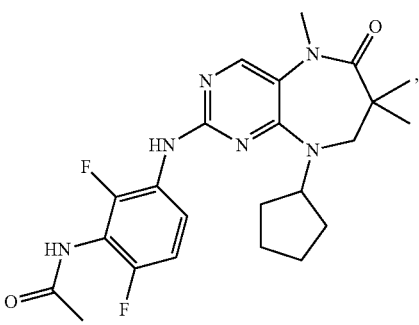
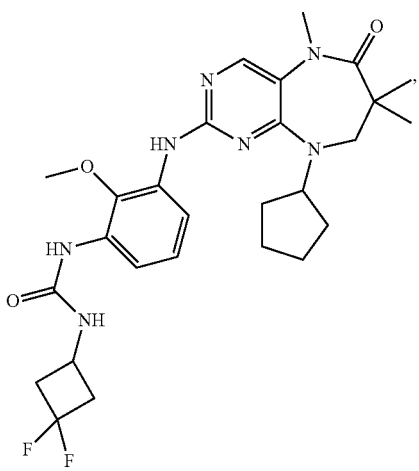
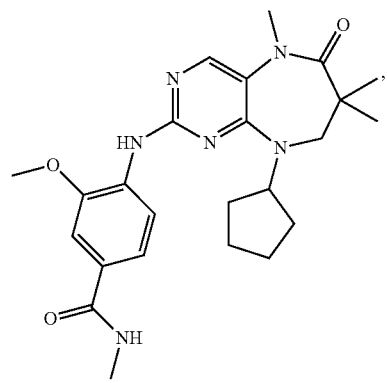

181
-continued
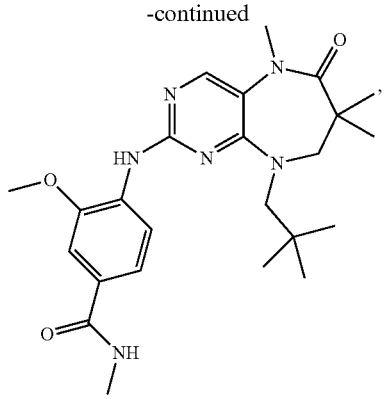
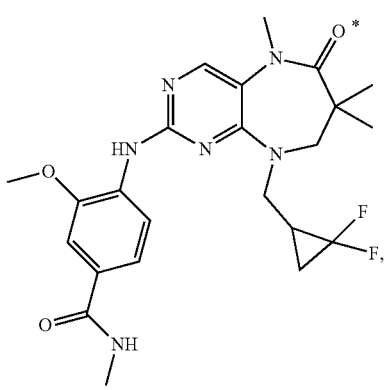
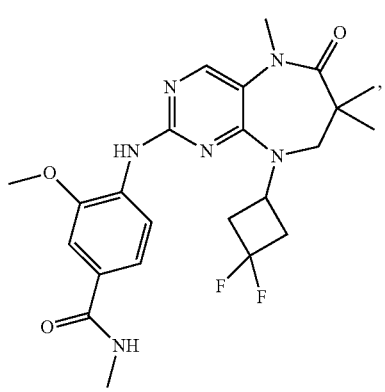
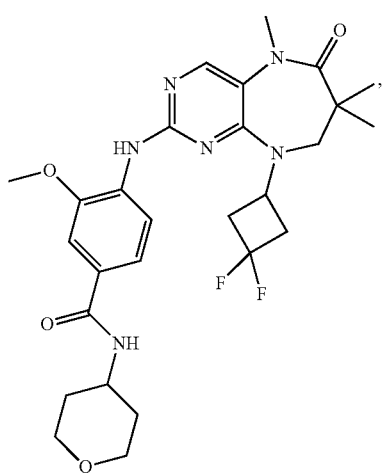
182
-continued
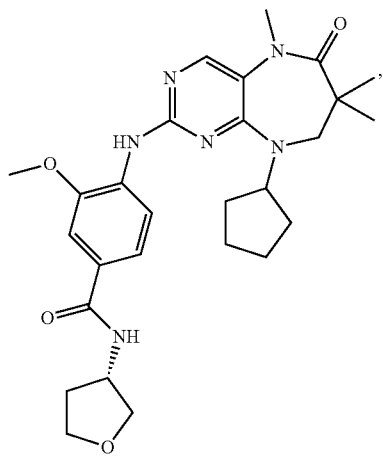
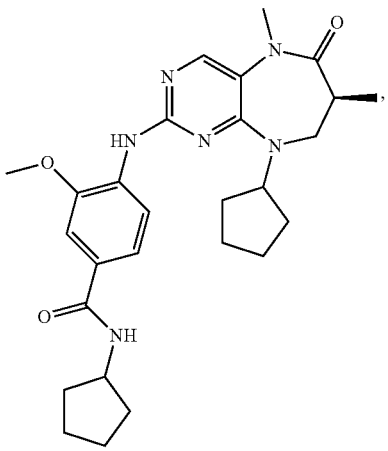
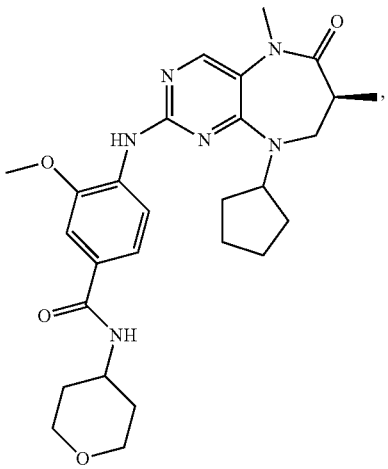

183
-continued
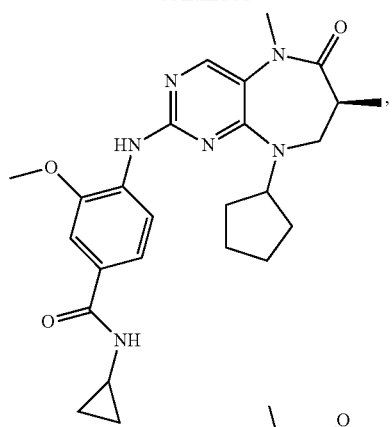
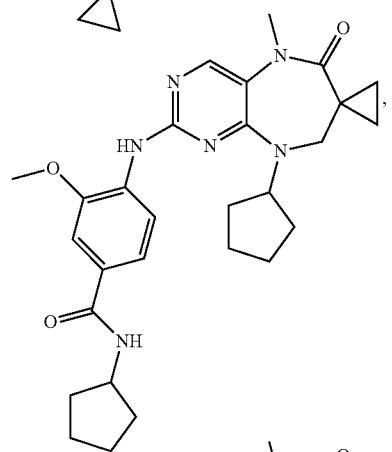
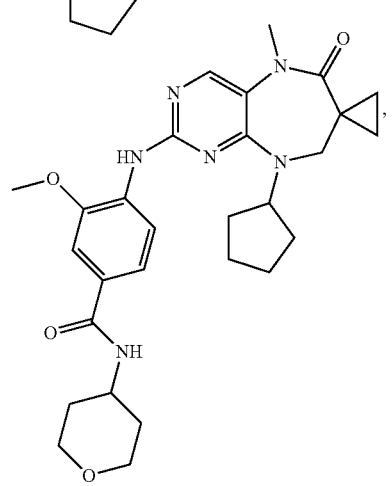
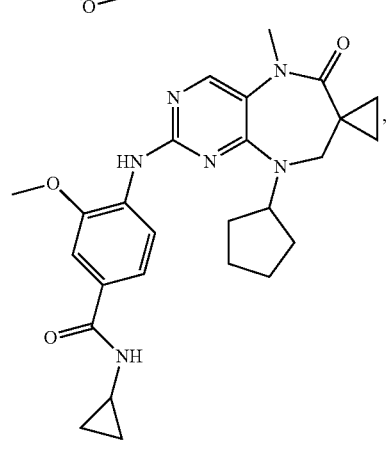
184
-continued
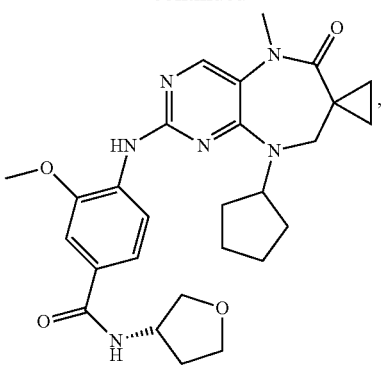
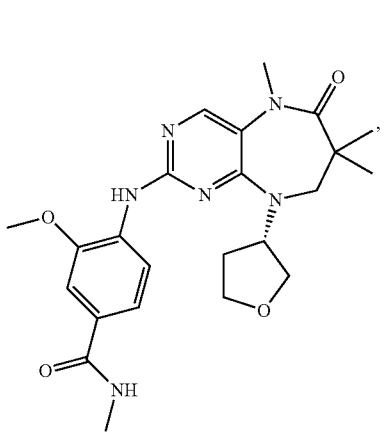
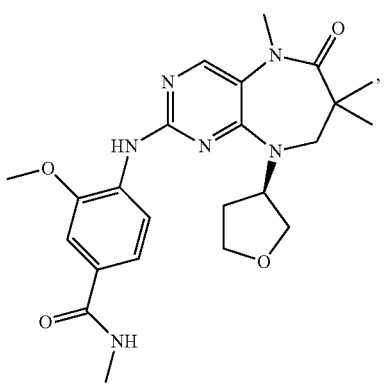
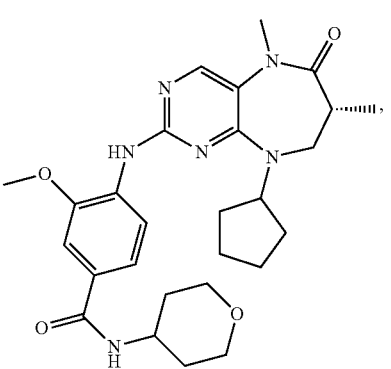

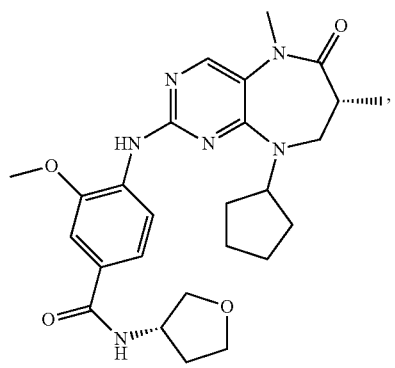
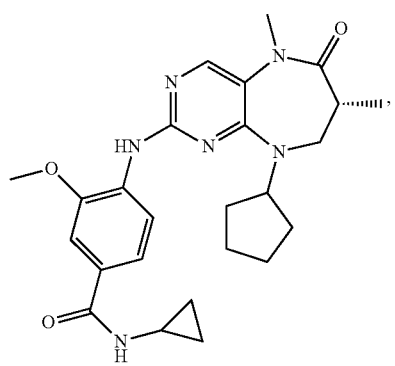
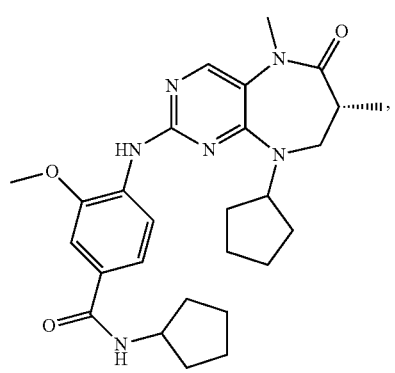
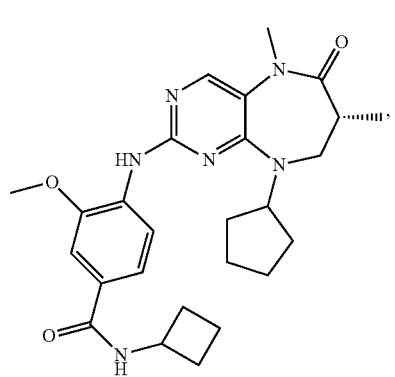
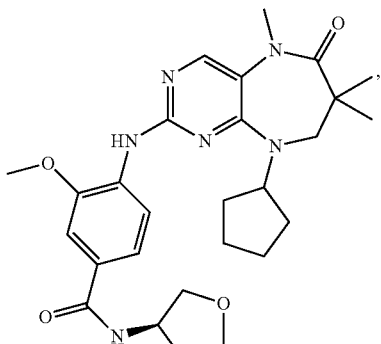
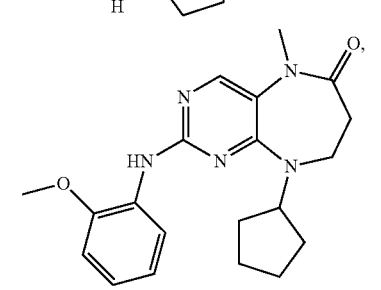
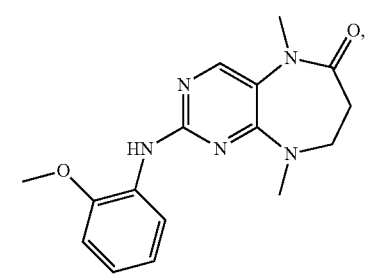
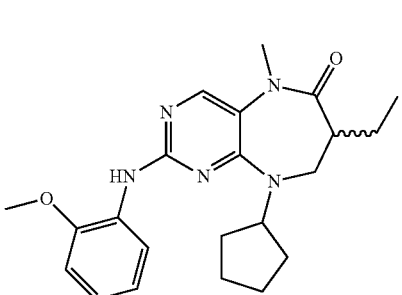
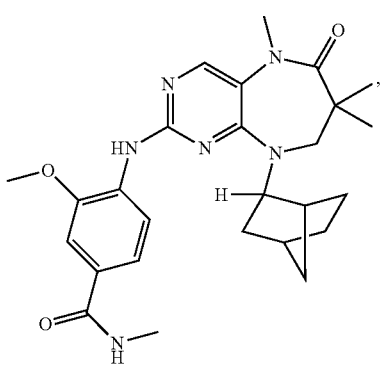

187
-continued
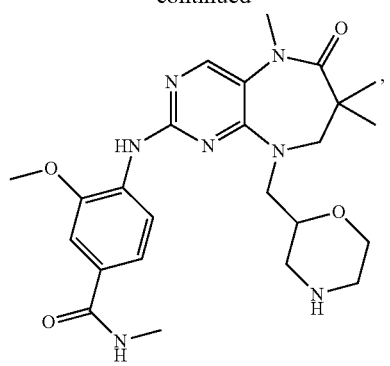
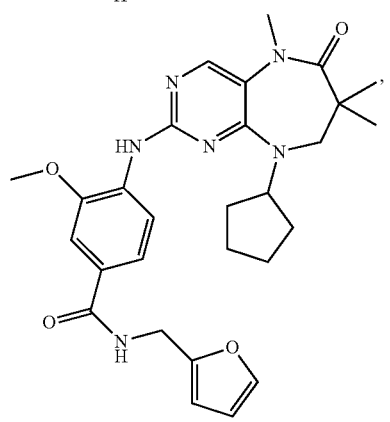
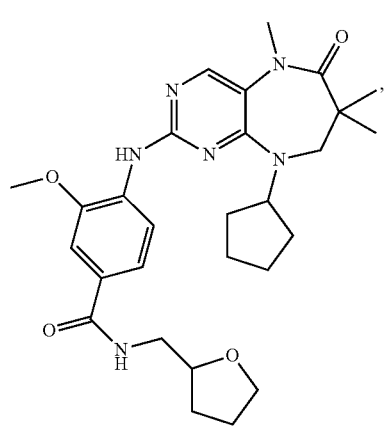
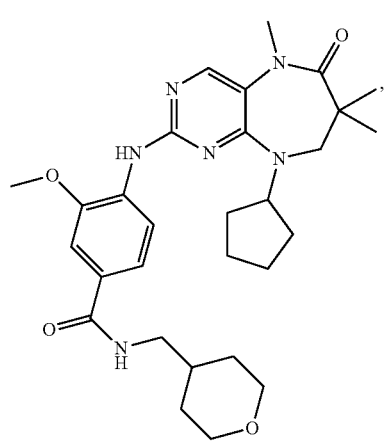
188
-continued
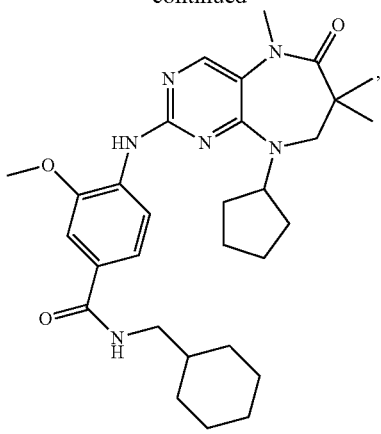
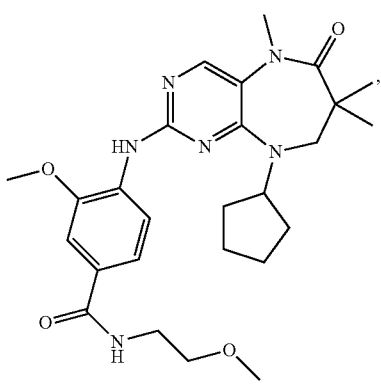
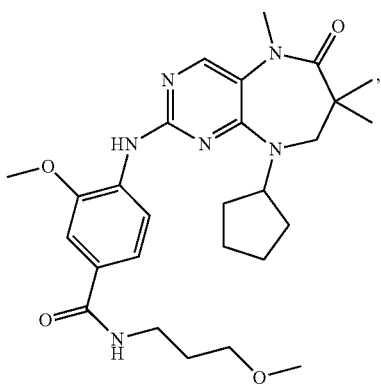
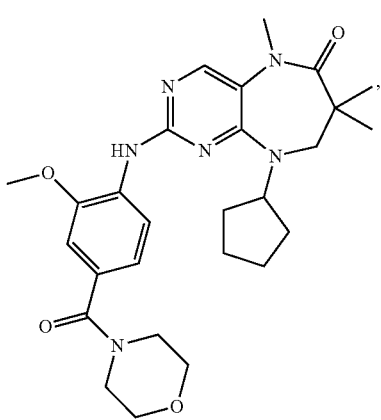

| 189 | 190 |
|---|---|
| -continued | -continued |
| 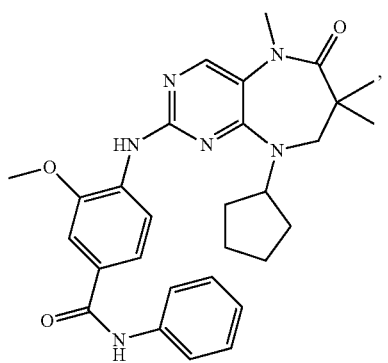 | 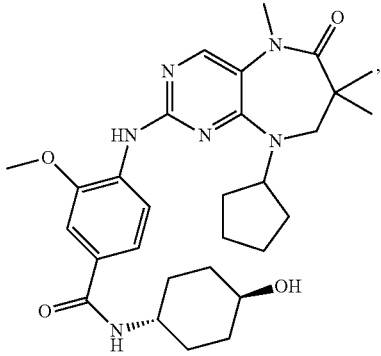 |
| 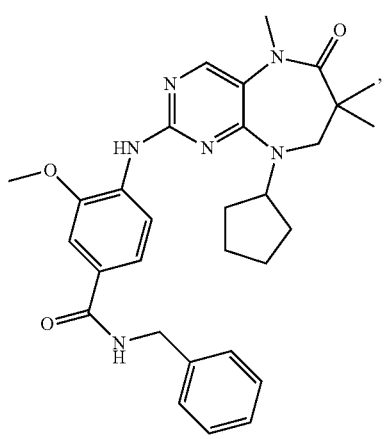 | 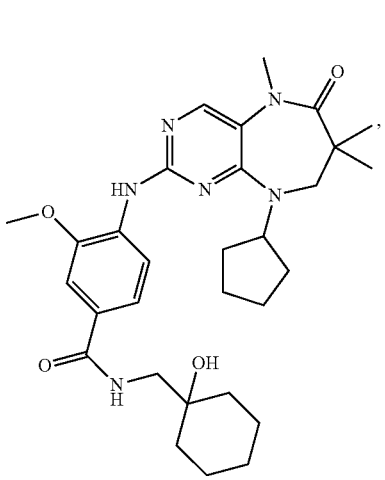 |
| 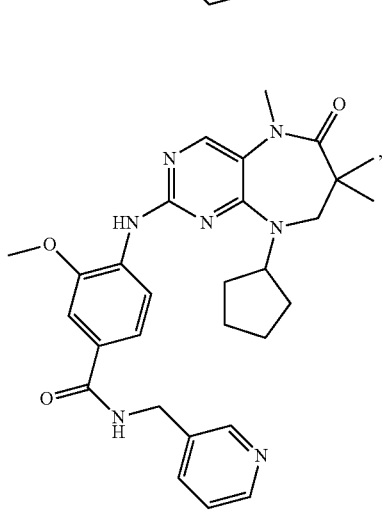 | 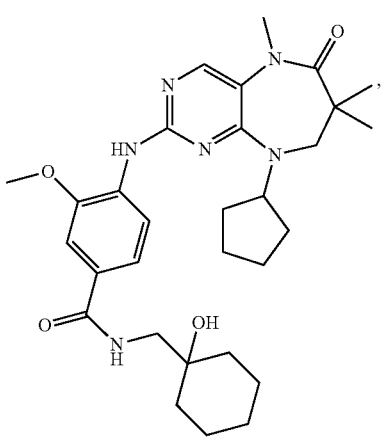 |
| 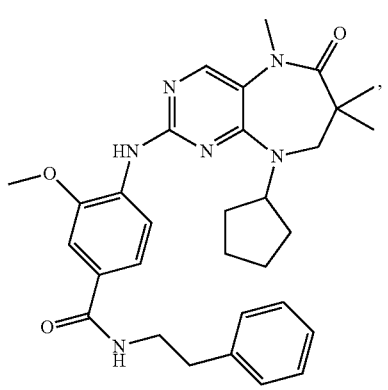 | 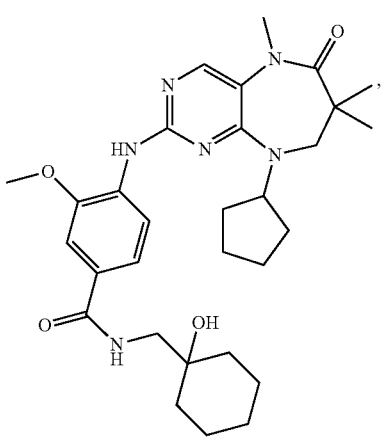 |

191
-continued
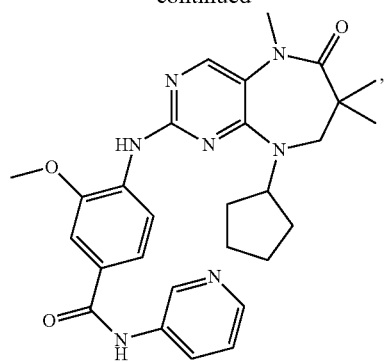
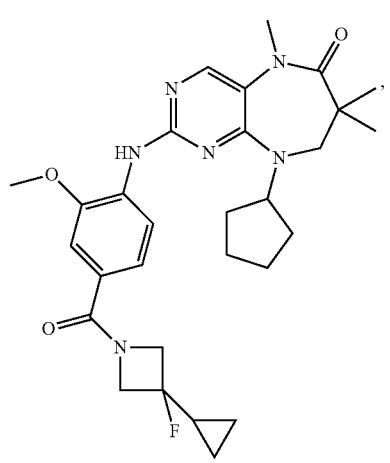
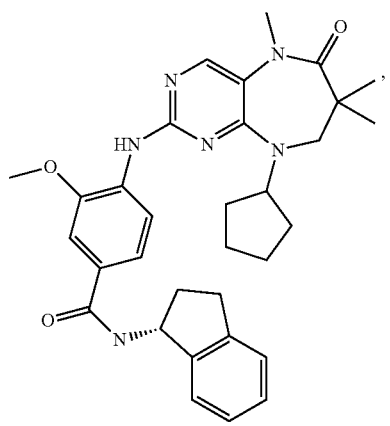
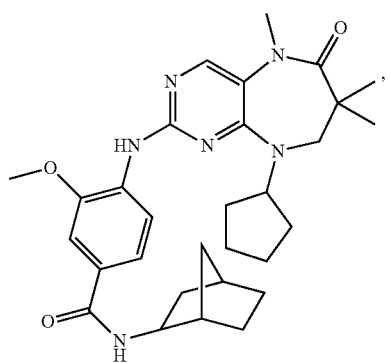
192
-continued
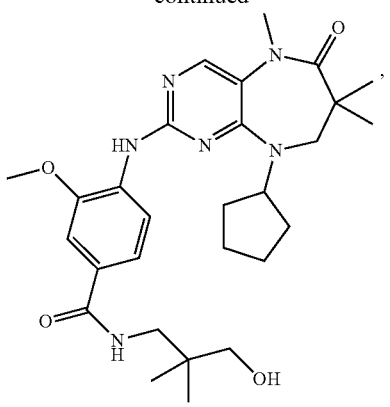
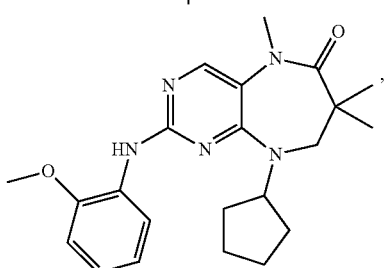
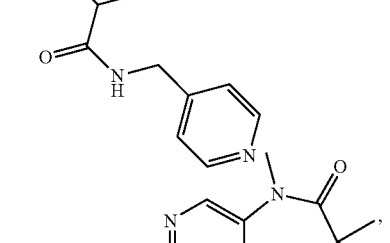
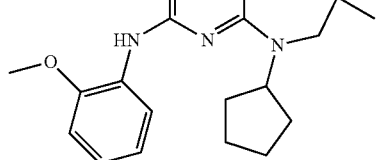
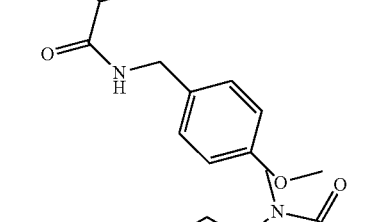
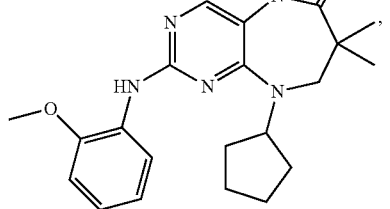
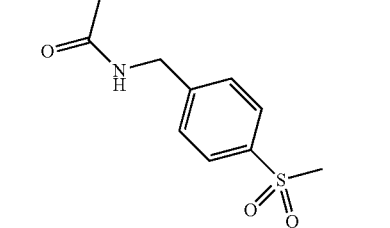

193
-continued
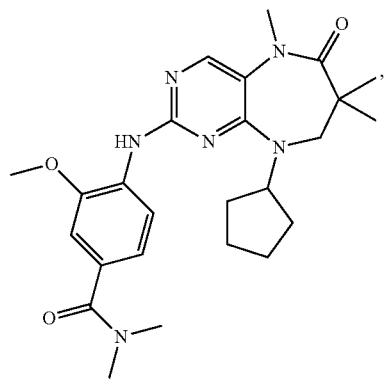
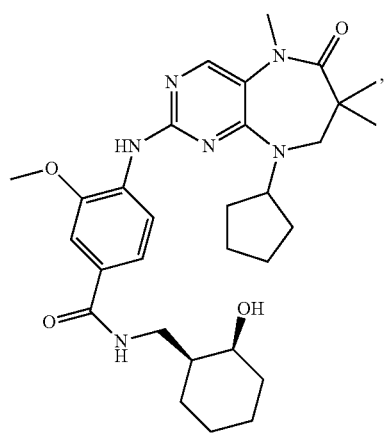
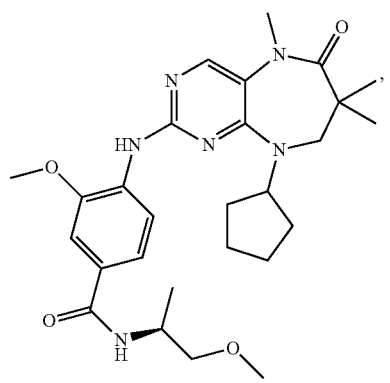
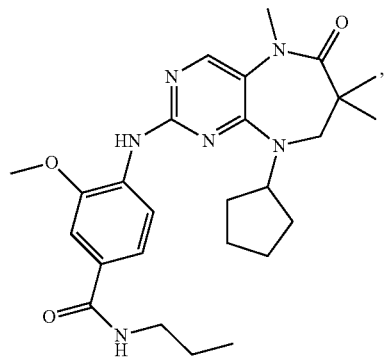
194
-continued
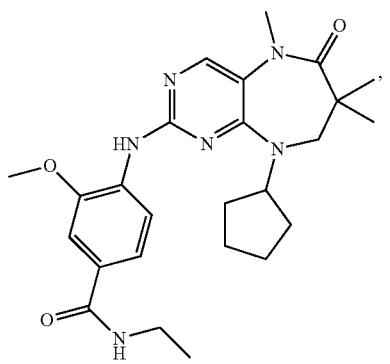
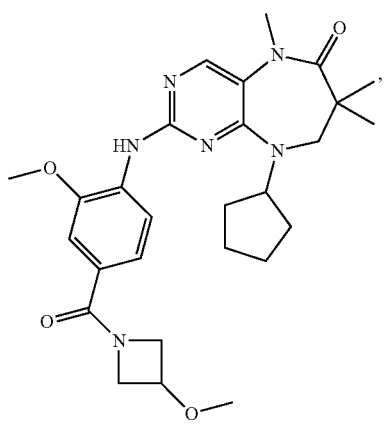
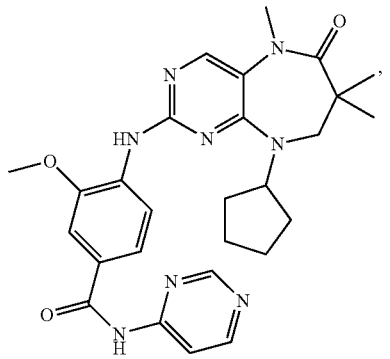
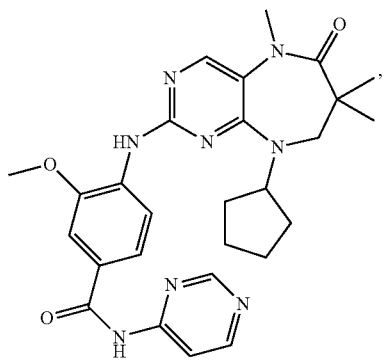

195
-continued
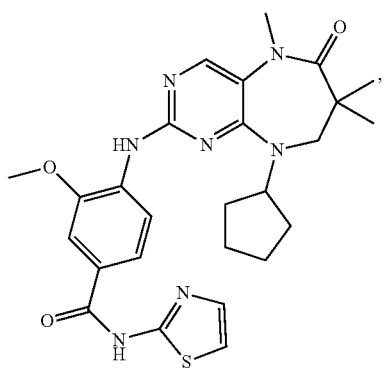
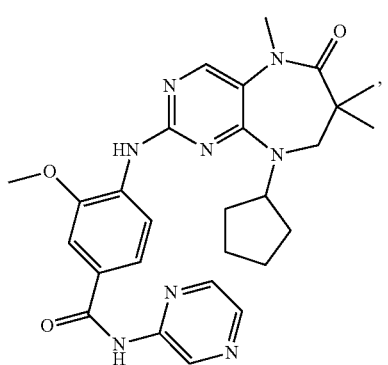
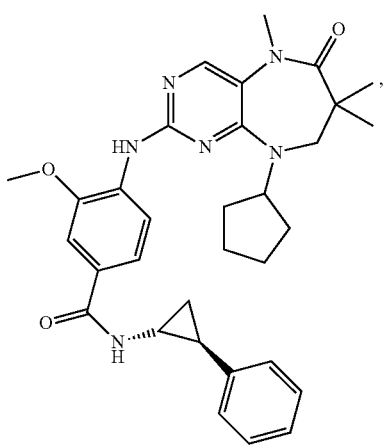
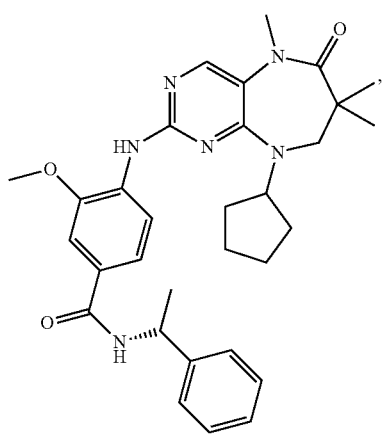
196
-continued
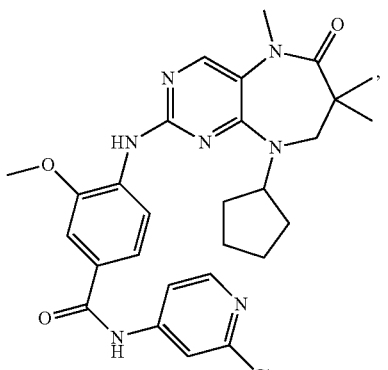
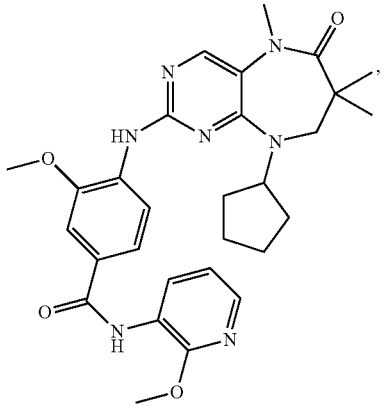
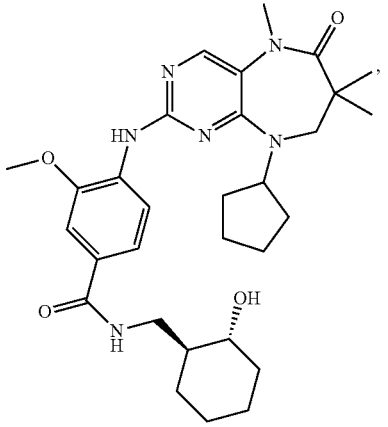
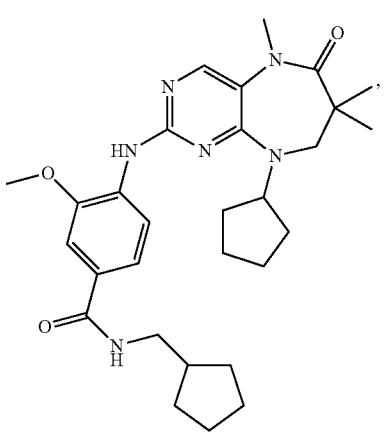

197
-continued
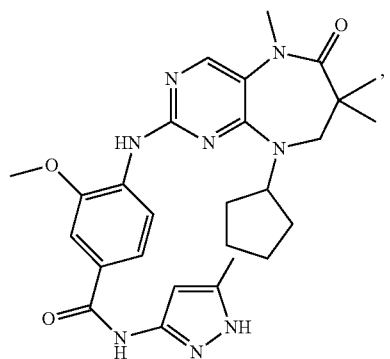
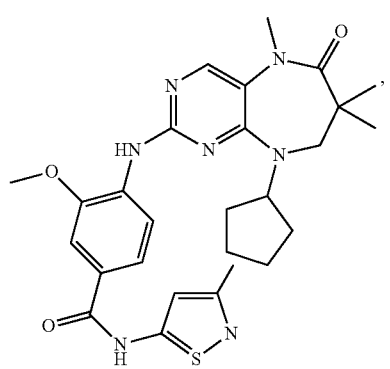
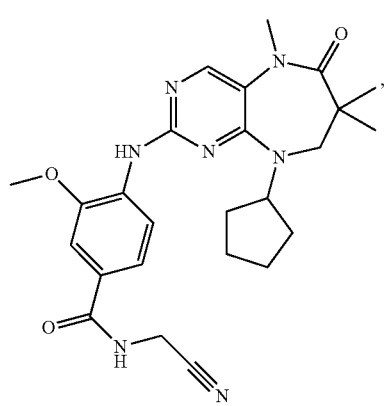
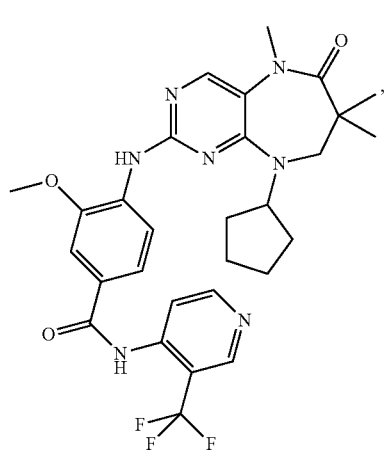
198
-continued
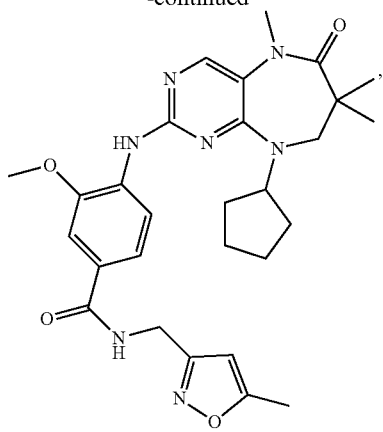
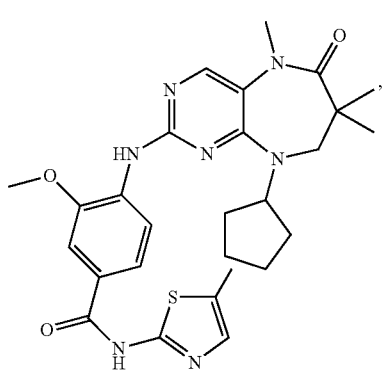
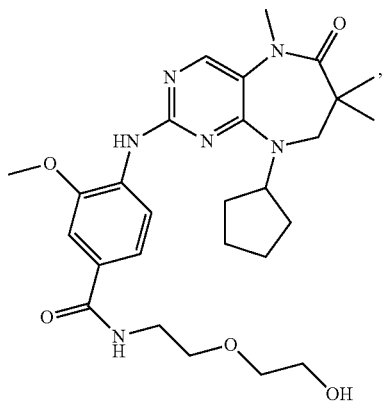
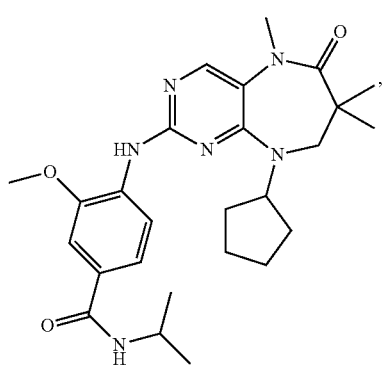

199
-continued
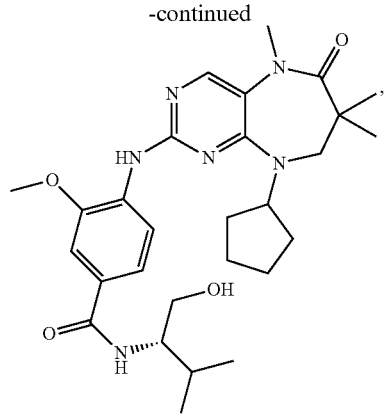
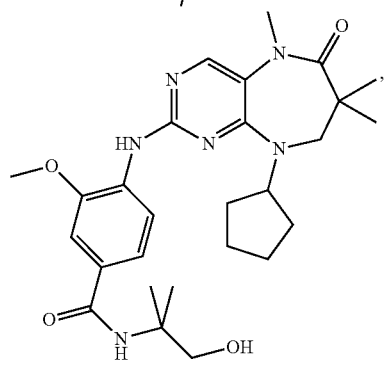
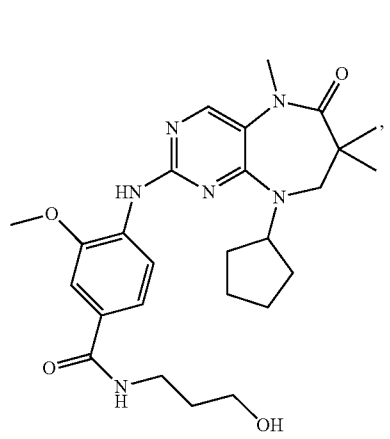
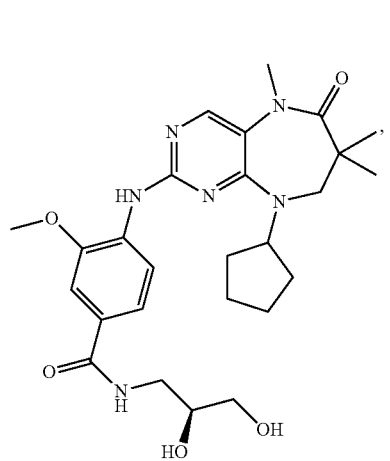
200
-continued
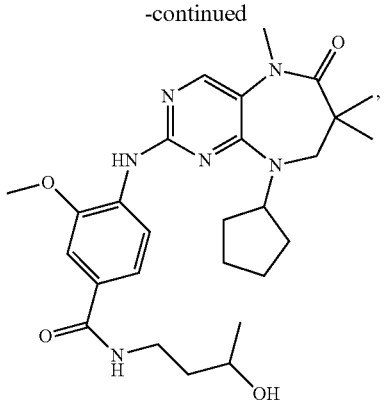
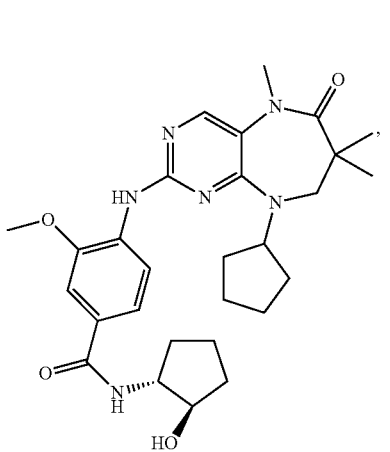
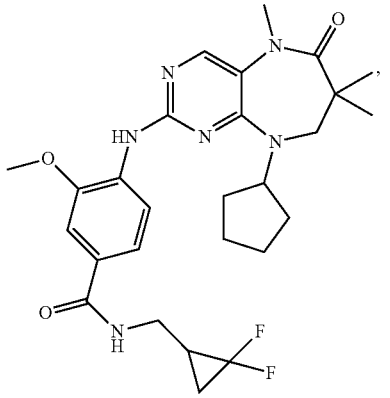
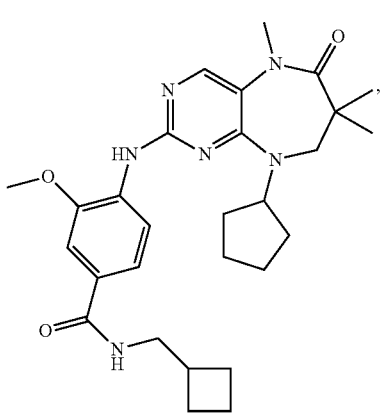

201
-continued
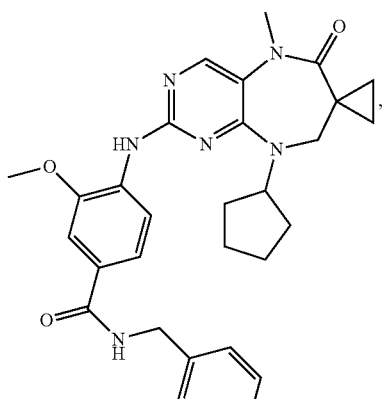
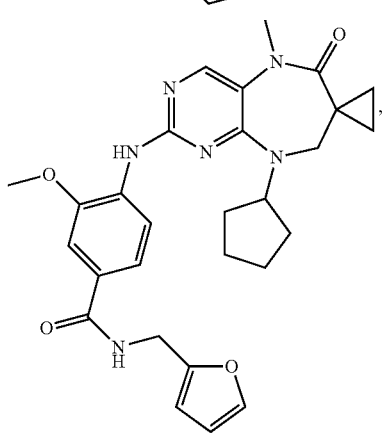
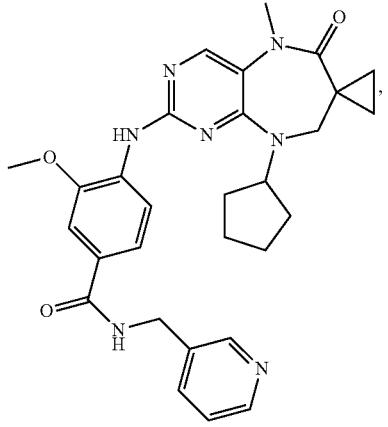
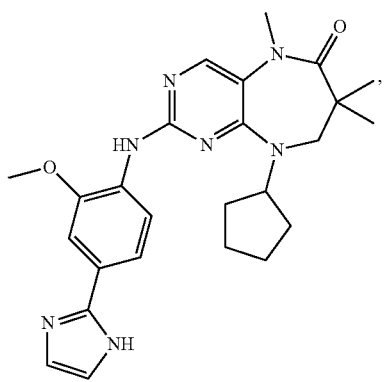
202
-continued
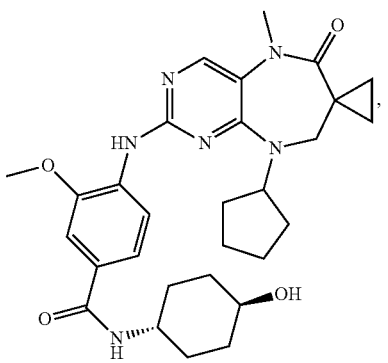
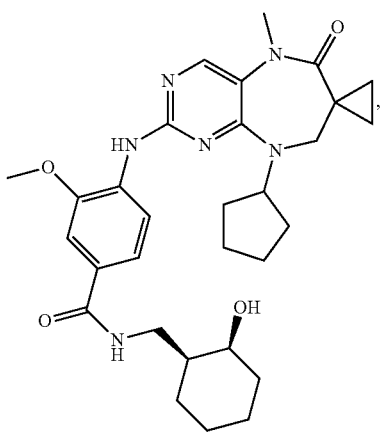
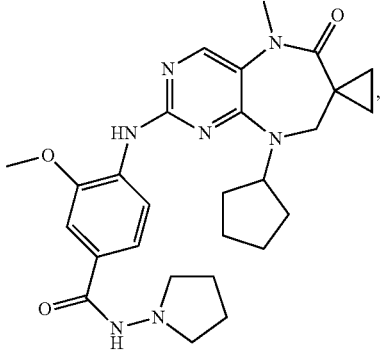
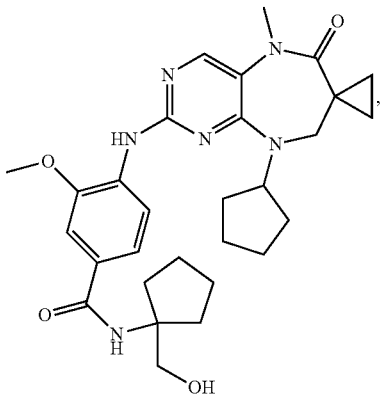

203
-continued
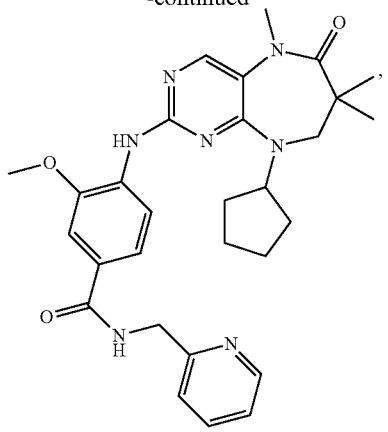
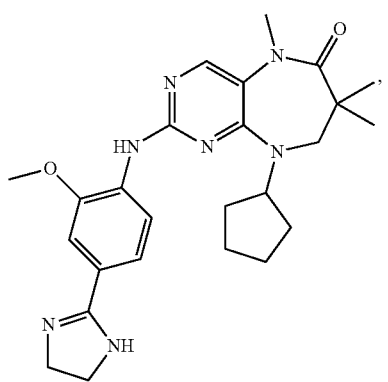
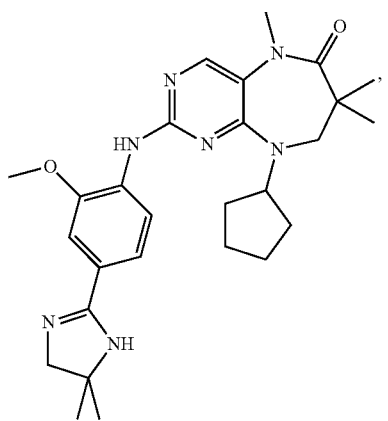
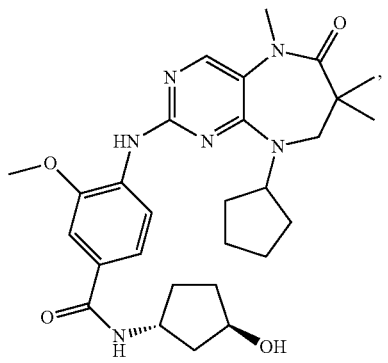
204
-continued
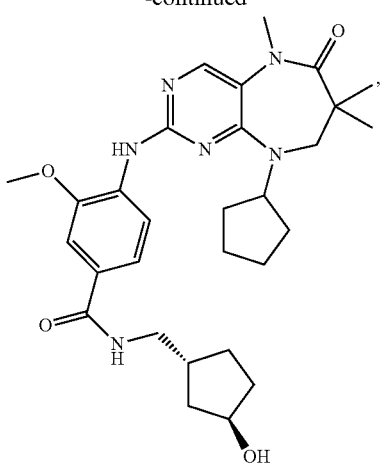
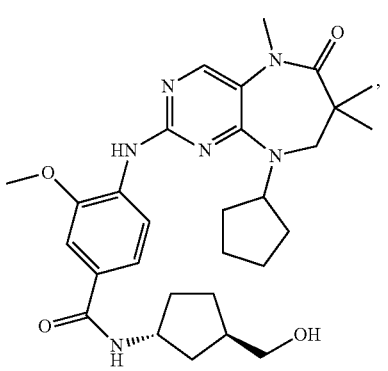
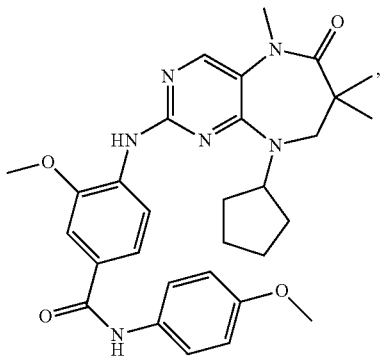
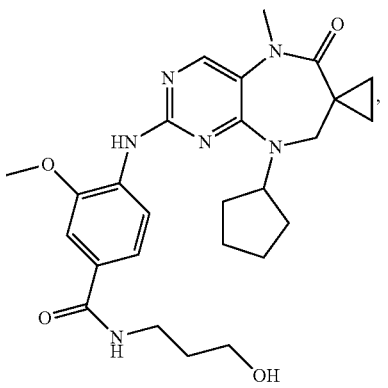

205
-continued
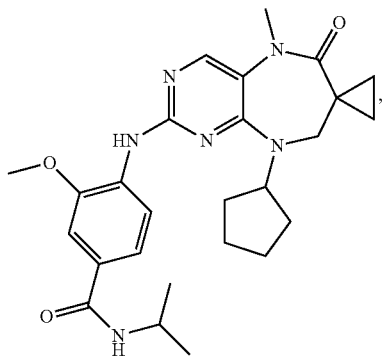
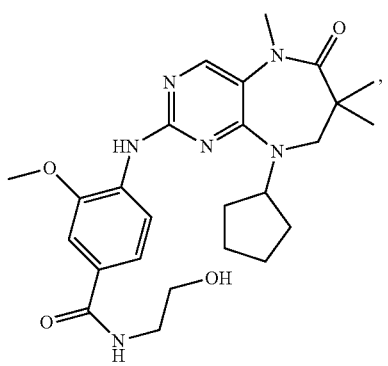
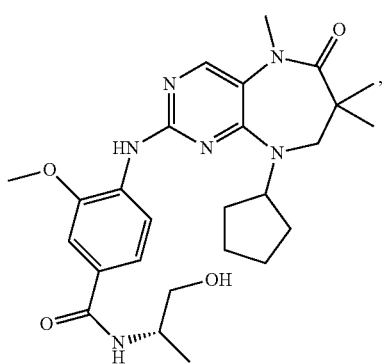
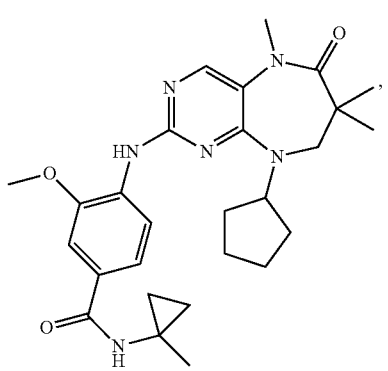
206
-continued
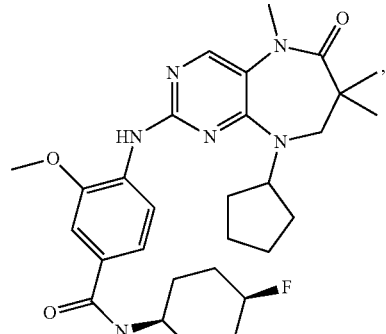
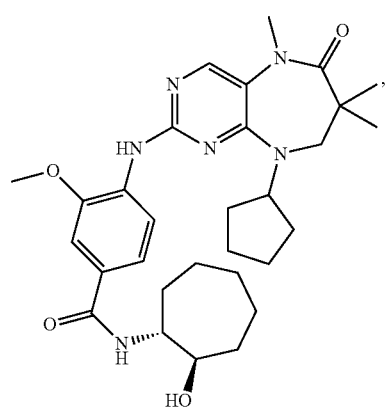
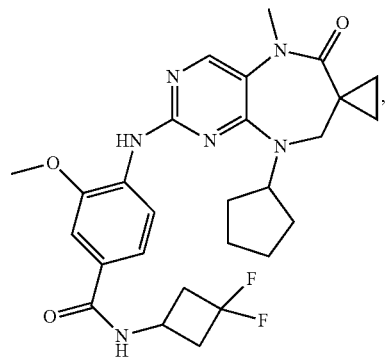
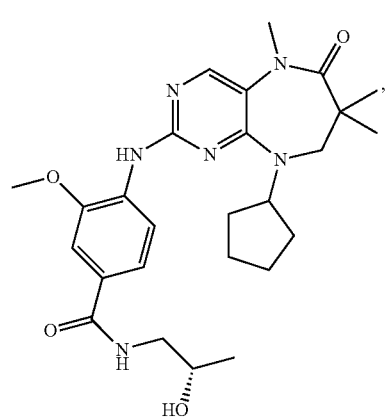

207
-continued
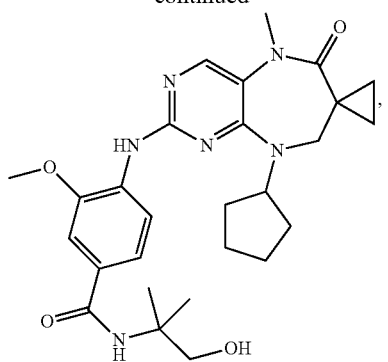
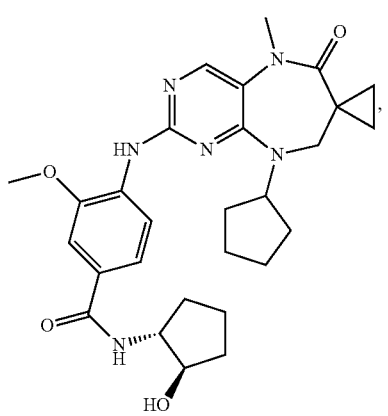
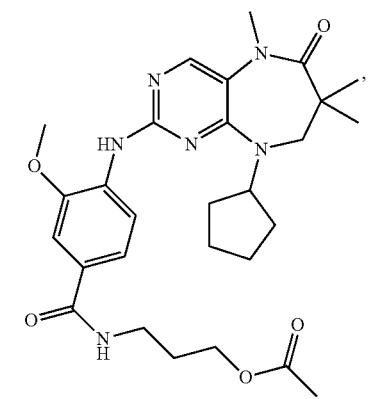
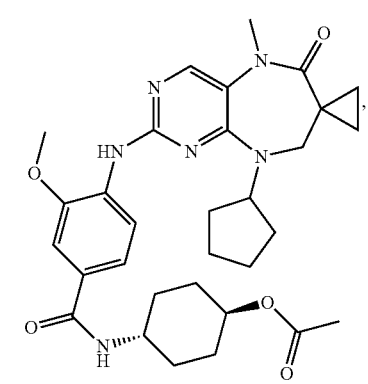
208
-continued
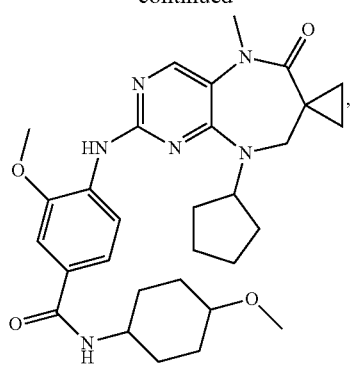
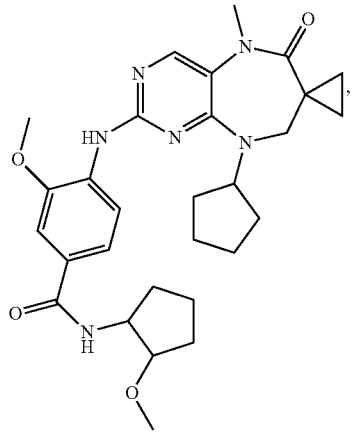
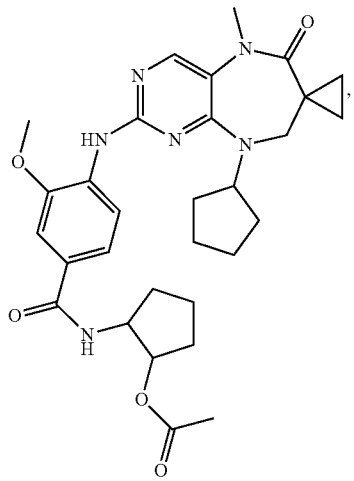
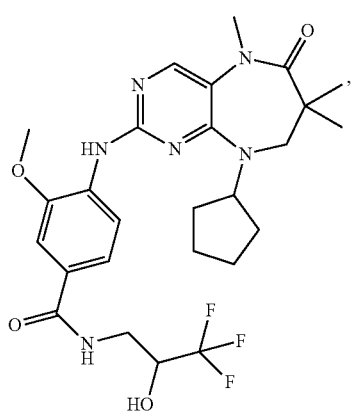

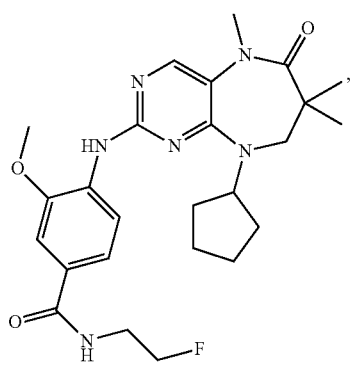
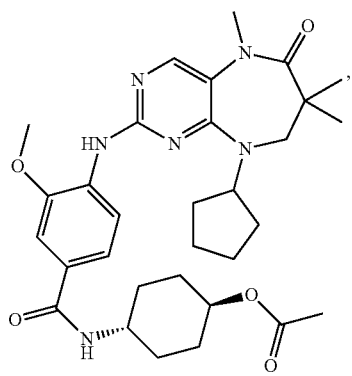
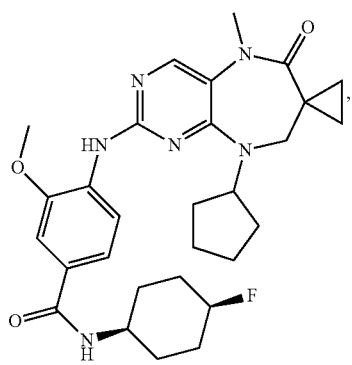
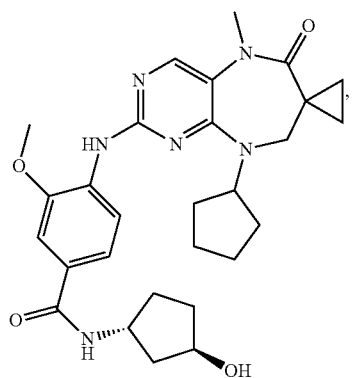
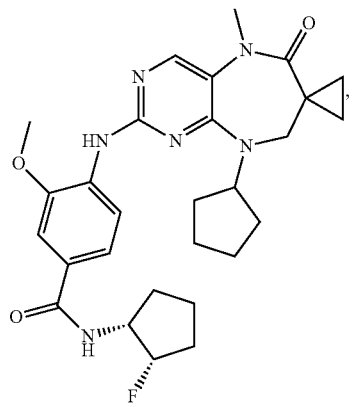
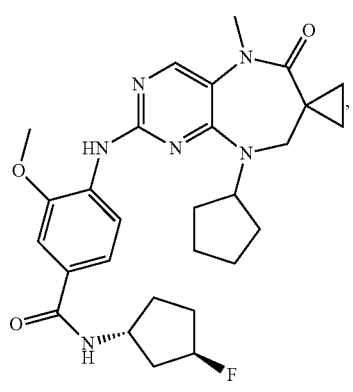
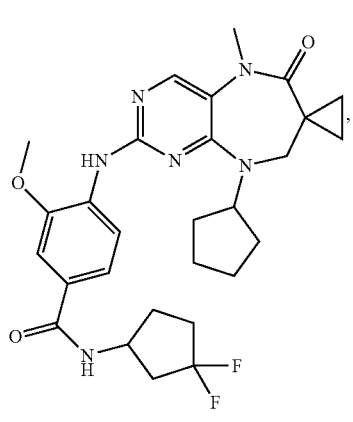
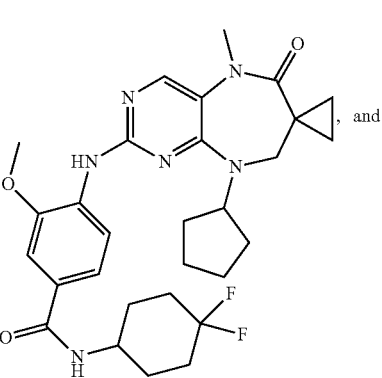

-continued
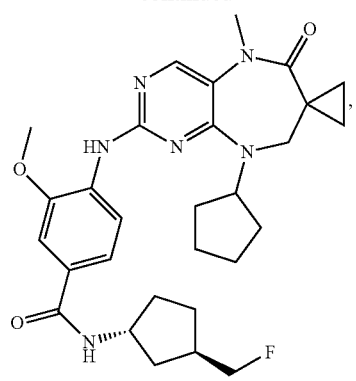
or a pharmaceutically acceptable salt thereof.
35. The method of claim 1, wherein the compound of Structural Formula (I) is represented by any one of the following structural formulae:
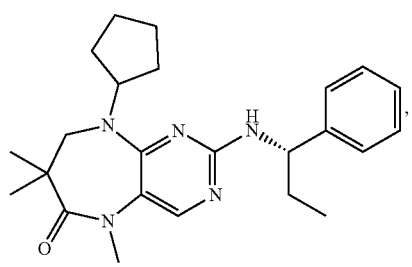
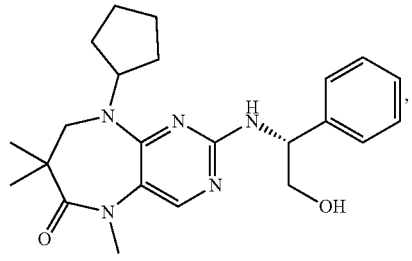
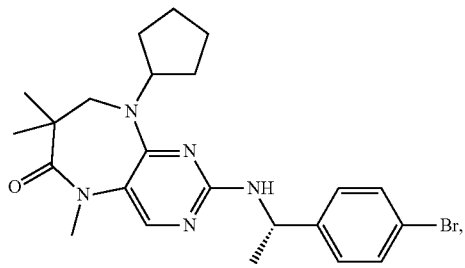
-continued
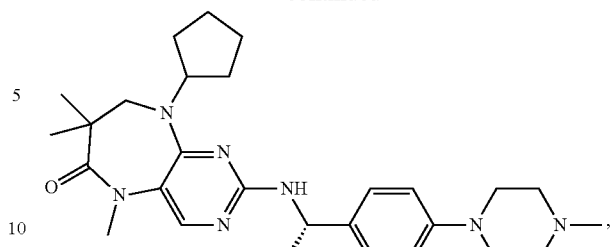
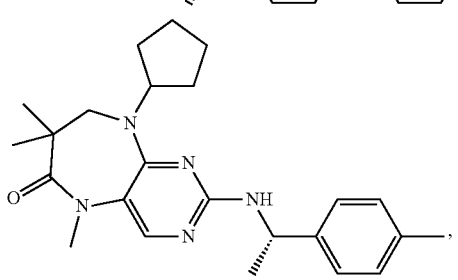
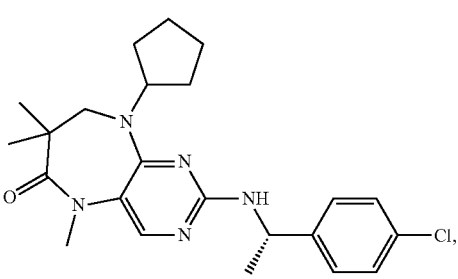
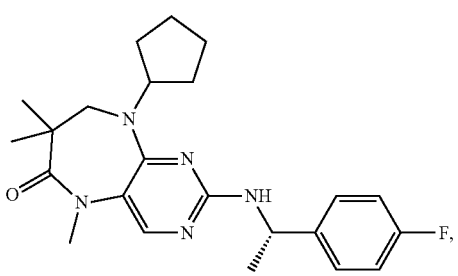
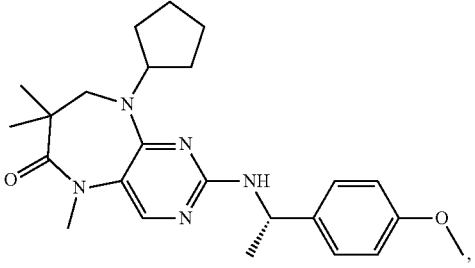
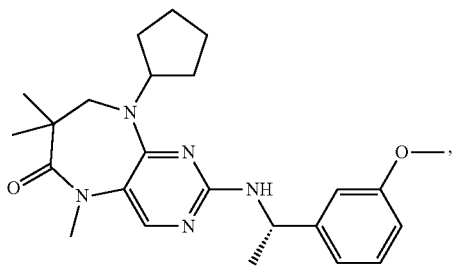

213
-continued
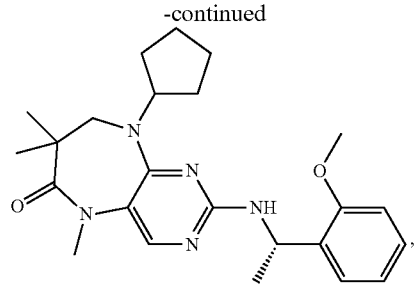
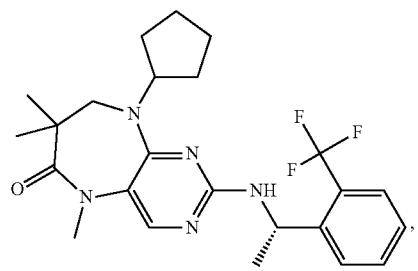
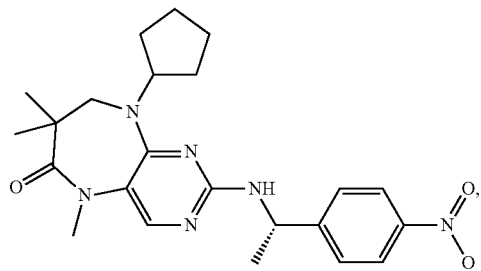
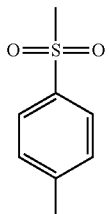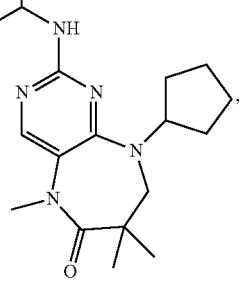
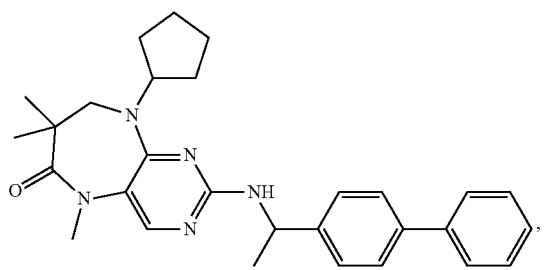
214
-continued
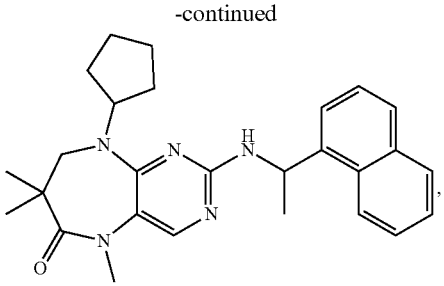
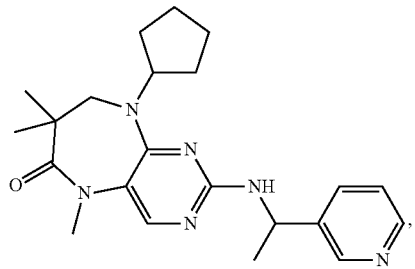
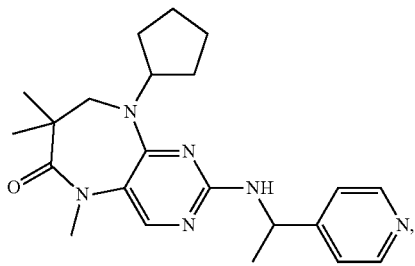
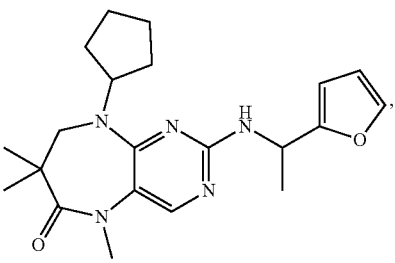
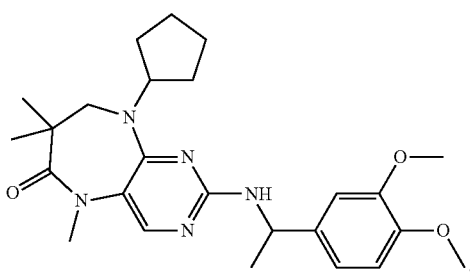
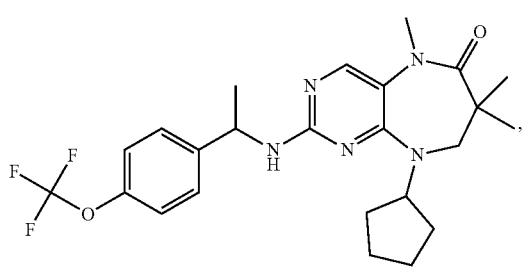

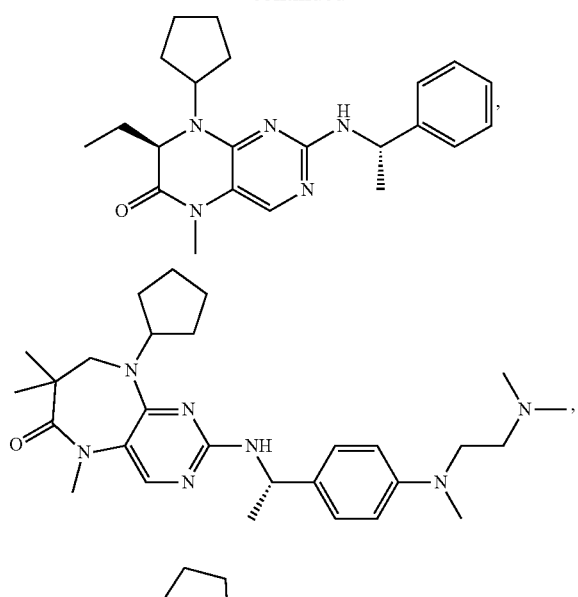
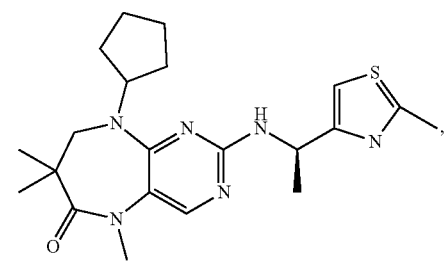
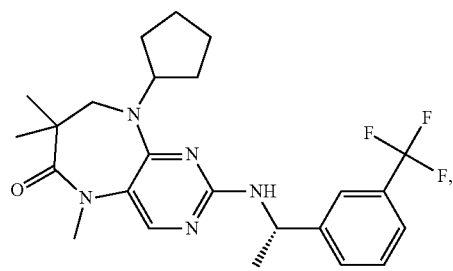
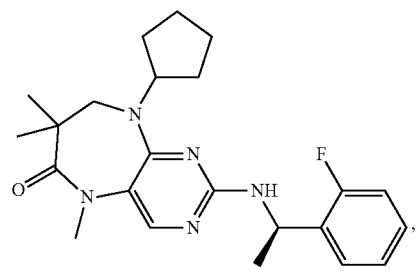
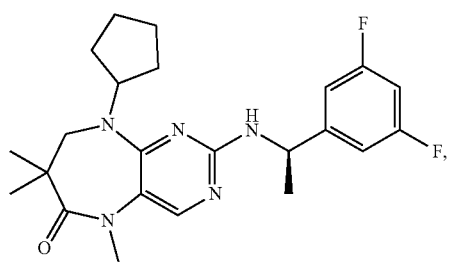
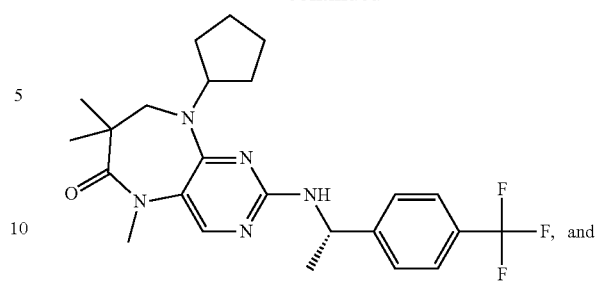
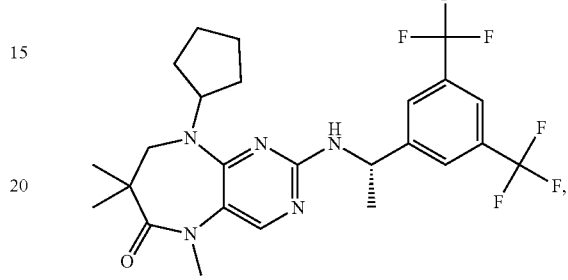
or a pharmaceutically acceptable salt thereof.
36. The method of claim 1, wherein the compound produced by the method is represented by any one of the following structural formulae:
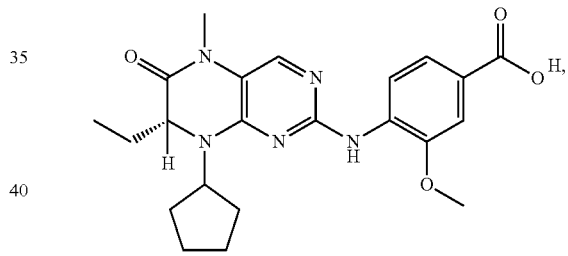
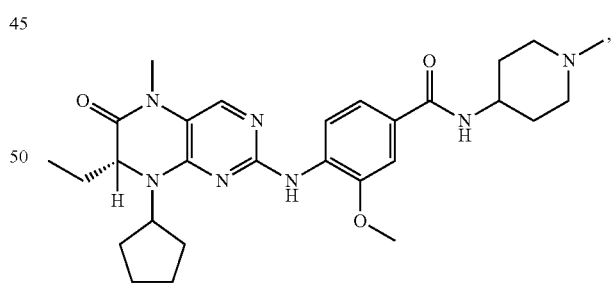
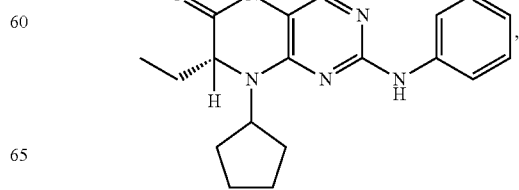

217
-continued
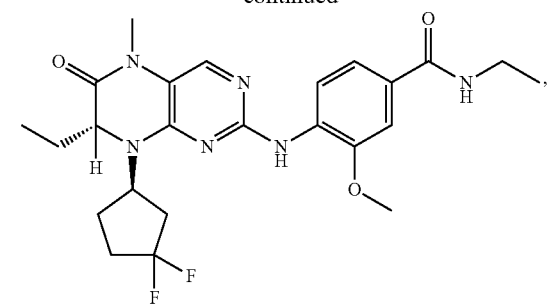
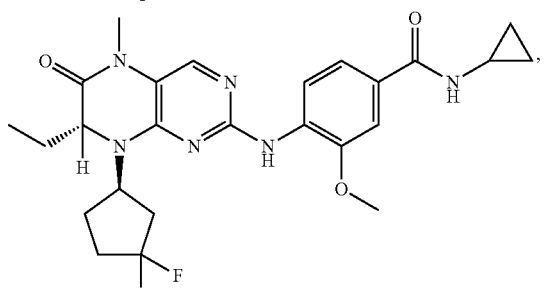
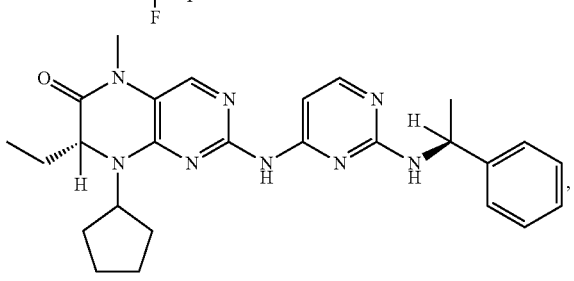
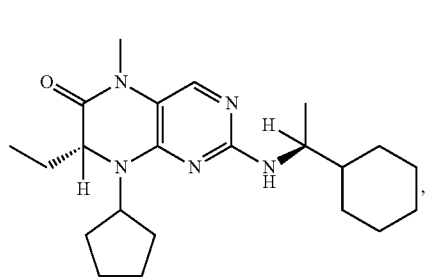
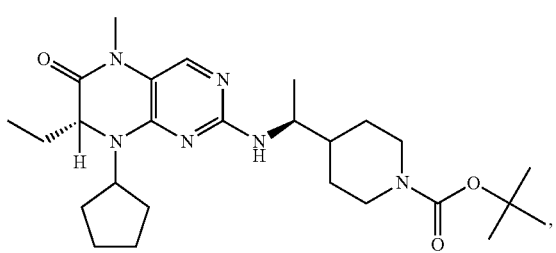
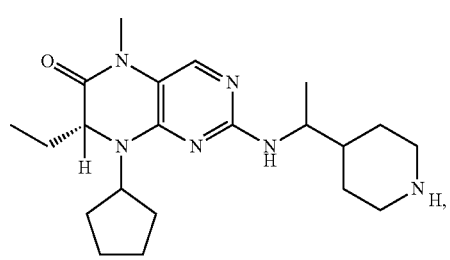
218
-continued
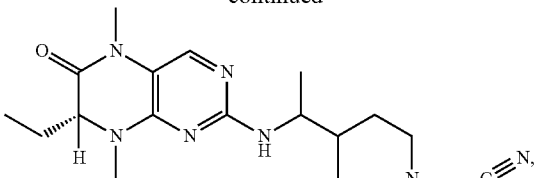
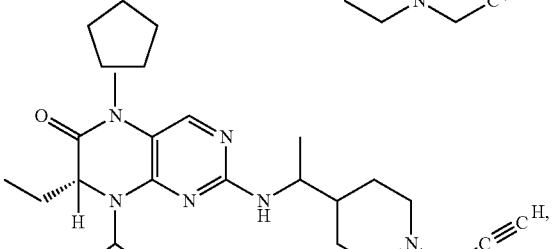
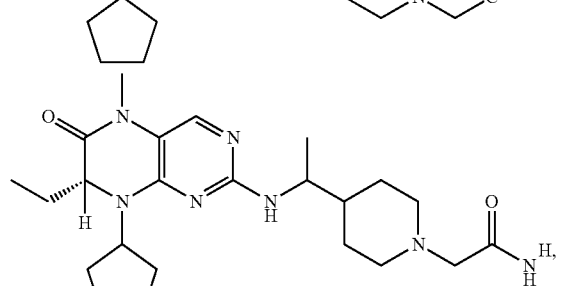
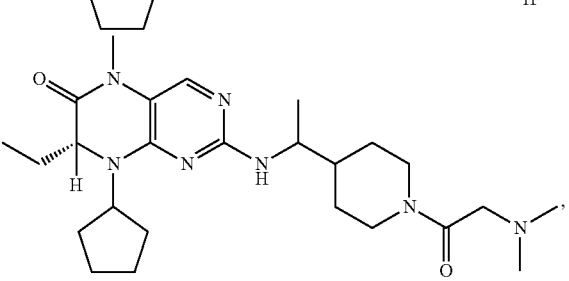
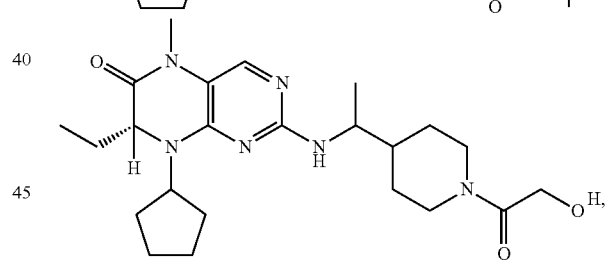
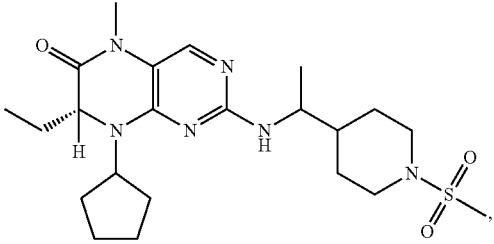
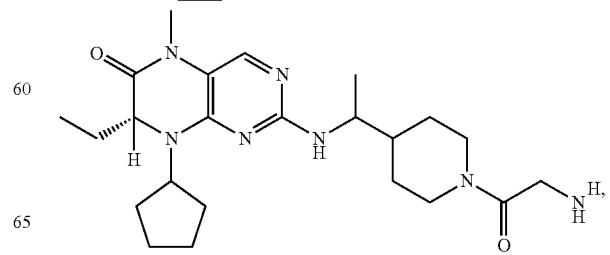

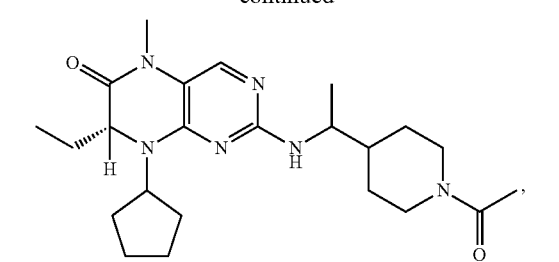

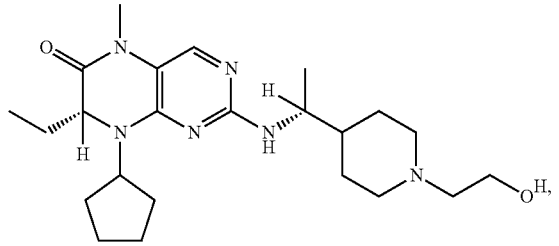

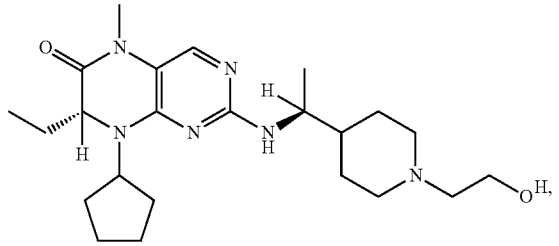

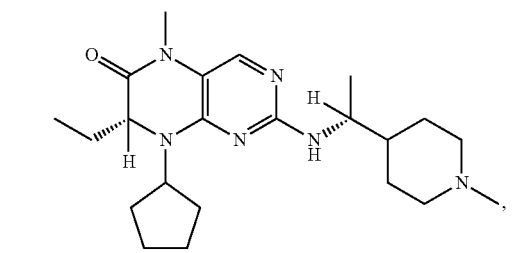

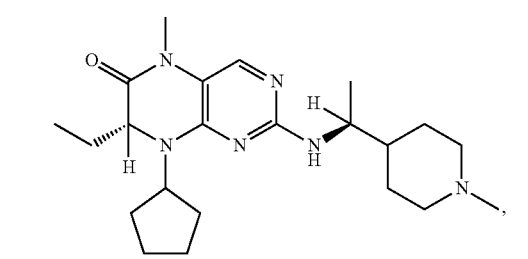

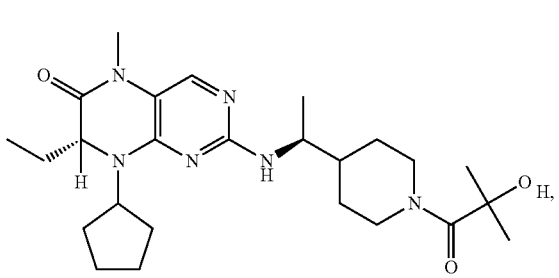

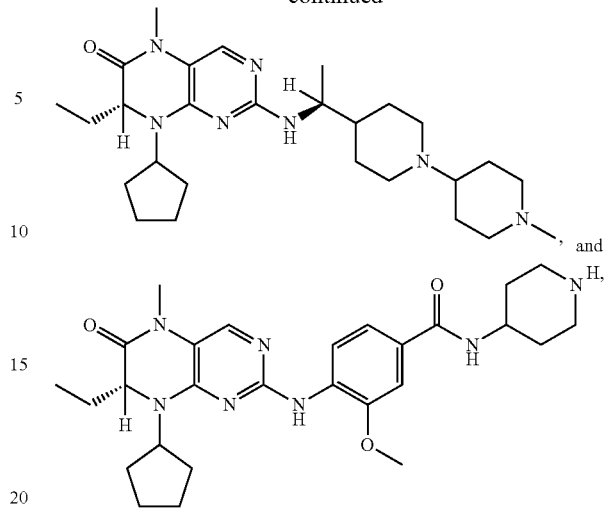

or a pharmaceutically acceptable salt thereof.

37. The method of claim 1, wherein the compound represented by Structural Formula (I) is represented by the following structural formula:

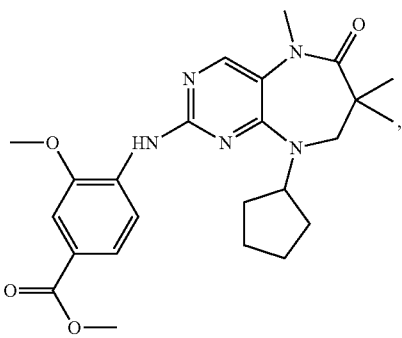

or a pharmaceutically acceptable salt thereof.

38. The method of claim 1, wherein the compound represented by Structural Formula (I) is represented by the following structural formula:

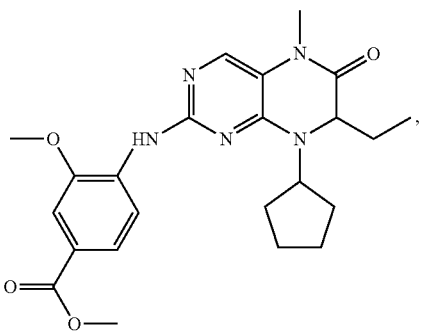 [SMILES: CCC1C(=O)N(C)c2cnc(Nc3ccc(C(=O)OC)cc3OC)nc2N1C1CCCC1]

or a pharmaceutically acceptable salt thereof.

* * * * *